United States Patent
(12) United States Patent
Yue et al.

(10) Patent No.: US 12,338,217 B2
(45) Date of Patent: Jun. 24, 2025

(54) NITROGEN-CONTAINING COMPOUND, ELECTRONIC ELEMENT AND ELECTRONIC DEVICE

(71) Applicant: SHAANXI LIGHTE OPTOELECTRONICS MATERIAL CO., LTD., Xi'an (CN)

(72) Inventors: Fumin Yue, Xi'an (CN); Chaochao Li, Xi'an (CN); Jiacong Xu, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/728,862

(22) PCT Filed: May 15, 2023

(86) PCT No.: PCT/CN2023/094373
§ 371 (c)(1),
(2) Date: Jul. 12, 2024

(87) PCT Pub. No.: WO2024/037073
PCT Pub. Date: Feb. 22, 2024

(65) Prior Publication Data

US 2025/0115554 A1 Apr. 10, 2025

(30) Foreign Application Priority Data

Aug. 17, 2022 (CN) ......................... 202210988201.1

(51) Int. Cl.
*C07D 209/90* (2006.01)
*C07B 59/00* (2006.01)
(Continued)

(52) U.S. Cl.
CPC .......... *C07D 209/90* (2013.01); *C07B 59/004* (2013.01); *C07D 403/12* (2013.01);
(Continued)

(58) Field of Classification Search
None
See application file for complete search history.

(56) References Cited

FOREIGN PATENT DOCUMENTS

| | | | |
|---|---|---|---|
| CN | 103827257 | A | 5/2014 |
| CN | 105980521 | A | 9/2016 |

(Continued)

*Primary Examiner* — Anthony Ho
(74) *Attorney, Agent, or Firm* — Rodney J. Fuller; Booth Udall Fuller, PLC

(57) ABSTRACT

The present disclosure belongs to the technical field of organic materials, and relates to a nitrogen-containing compound, an electronic element and an electronic device. The compound has a structure as shown in formula (1) below. The nitrogen-containing compound of the present disclosure can improve the performance of an electronic element.

(1)

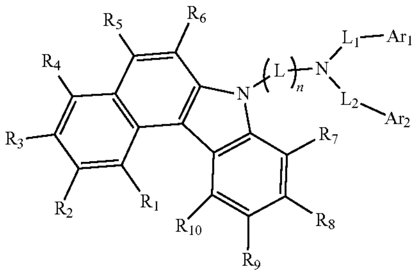

11 Claims, 1 Drawing Sheet

(51) Int. Cl.

| | |
|---|---|
| ***C07D 403/12*** | (2006.01) |
| ***C07D 405/12*** | (2006.01) |
| ***C07D 409/12*** | (2006.01) |
| ***H10K 85/60*** | (2023.01) |

(52) U.S. Cl.

CPC ......... *C07D 405/12* (2013.01); *C07D 409/12* (2013.01); *H10K 85/615* (2023.02); *H10K 85/631* (2023.02); *H10K 85/6572* (2023.02); *H10K 85/6574* (2023.02); *H10K 85/6576* (2023.02); *C07B 2200/05* (2013.01)

(56) References Cited

FOREIGN PATENT DOCUMENTS

| | | | |
|---|---|---|---|
| CN | 108780853 | A | 11/2018 |
| CN | 112300053 | A | 2/2021 |
| CN | 115650899 | A | 1/2023 |
| CN | 116947735 | A | 10/2023 |
| KR | 10-2016-0029721 | A | 3/2016 |
| KR | 10-2017-0058177 | A | 5/2017 |

NITROGEN-CONTAINING COMPOUND, ELECTRONIC ELEMENT AND ELECTRONIC DEVICE

CROSS-REFERENCE TO RELATED DISCLOSURES

This application is the U.S. National Stage of International Patent Application No. PCT/CN2023/094373, filed on May 15, 2023, which claims the benefit and priority of Chinese patent disclosure No. 202210988201.1 filed on Aug. 17, 2022, the contents of each of which are incorporated herein by reference in their entireties.

FIELD OF THE INVENTION

The present disclosure belongs to the technical field of organic materials, and in particular provides a nitrogen-containing compound, an electronic element and an electronic device.

BACKGROUND OF THE INVENTION

Organic electroluminescent devices, also known as organic light-emitting diodes, refer to the phenomenon that organic light-emitting materials emit light when excited by current under the action of an electric field. It is a process of converting electrical energy into light energy. Compared with inorganic light emitting materials, organic light emitting diodes OLEDs have the advantages of active light emission, large optical path range, low driving voltage, high brightness, high efficiency, low energy consumption and simple manufacturing process. It is precisely because of these advantages that organic light-emitting materials and devices have become one of the most popular scientific research topics in the scientific community and industry.

Organic electroluminescent devices generally comprise an anode, a hole transport layer, an electron blocking layer, an organic light emitting layer, an electron transport layer, an electron injection layer and a cathode that are stacked in sequence. When a voltage is applied to the cathode and anode, the two electrodes generate an electric field. Under the action of the electric field, the electrons on the cathode side move toward the organic light emitting layer, and the holes on the anode side also move toward the organic light emitting layer. The electrons and holes combine in the organic light emitting layer to form excitons, and the excitons in an excited state release energy outwards, thereby causing the organic light emitting layer to emit light.

Currently, there are problems such as reduced luminous efficiency and shortened lifespan during the use of organic electroluminescent devices, resulting in a decline in the performance of organic electroluminescent devices.

SUMMARY OF THE INVENTION

In view of the above problems existing in the prior art, the present disclosure aims at providing a nitrogen-containing compound, an electronic element and an electronic device using the same. The nitrogen-containing compound, when used in an electronic element, can improve the performance of the electronic element.

In order to achieve the above object, the first aspect of the present disclosure provides a nitrogen-containing compound having a structure as shown in the following Formula 1:

Formula 1

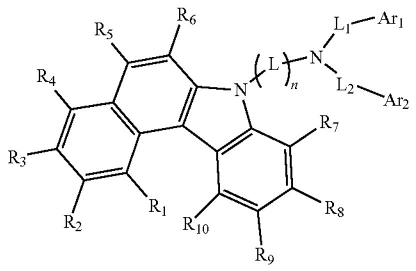

wherein, $R_2$ to $R_9$ are identical or different, and each is independently hydrogen or deuterium;

$R_1$ and $R_{10}$ are identical or different, and each is independently selected from hydrogen, deuterium, and group A, and only one of $R_1$ and $R_{10}$ is selected from group A, and the group A is selected from an aryl having 6 to 12 carbon atoms, and a deuterated aryl having 6 to 12 carbon atoms;

$Ar_1$ and $Ar_2$ are identical or different, and each is independently selected from a substituted or unsubstituted aryl having 6 to 30 carbon atoms, and a substituted or unsubstituted heteroaryl having 5 to 30 carbon atoms;

each L is independently selected from a substituted or unsubstituted arylene having 6 to 30 carbon atoms, and a substituted or unsubstituted heteroarylene having 5 to 30 carbon atoms, n represents the number of L, n is selected from 1 and 2, and when n is 2, each L is identical or different;

$L_1$ and $L_2$ are identical or different, and each is independently selected from a single bond, a substituted or unsubstituted arylene having 6 to 30 carbon atoms, and a substituted or unsubstituted heteroarylene having 5 to 30 carbon atoms;

substituent(s) in L, $L_1$, $L_2$, $Ar_1$, and $Ar_2$ are identical or different, and each is independently selected from deuterium, a halogen, cyano, an alkyl having 1 to 10 carbon atoms, an aryl having 6 to 18 carbon atoms, a heteroaryl having 5 to 18 carbon atoms, a deuterated alkyl having 1 to 10 carbon atoms, a haloalkyl having 1 to 10 carbon atoms, and a trialkylsiyl having 3 to 12 carbon atoms; in $Ar_1$ and $Ar_2$, optionally, any two adjacent substituents form a saturated or unsaturated ring having 3 to 15 carbon atoms.

A second aspect of the present disclosure provides an electronic element, comprising an anode and a cathode disposed opposite to each other, and a functional layer disposed between the anode and the cathode; wherein the functional layer comprises the nitrogen-containing compound described in the first aspect of the present disclosure.

A third aspect of the present disclosure provides an electronic device, comprising the electronic element described in the second aspect of the present disclosure.

The nitrogen-containing compound of the present disclosure has a specific benzocarbazolyl

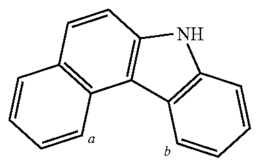 [SMILES: c1ccc2c(c1)ccc1[nH]c3ccccc3c12]

as the parent nucleus, and the position a or position b of the parent nucleus linked with a smaller aryl such as phenyl, biphenyl, or naphthyl (hereinafter collectively referred to as small-structure aryl), the conjugation of these small-structure aryl with benzocarbazolyl rings will make the electron cloud density distribution wider and increase the hole mobility of the molecule, thereby improving the efficiency of the obtained OLED device.

BRIEF DESCRIPTION OF THE DRAWINGS

The accompanying drawings are intended to provide a further understanding of the present disclosure and form a part of the specification. The accompanying drawings, together with the following specific embodiments, are used to illustrate the present disclosure, but do not constitute any limitation to the present disclosure.

LIST OF REFERENCE SIGNS

Figure 1:
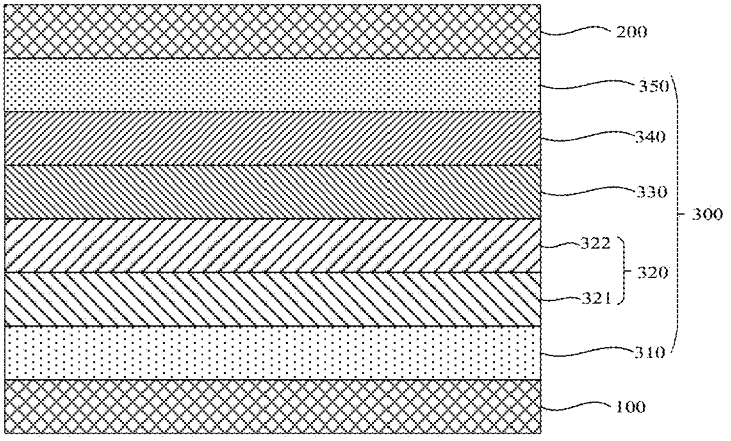
FIG. 1 is a schematic structural diagram of an organic electroluminescent device according to an embodiment of the present disclosure.

100: anode; 200: cathode; 300: functional layer; 310: hole injection layer; 320: hole transport layer; 321: first hole transport layer; 322: second hole transport layer; 330: organic light emitting layer; 340: electron transport layer; 350: electron injection layer; 360: photoelectric conversion layer; 400: first electronic device; 500: second electronic device.

DETAILED DESCRIPTION OF THE EMBODIMENTS

Specific embodiments of the present disclosure will be described in detail below with reference to the accompanying drawings. It should be understood that the specific embodiments described here are only used to illustrate and explain the present disclosure, and are not intended to limit the present disclosure.

Exemplary embodiments will now be described more comprehensively with reference to the accompanying drawings. The exemplary embodiments, however, can be implemented in a variety of forms and should not be interpreted as being limited to the examples set forth herein. On the contrary, these embodiments are provided to make the present disclosure more comprehensive and complete, and to communicate the concepts of these exemplary embodiments fully to those skilled in the art. Features, structures, or characteristics described can be combined in one or more embodiment(s) in any suitable manner. In the following description, many specific details are provided to give a full understanding of the embodiments of the present disclosure.

In the present disclosure, the expression "each . . . independently" may be used interchangeably with the expressions ". . . respectively and independently", and ". . . each independently", and all these expressions should be interpreted in a broad sense. They can not only mean that, in different groups, specific options expressed between the same symbols do not affect each other, but also mean that in a same group, specific options expressed between the same symbols do not affect each other. For example, the meaning of "

Q-1

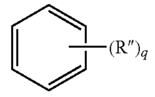

Q-2

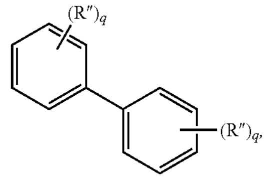

where each q is independently 0, 1, 2, or 3, and each R" is independently selected from hydrogen, deuterium, fluorine and chlorine" is as follows: Formula Q-1 represents that q substituents R" exist on a benzene ring, each R" can be identical or different, and options of each R" do not affect each other; and Formula Q-2 represents that each benzene ring of biphenyl has q substituents R", the number q of substituents R" on the two benzene rings can be identical or different, each R" can be identical or different, and options of each R" do not affect each other.

In the present disclosure, the term "optional" or "optionally" means that the subsequently described event or circumstance may but not need to occur, and the description includes instances where the event or circumstance does or does not occur. As an example, "optionally, any two adjacent substituents form a ring" means that the two substituents may but not need to form a ring, i.e., including instance where the two adjacent substituents form a ring and instance where the two adjacent substituents do not form a ring.

In the present disclosure, the term "substituted or unsubstituted" means that the functional group defined by the term may or may not have a substituent (hereinafter referred to as Rc for ease of description). For example, "substituted or unsubstituted aryl" refers to an aryl with a substituent Rc or an aryl without a substituent. The above substituent Rc, may be, for example, deuterium (D), halogen, cyano, alkyl, aryl, heteroaryl, deuterated alkyl, haloalkyl, trialkylsilyl, etc. In the present disclosure, the "substituted" functional group can be substituted by one or more of the above Rc; when two Rc are linked to the same atom, the two Rc can exist independently or link to each other to form a spiro ring with the atom; when there are two adjacent Rc on the functional group, the two adjacent Rc can exist independently or be fused to form a ring with the functional group to which they linked.

In the present disclosure, the number of carbon atoms of a substituted or unsubstituted functional group is the total number of all carbon atoms. For example, if $L_1$ is a substituted arylene having 20 carbon atoms, then the total number of all carbon atoms of the arylene and substituent(s) thereof is 20.

In the present disclosure, aryl refers to any functional group or substituent derived from an aromatic carbon ring. An aryl may be a monocyclic aryl (e.g., phenyl) or a polycyclic aryl. In other words, an aryl may be a monocyclic aryl, a fused aryl, two or more monocyclic aryls linked by carbon-carbon bond conjugation, a monocyclic aryl and a fused aryl linked by carbon-carbon bond conjugation, or two or more fused aryls linked by carbon-carbon bond conjugation. That is, unless otherwise specified, two or more aromatic groups linked by carbon-carbon bond conjugation may also be regarded as an aryl in the present disclosure. Among them, fused aryl may include, for example, bicyclic fused aryl (e.g., naphthyl), tricyclic fused aryl (e.g., phenanthryl, fluorenyl, anthryl), etc. An aryl does not contain heteroatoms such as B, N, O, S, P, Se, Si, etc. For example, In the present disclosure, naphthyl, terphenyl, etc. are aryl. Examples of aryl may include, but are not limited to, phenyl, naphthyl, fluorenyl, anthryl, phenanthryl, biphenyl, terphenyl, tetraphenyl, pentaphenyl, benzo[9,10]phenanthryl, pyrenyl, benzofluoranthenyl, chrysenyl, etc. In the present disclosure, arylene refers to a divalent group formed by further removing one hydrogen atom from an aryl.

In the present disclosure, the substituted aryl may be the aryl in which one or more hydrogen atom(s) are substituted by deuterium, halogen, cyano, aryl, heteroaryl, trialkylsilyl, alkyl, etc. A deuterated aryl may be the aryl in which one or more hydrogen atom(s) are substituted by deuterium. Specific examples of heteroaryl-substituted aryl include, but are not limited to, dibenzofuranyl-substituted phenyl, dibenzothienyl-substituted phenyl, pyridyl-substituted phenyl, carbazolyl-substituted phenyl, etc. It should be understood that the number of carbon atoms of a substituted aryl refers to the total number of carbon atoms of the aryl and substituent(s) on the aryl. For example, a substituted aryl having 30 carbon numbers means that the total number of carbon atoms in the aryl and substituent(s) thereof is 30. “More” means one, two or more than two.

In the present disclosure, the number of carbon atoms of substituted or unsubstituted aryl may be 6 to 30. For example, the number of carbon atoms of substituted or unsubstituted aryl is 6, 7, 8, 9, 10, 11, 12, 13, 14, 15, 16, 17, 18, 19, 20, 21, 22, 23, 24, 25, 26, 27, 28, 29, or 30.

In the present disclosure, heteroaryl refers to a monovalent aromatic ring or a derivative thereof containing at least 1 heteroatom. The heteroatom(s) may be one or more selected from B, O, N, P, Si, Se, and S. A heteroaryl may be a monocyclic heteroaryl or polycyclic heteroaryl. In other words, a heteroaryl may be a single aromatic ring system, or a plurality of aromatic ring systems linked by carbon-carbon bond conjugation, with any one of the aromatic ring systems being an aromatic monocyclic ring or a fused aromatic ring. For example, heteroaryl may include, but are not limited to, thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl and N-arylcarbazolyl (such as N-phenylcarbazolyl), N-heteroarylcarbazolyl (such as N-pyridylcarbazolyl), N-alkylcarbazolyl (such as N-methylcarbazolyl), etc., but are not limited thereto. Among them, thienyl, furyl, phenanthrolinyl, etc. are heteroaryl with a single aromatic ring system type, and N-arylcarbazolyl and N-heteroarylcarbazolyl are plurality of aromatic ring system types linked by carbon-carbon bond conjugation. In the present disclosure, the heteroarylene refers to a divalent group formed by further removing one hydrogen atom from a heteroaryl.

In the present disclosure, the substituted heteroaryl may be the heteroaryl in which one or more hydrogen atom(s) are substituted by deuterium, halogen, aryl, heteroaryl, trialkylsilyl, alkyl, haloalkyl, deuterated alkyl, etc. Specific examples of aryl-substituted heteroaryl include, but are not limited to, phenyl-substituted dibenzofuranyl, phenyl-substituted dibenzothienyl, phenyl-substituted pyridyl, etc. It should be understood that the number of carbon atoms of a substituted heteroaryl refers to the total number of carbon atoms of the heteroaryl and substituent(s) on the heteroaryl.

In the present disclosure, the number of carbon atoms of substituted or unsubstituted heteroaryl may be 5 to 30. For example, the number of carbon atoms of substituted or unsubstituted heteroaryl may be 5, 6, 7, 8, 9, 10, 11, 12, 13, 14, 15, 16, 17, 18, 19, 20, 21, 22, 23, 24, 25, 26, 27, 28, 29, or 30.

In the present disclosure, a non-positional linkage bond is single bond “—§—” extending from a ring system, and it indicates that one end of the linkage bond can be linked to any position in the ring system through which the bond passes, and the other end is linked to the rest of the compound molecule. For example, as shown in Formula (f) below, the naphthyl represented by Formula (f) is linked to other positions of the molecule via two non-positional bonds passing through the two rings, which indicates any of possible linkages shown in Formulae (f-1) to (f-10):

(f)

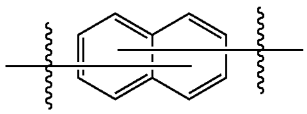

(f-1)

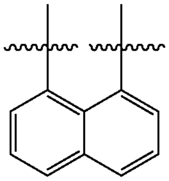

(f-2)

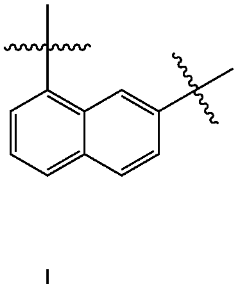

(f-3)

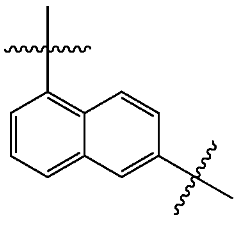

-continued (f-4)

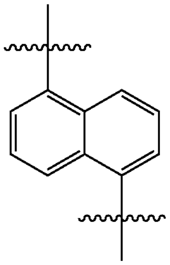

(f-5)

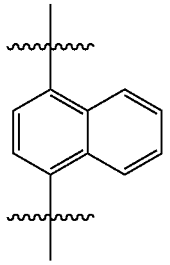

(f-6)

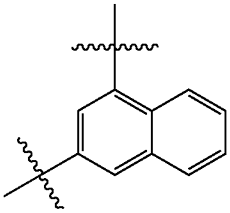

(f-7)

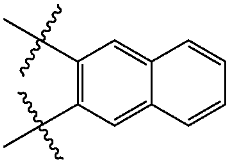

(f-8)

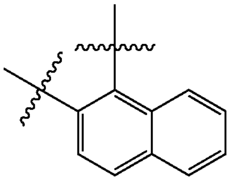

(f-9)

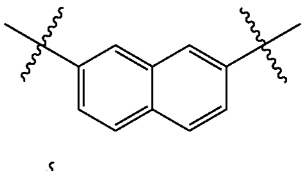

(f-10)

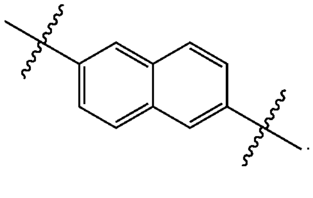

As another example, as shown in Formula (X') below, dibenzofuranyl represented by Formula (X') is linked to other positions of the molecule via a non-positional bond extending from the center of a side benzene ring, which indicates any of possible linkages shown in Formulae (X'-1) to (X'-4):

(X')

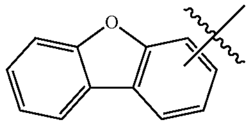

(X'-1)

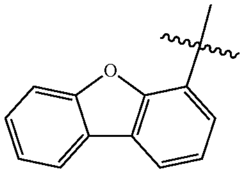

(X'-2)

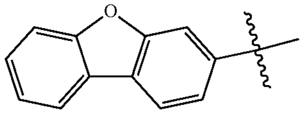

(X'-3)

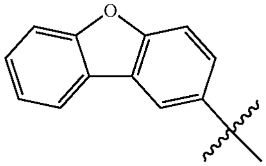

(X'-4)

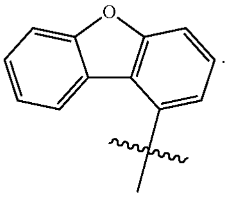

A non-positional substituent of the present disclosure refers to a substituent linked via single bond extending from the center of a ring system, and it means that the substituent may be linked to any possible position in the ring system. For example, as shown in Formula (Y) below, the substituent R' represented by Formula (Y) is linked to a quinoline ring via a non-positional bond, which indicates any of possible linkages shown in Formulae (Y-1) to (Y-7):

(Y)

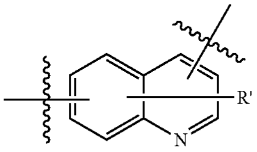

(Y-1)

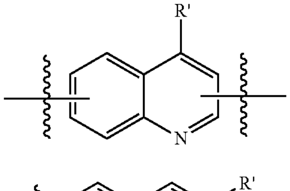

(Y-2)

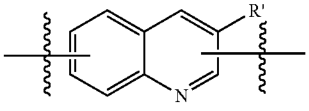

-continued (Y-3)

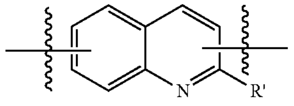

(Y-4)

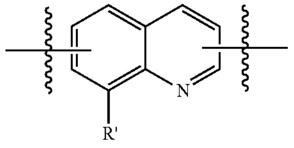

(Y-5)

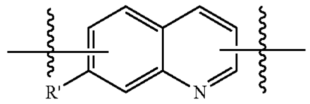

(Y-6)

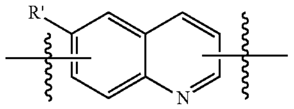

(Y-7)

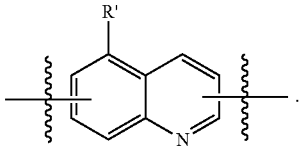

In the present disclosure, an alkyl having 1 to 10 carbon atoms may include a linear alkyl having 1 to 10 carbon atoms and a branched alkyl having 3 to 10 carbon atoms. The number of carbon atoms may be, for example, 1, 2, 3, 4, 5, 6, 7, 8, 9, or 10. Specific examples of alkyl with 1 to 10 carbon atoms include, but are not limited to, methyl, ethyl, n-propyl, isopropyl, n-butyl, isobutyl, tert-butyl, n-pentyl, isopentyl, neopentyl, cyclopentyl, n-hexyl, heptyl, n-octyl, 2-ethylhexyl, nonyl, decyl, 3,7-dimethyloctyl, etc.

In the present disclosure, halogen may be, for example, fluorine, chlorine, bromine, iodine, etc.

In the present disclosure, the number of carbon atoms of the trialkylsilyl as a substituent may be 3 to 12, for example, 3, 6, 7, 8, 9, 10, 11, or 12. Specific examples of trialkylsilyl include, but are not limited to, trimethylsilyl, ethyldimethylsilyl, triethylsilyl, etc.

In the present disclosure, the number of carbon atoms of the haloalkyl as a substituent may be 1 to 10, and the number of carbon atoms may be, for example, 1, 2, 3, 4, 5, 6, 7, 8, 9, or 10. For example, the haloalkyl may be a fluoroalkyl having 1 to 5 carbon atoms. Specific examples of haloalkyl include, but are not limited to, trifluoromethyl.

In the present disclosure, the number of carbon atoms of the aryl as a substituent may be 6 to 18, and the number of carbon atoms may be, for example, 6, 10, 12, 13, 14, 15, 18, etc. Specific examples of aryl as substituent(s) include, but are not limited to, phenyl, naphthyl, biphenyl, fluorenyl, phenanthryl, etc.

In the present disclosure, the number of carbon atoms of the heteroaryl as a substituent may be 5 to 18, and the number of carbon atoms may be, for example, 5, 6, 8, 9, 10, 11, 12, 18, etc. Specific examples of heteroaryl as substituent(s) include, but are not limited to, pyridyl, quinolyl, dibenzofuranyl, dibenzothienyl, carbazolyl, etc.

In a first aspect, the present disclosure provides a nitrogen-containing compound having a structure as shown in the following Formula 1:

Formula 1

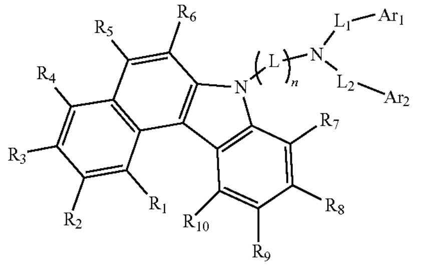

wherein, $R_2$ to $R_9$ ($R_2$, $R_3$, $R_4$, $R_5$, $R_6$, $R_7$, $R_8$, and $R_9$) are identical or different, and each is independently hydrogen (H) or deuterium (D);

$R_1$ and $R_{10}$ are identical or different, and each is independently selected from hydrogen, deuterium, and group A, and only one of $R_1$ and $R_{10}$ is selected from group A, and the group A is selected from an aryl having 6 to 12 carbon atoms, and a deuterated aryl having 6 to 12 carbon atoms;

$Ar_1$ and $Ar_2$ are identical or different, and each is independently selected from a substituted or unsubstituted aryl having 6 to 30 carbon atoms, and a substituted or unsubstituted heteroaryl having 5 to 30 carbon atoms;

each L is independently selected from a substituted or unsubstituted arylene having 6 to 30 carbon atoms, and a substituted or unsubstituted heteroarylene having 5 to 30 carbon atoms, n represents the number of L, and n is selected from 1 and 2, when n is 2, each L is identical or different;

$L_1$ and $L_2$ are identical or different, and each is independently selected from a single bond, a substituted or unsubstituted arylene having 6 to 30 carbon atoms, and a substituted or unsubstituted heteroarylene having 5 to 30 carbon atoms;

substituent(s) in L, $L_1$, $L_2$, $Ar_1$, and $Ar_2$ are identical or different, and each is independently selected from deuterium, a halogen, cyano, an alkyl having 1 to 10 carbon atoms, an aryl having 6 to 18 carbon atoms, a heteroaryl having 5 to 18 carbon atoms, a deuterated alkyl having 1 to 10 carbon atoms, a haloalkyl having 1 to 10 carbon atoms, and a trialkylsiyl having 3 to 12 carbon atoms; in Arm and $Ar_2$, optionally, any two adjacent substituents form a saturated or unsaturated ring having 3 to 15 carbon atoms.

In some embodiments, $R_1$ is group A, and $R_2$ to $R_{10}$ are each independently hydrogen or deuterium.

In other embodiments, $R_{10}$ is group A, and $R_1$ to $R_9$ are each independently hydrogen or deuterium.

Optionally, group A is selected from a deuterium-substituted or unsubstituted phenyl, a deuterium-substituted or unsubstituted naphthyl, and a deuterium-substituted or unsubstituted biphenyl.

Further optionally, group A is selected from the group consisting of the following groups:

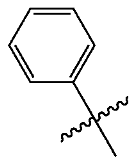

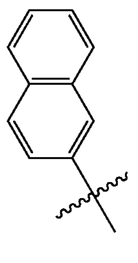

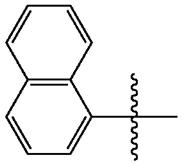

-continued

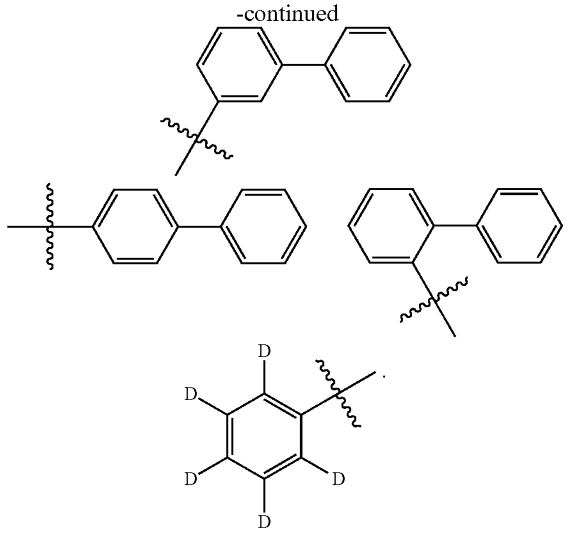

In the present disclosure, $Ar_1$ and $Ar_2$, for example, may each be independently selected from: a substituted or unsubstituted aryl having 6, 7, 8, 9, 10, 11, 12, 13, 14, 15, 16, 17, 18, 19, 20, 21, 22, 23, 24, or 25 carbon atoms, and a substituted or unsubstituted heteroaryl having 5, 6, 7, 8, 9, 10, 11, 12, 13, 14, 15, 16, 17, 18, 19, 20, 21, 22, 23, 24, or 25 carbon atoms.

Optionally, $Ar_1$ and $Ar_2$ are identical or different, and each is independently selected from a substituted or unsubstituted aryl having 6 to 25 carbon atoms, and a substituted or unsubstituted heteroaryl having 12 to 25 carbon atoms.

In some embodiments, $Ar_1$ and $Ar_2$ are each independently selected from a substituted or unsubstituted phenyl, a substituted or unsubstituted naphthyl, a substituted or unsubstituted biphenyl, a substituted or unsubstituted terphenyl, a substituted or unsubstituted phenanthryl, a substituted or unsubstituted anthryl, a substituted or unsubstituted fluorenyl, a substituted or unsubstituted triphenylene, a substituted or unsubstituted pyridyl, a substituted or unsubstituted dibenzofuranyl, a substituted or substituted dibenzothienyl, and a substituted or unsubstituted carbazolyl.

Optionally, substituent(s) in $Ar_1$ and $Ar_2$ are identical or different, and are each independently selected from deuterium, fluorine, cyano, an alkyl having 1 to 5 carbon atoms, an aryl having 6 to 12 carbon atoms, a heteroaryl having 5 to 12 carbon atoms, a deuterated alkyl having 1 to 5 carbon atoms, a haloalkyl having 1 to 5 carbon atoms, and a trialkylsilyl having 3 to 7 carbon atoms; optionally, in $Ar_1$ and $Ar_2$, any two adjacent substituents form a saturated or unsaturated ring having 5 to 15 carbon atoms.

In some embodiments, substituent(s) in $Ar_1$ and $Ar_2$ are each independently selected from deuterium, fluorine, cyano, methyl, ethyl, n-propyl, isopropyl, tert-butyl, phenyl, naphthyl, biphenyl, pyridyl, dibenzothienyl, dibenzofuranyl, carbazolyl, trideuteromethyl, trifluoromethyl, and trimethylsilyl; optionally, in $Ar_1$ and $Ar_2$, any two adjacent substituents form a benzene ring, a cyclopentane, a cyclohexane, or a fluorene ring.

In some embodiments, $Ar_1$ and $Ar_2$ are each independently selected from a substituted or unsubstituted group V, the unsubstituted group V is selected from the following groups:

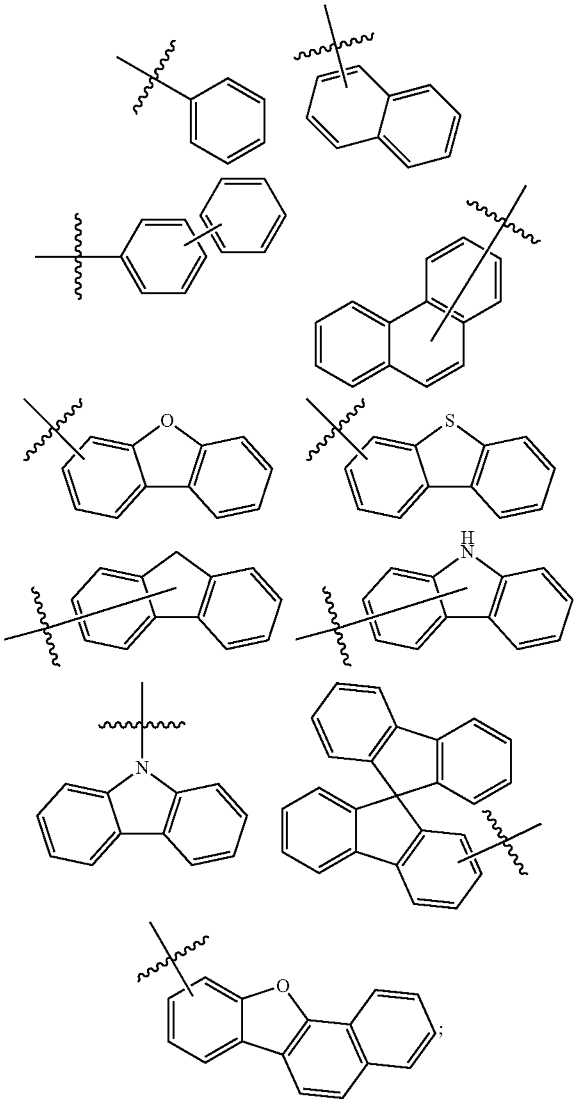

the substituted group V has one or more substituent(s), and each substituent is independently selected from deuterium, fluorine, cyano, methyl, ethyl, isopropyl, tert-butyl, trimethylsilyl, trideuteromethyl, trifluoromethyl, phenyl, naphthyl, and pyridyl.

Optionally, $Ar_1$ and $Ar_2$ are each independently selected from the following groups:

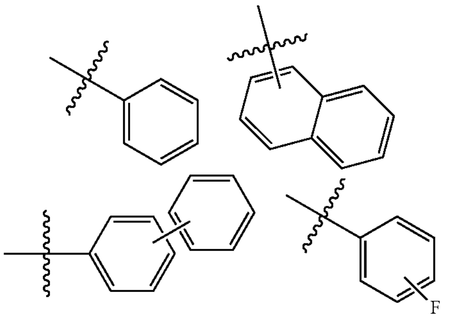

-continued
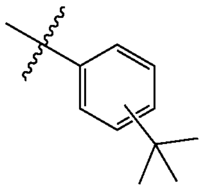
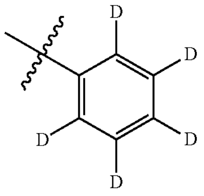
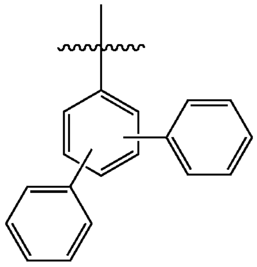
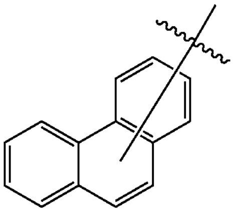
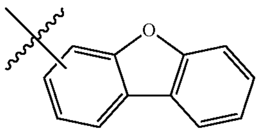
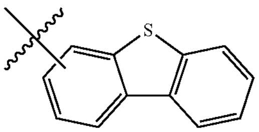
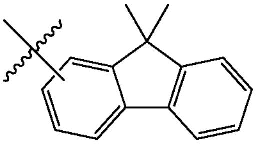
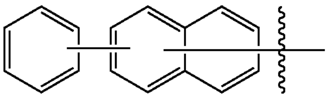
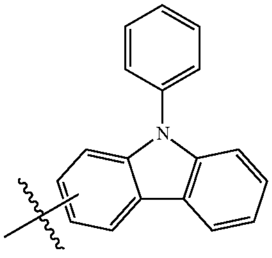
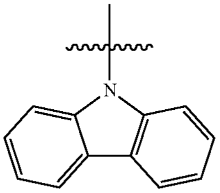
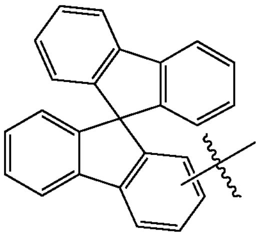
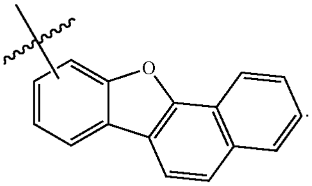
Further optionally, $Ar_1$ and $Ar_2$ are each independently selected from the group consisting of the following groups:
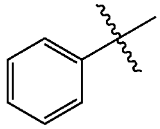
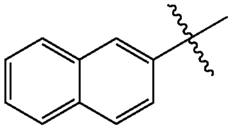
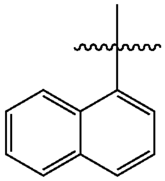
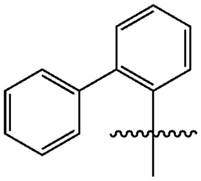
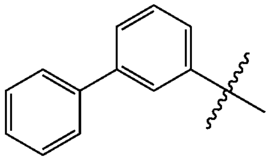
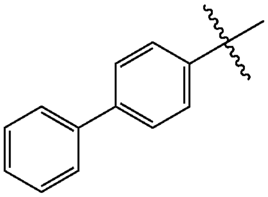
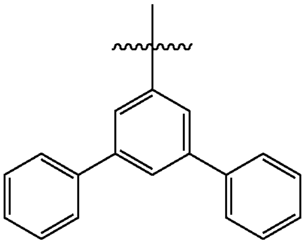
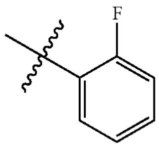
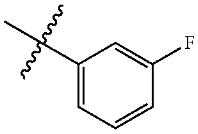
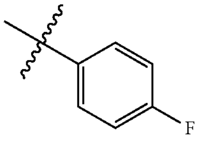
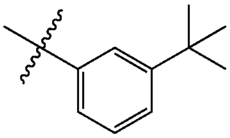
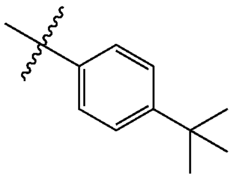
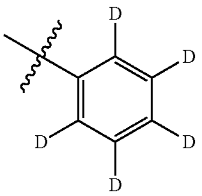
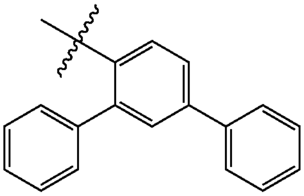
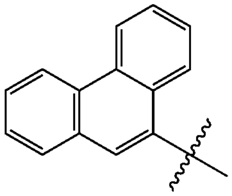
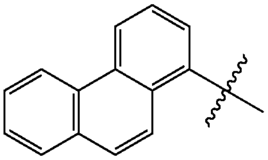
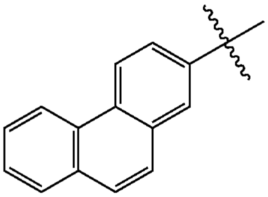
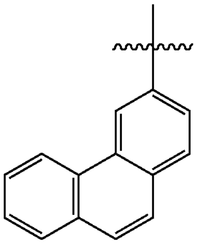

-continued

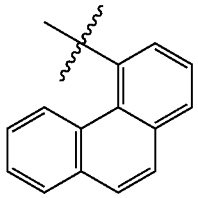
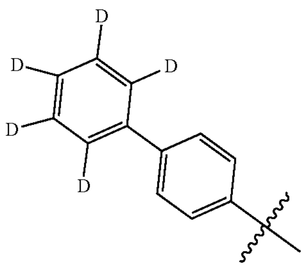
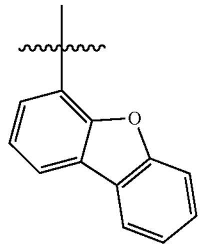
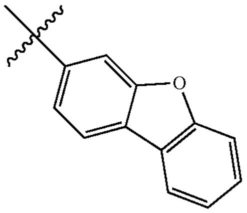
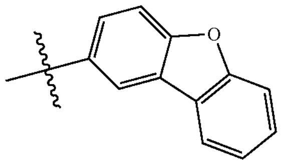
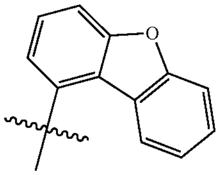
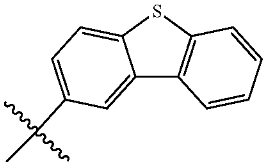
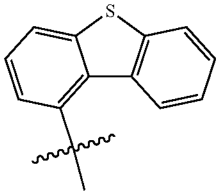
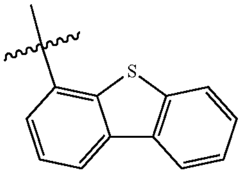
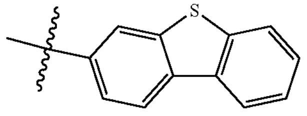
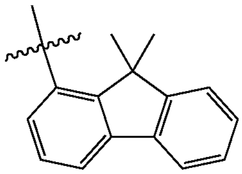
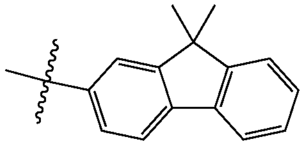
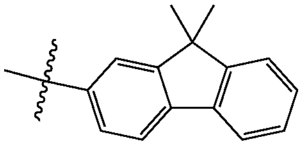
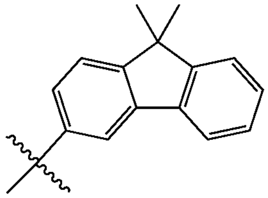
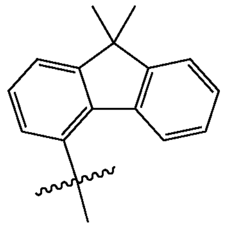
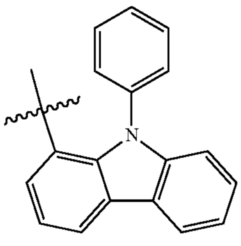

-continued

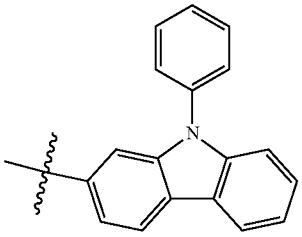
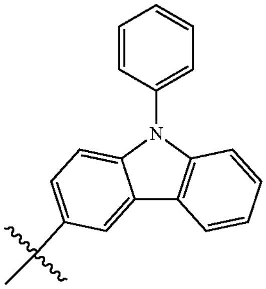
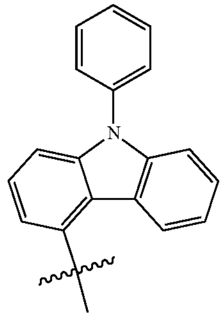
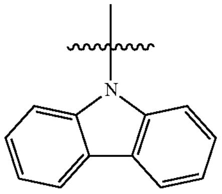
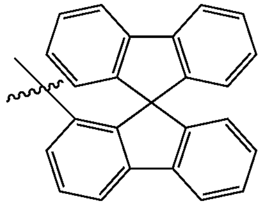
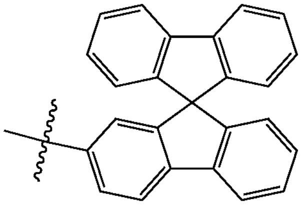
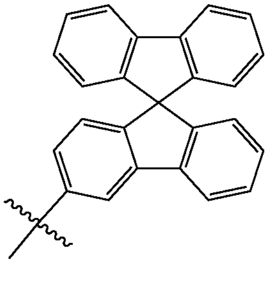
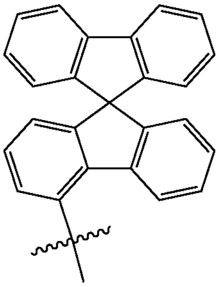
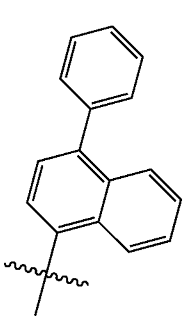
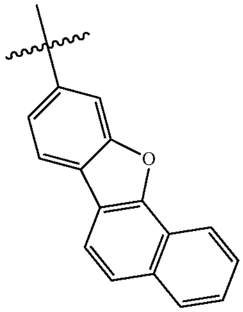
.

In the present disclosure, L may be selected from, for example: a substituted or unsubstituted arylene having 6, 7, 8, 9, 10, 11, 12, 13, 14, 15, 16, 17, 18, 19, or 20 carbon atoms, and a heteroarylene having 5, 6, 7, 8, 9, 10, 11, 12, 13, 14, 15, 16, 17, 18, 19, or 20 carbon atoms.

In some embodiments, each L is independently selected from a substituted or unsubstituted arylene having 6 to 15 carbon atoms, and a substituted or unsubstituted heteroarylene having 10 to 18 carbon atoms.

In the present disclosure, $L_1$ and $L_2$ may be selected from, for example: a single bond, a substituted or unsubstituted arylene having 6, 7, 8, 9, 10, 11, 12, 13, 14, 15, 16, 17, 18, 19, or 20 carbon atoms, and a heteroarylene having 5, 6, 7, 8, 9, 10, 11, 12, 13, 14, 15, 16, 17, 18, 19, or 20 carbon atoms.

Optionally, $L_1$ and $L_2$ are identical or different, and each is independently selected from a single bond, a substituted or unsubstituted arylene having 6 to 18 carbon atoms, and a substituted or unsubstituted heteroarylene having 10 to 18 carbon atoms.

In some embodiments, L is selected from a substituted or unsubstituted phenylene, a substituted or unsubstituted naphthylene, a substituted or unsubstituted biphenylene, a substituted or unsubstituted phenanthrylene, a substituted or unsubstituted fluorenylene, a substituted or unsubstituted pyridylene, a substituted or unsubstituted dibenzothienylene, a substituted or unsubstituted dibenzofuranylene, and a substituted or unsubstituted carbazolylene.

In some embodiments, $L_1$ and $L_2$ are each independently selected from a single bond, a substituted or unsubstituted phenylene, a substituted or unsubstituted naphthylene, a substituted or unsubstituted biphenylene, a substituted or unsubstituted phenanthrylene, a substituted or unsubstituted fluorenylene, a substituted or unsubstituted pyridylene, a substituted or unsubstituted dibenzothienylene, a substituted or unsubstituted dibenzofuranylene, and a substituted or unsubstituted carbazolylene.

Optionally, substituent(s) in L, $L_1$, and $L_2$ are identical or different, and are each independently selected from deuterium, fluorine, cyano, an alkyl having 1 to 4 carbon atoms, and an aryl having 6 to 10 carbon atoms.

Optionally, substituent(s) in L, $L_1$, and $L_2$ are identical or different, and are each independently selected from deuterium, fluorine, cyano, methyl, ethyl, isopropyl, tert-butyl, phenyl, and naphthyl.

In the present disclosure, when n is equal to 2, the structure of

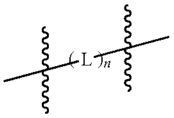

is

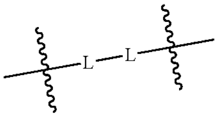

the two L may be identical or different.

In some embodiments, when n is equal to 2, one of the two L is a substituted or unsubstituted phenylene, and the other is a substituted or unsubstituted phenylene, or a substituted or unsubstituted naphthylene.

In some embodiments, each L is independently selected from a substituted or unsubstituted group W, and $L_1$ and $L_2$ are each independently selected from a single bond, and a substituted or unsubstituted group W, wherein, the unsubstituted group W is selected from the following groups:

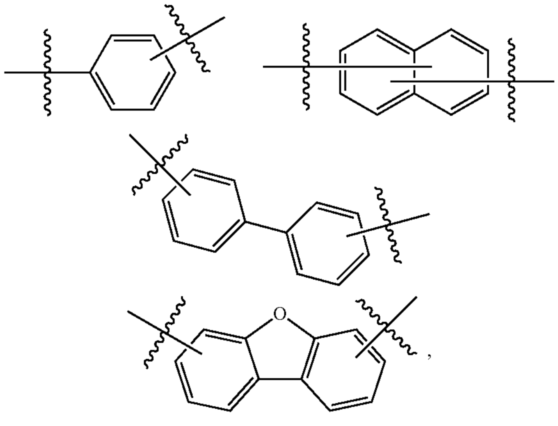

the substituted group W has one or more substituent(s), and each substituent is independently selected from deuterium, fluorine, cyano, an alkyl having 1 to 4 carbon atoms, phenyl, trimethylsilyl, trideuteromethyl, and trifluoromethyl.

Optionally, each L is independently selected from the group consisting of the following groups:

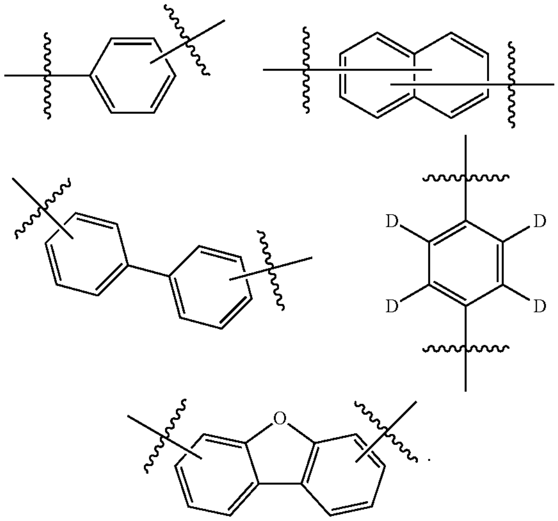

Optionally,

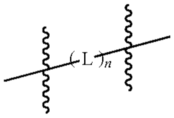

is selected from the group consisting of the following groups:

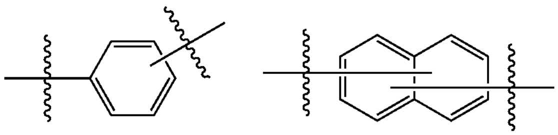

-continued
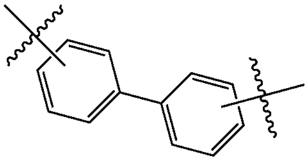
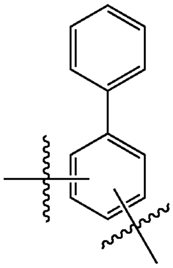
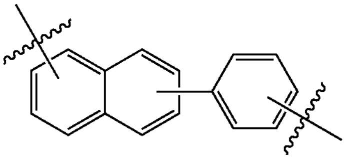
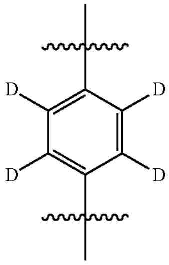
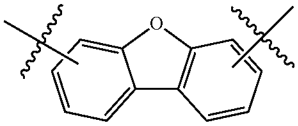.
Optionally,
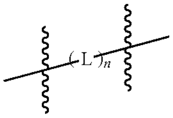
is selected from the group consisting of the following groups:
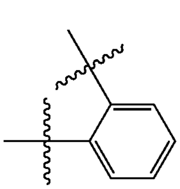
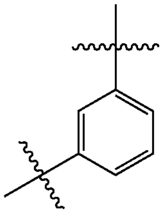
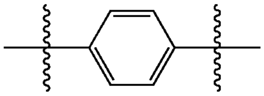
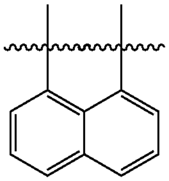
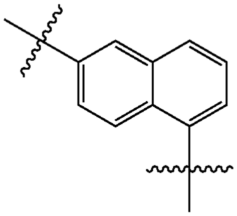
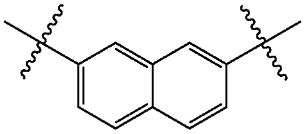
-continued
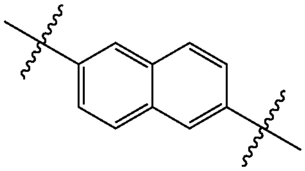
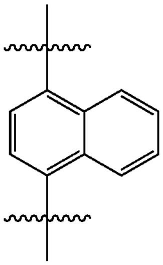
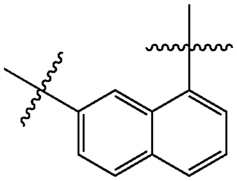
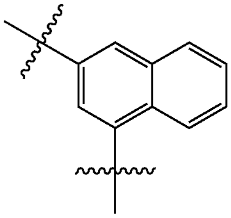
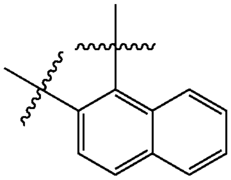
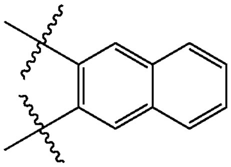
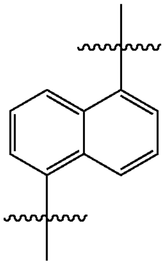
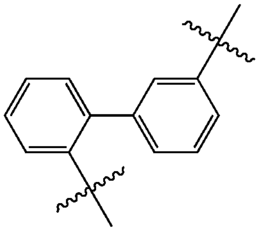
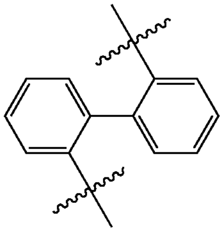
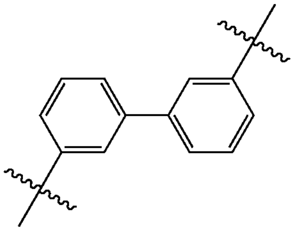
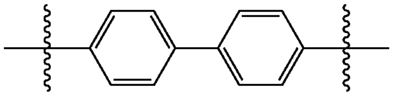
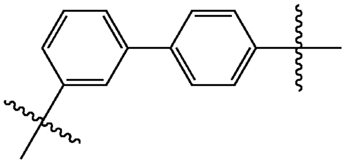
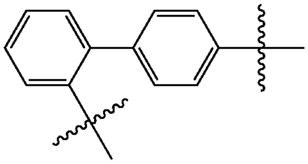

-continued
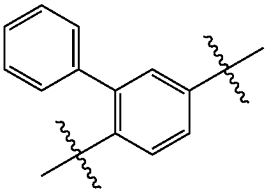
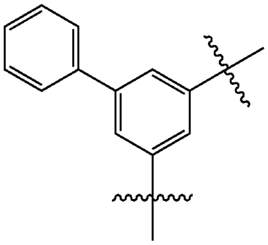
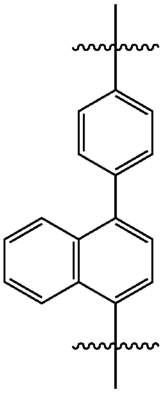
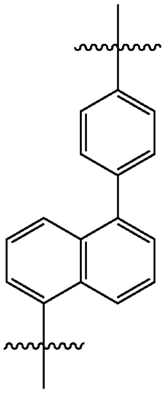
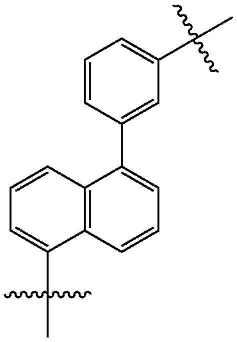
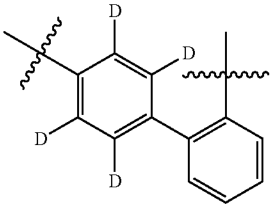
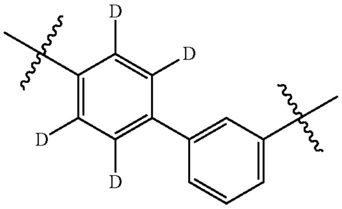
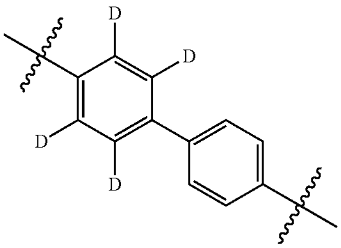
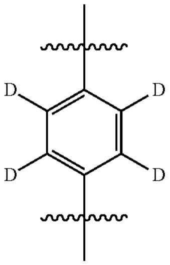
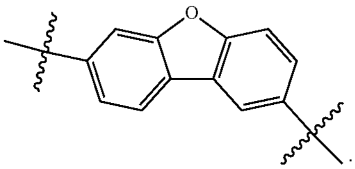
Optionally, $L_1$ and $L_2$ are each independently selected from the group consisting of a single bond and the following groups:
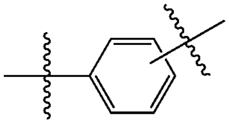
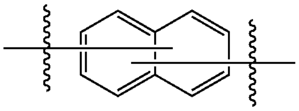
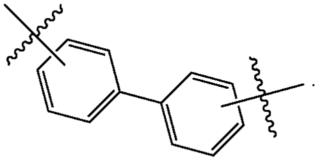
Further optionally, $L_1$ and $L_2$ are each independently selected from the group consisting of a single bond and the following groups:
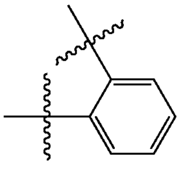
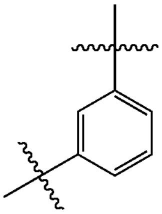
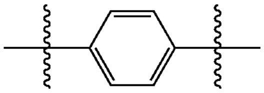
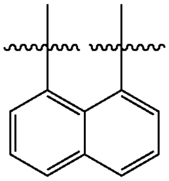
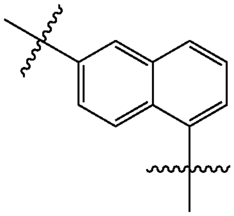
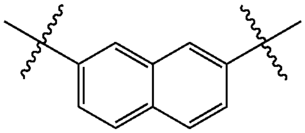
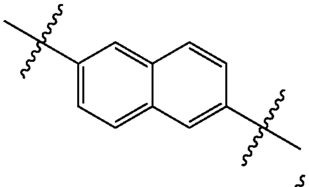
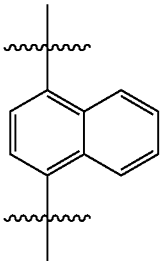
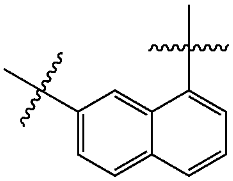
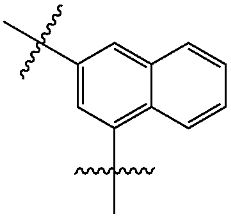

-continued
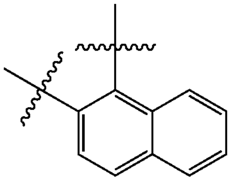
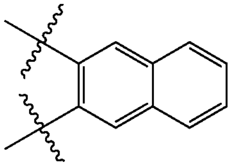
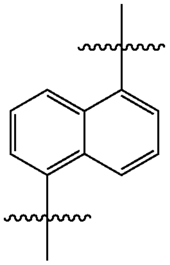
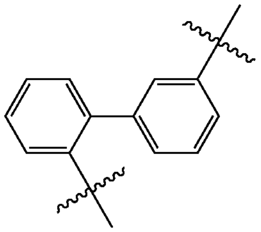
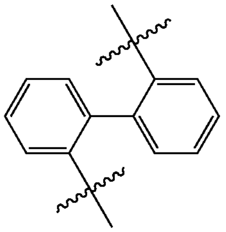
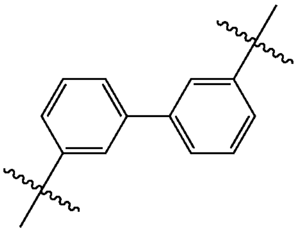
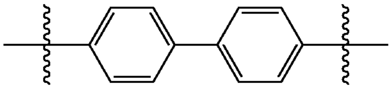
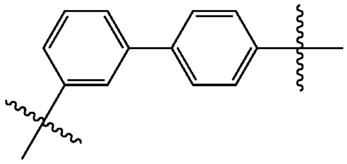
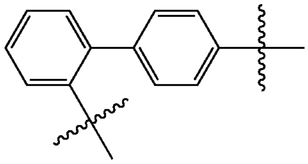
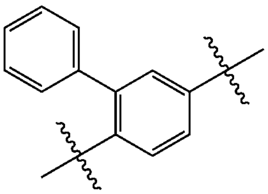
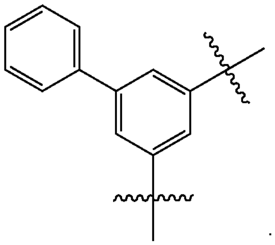
In some embodiments,
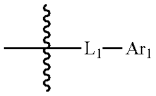
and
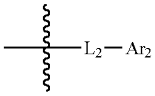
are each independently selected from the group consisting of the following groups:
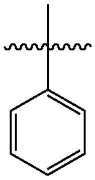
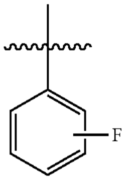
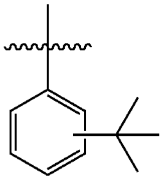
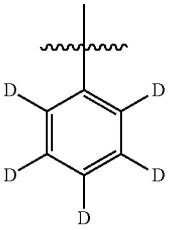
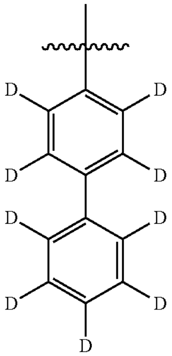
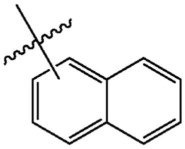
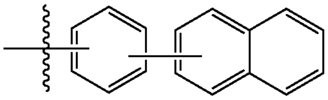
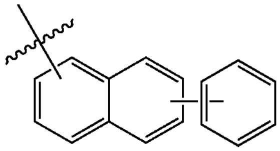
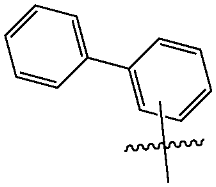
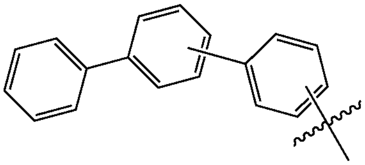
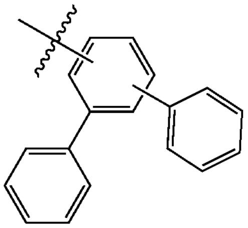
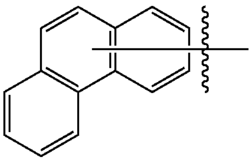
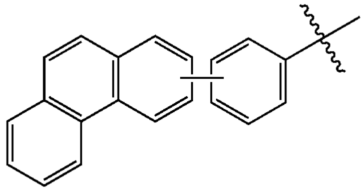

-continued
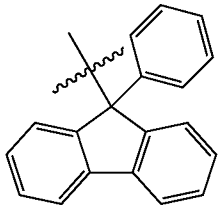
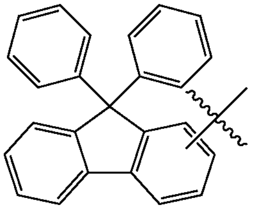
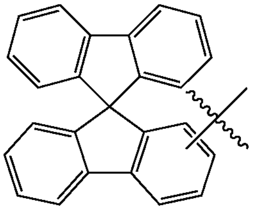
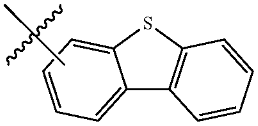
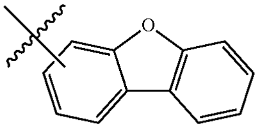
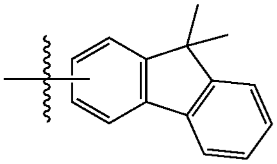
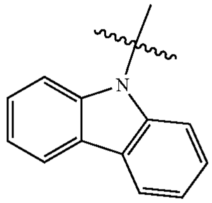
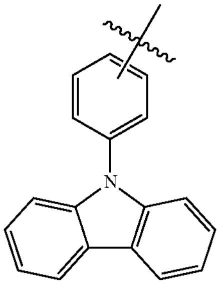
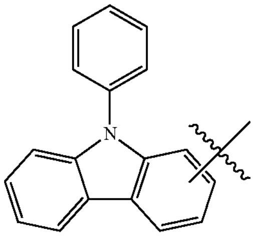
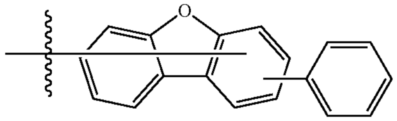
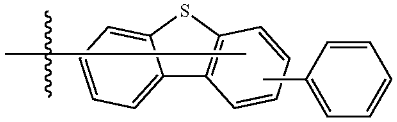
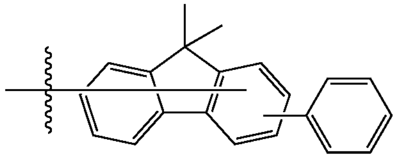
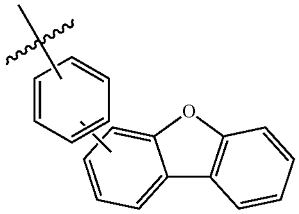
-continued
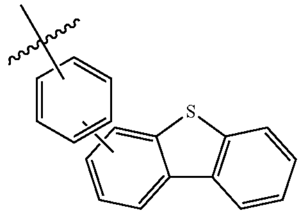
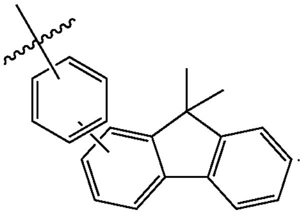
In some more specific embodiments, the nitrogen-containing compound is selected from the group consisting of the following compounds:
1
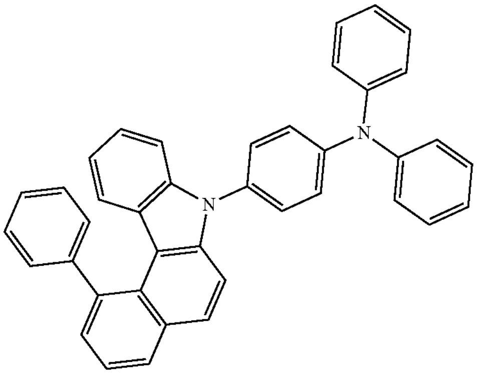
2
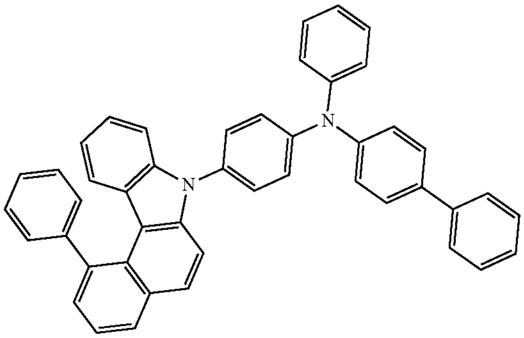
3
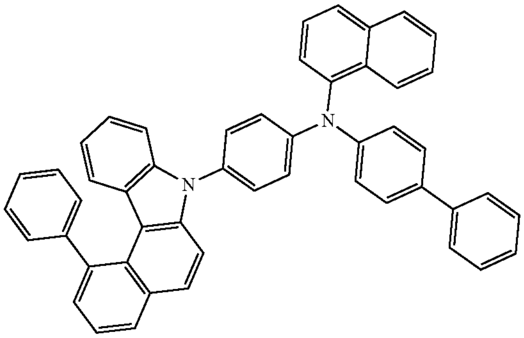

-continued
4
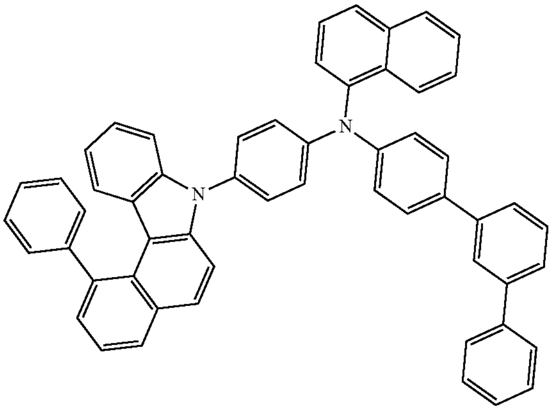
5
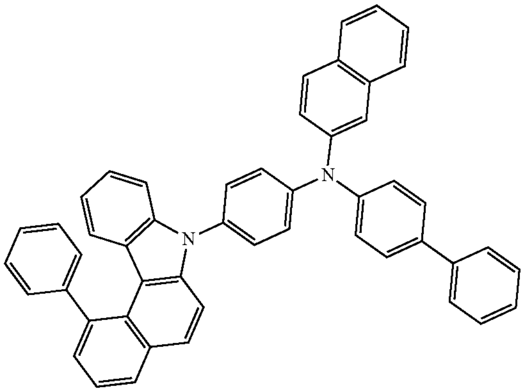
6
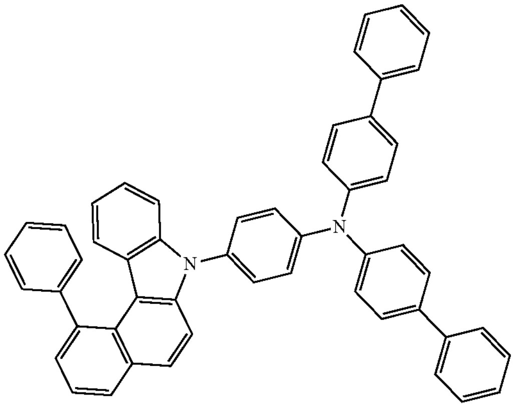
7
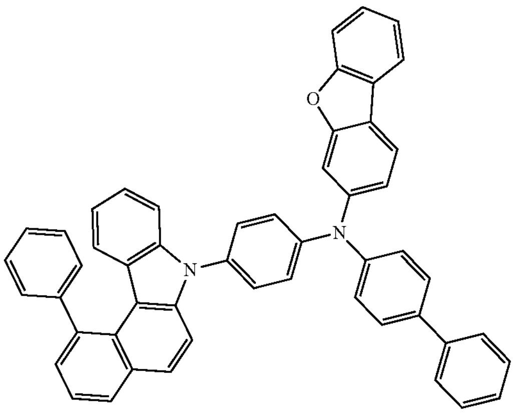
-continued
8
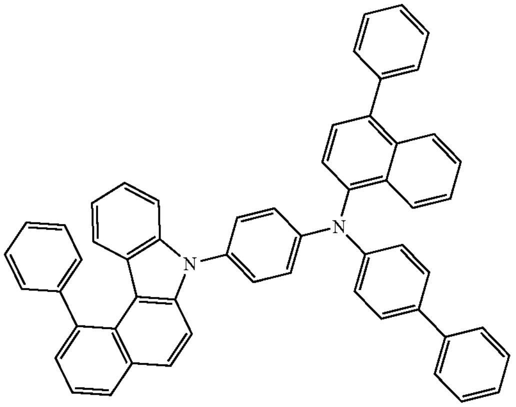
9
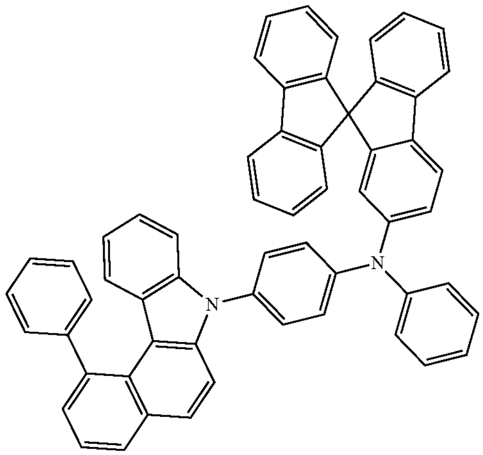
10
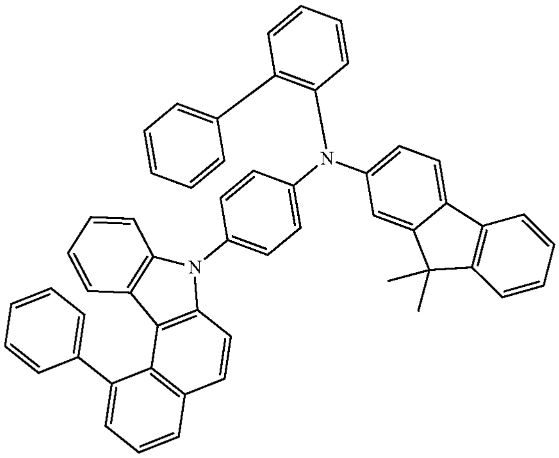

-continued
11
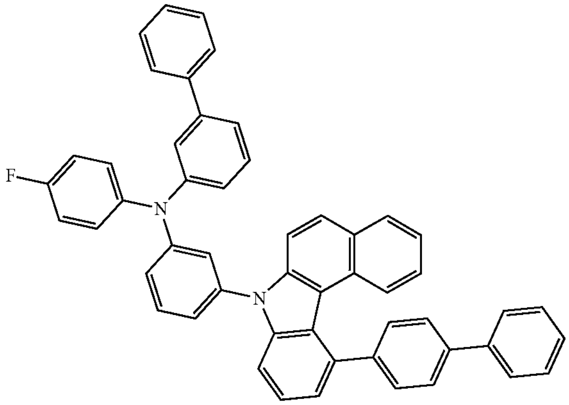
12
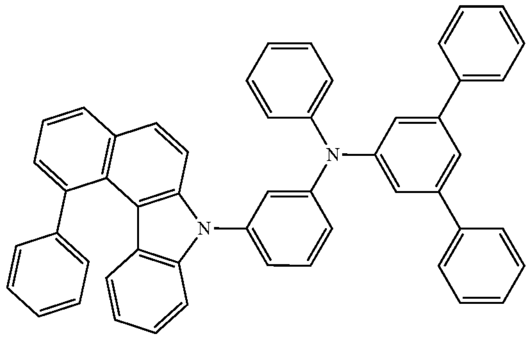
13
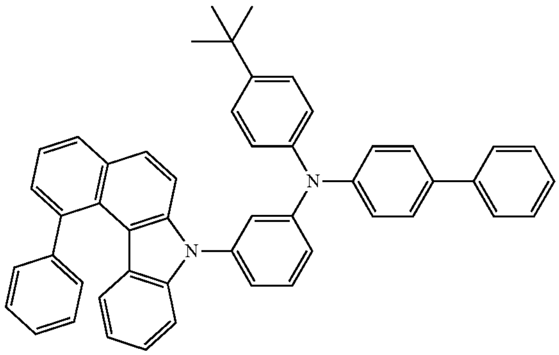
14
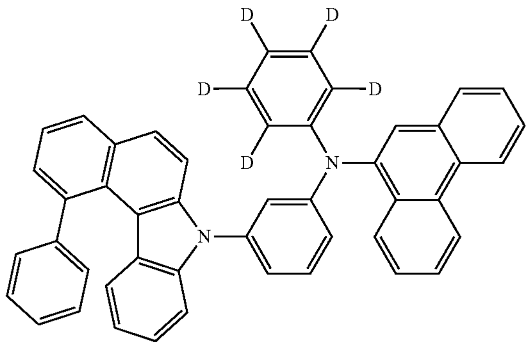
-continued
15
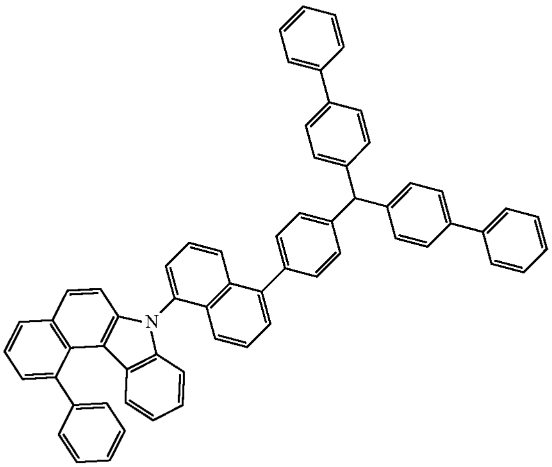
16
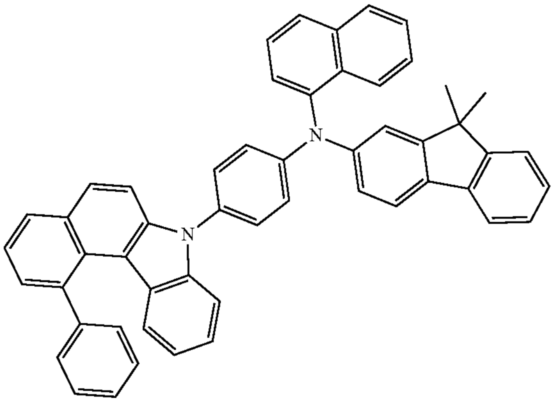
17
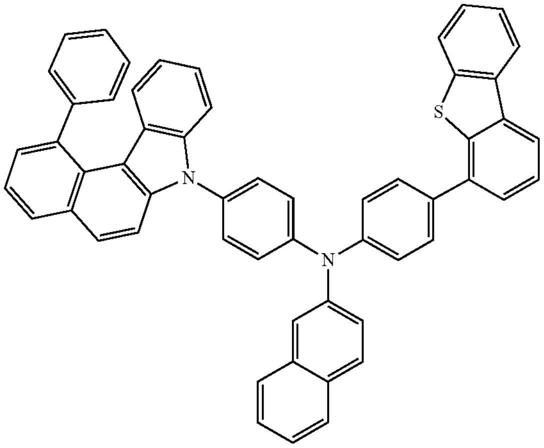

-continued
18
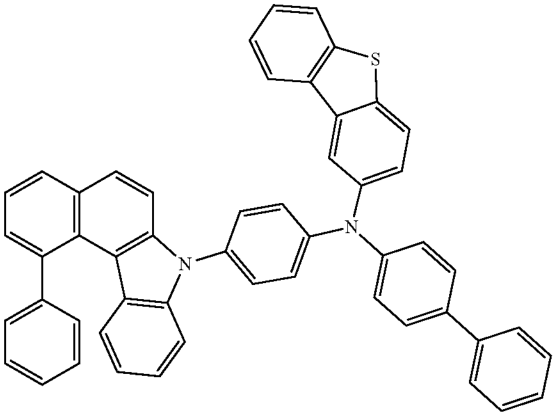
19
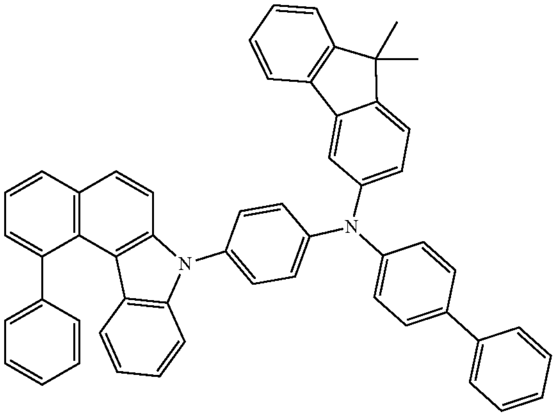
20
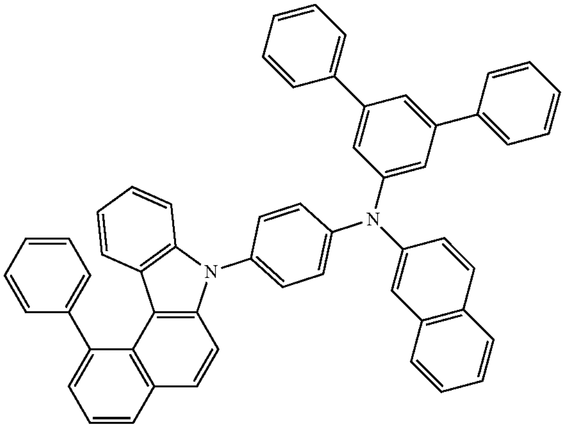
-continued
21
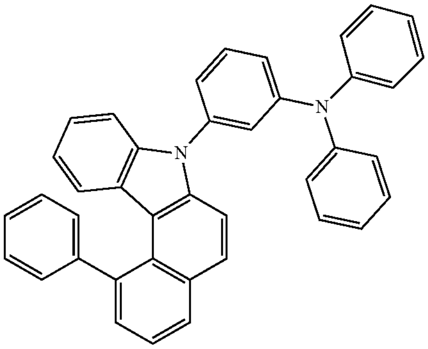
22
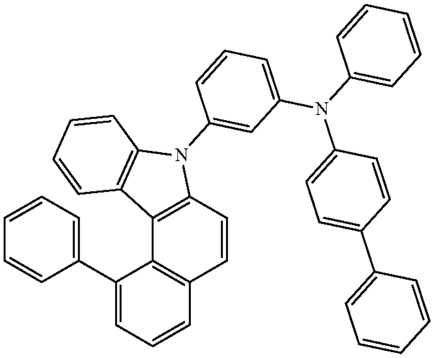
23
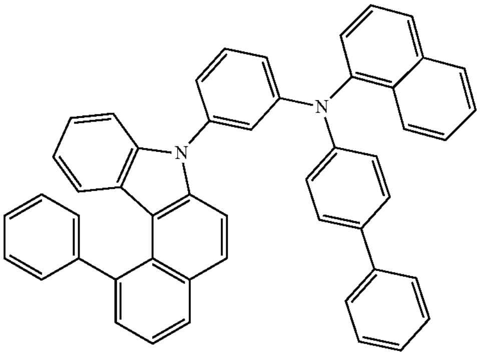
24
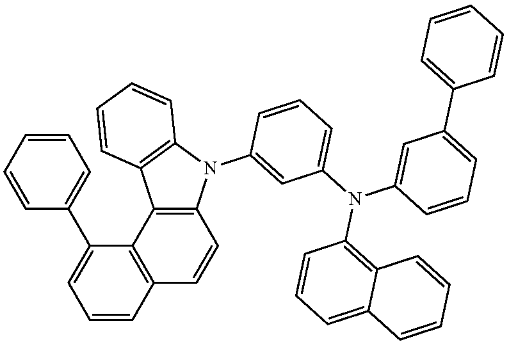

-continued
25
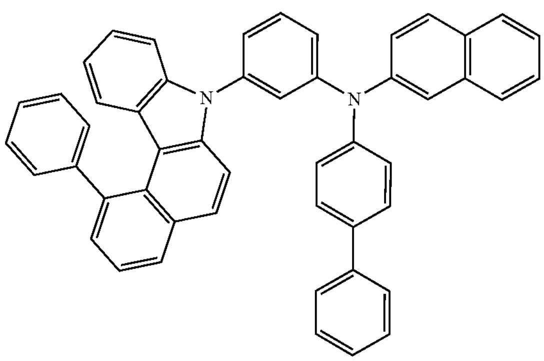
26
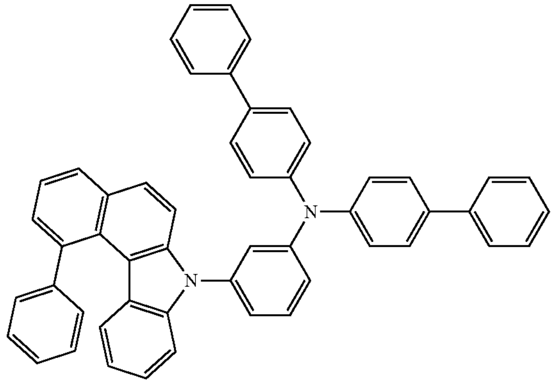
27
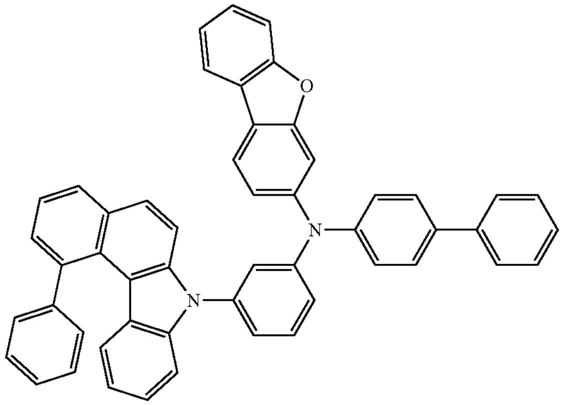
28
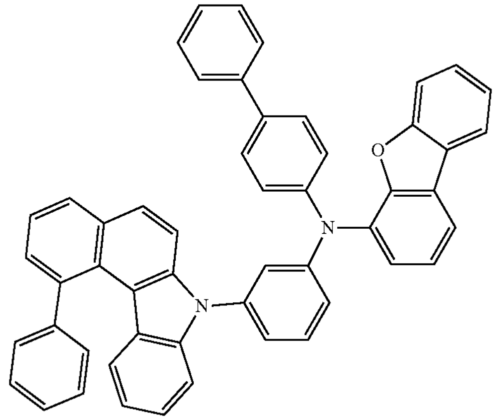
-continued
29
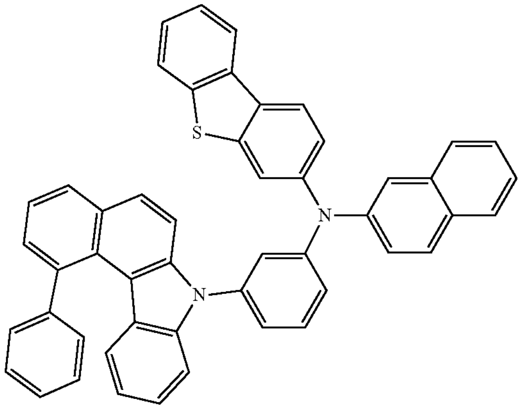
30
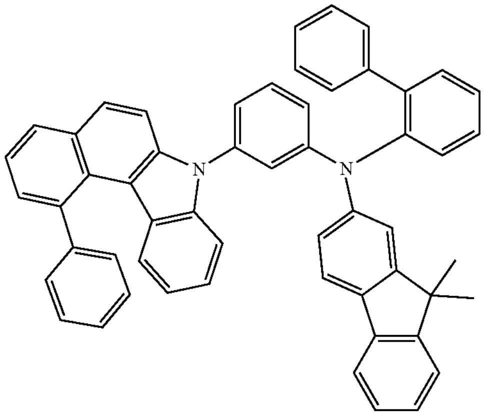
31
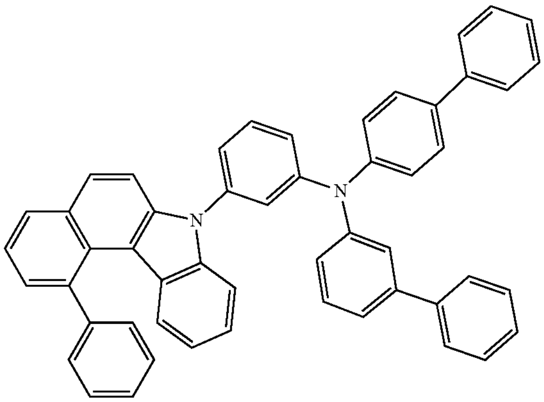

-continued
32
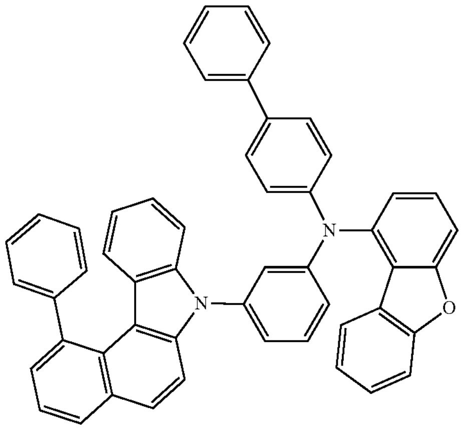
33
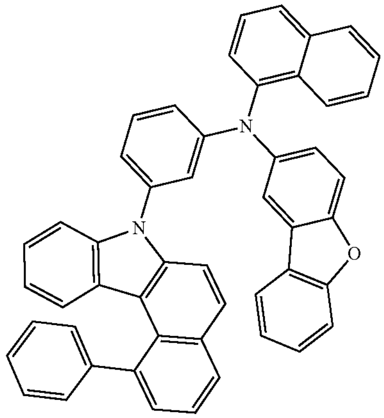
34
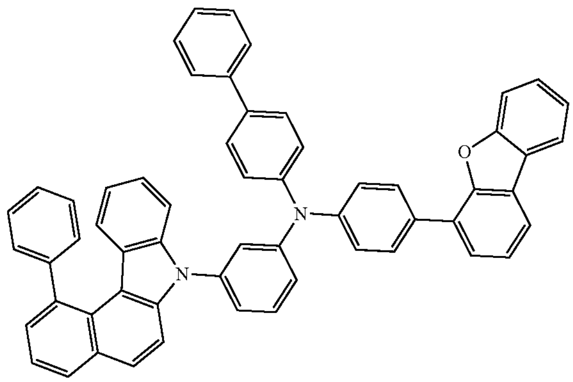
-continued
35
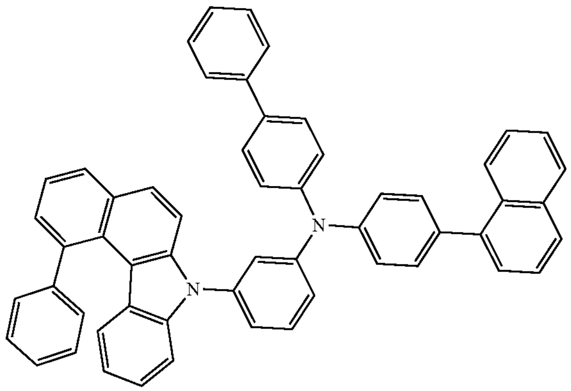
36
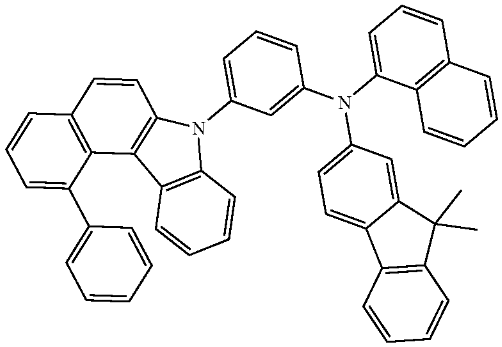
37
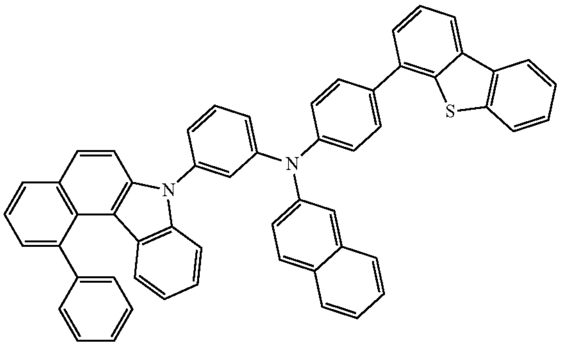
38
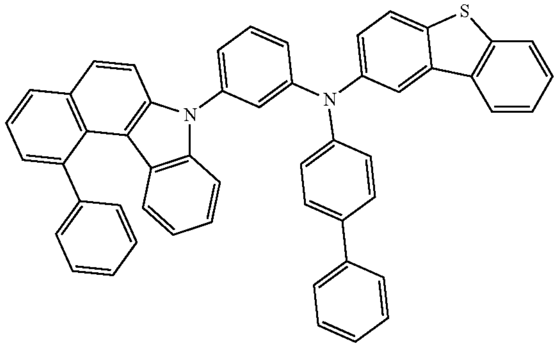

-continued
39
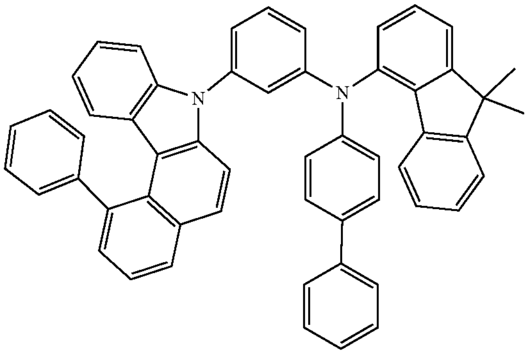
40
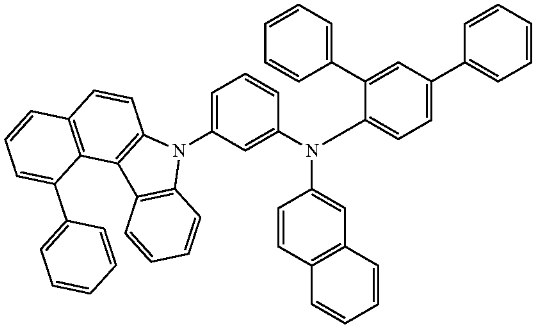
41
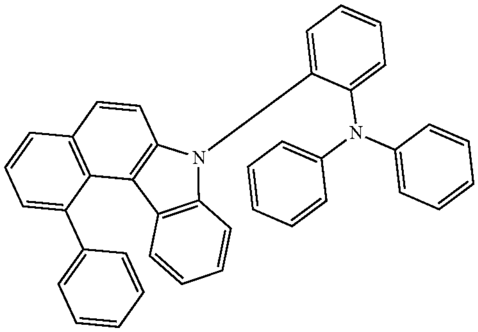
42
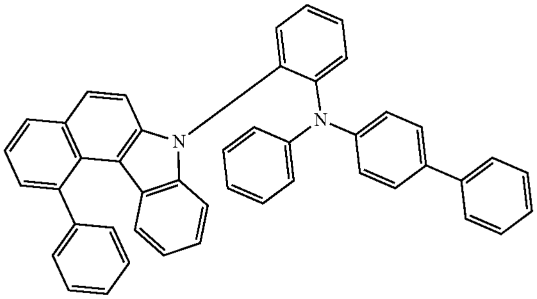
-continued
43
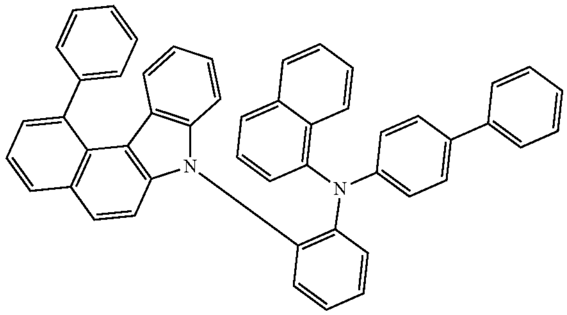
44
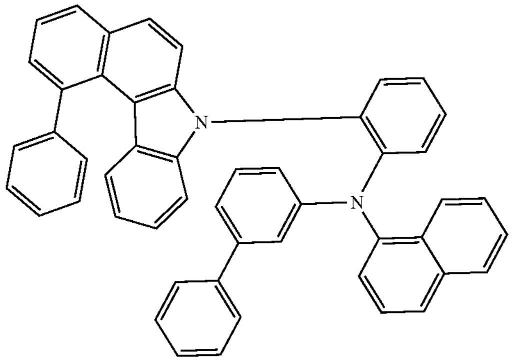
55
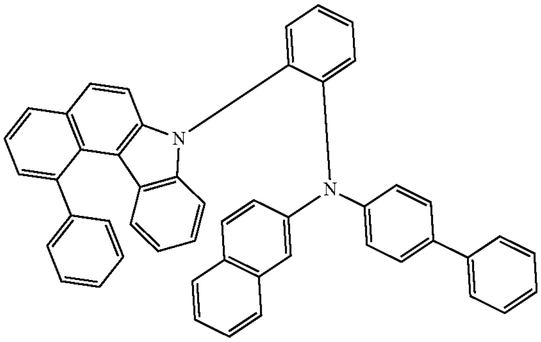
56
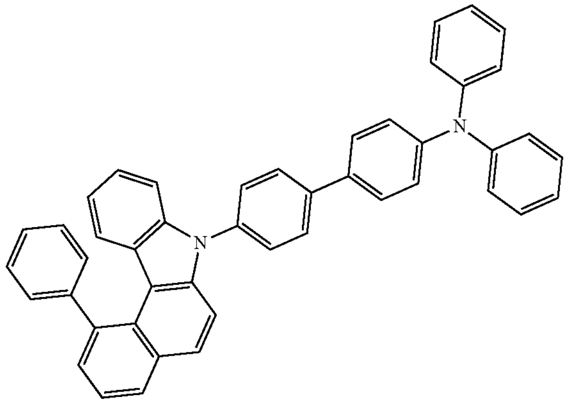

-continued
57
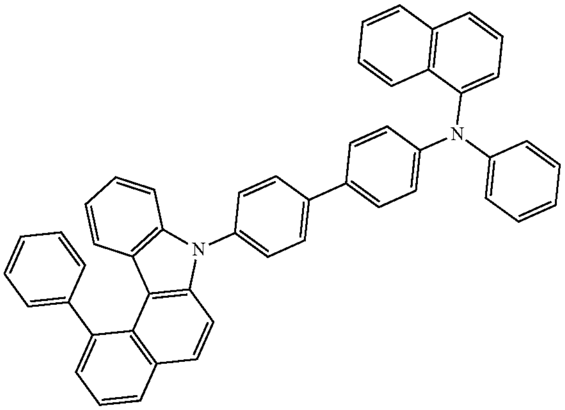
58
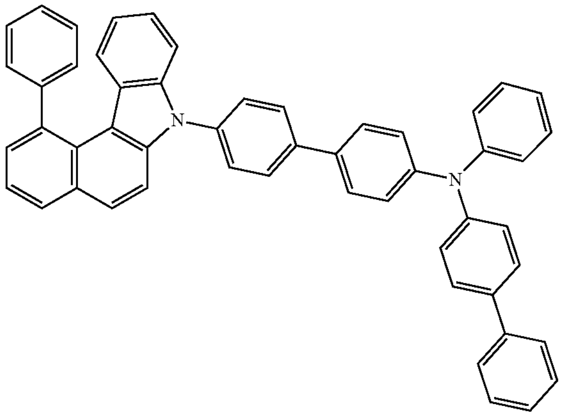
59
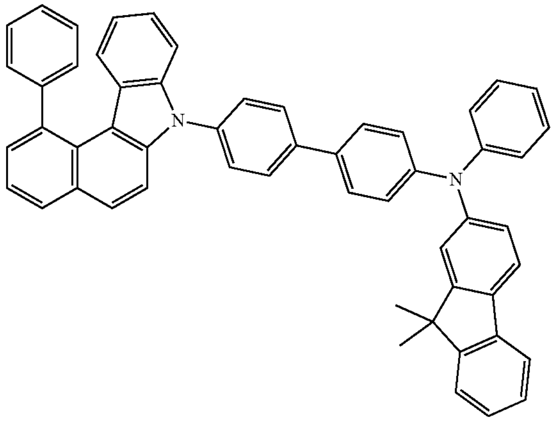
-continued
60
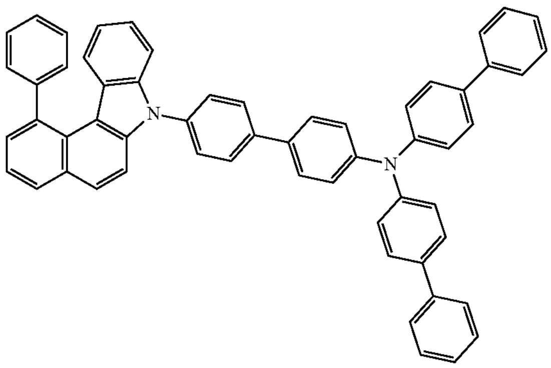
61
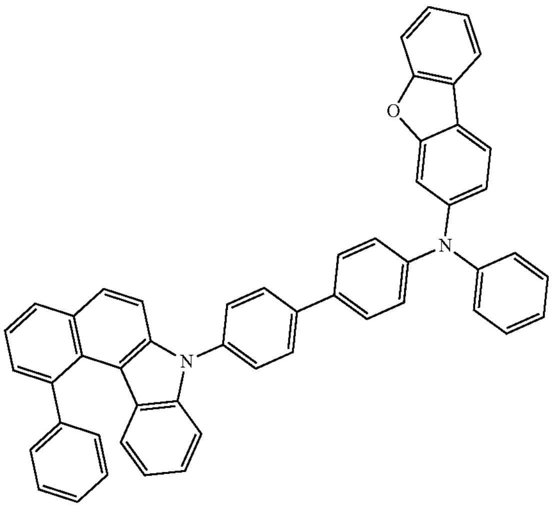
62
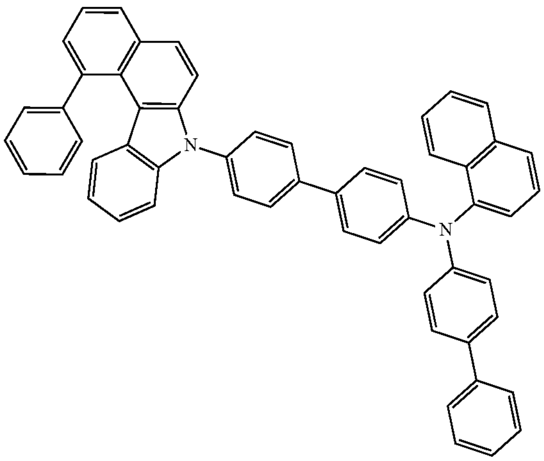

-continued
63
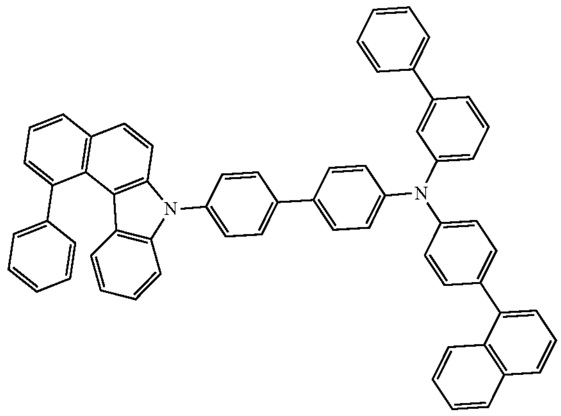
64
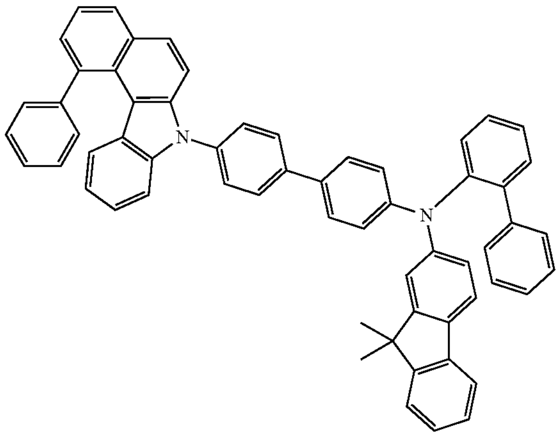
65
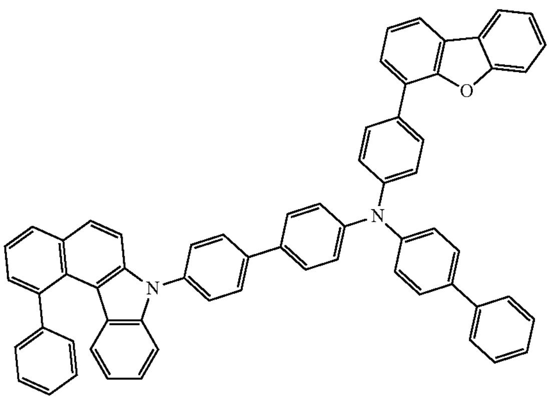
-continued
66
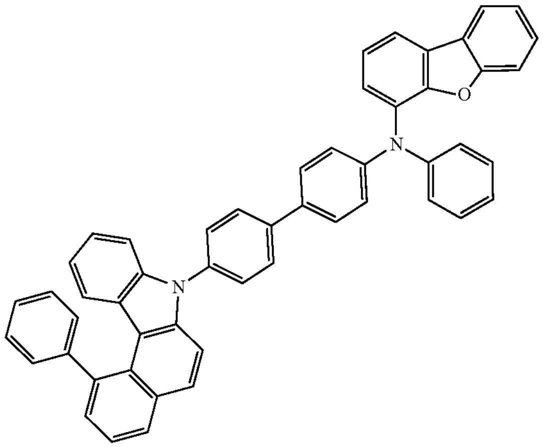
67
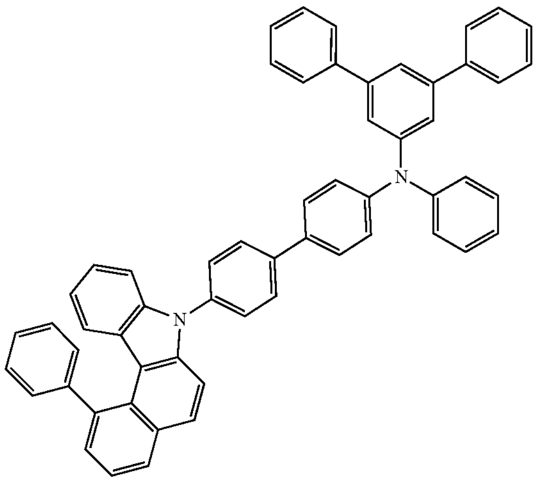
68
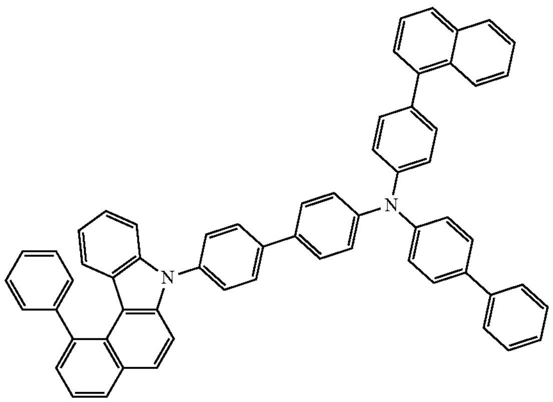

-continued
69
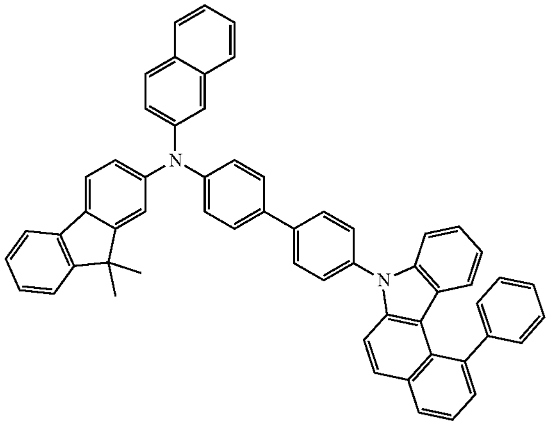
70
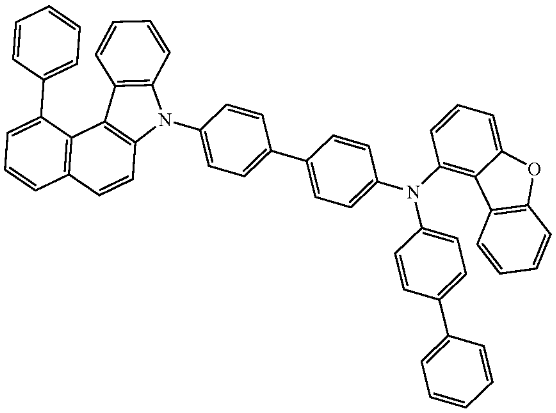
71
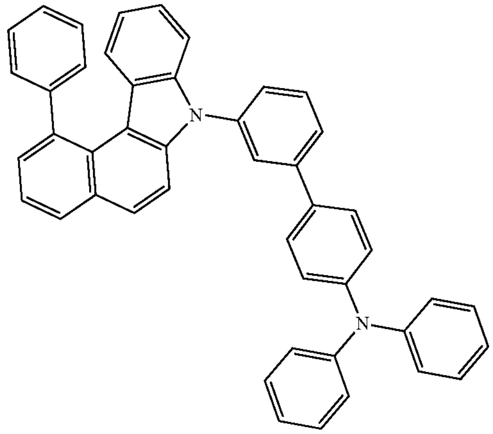
-continued
72
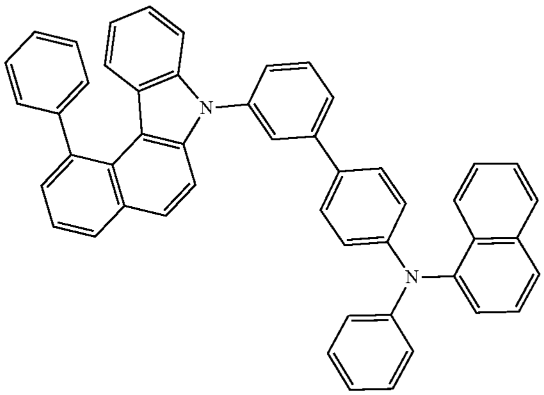
73
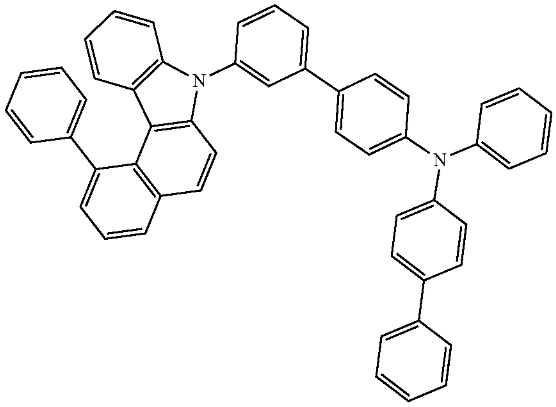
74
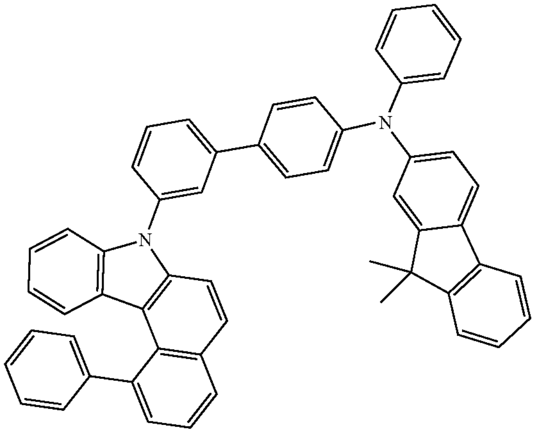

-continued
75
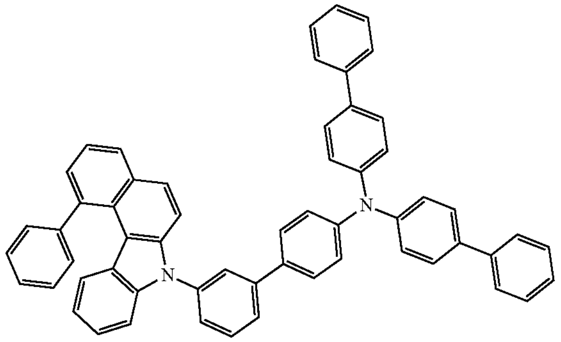
76
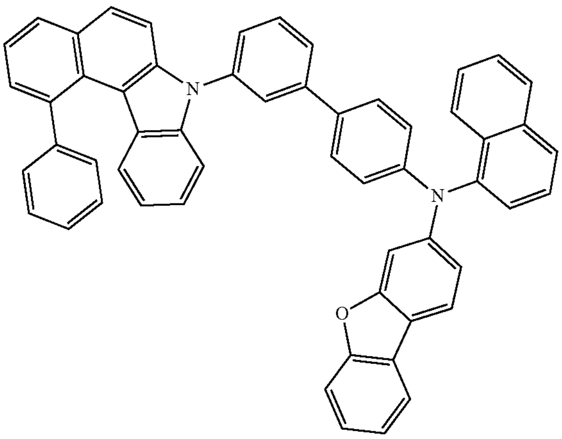
77
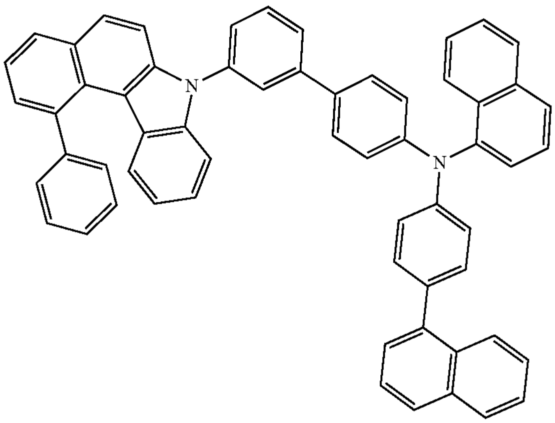
78
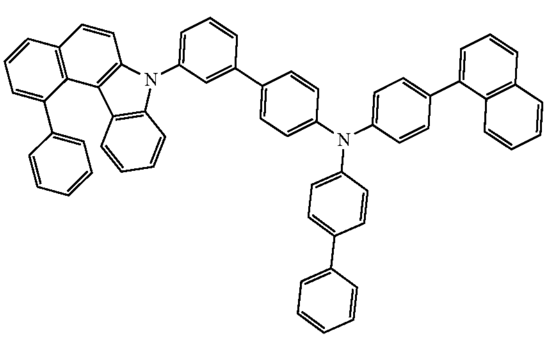
-continued
79
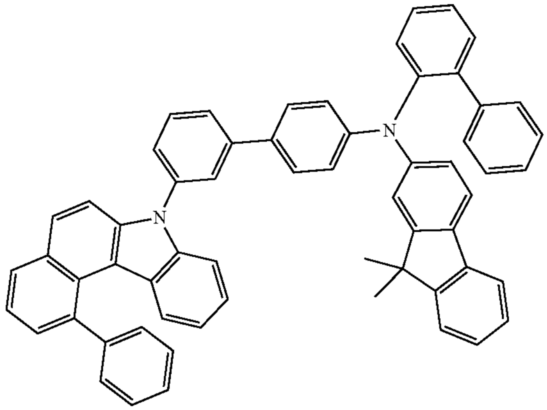
80
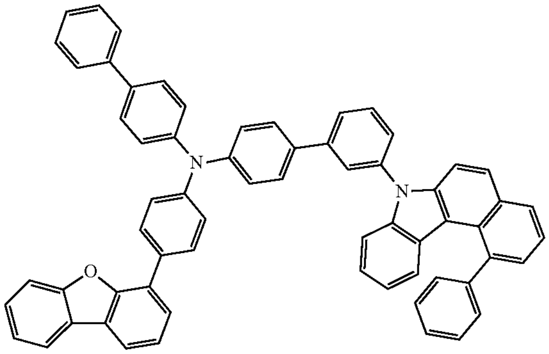
81
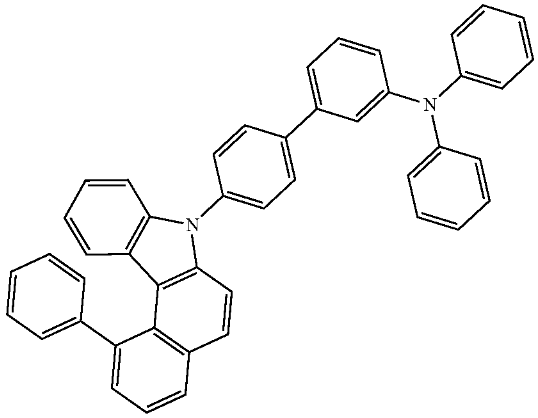

82
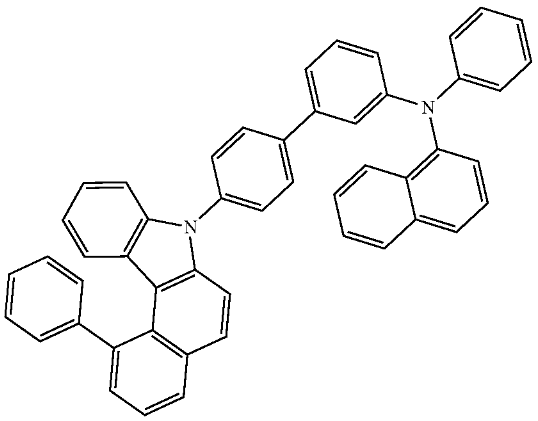
83
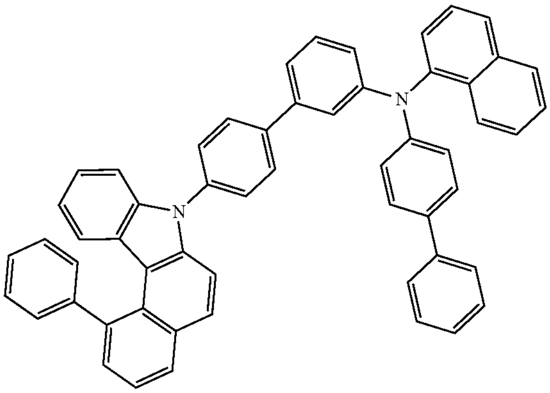
84
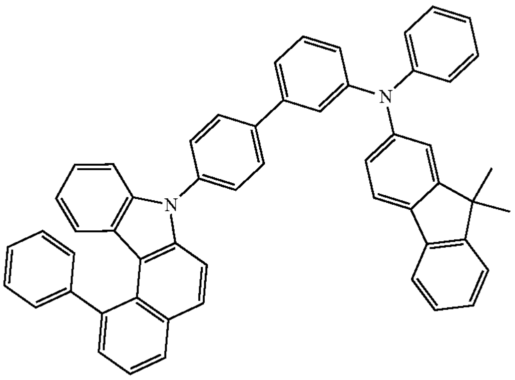
85
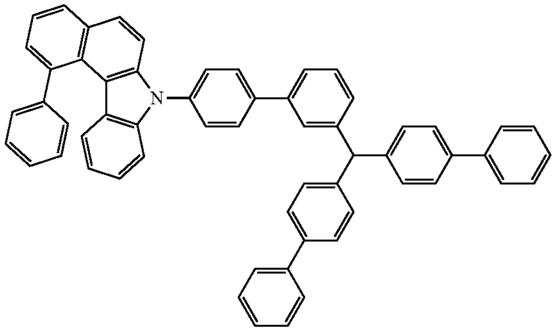
86
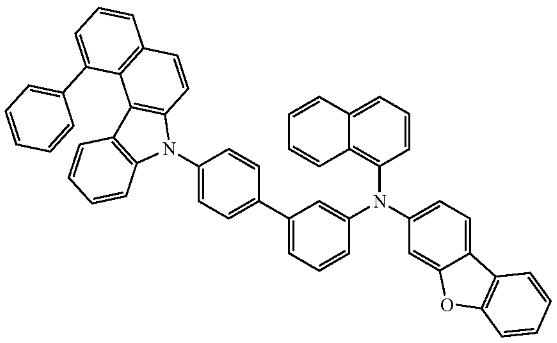
87
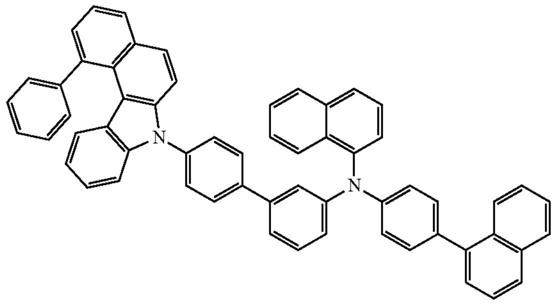
88
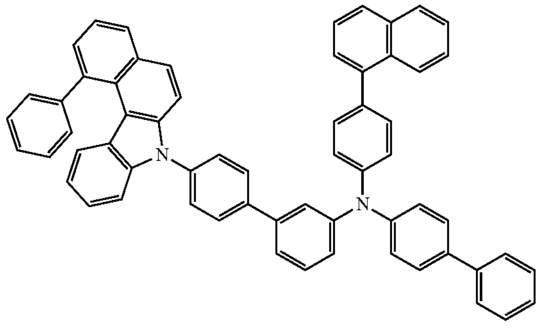
89
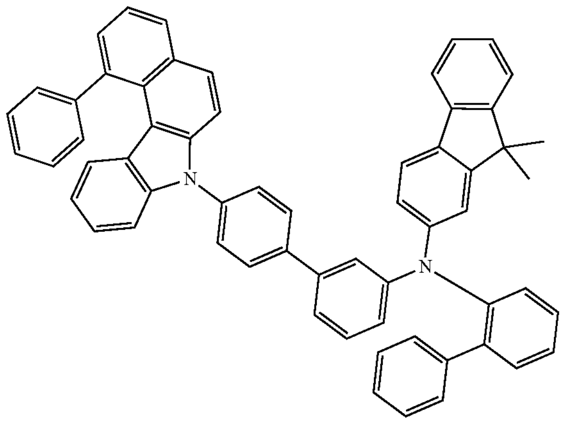

-continued
90
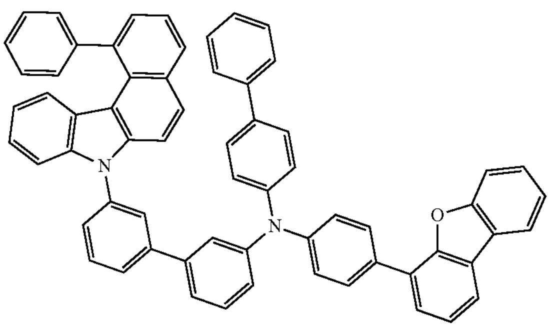
91
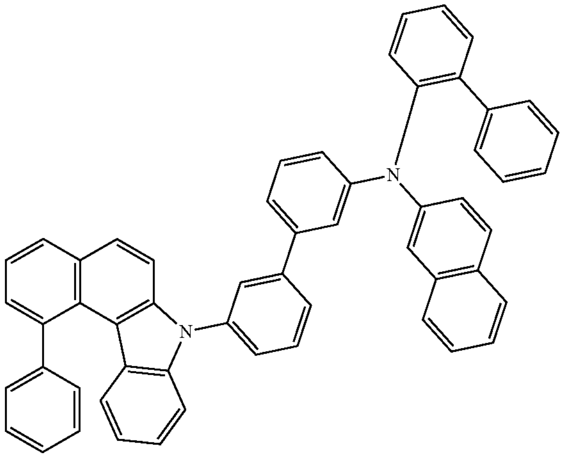
92
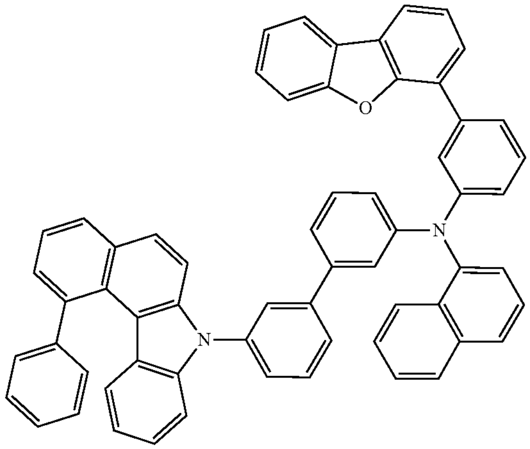
-continued
93
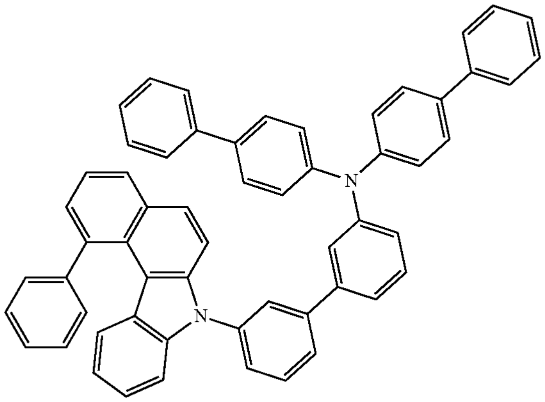
94
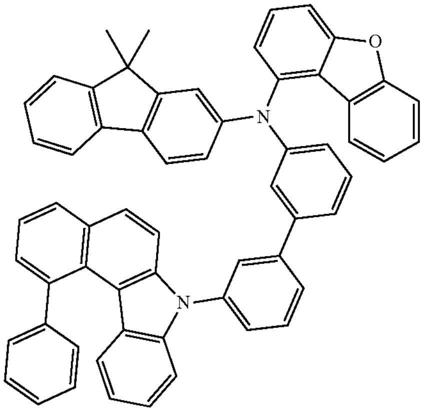
95
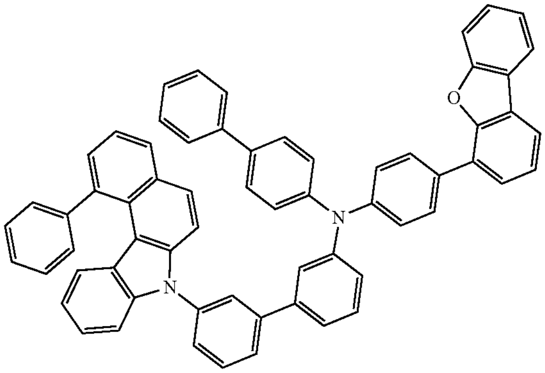

-continued
96
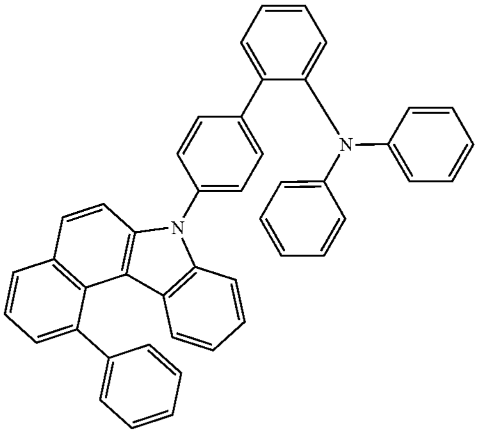
97
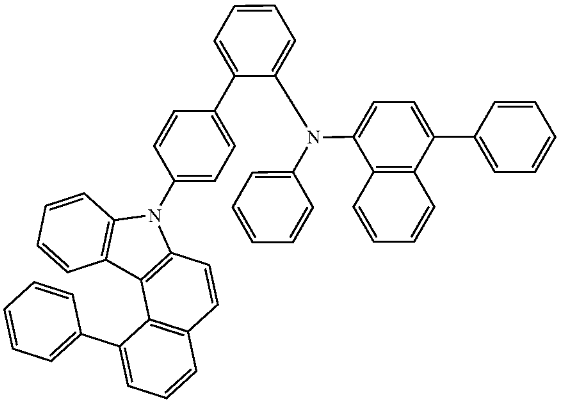
98
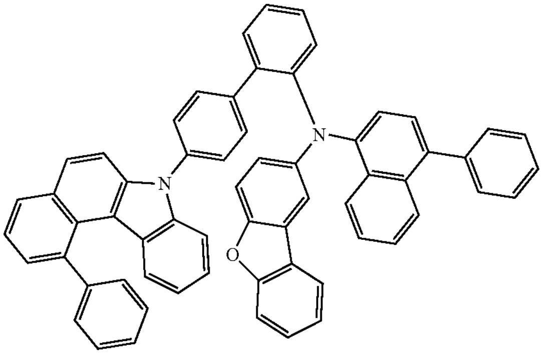
99
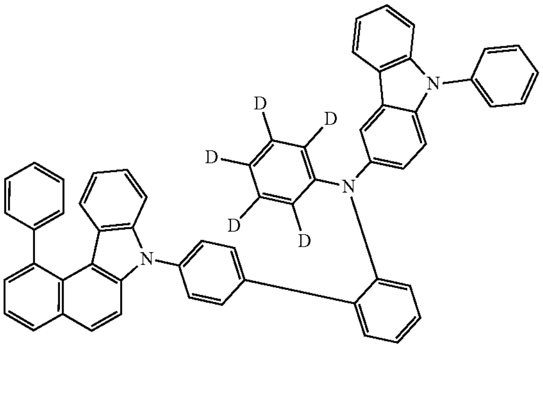
-continued
100
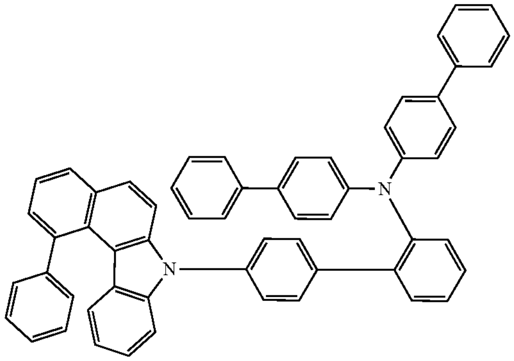
101
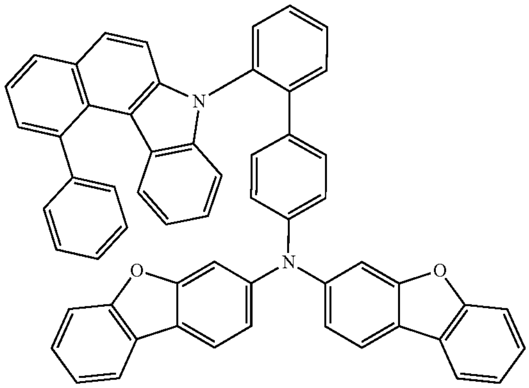
102
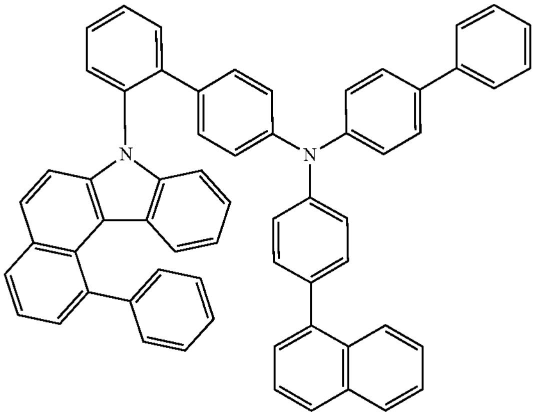
103
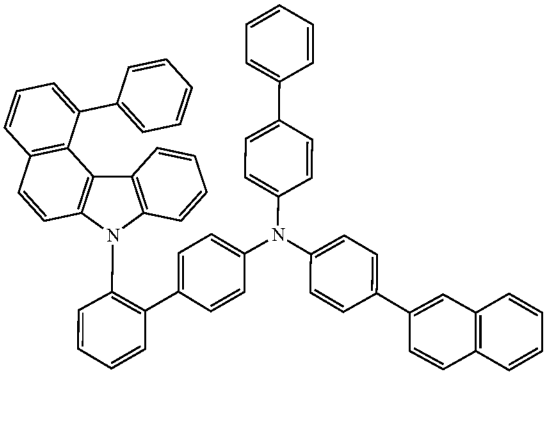

-continued
104
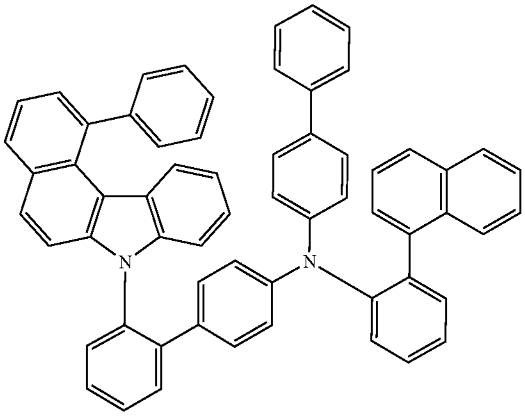
105
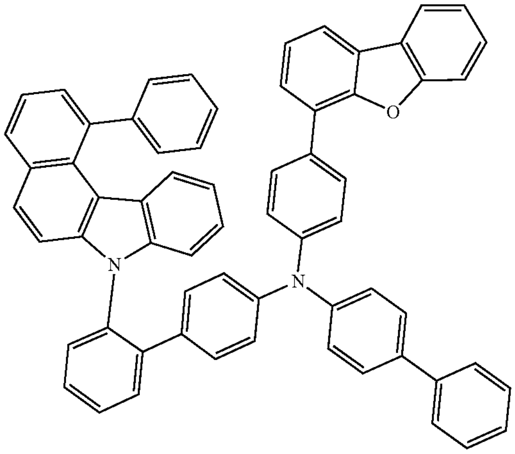
106
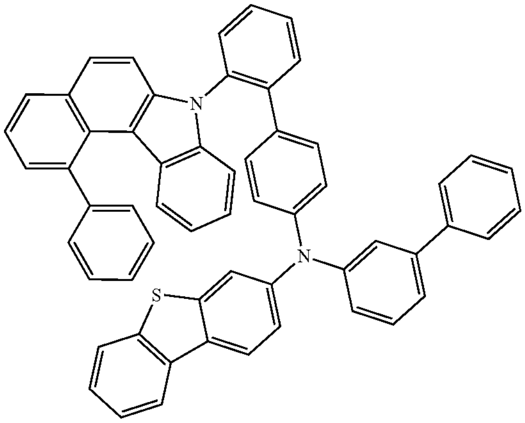
-continued
107
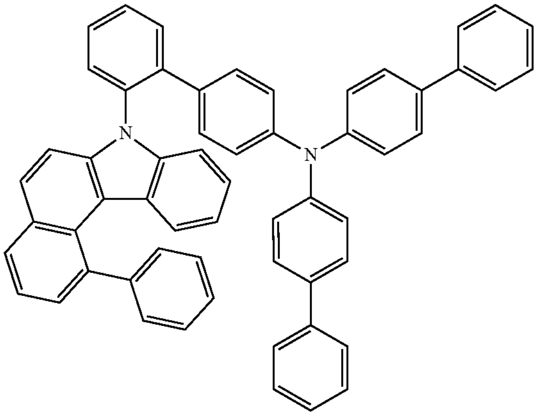
108
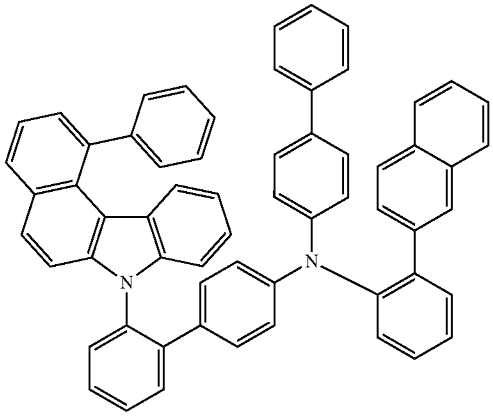
109
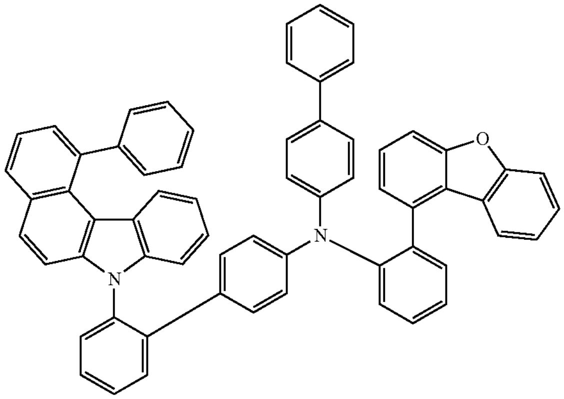

-continued
110
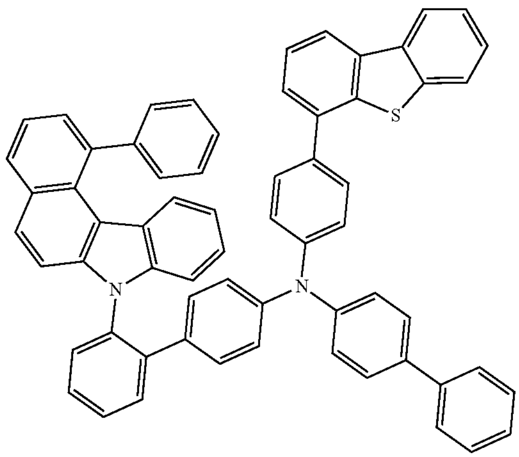
111
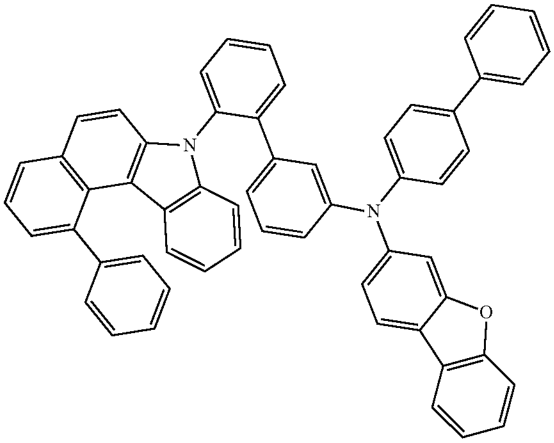
112
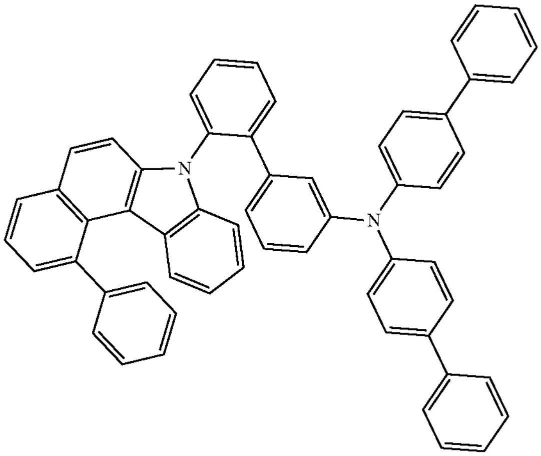
-continued
113
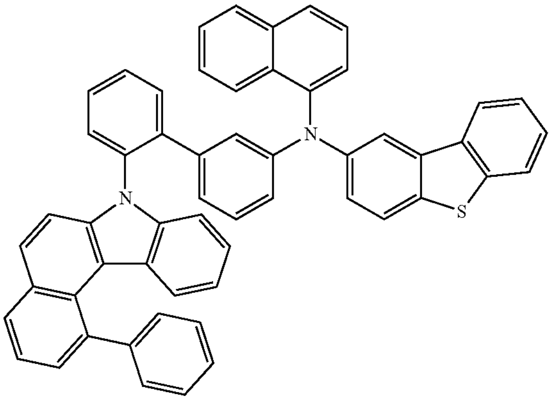
114
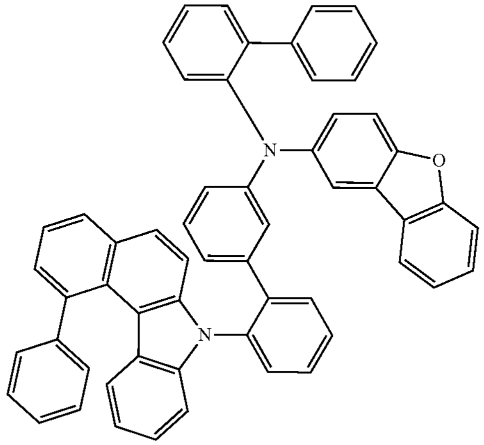
115
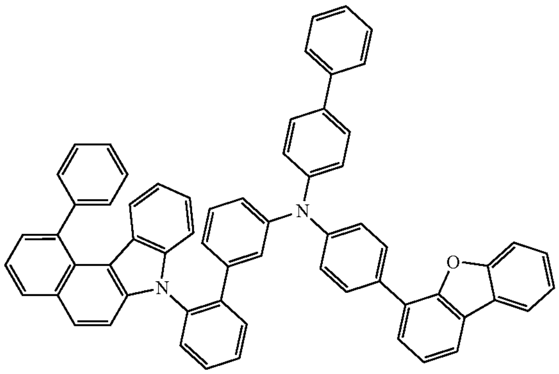
116
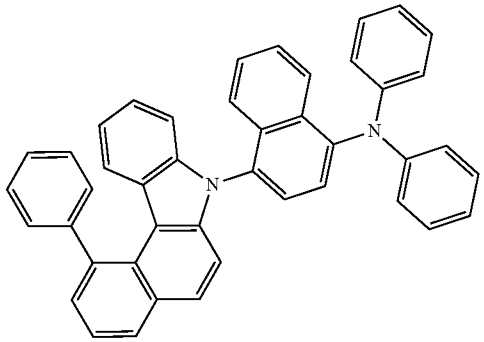

-continued
117
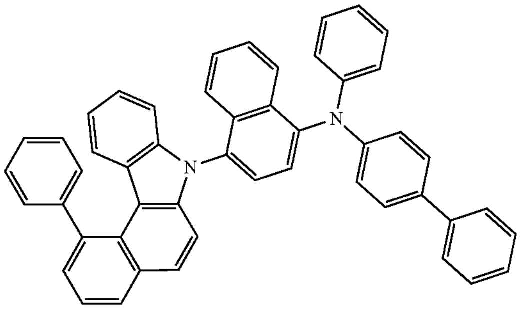
118
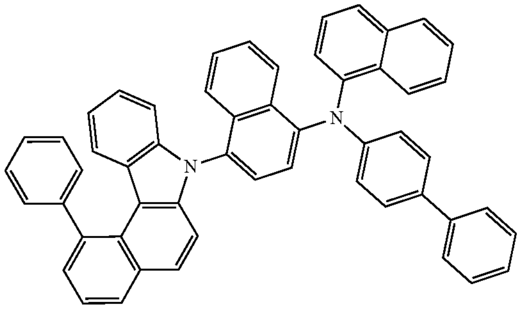
119
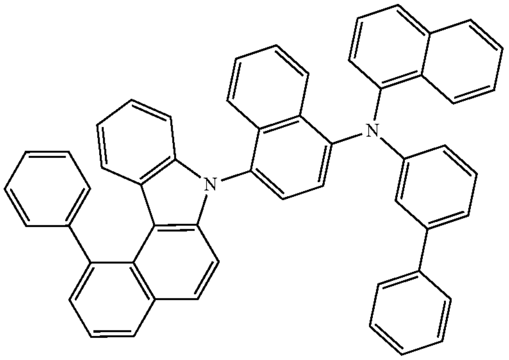
120
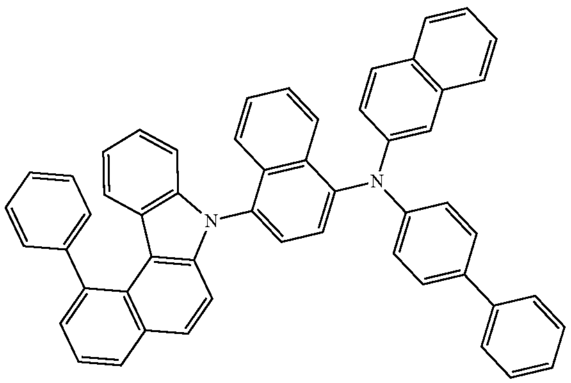
-continued
121
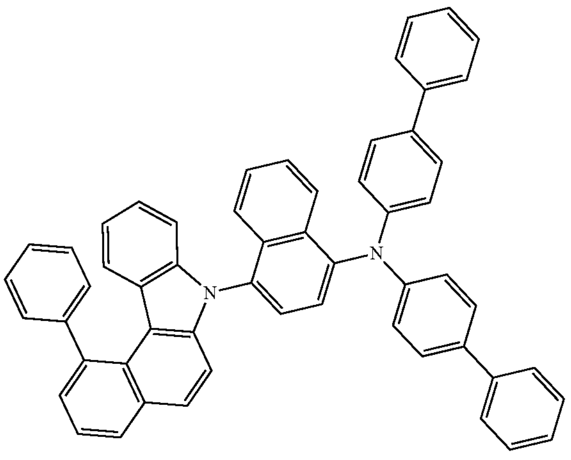
122
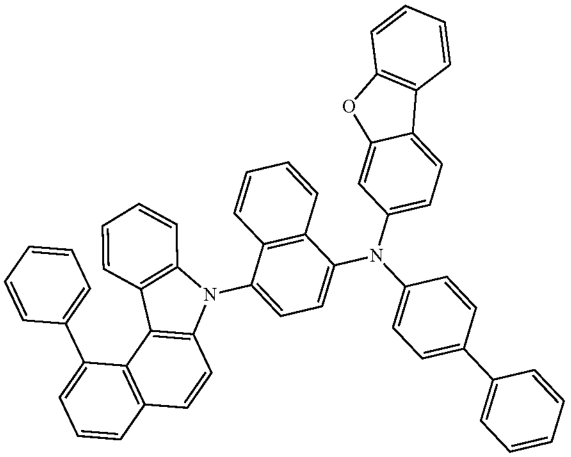
123
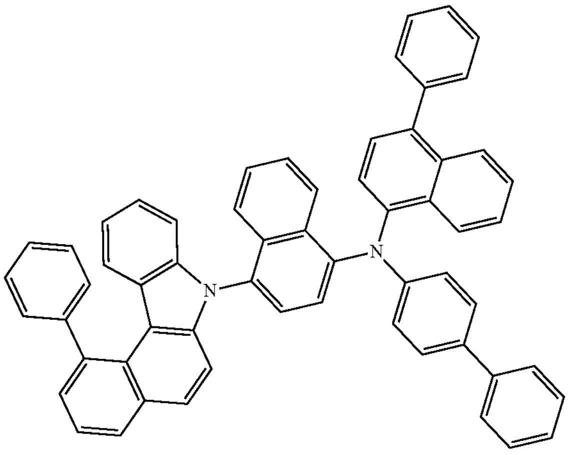

-continued
124
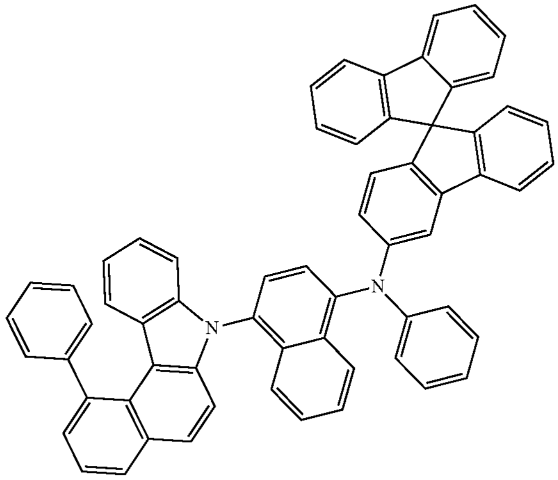
125
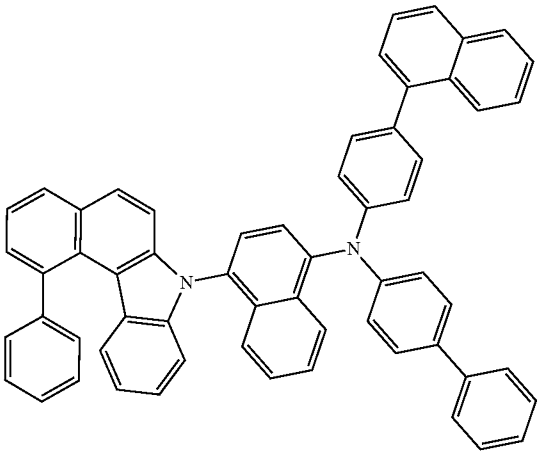
126
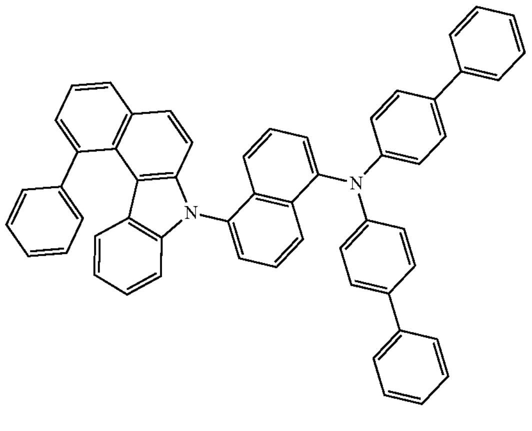
-continued
127
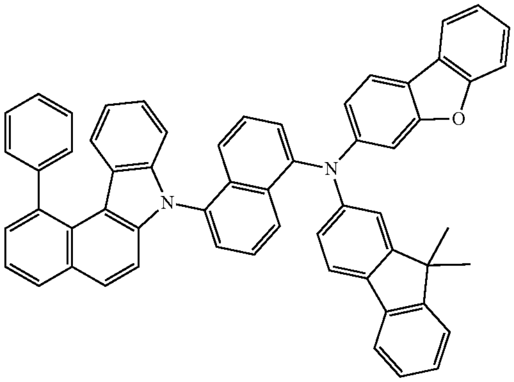
128
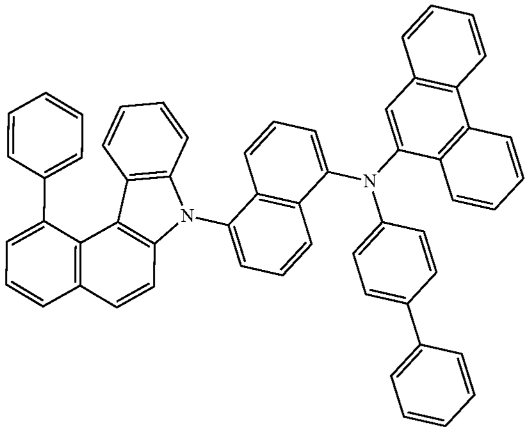
129
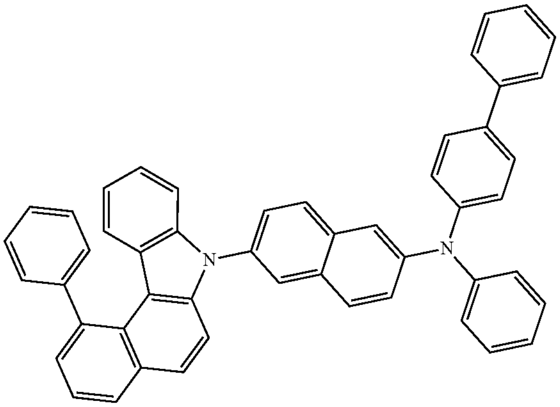

-continued
130
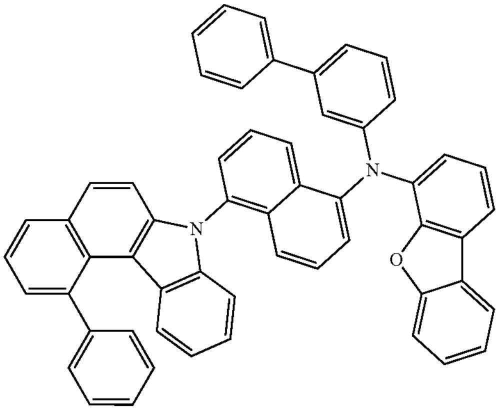
131
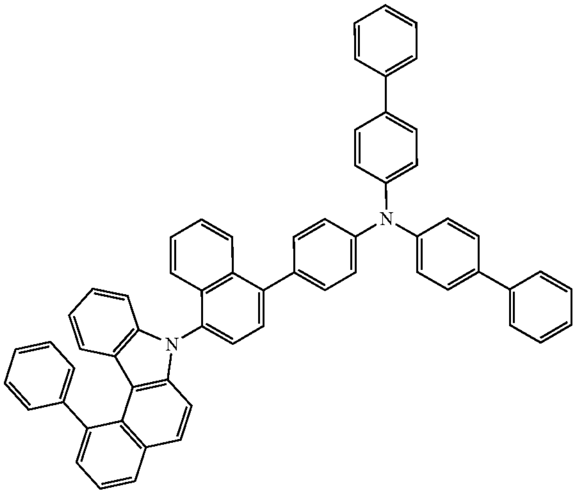
132
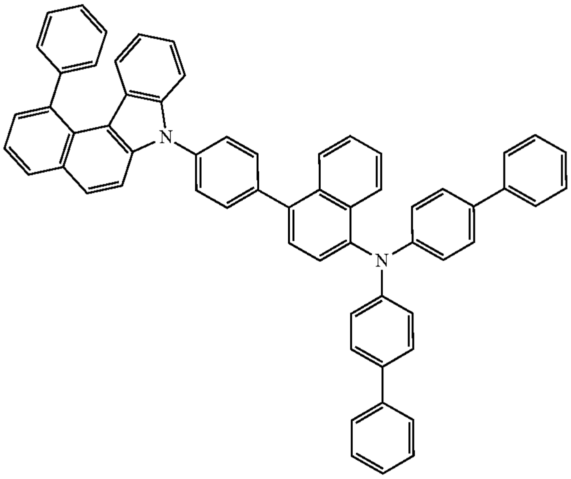
-continued
133
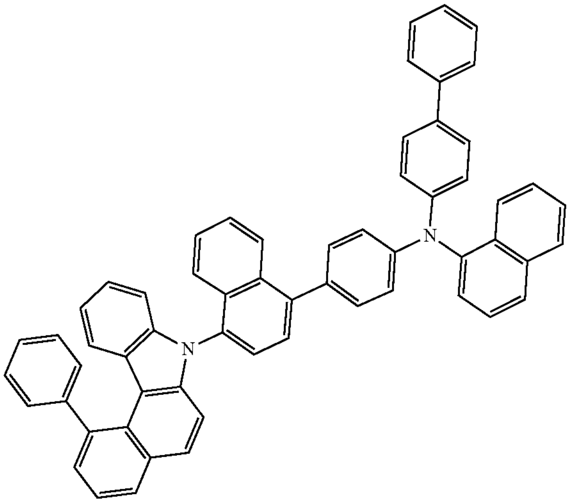
134
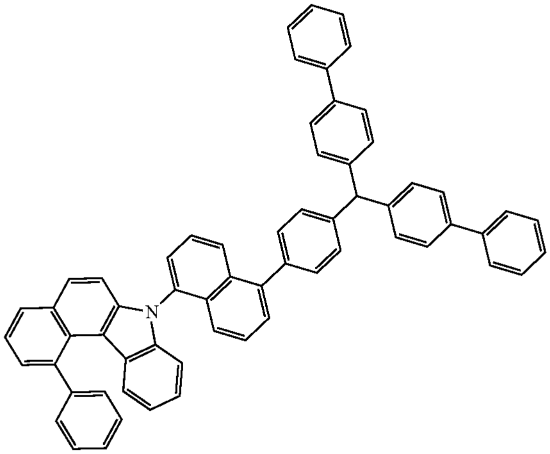
135
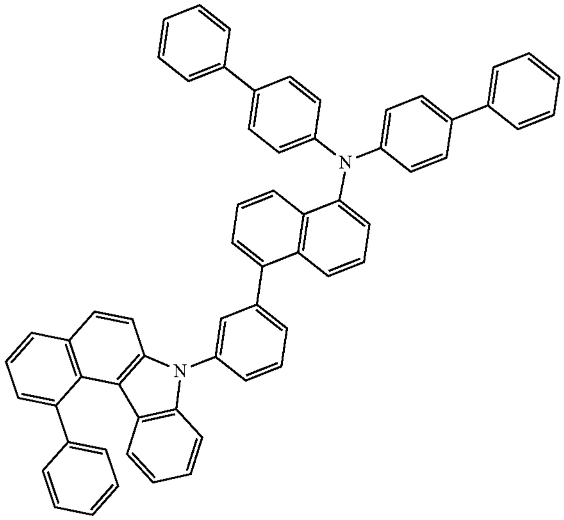

-continued
136
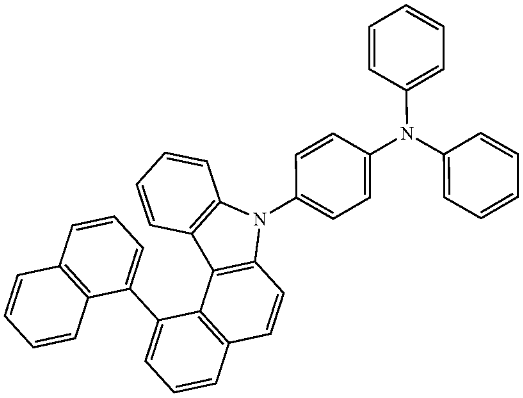
137
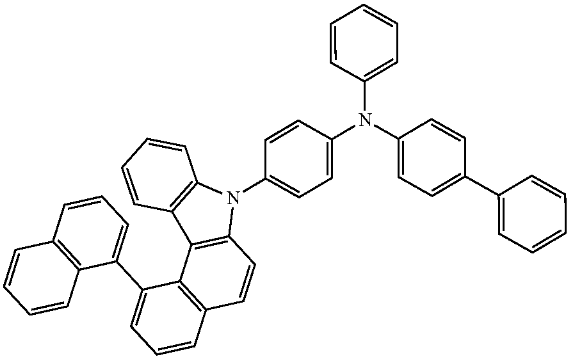
138
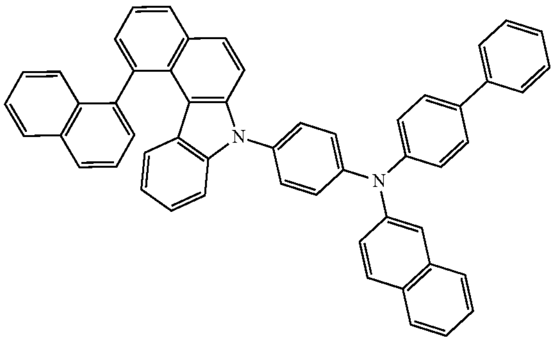
139
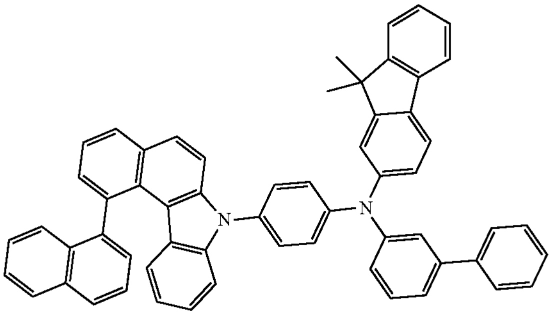
-continued
140
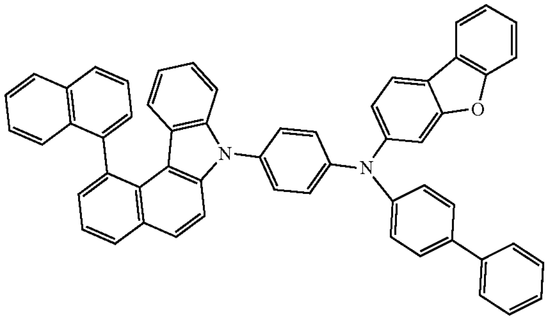
141
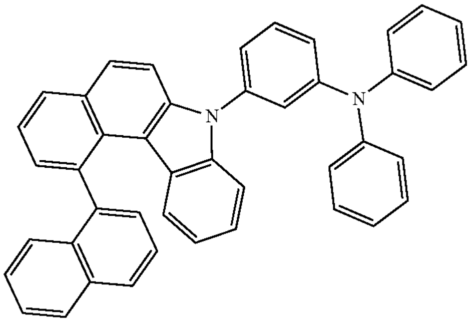
142
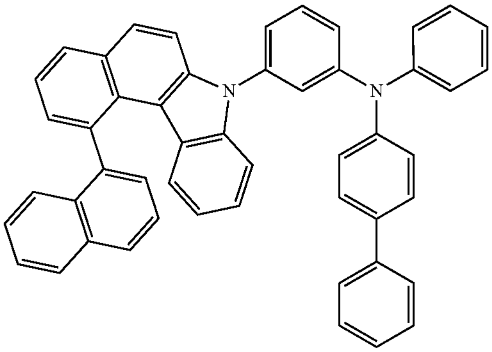
143
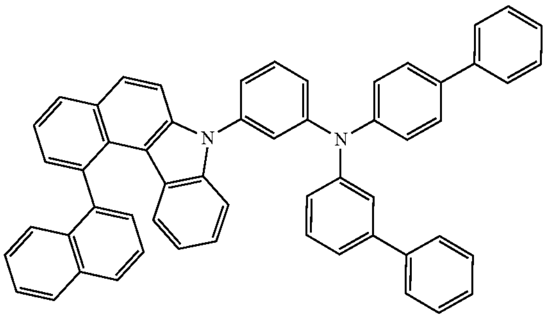

-continued
144
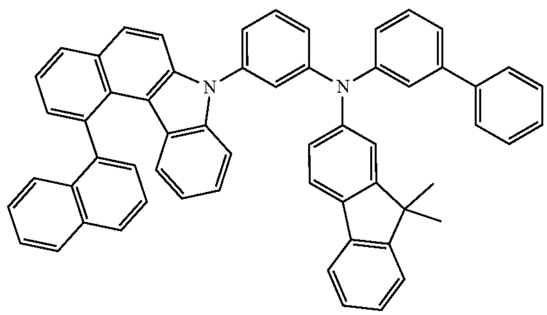
145
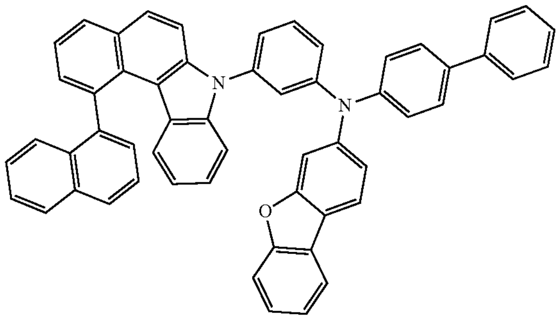
146
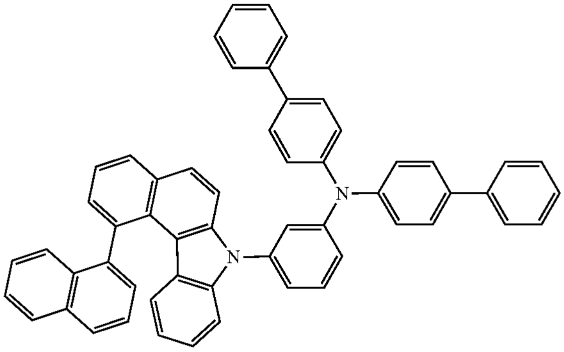
147
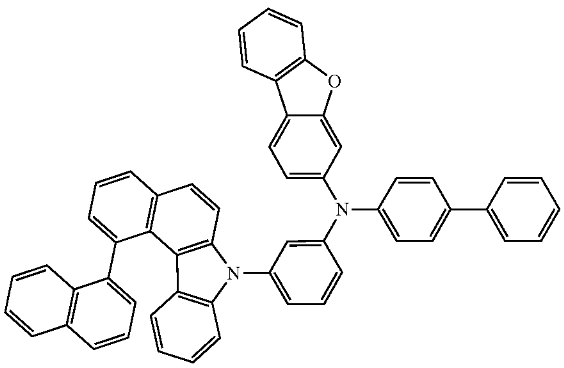
-continued
148
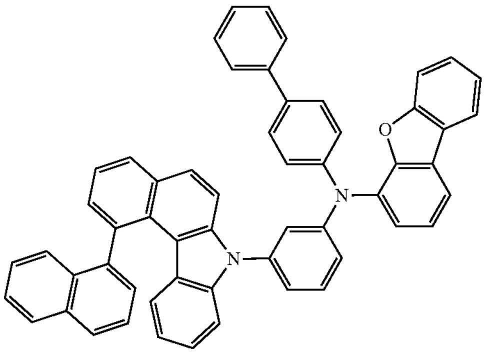
149
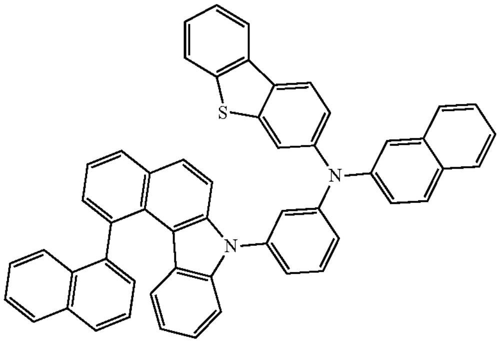
150
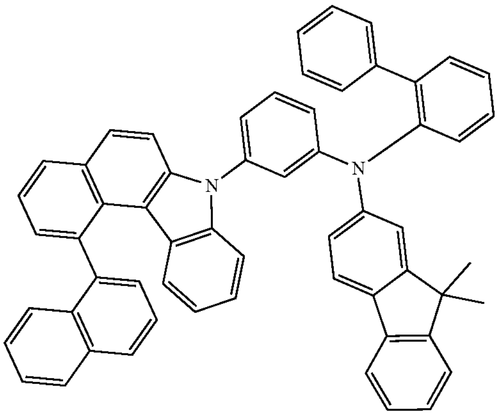
151
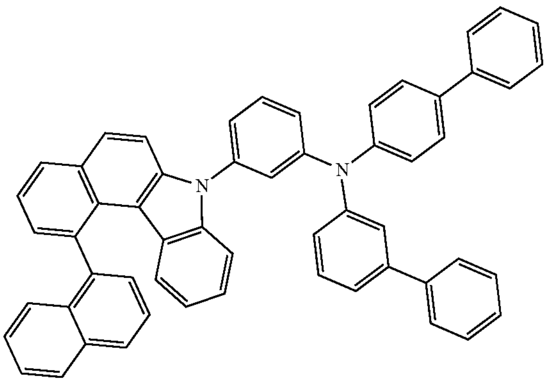

-continued
152
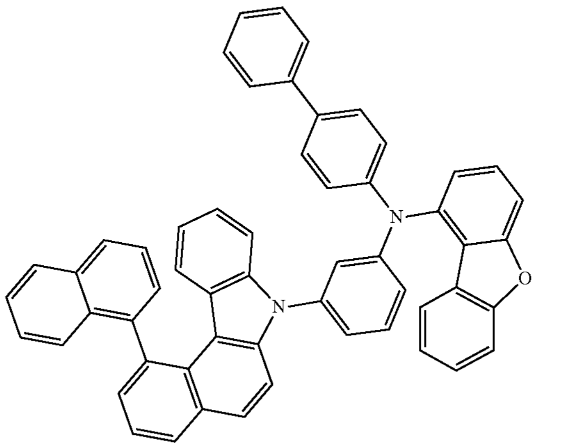
153
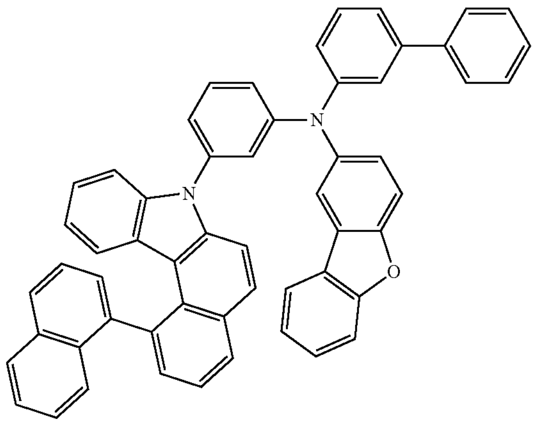
154
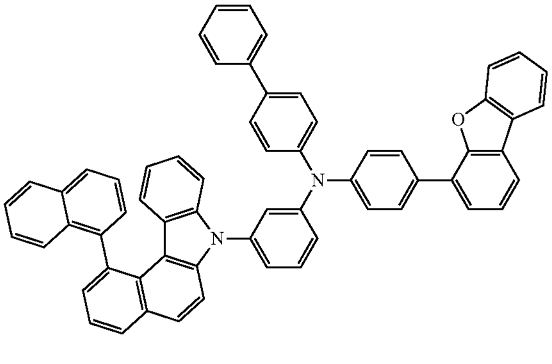
155
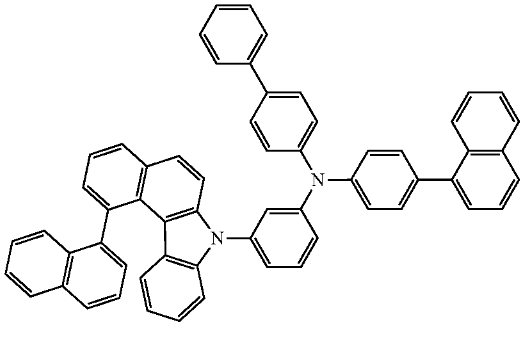
-continued
156
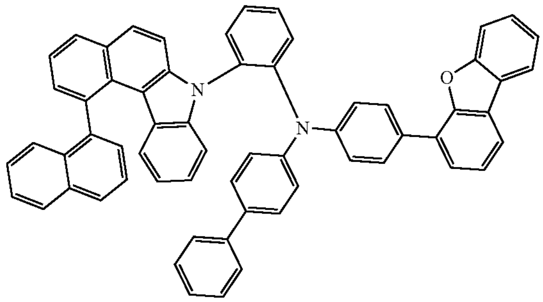
157
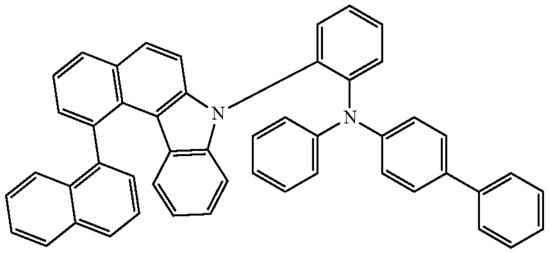
158
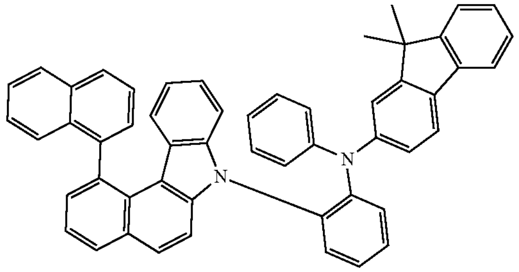
159
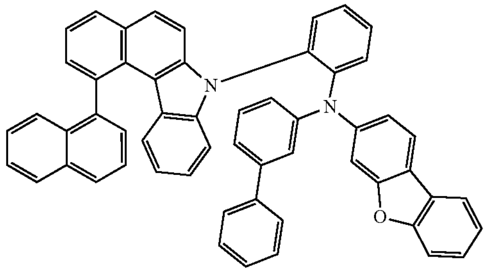
160
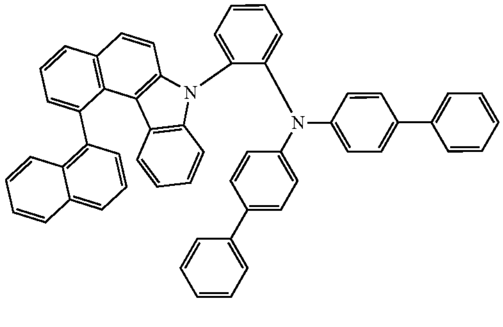

-continued
161
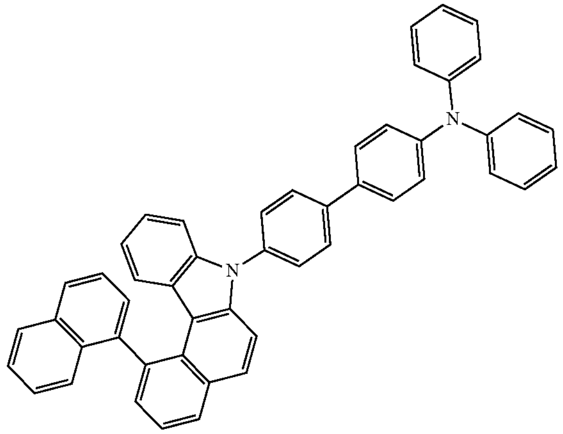
162
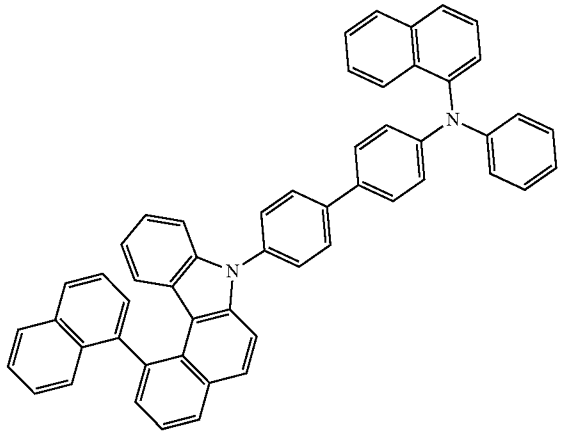
163
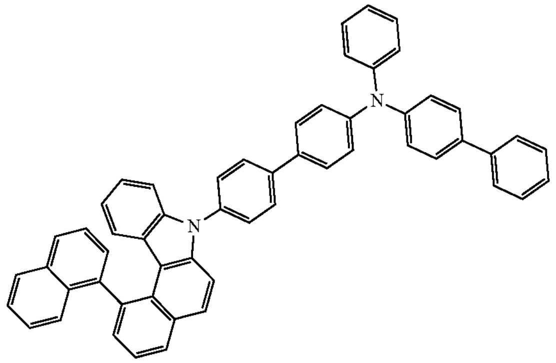
-continued
164
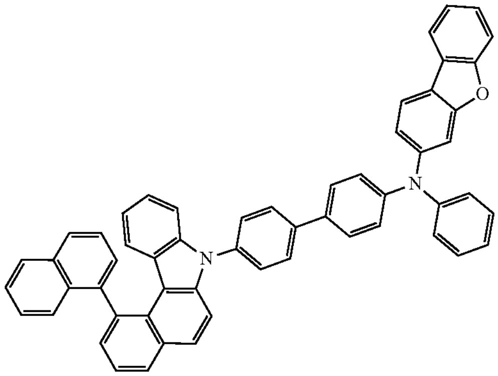
165
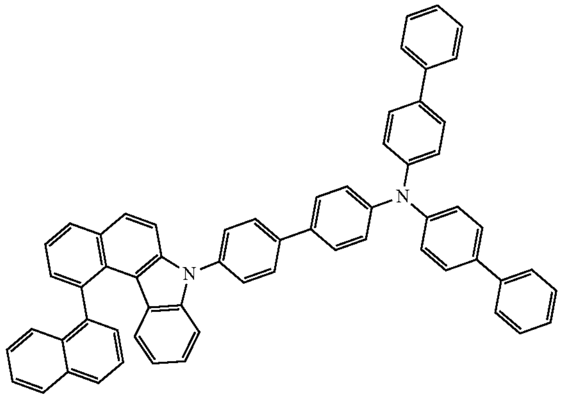
166
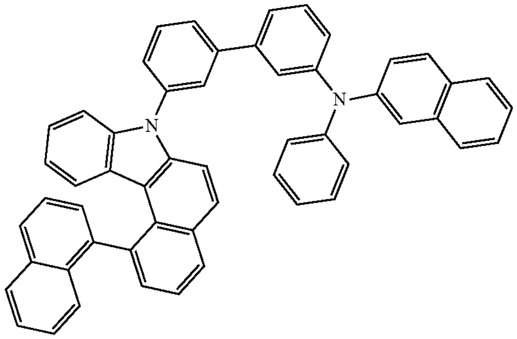
167
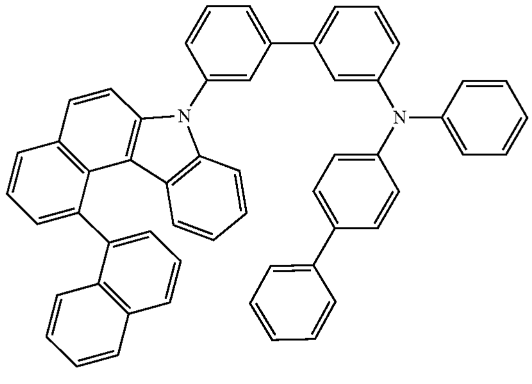

-continued
168
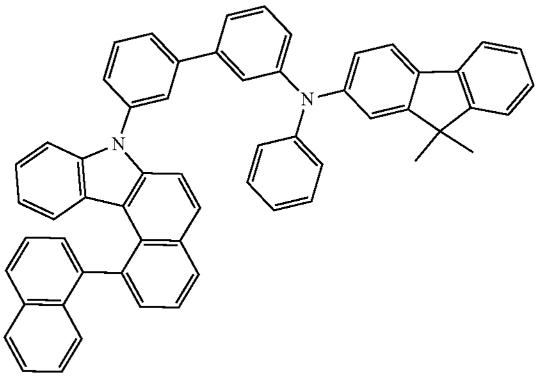
169
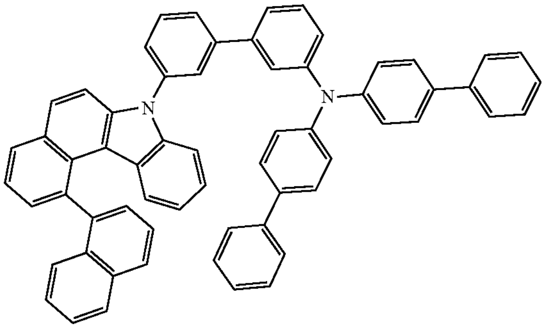
170
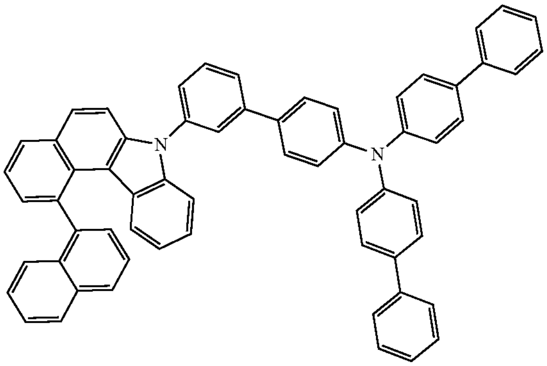
171
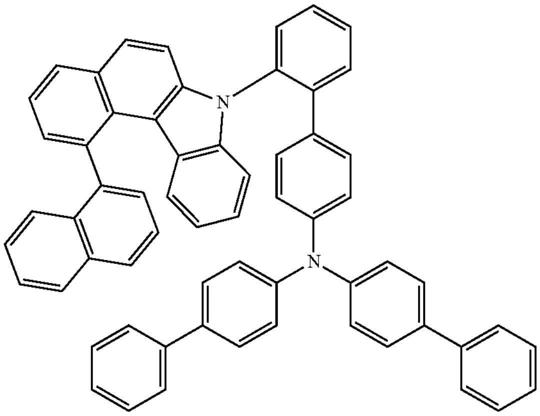
-continued
172
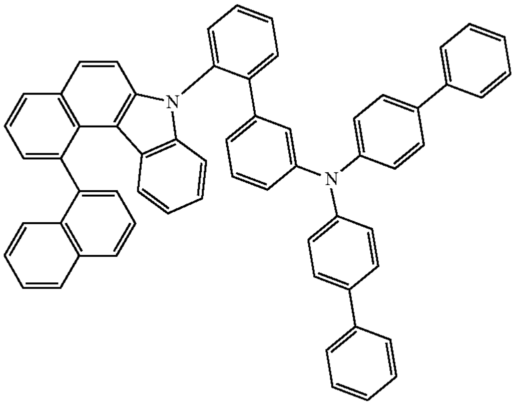
173
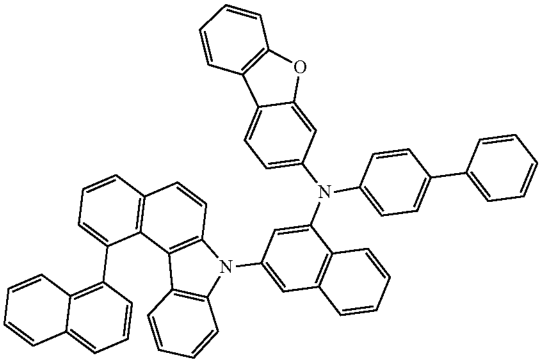
174
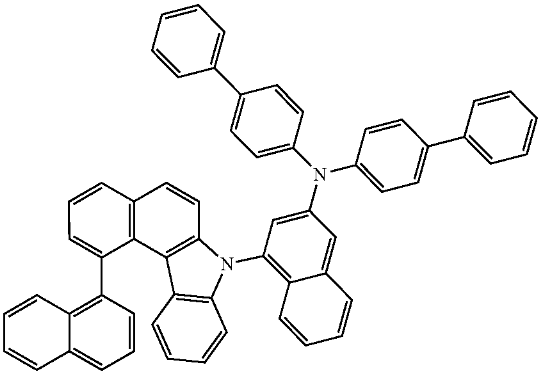
175
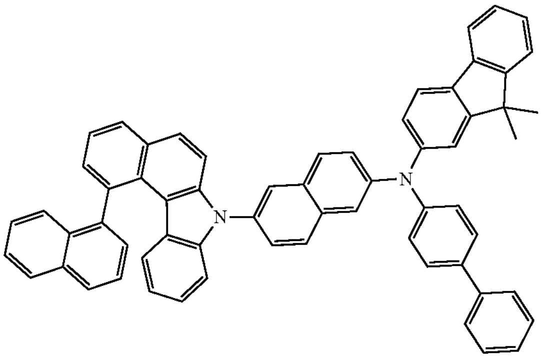

-continued
176
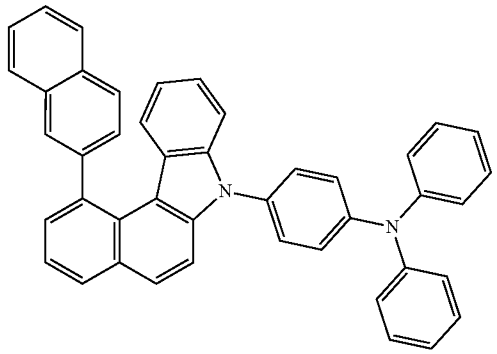
177
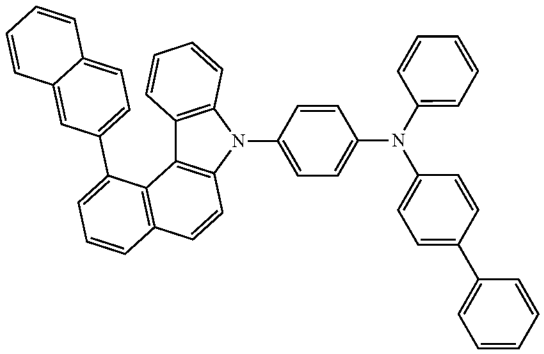
178
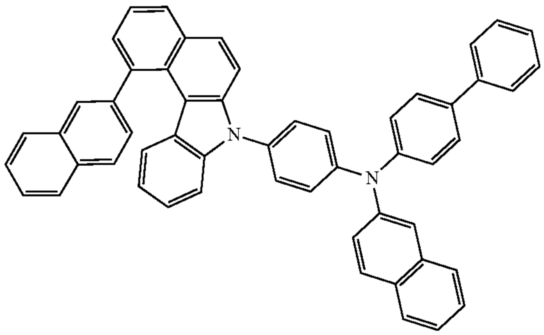
179
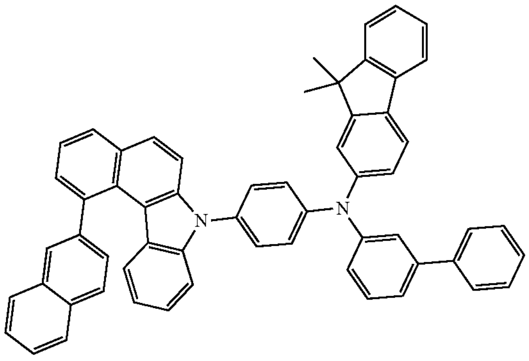
-continued
180
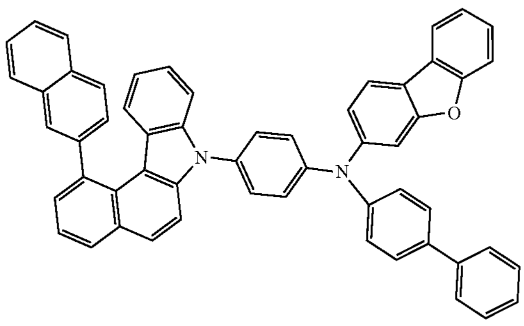
181
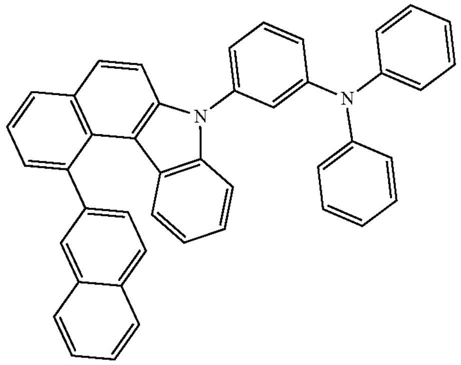
182
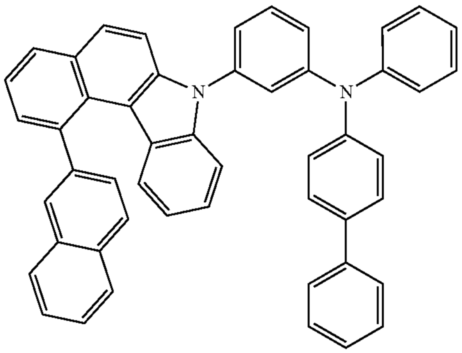
183
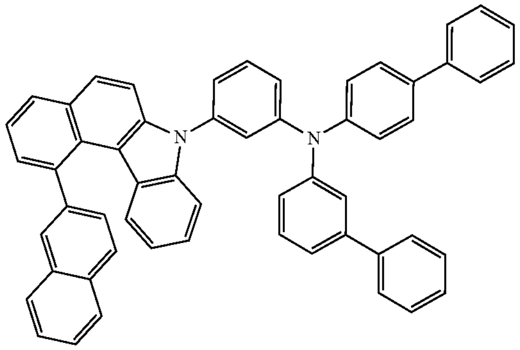

-continued
184
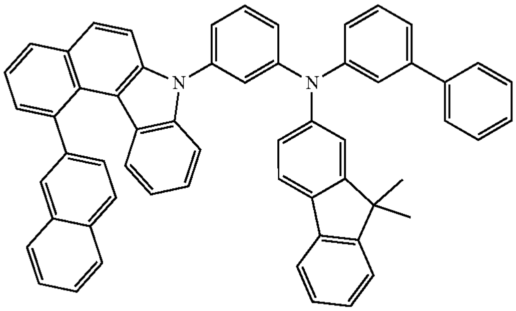
185
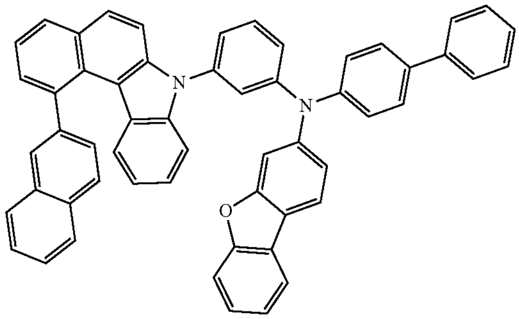
186
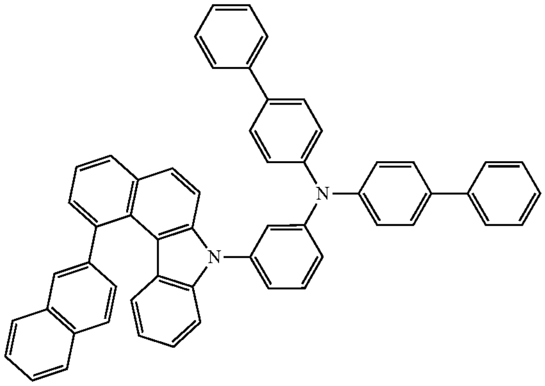
187
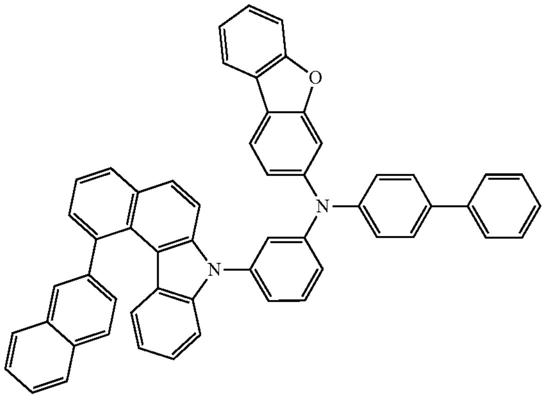
-continued
188
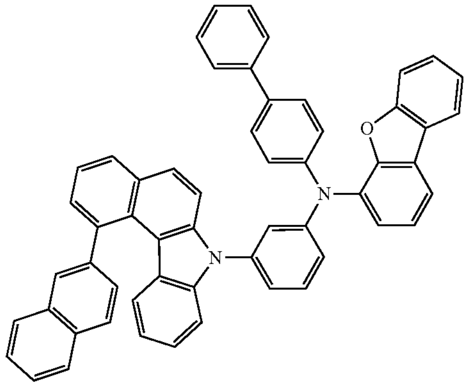
189
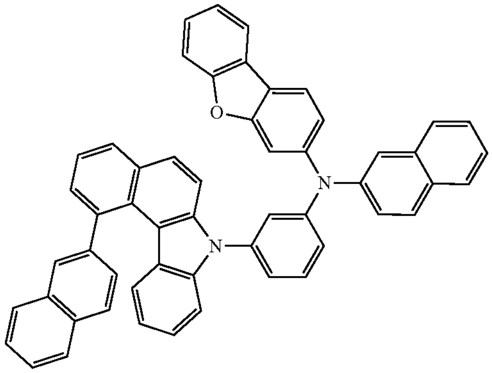
190
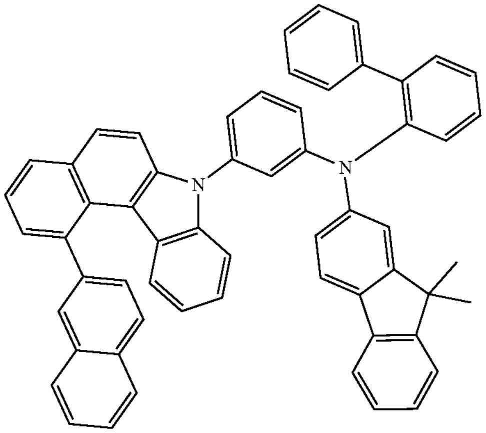
191
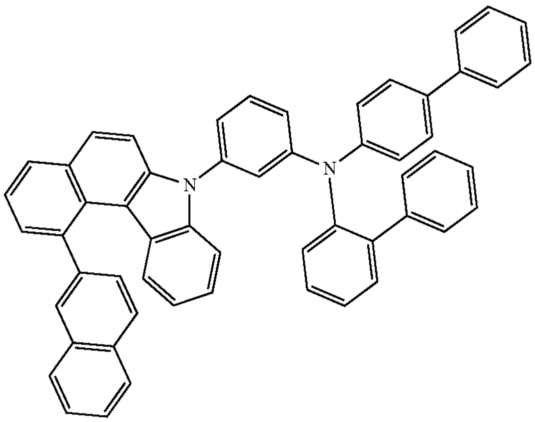

-continued
192
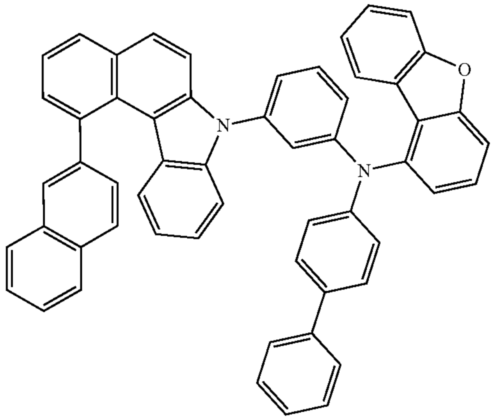
193
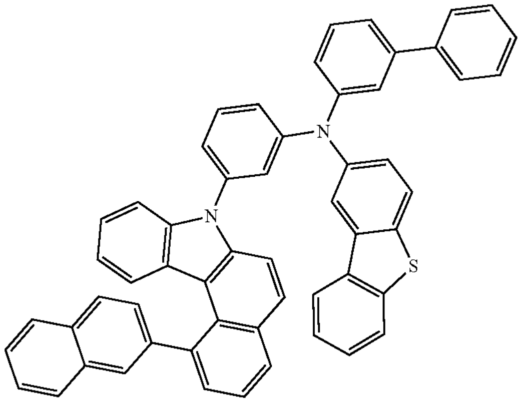
194
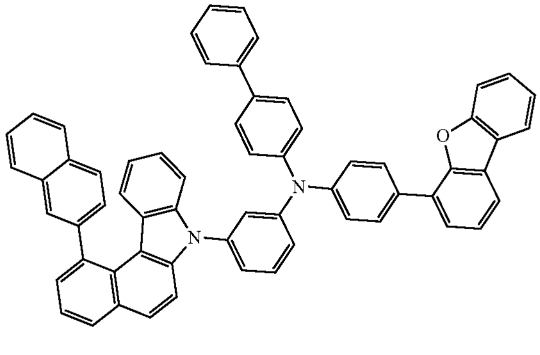
195
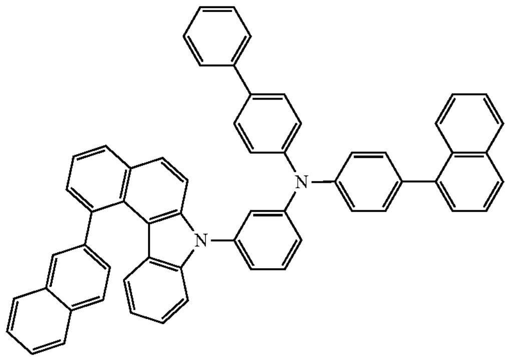
-continued
196
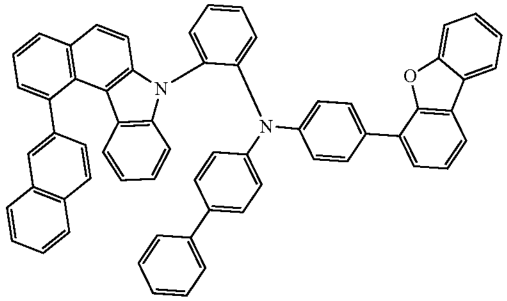
197
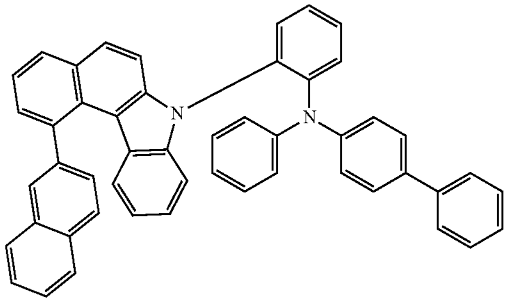
198
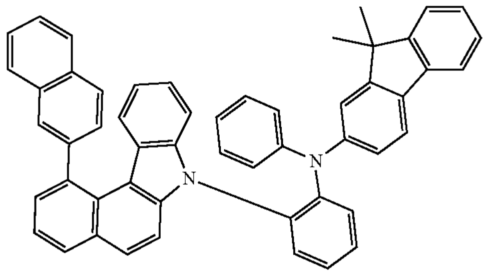
199
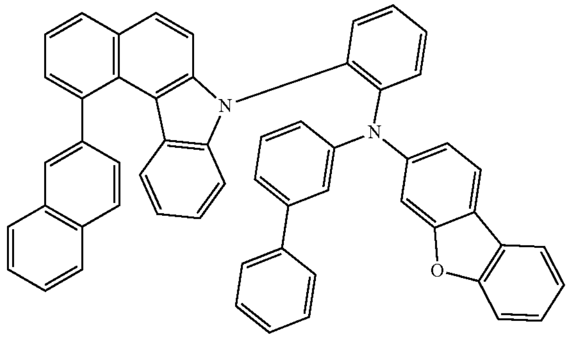
200
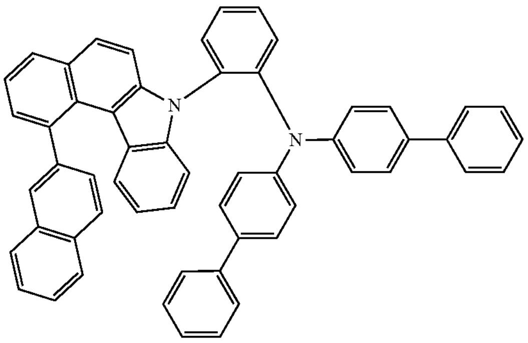

-continued
201
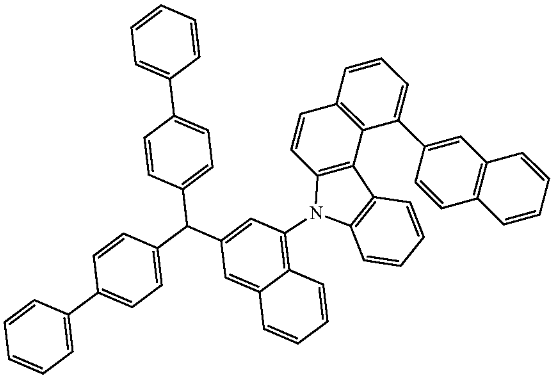
202
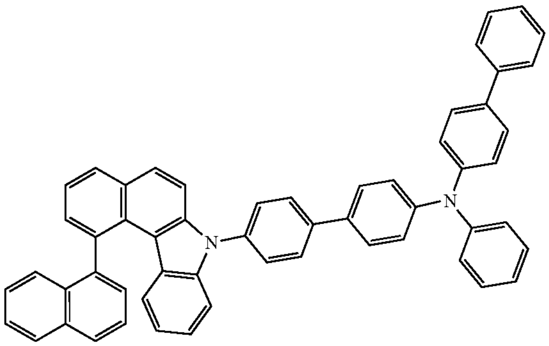
203
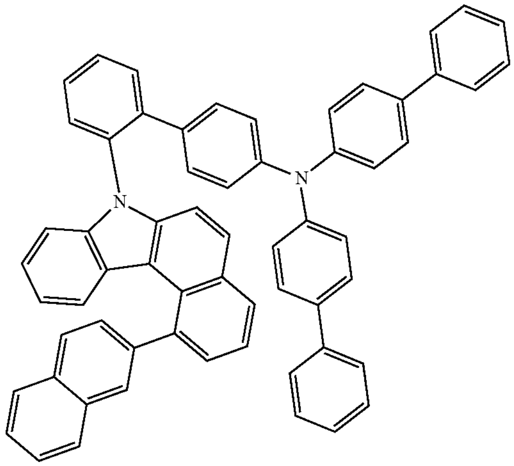
204
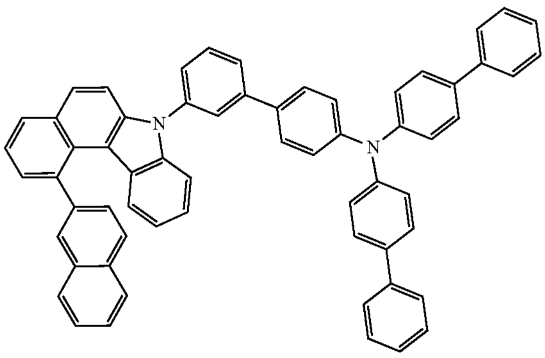
-continued
205
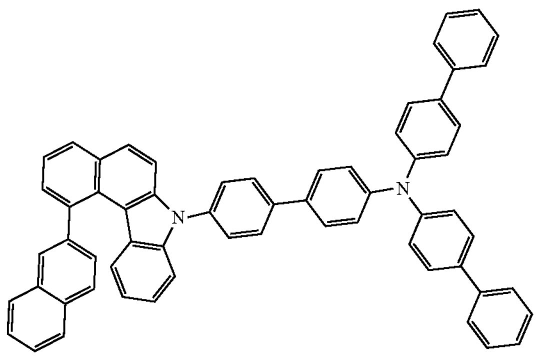
206
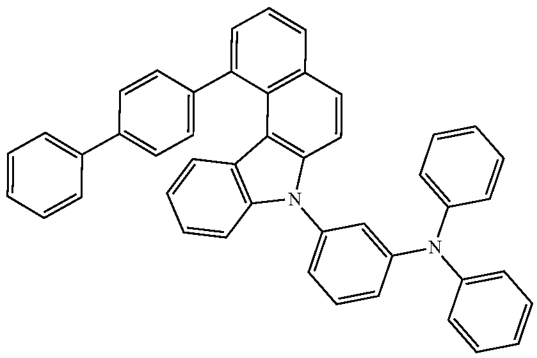
207
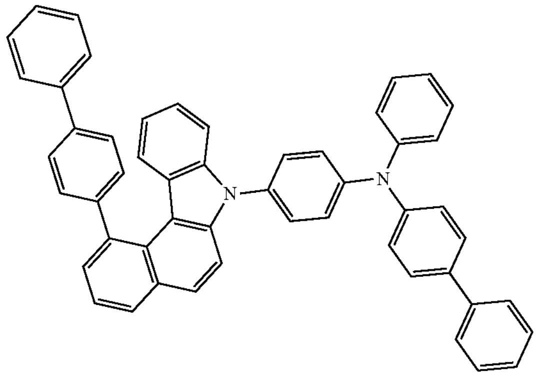
208
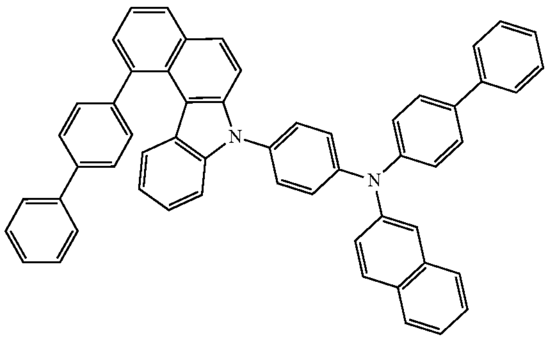

-continued
209
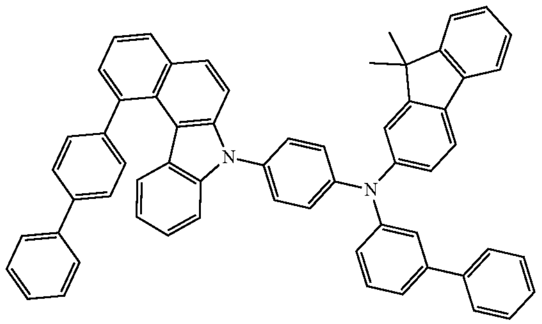
210
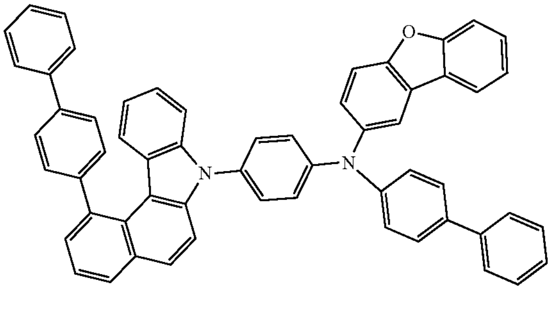
211
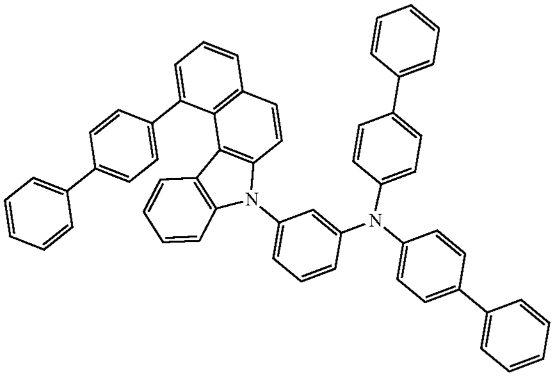
212
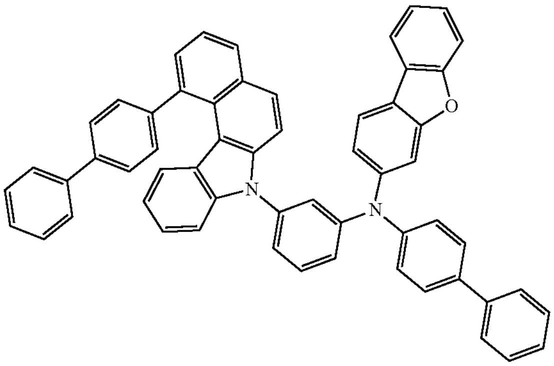
-continued
213
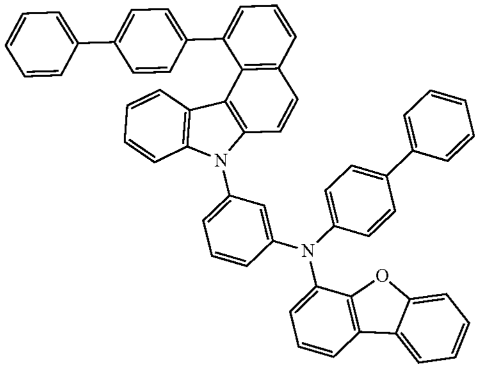
214
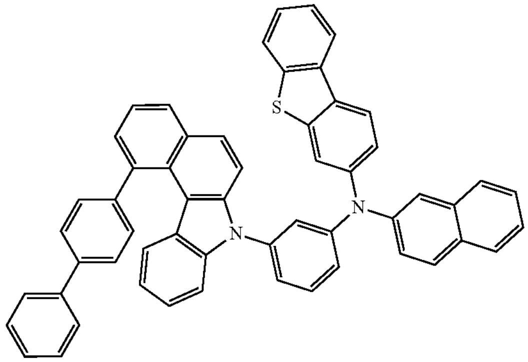
215
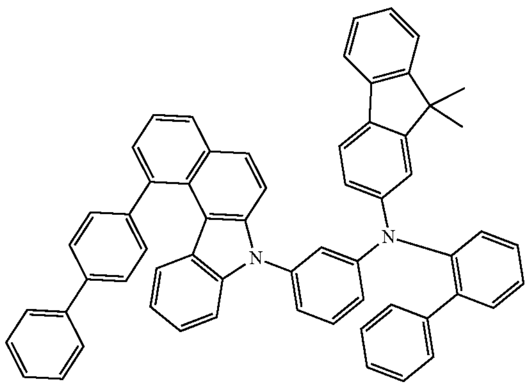
216
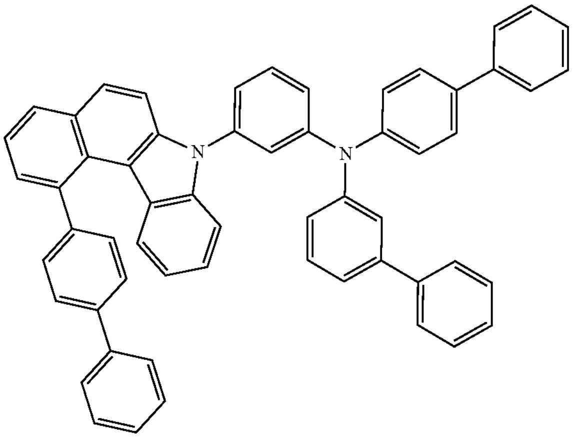

-continued
217
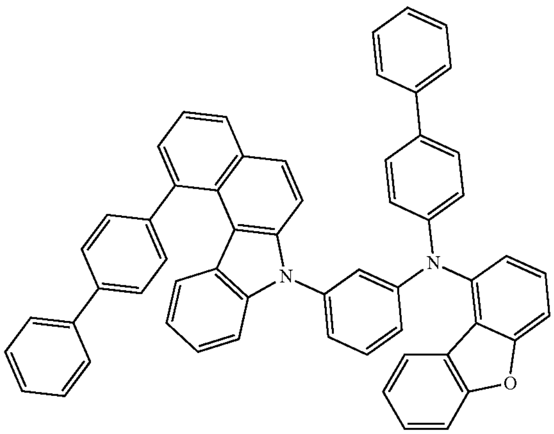
218
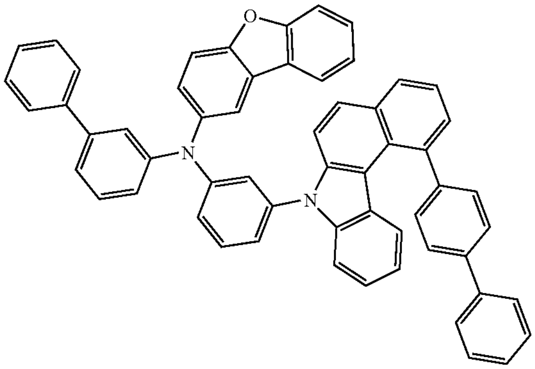
219
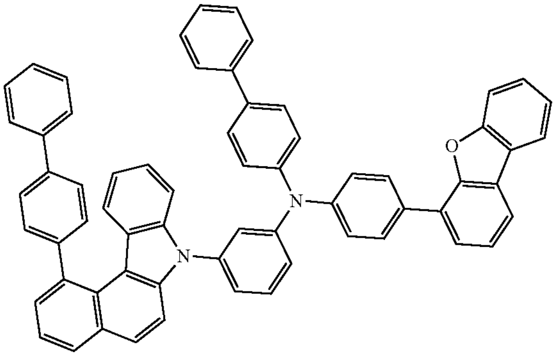
220
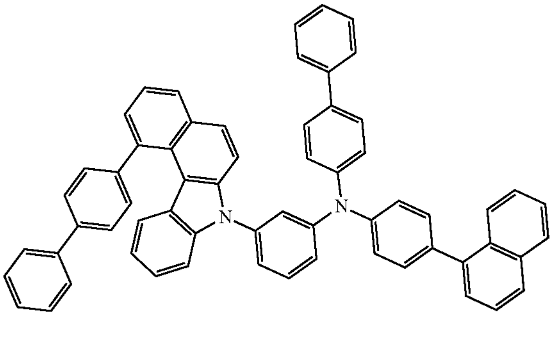
-continued
221
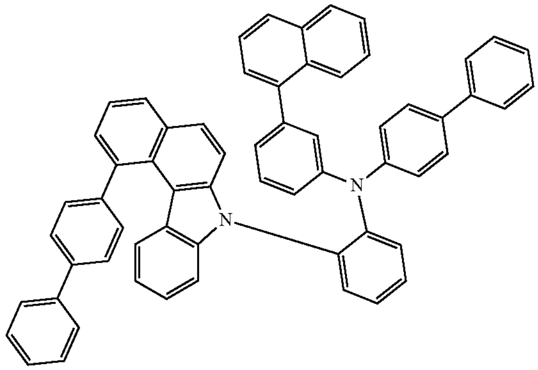
222
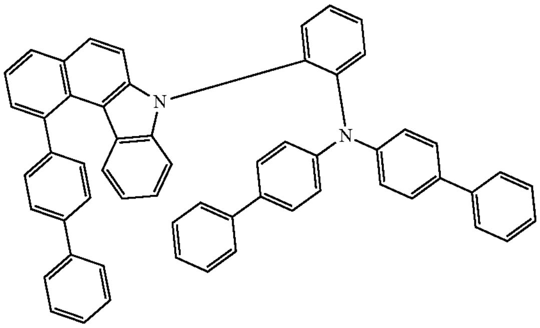
223
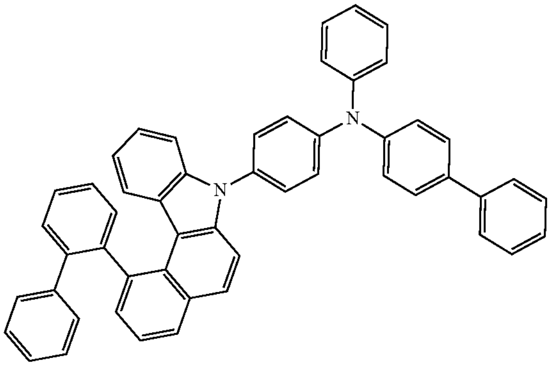
224
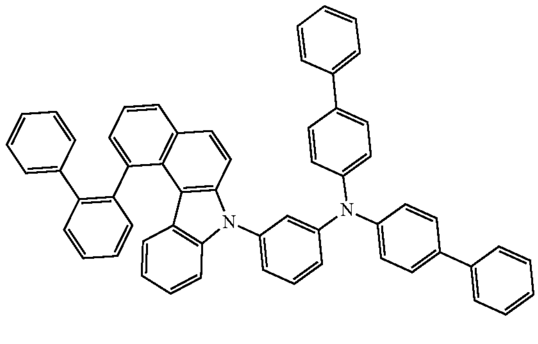

-continued
225
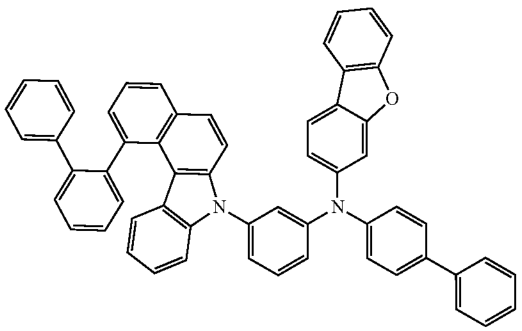
226
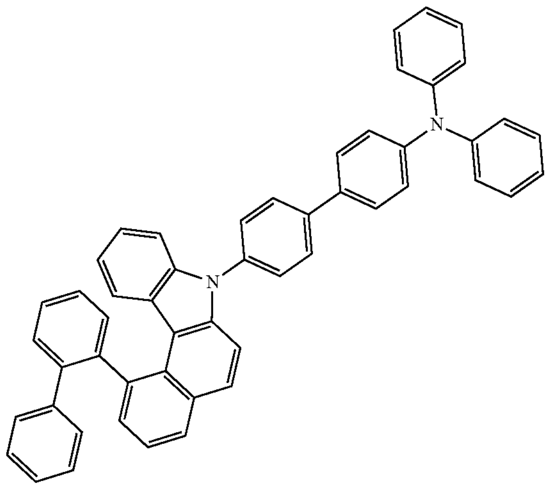
227
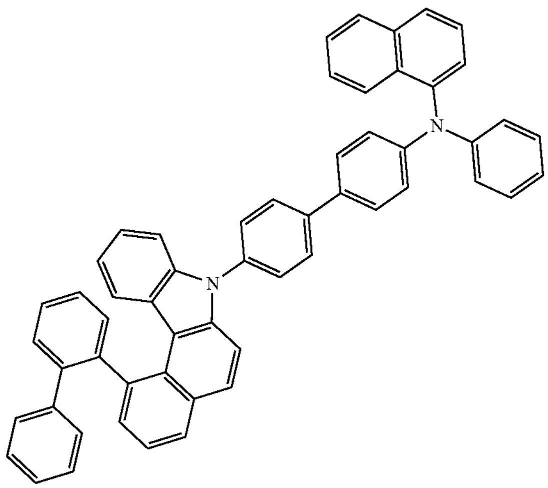
-continued
228
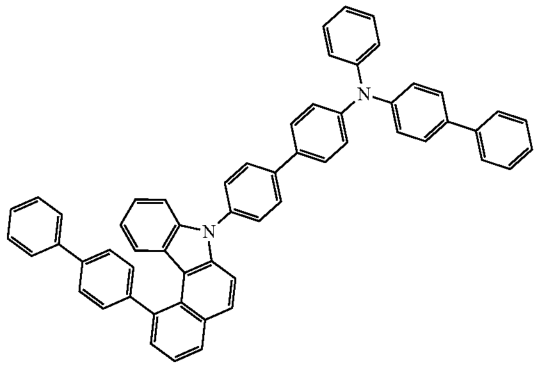
229
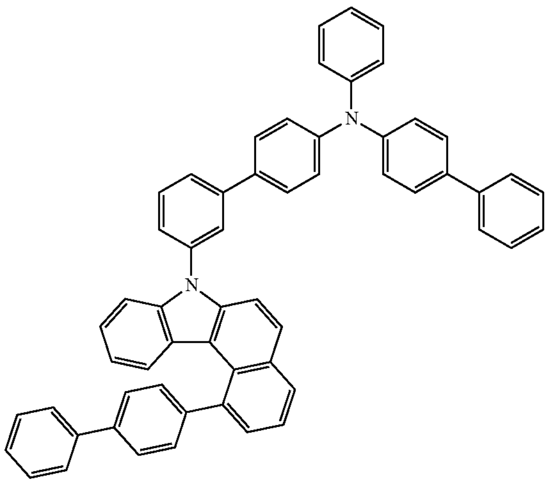
230
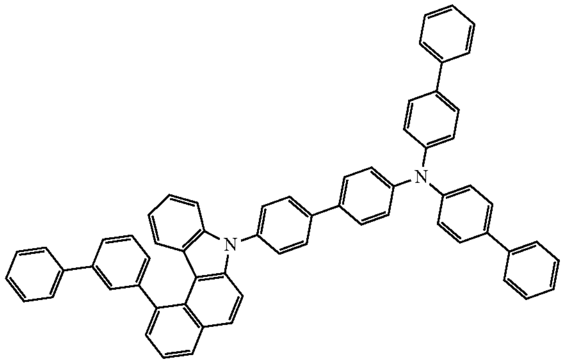

-continued
231
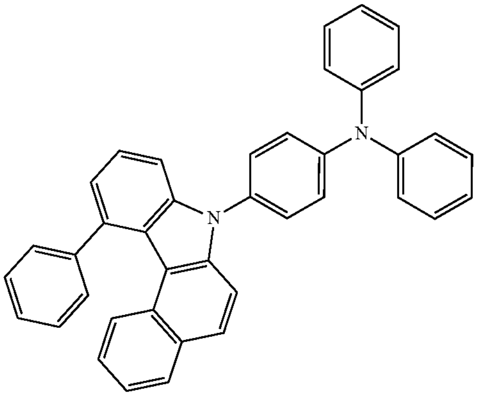
232
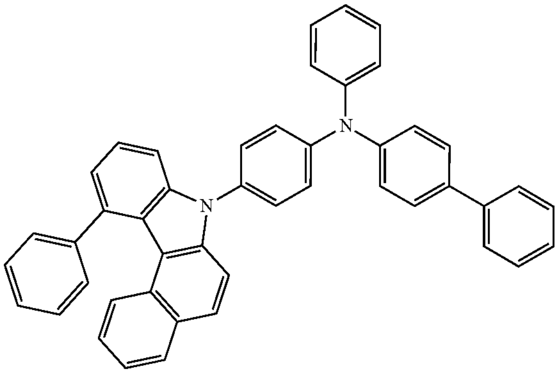
233
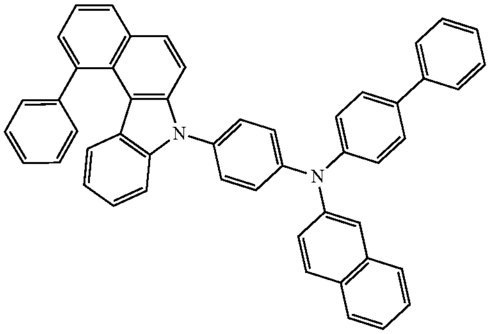
234
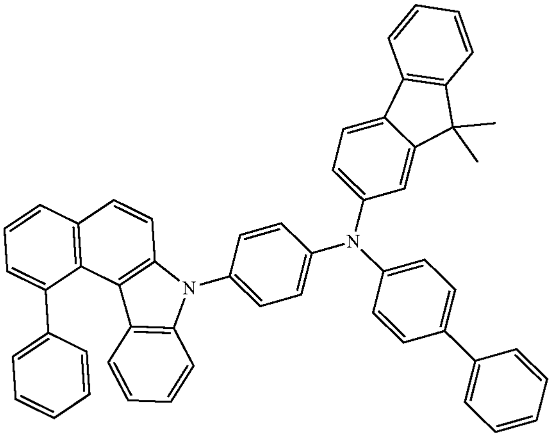
-continued
235
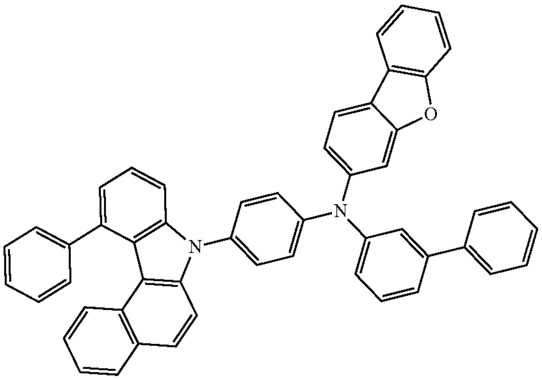
236
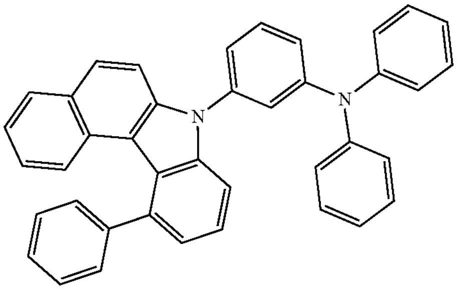
237
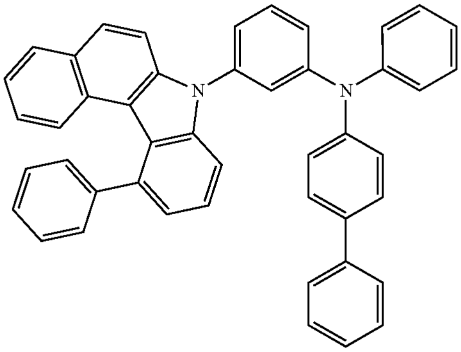
238
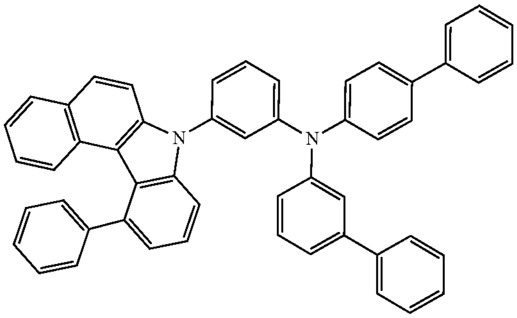

-continued
239
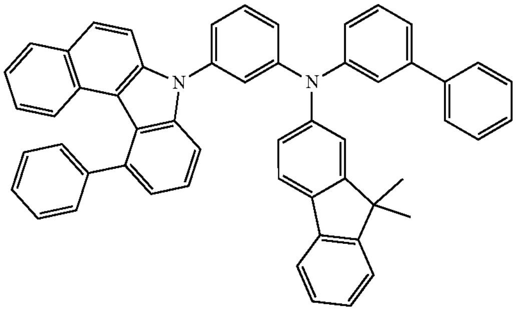
240
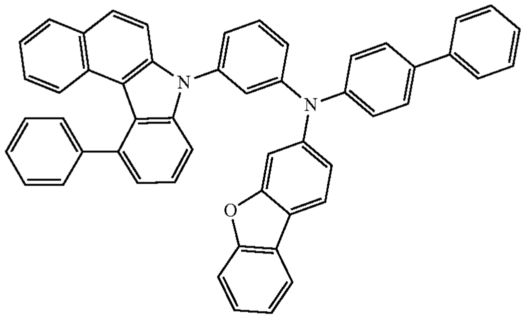
246
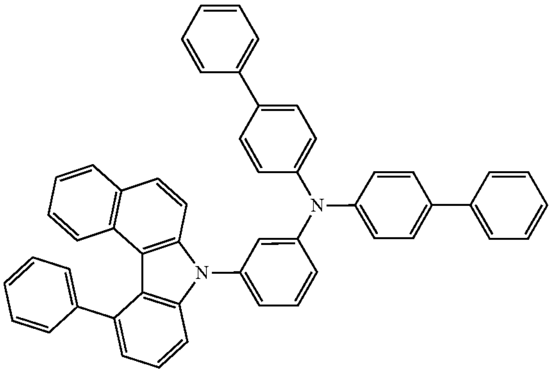
247
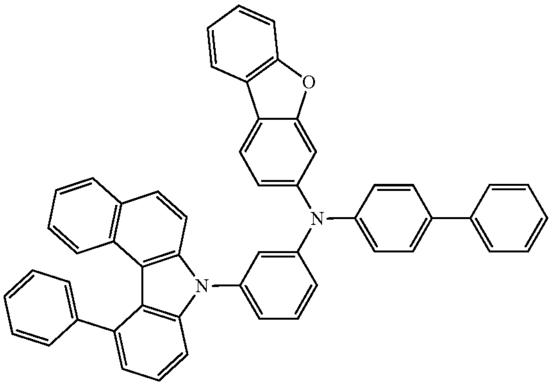
-continued
248
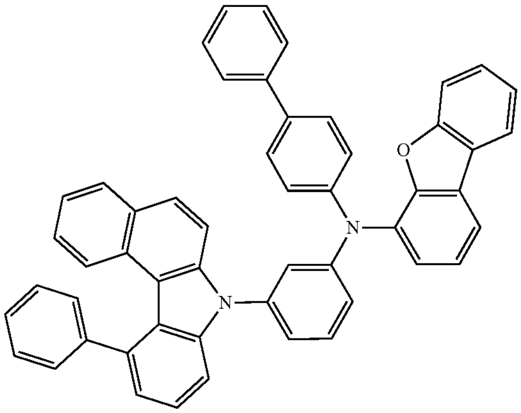
249
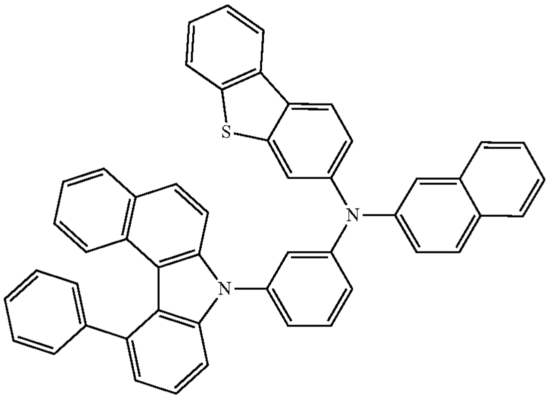
250
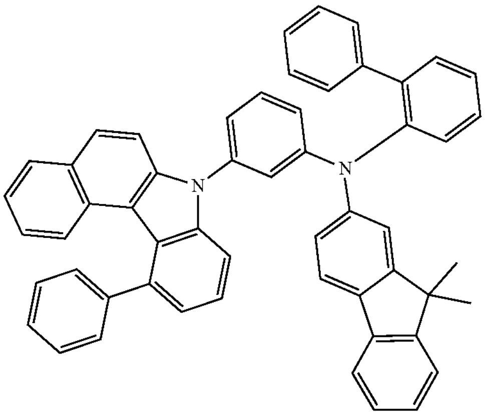

251
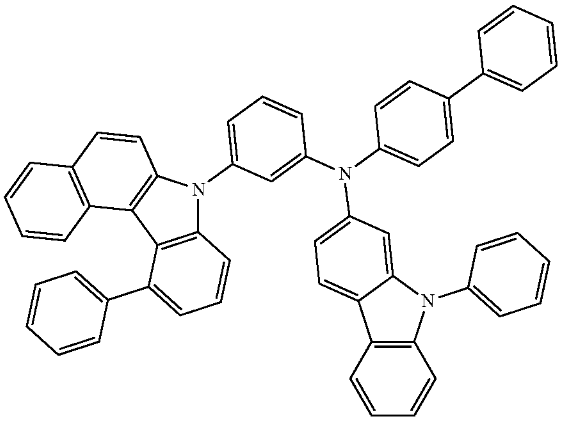
252
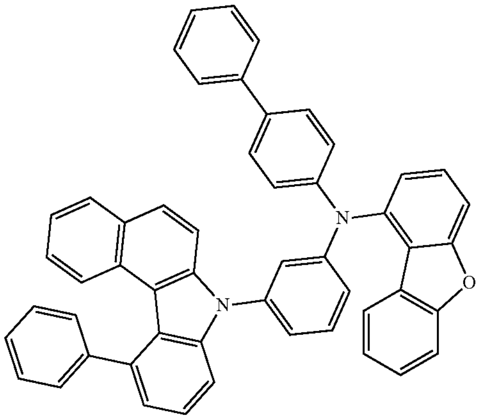
253
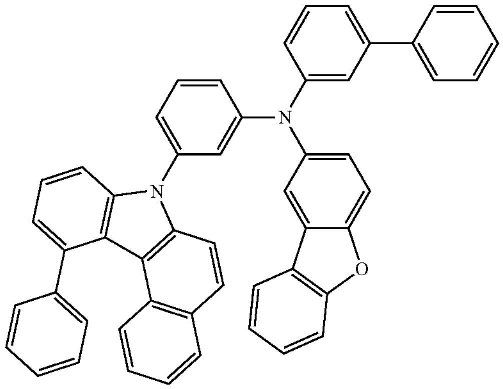
254
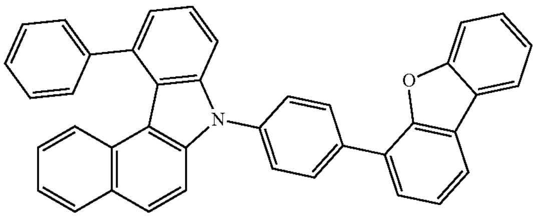
-continued
255
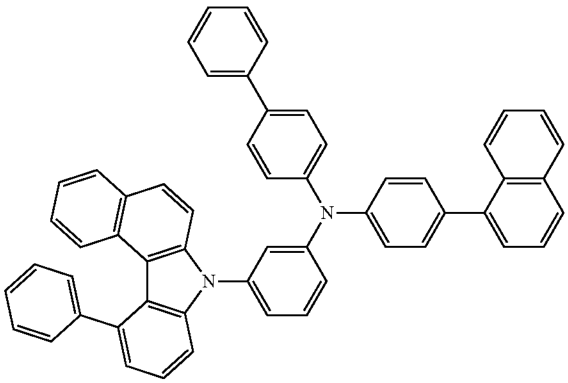
256
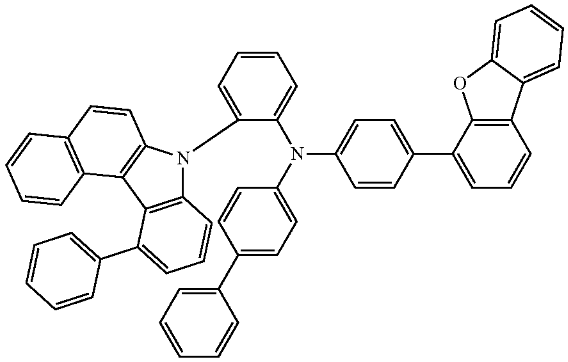
257
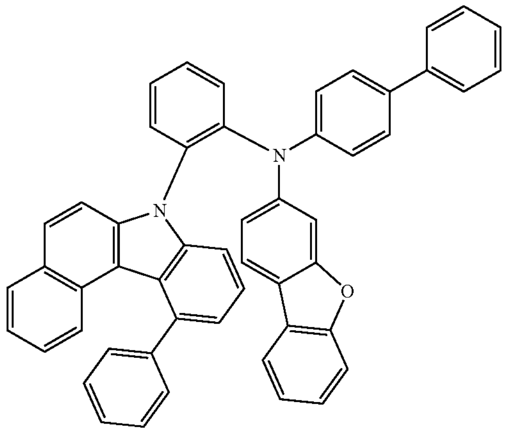
258
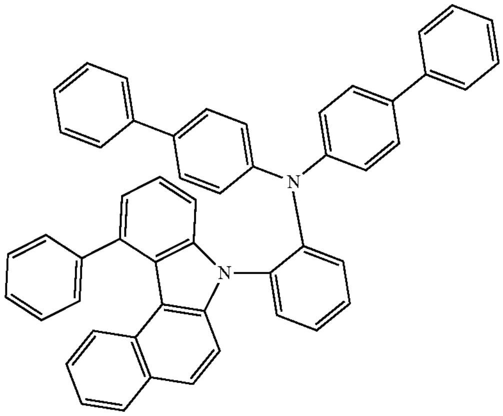

-continued
259
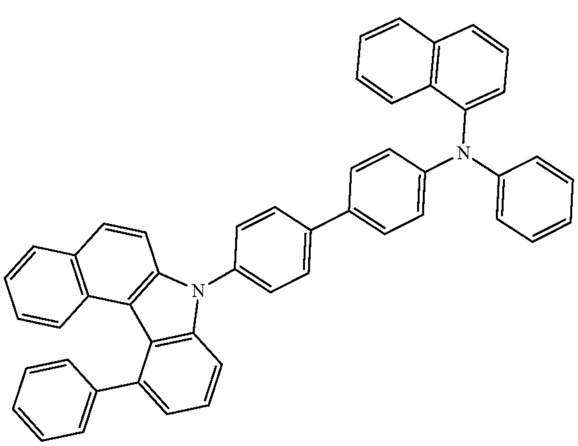
260
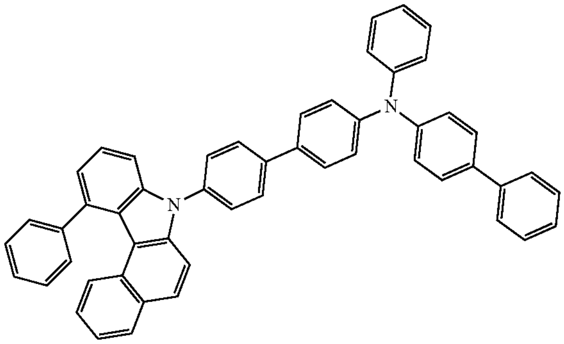
261
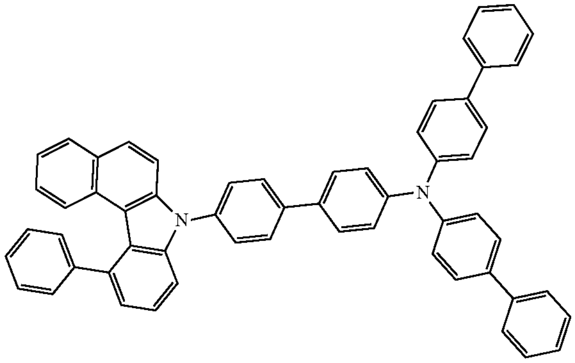
262
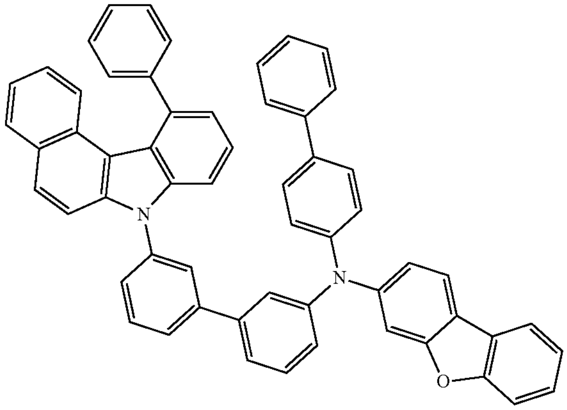
-continued
263
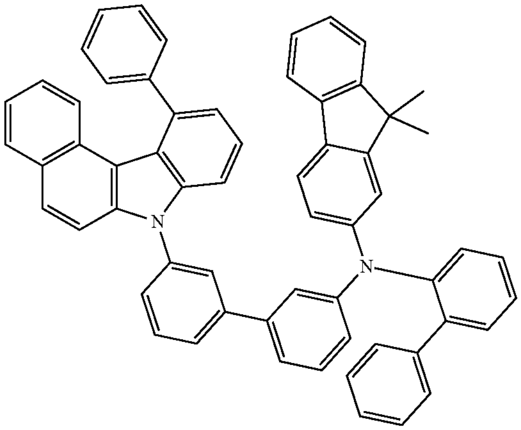
264
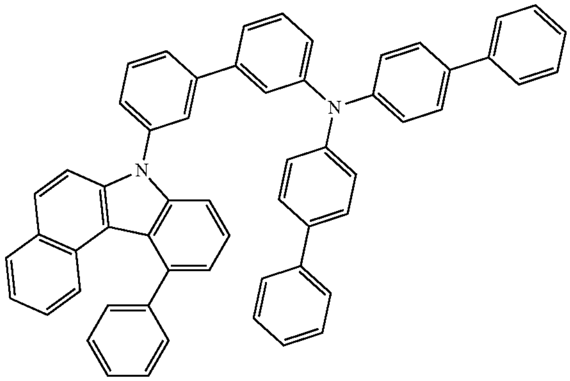
265
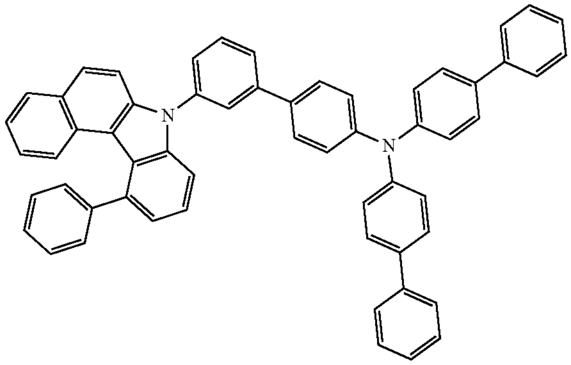
266
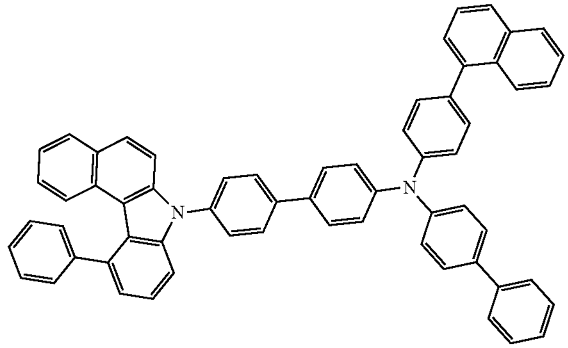

-continued
267
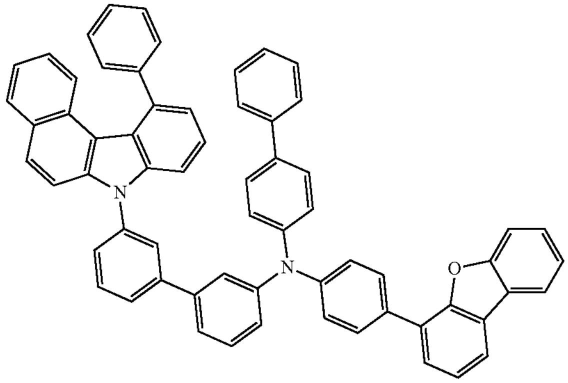
268
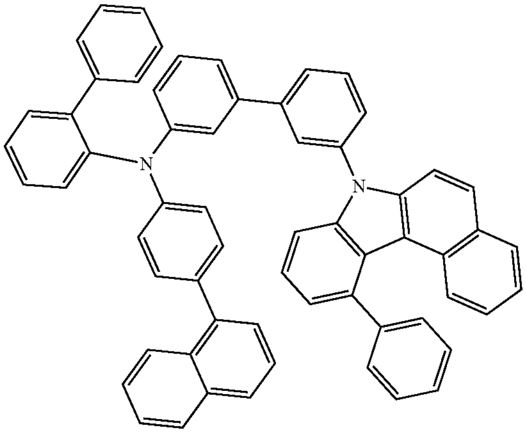
269
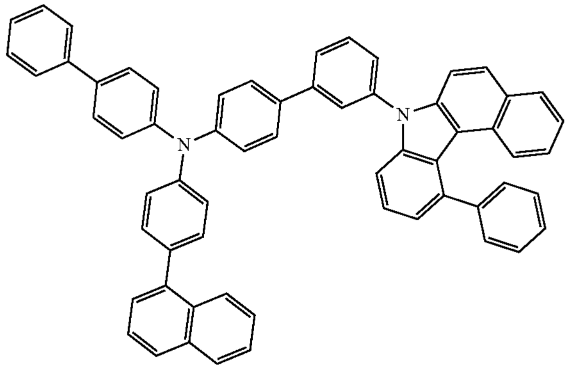
270
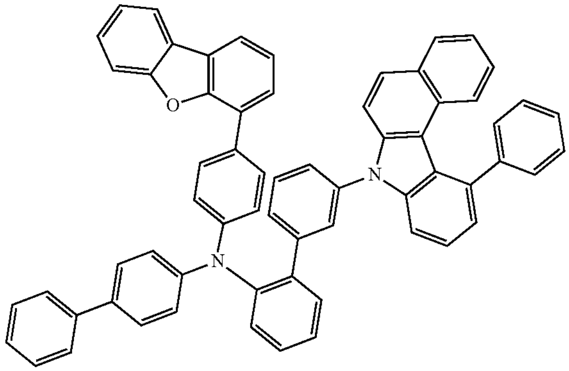
-continued
271
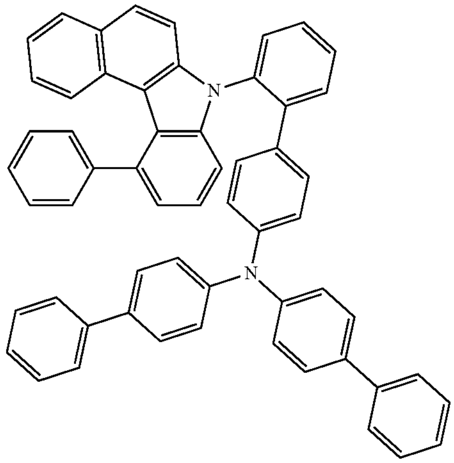
272
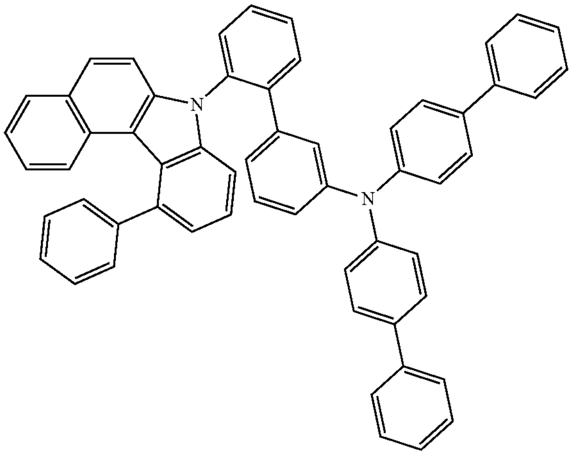
273
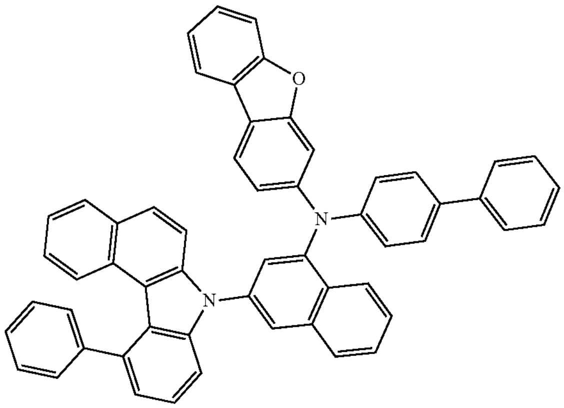

-continued
274
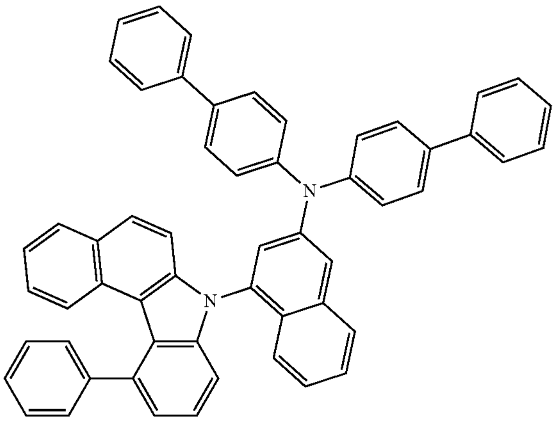
275
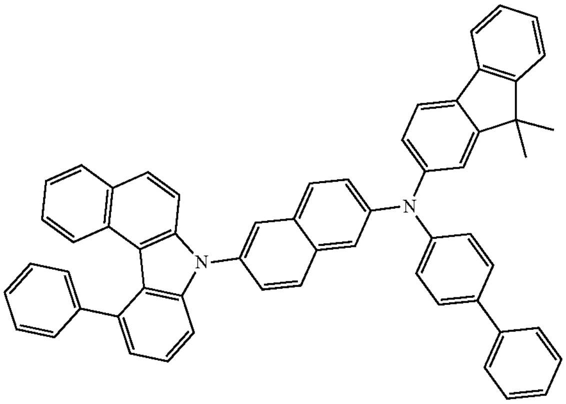
276
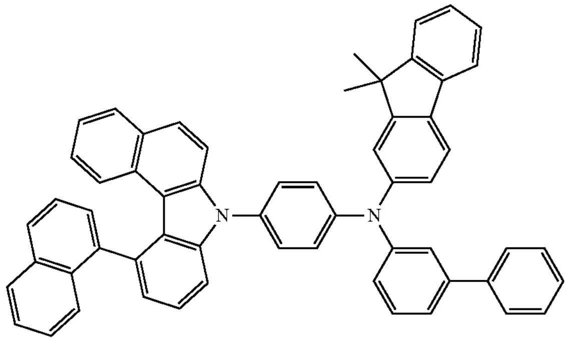
277
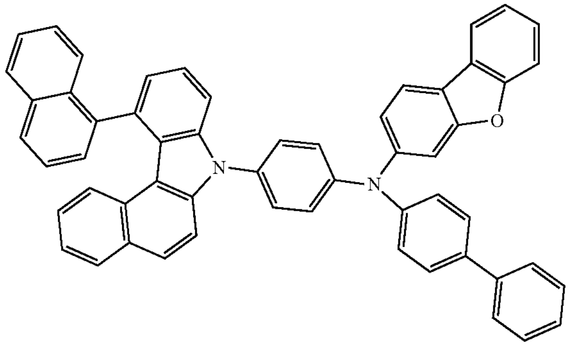
-continued
278
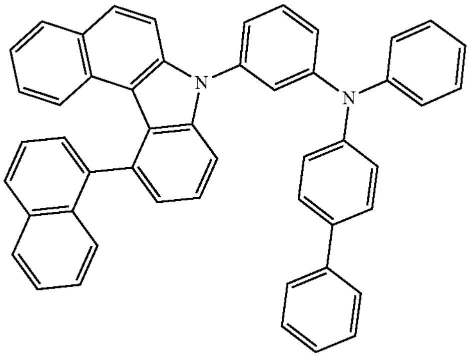
279
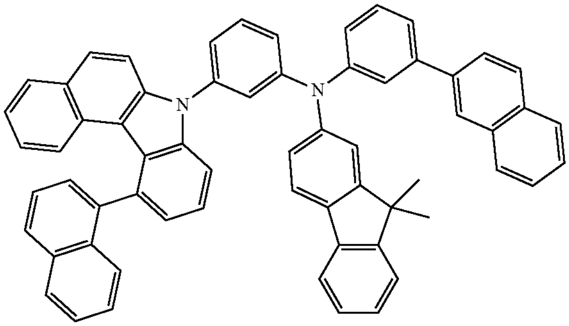
280
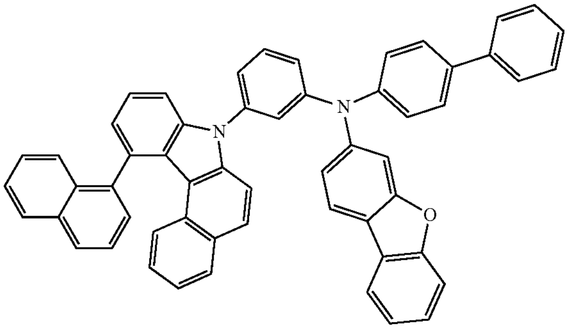
281
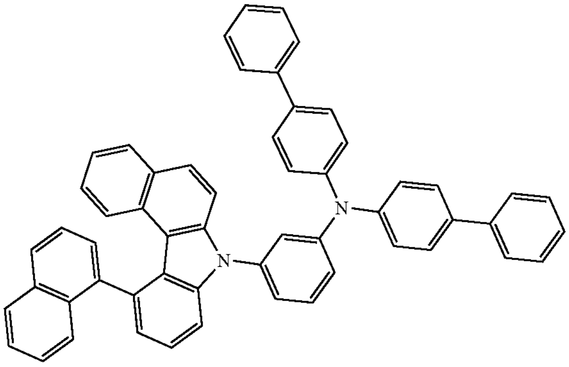

-continued
282
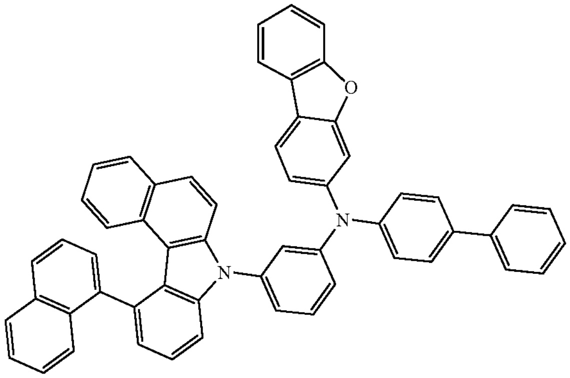
283
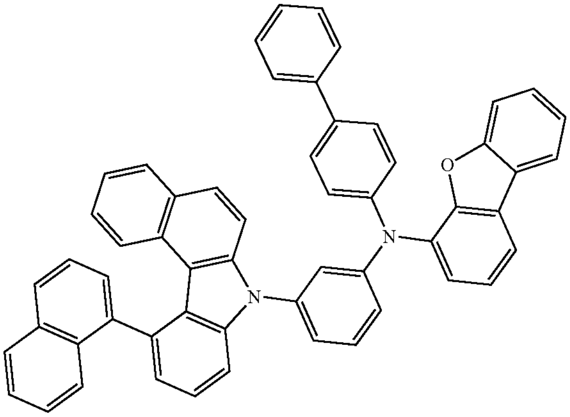
284
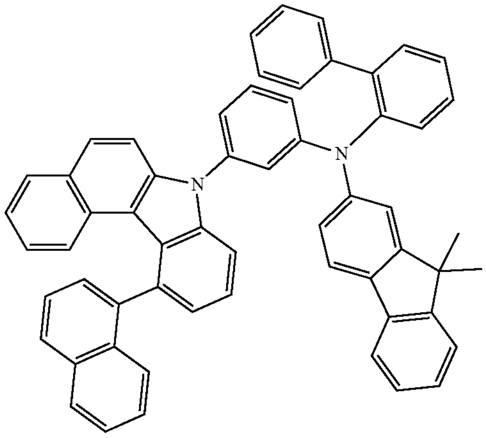
-continued
285
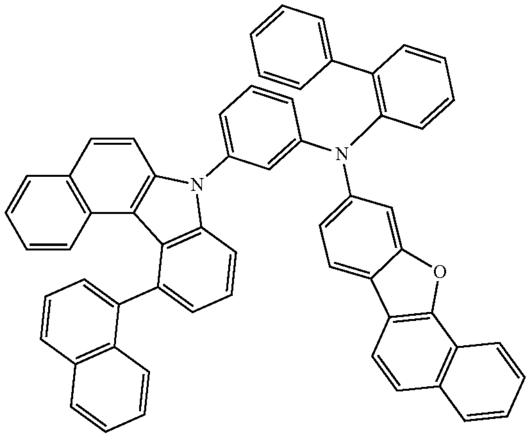
286
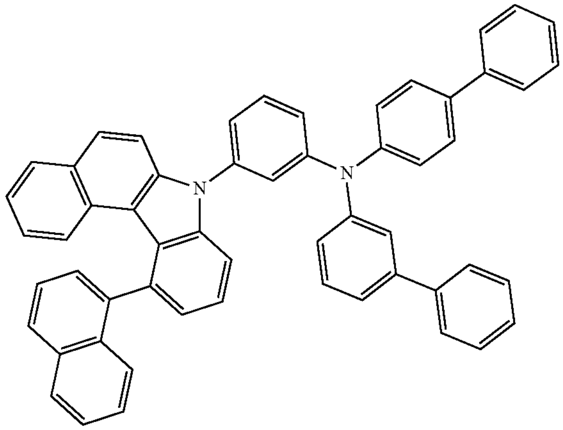
287
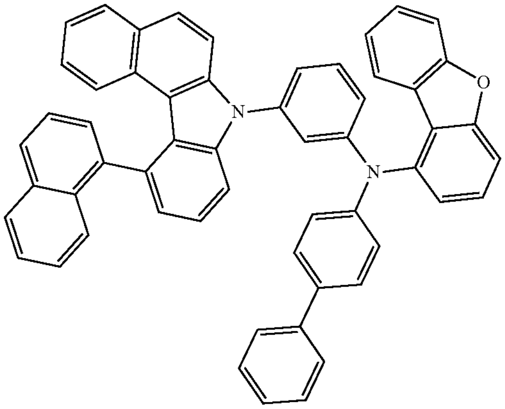

-continued
288
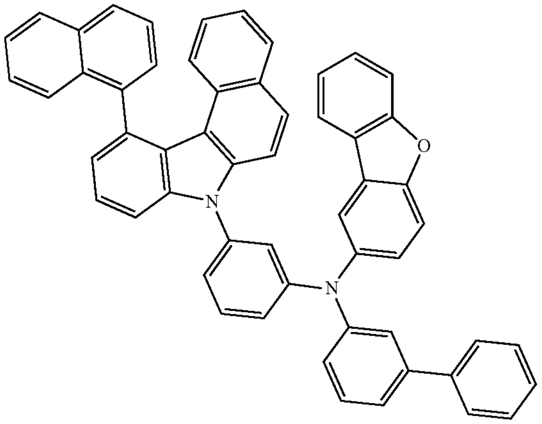
289
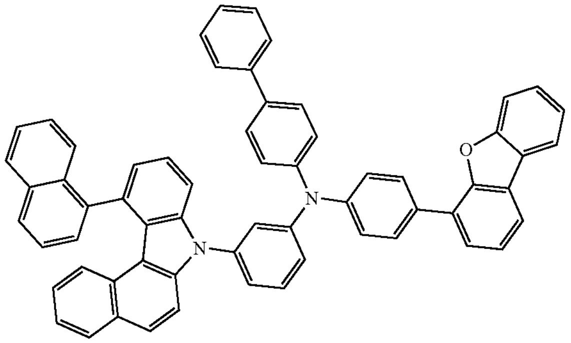
290
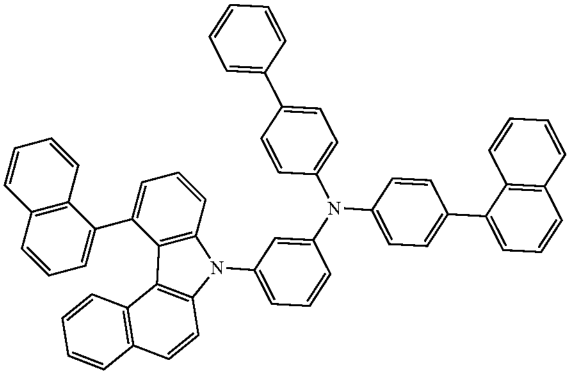
291
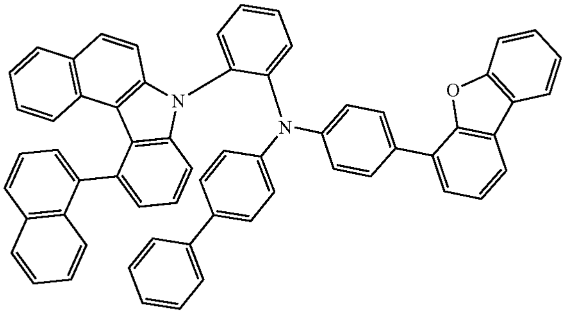
-continued
292
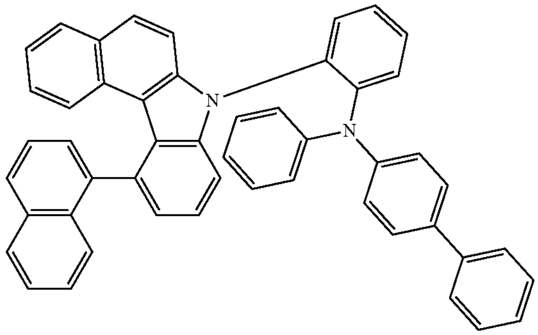
293
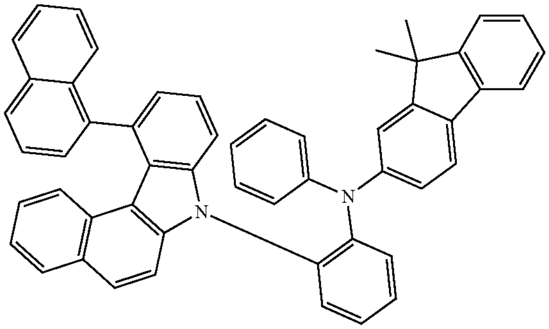
294
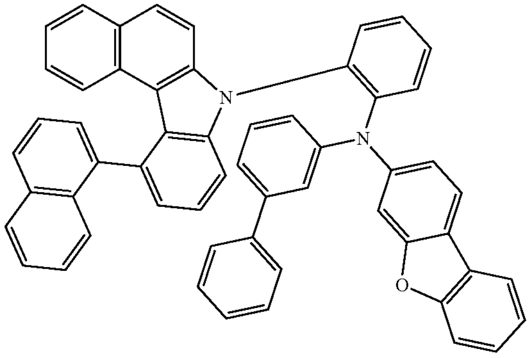
295
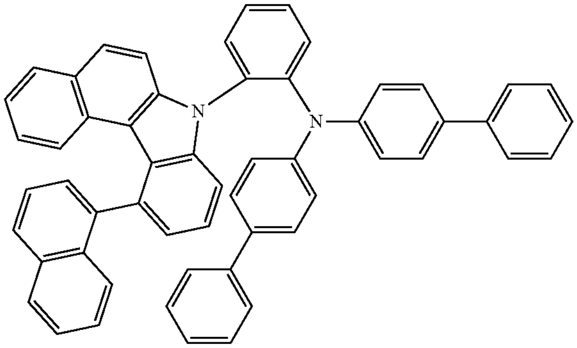

-continued
296
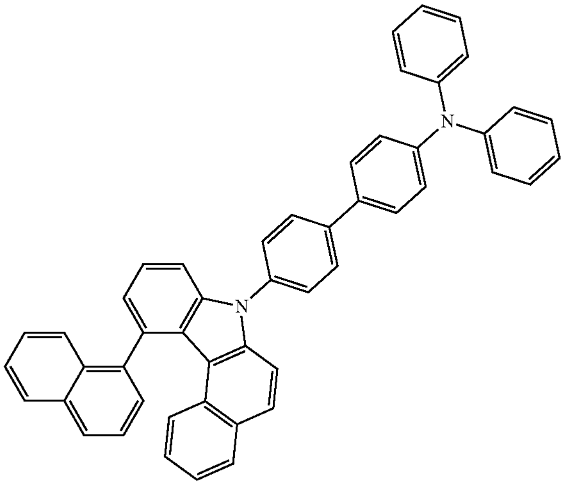
297
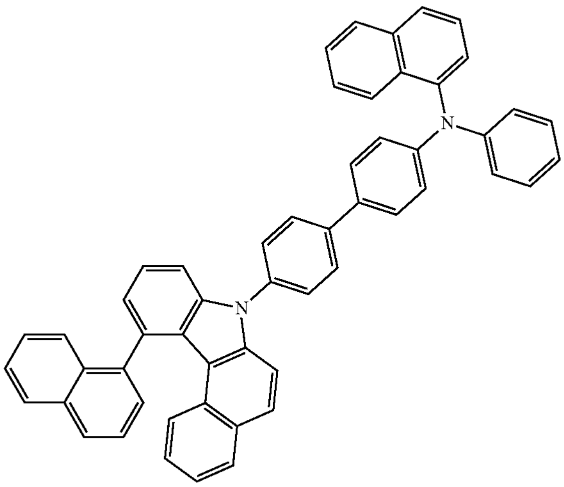
298
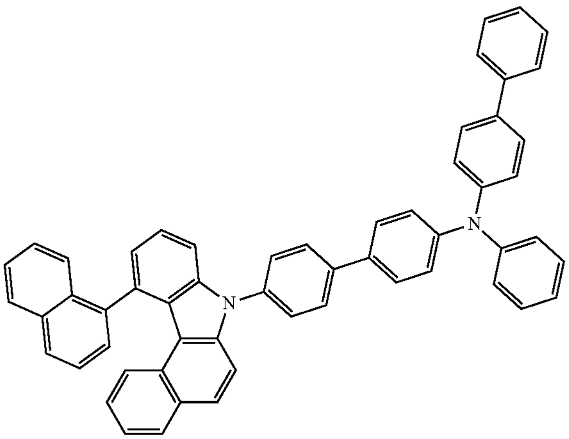
-continued
299
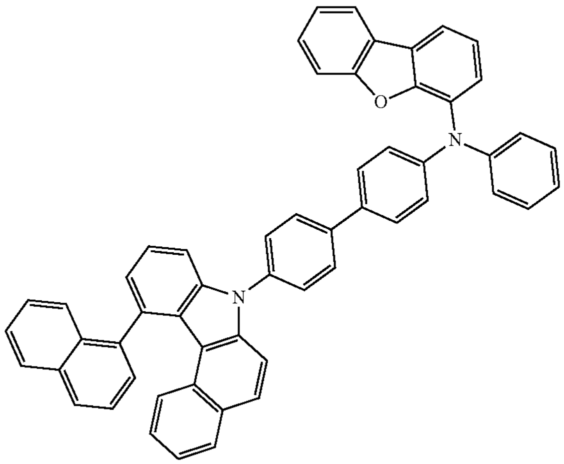
300
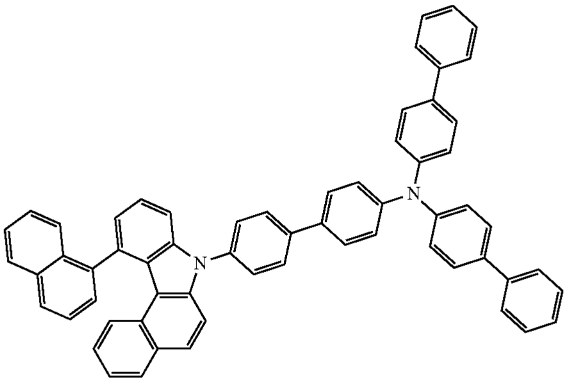
301
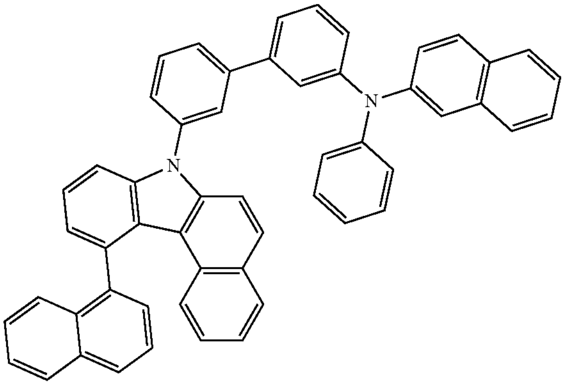

302
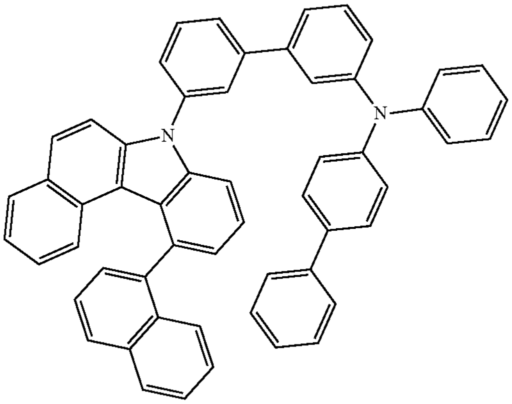
303
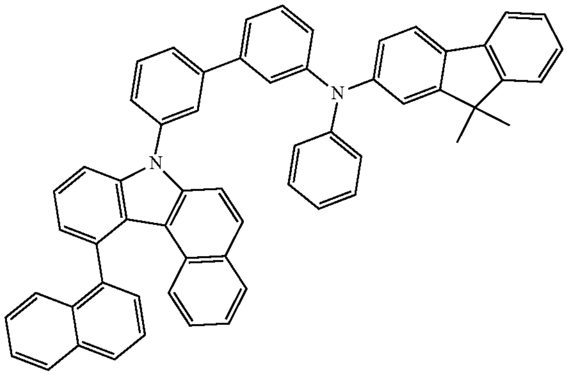
304
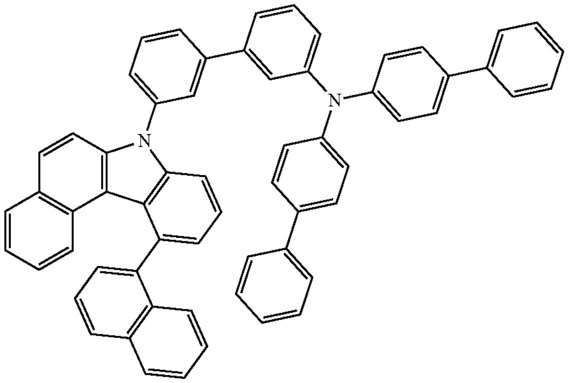
305
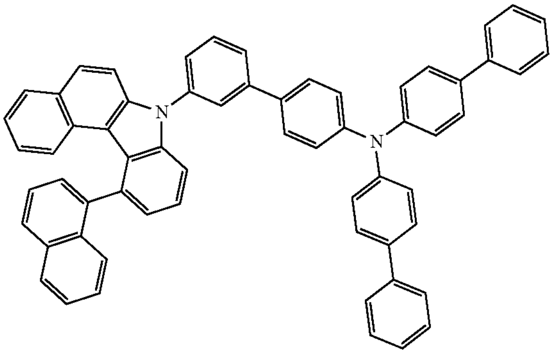
306
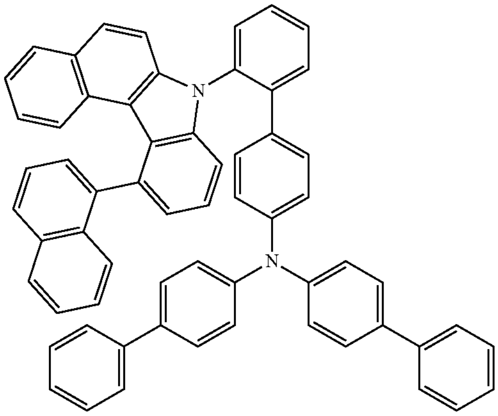
307
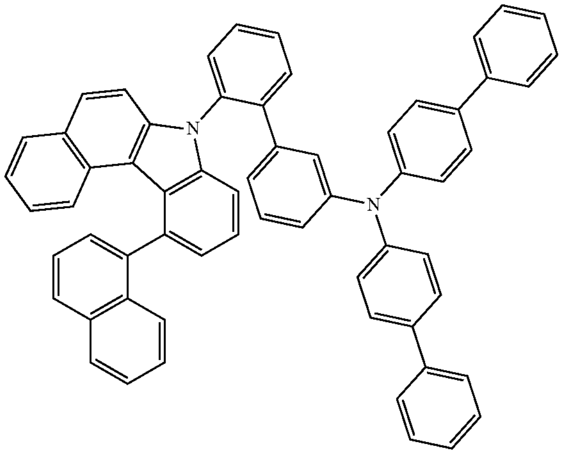
308
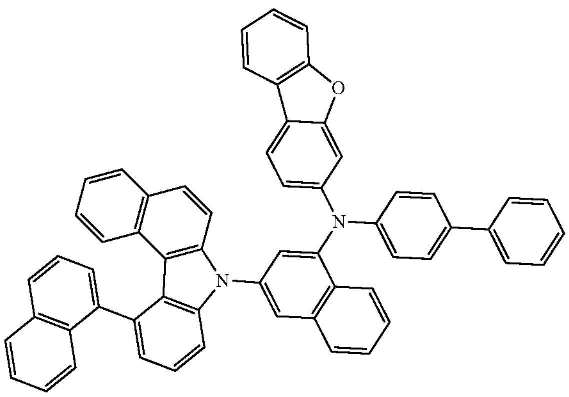

309
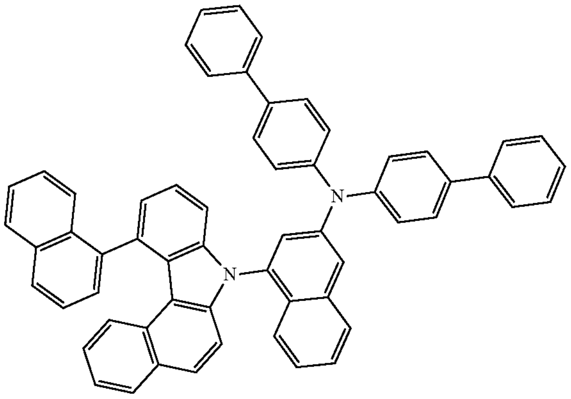
310
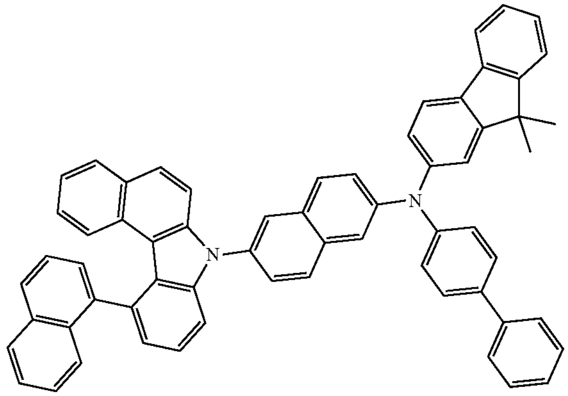
311
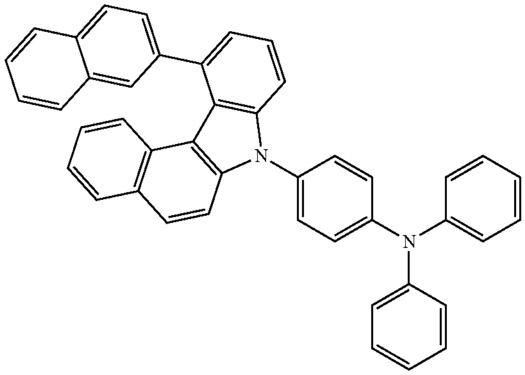
312
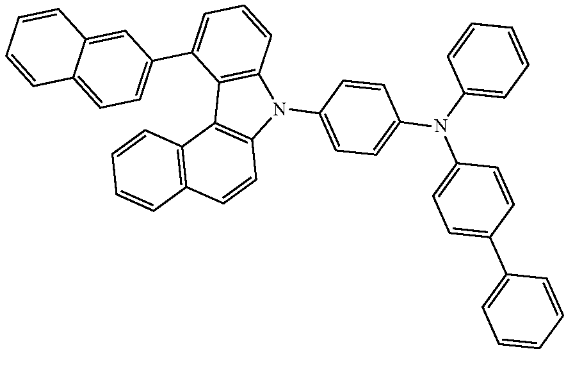
313
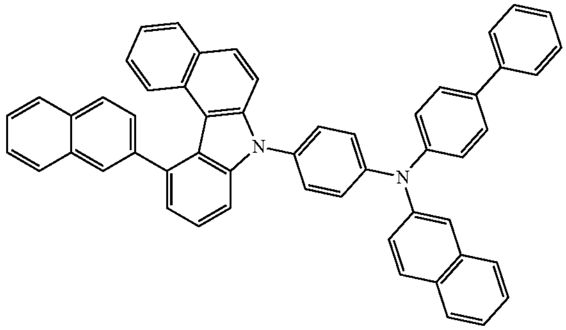
314
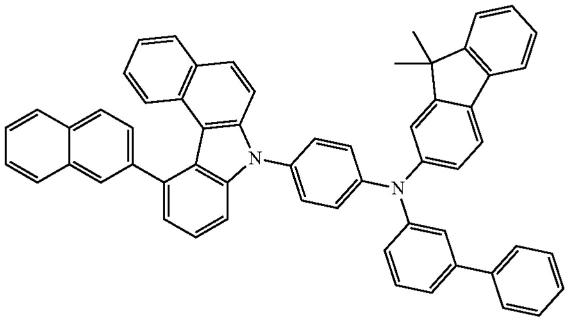
315
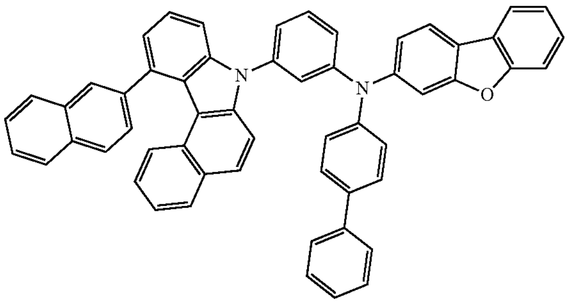
316
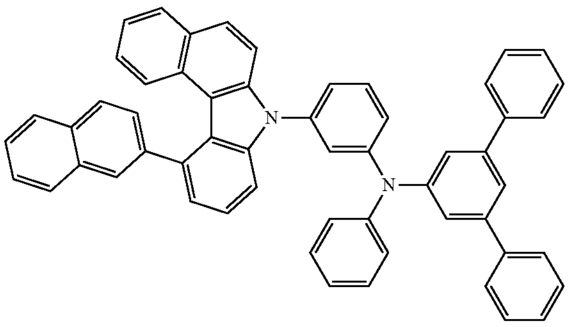

-continued
317
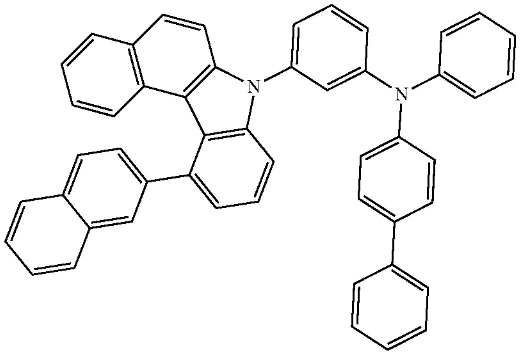
318
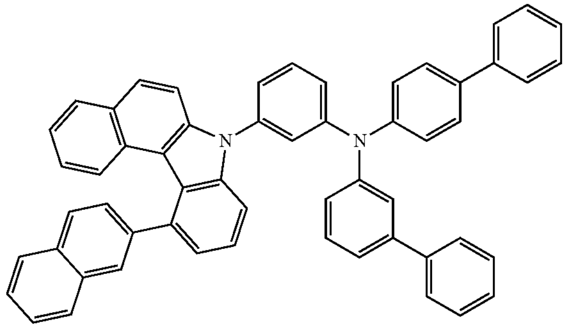
319
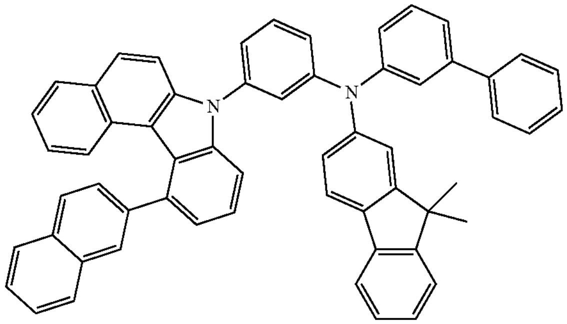
320
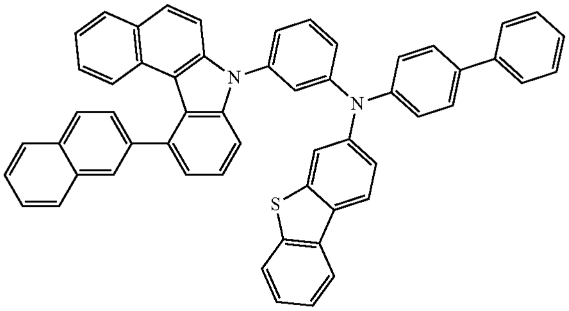
-continued
321
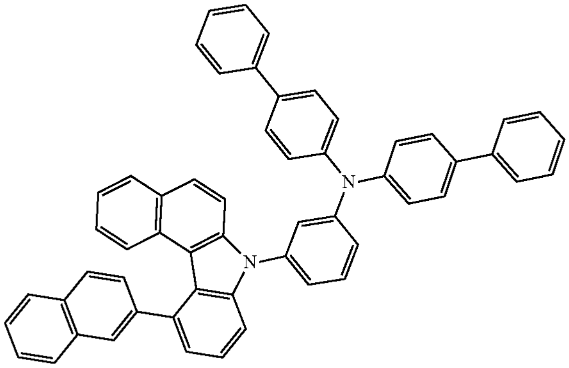
322
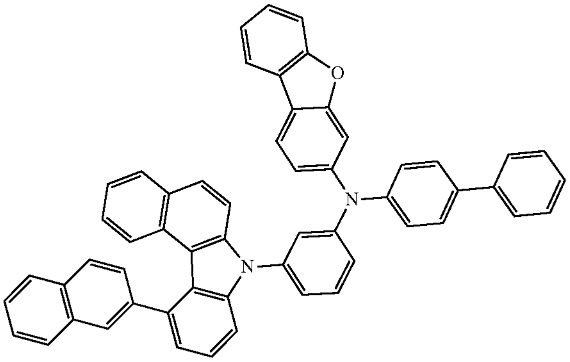
323
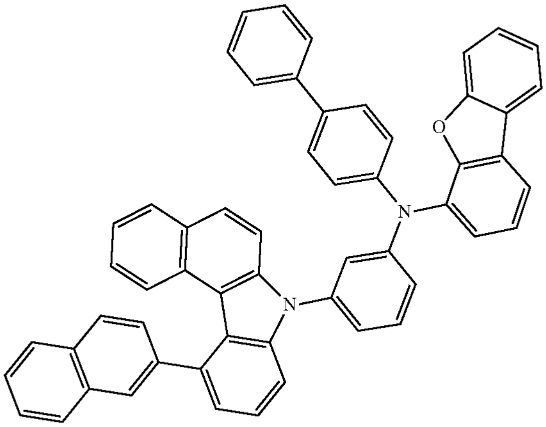

-continued
324
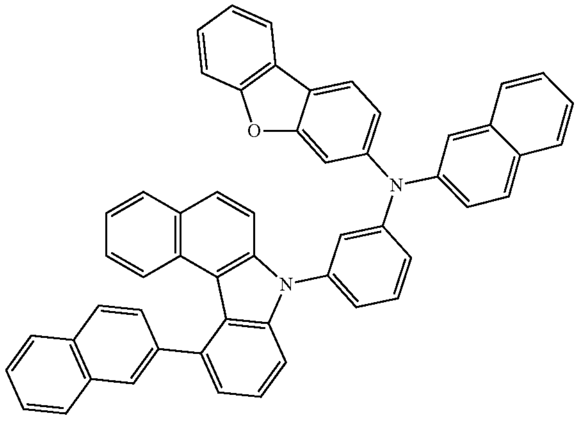
325
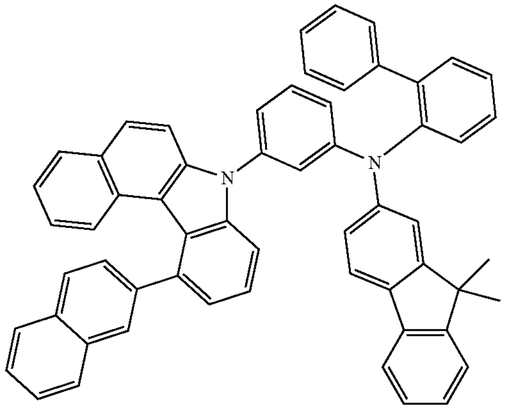
326
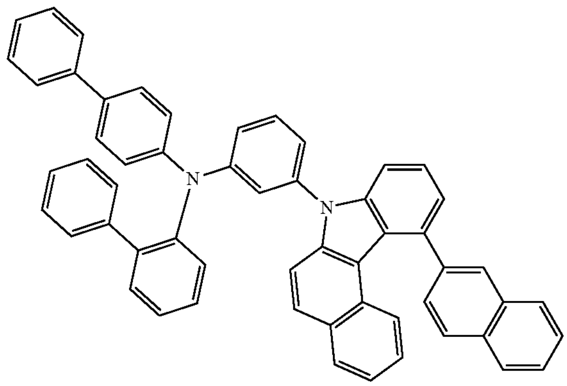
-continued
327
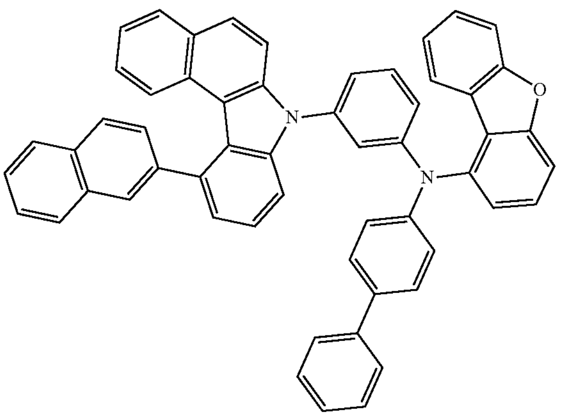
328
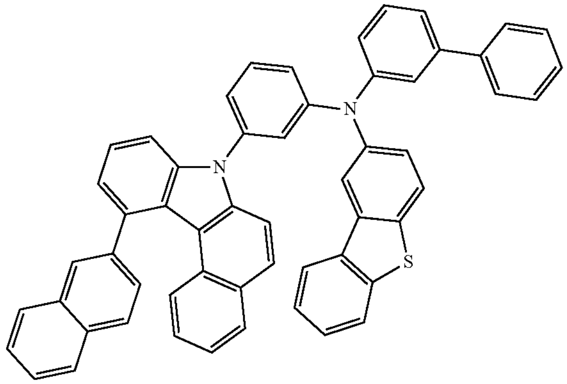
329
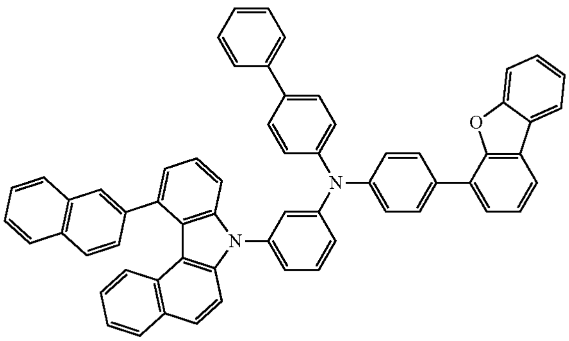
330
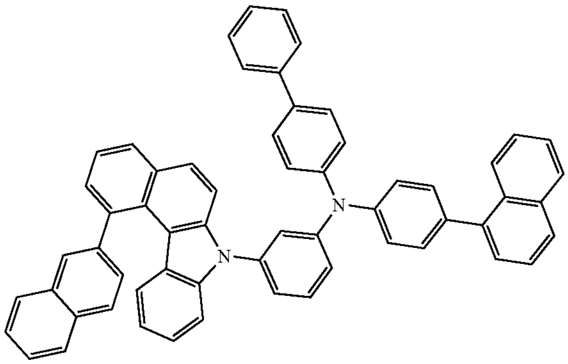

331
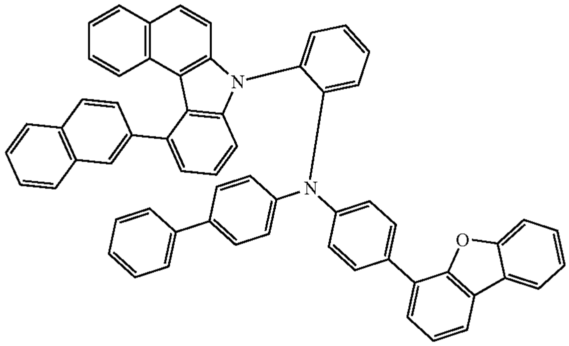
332
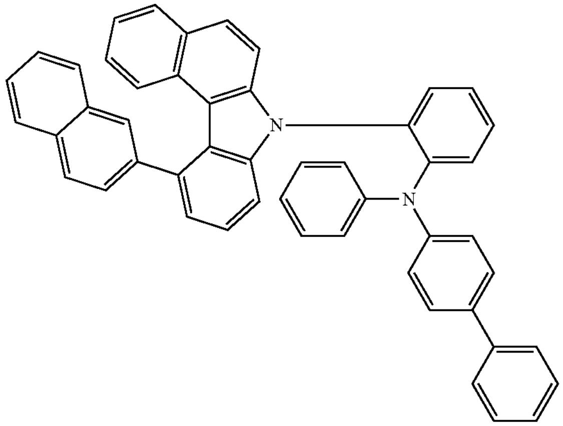
333
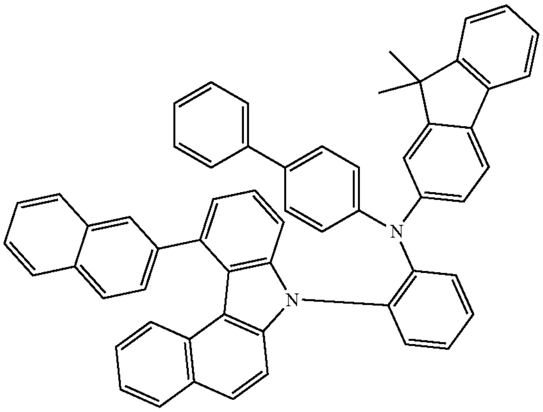
334
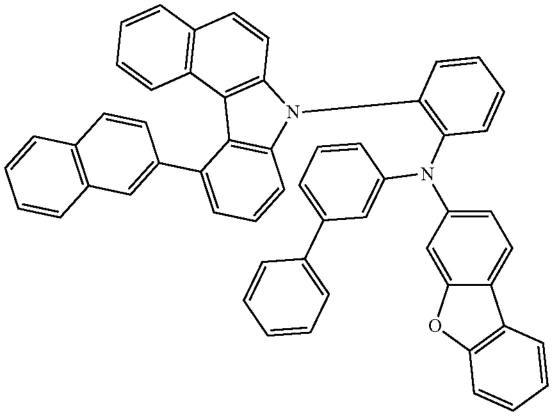
335
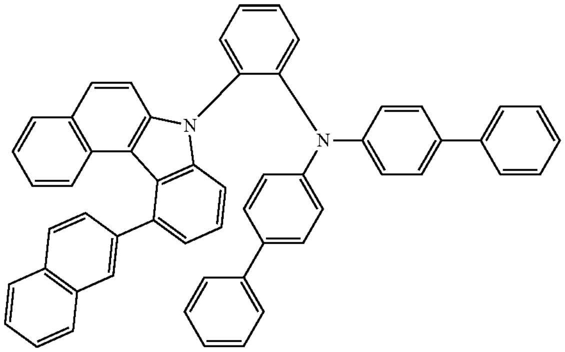
336
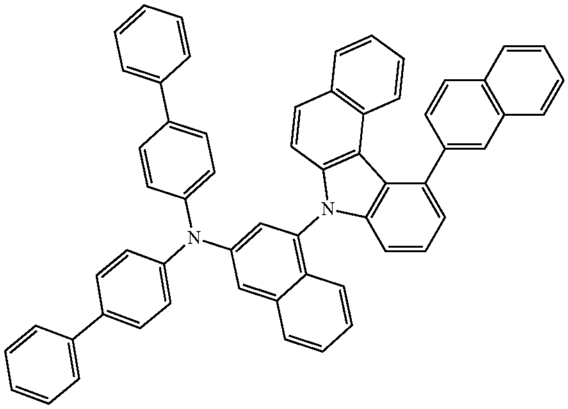
337
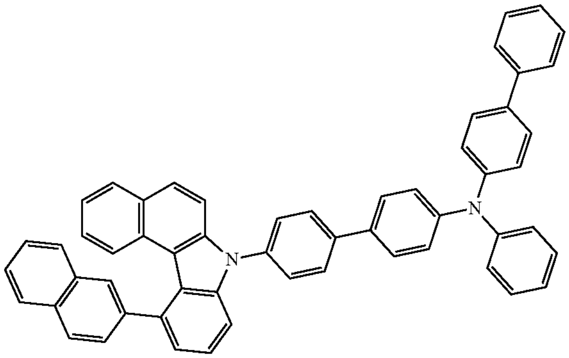

-continued
338
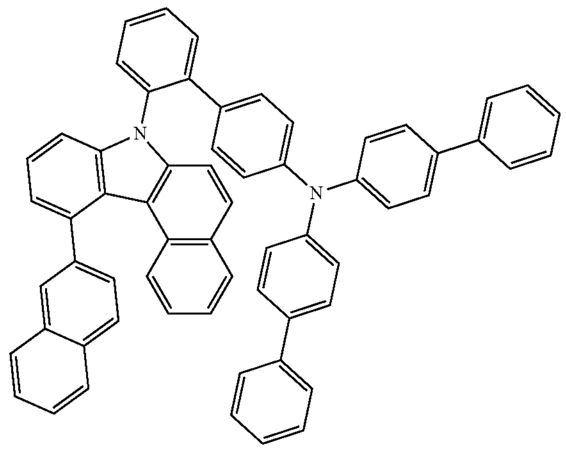
339
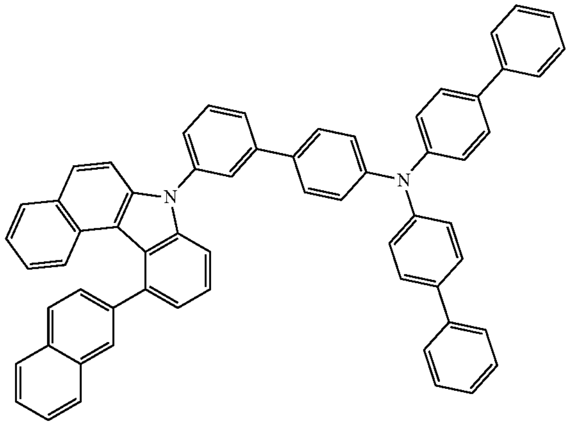
340
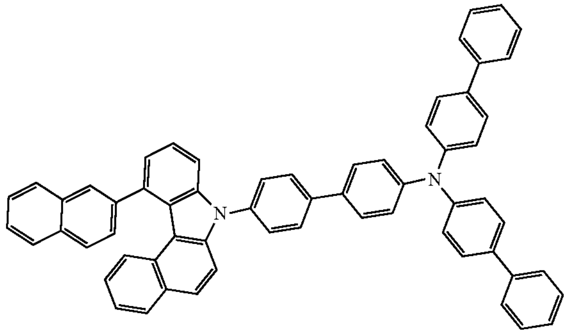
-continued
341
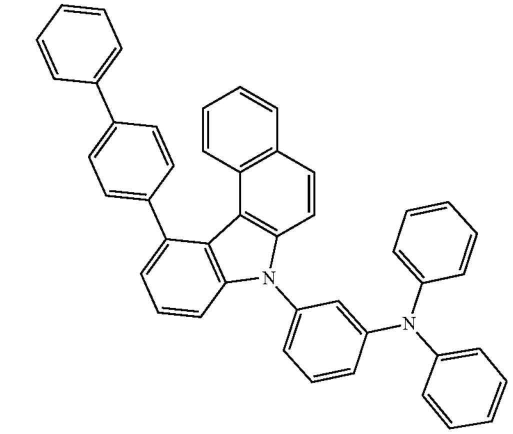
342
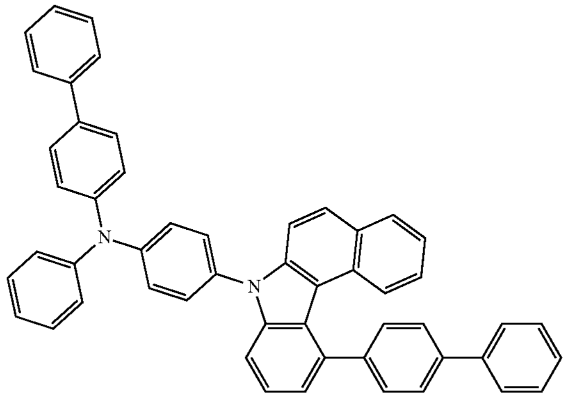
343
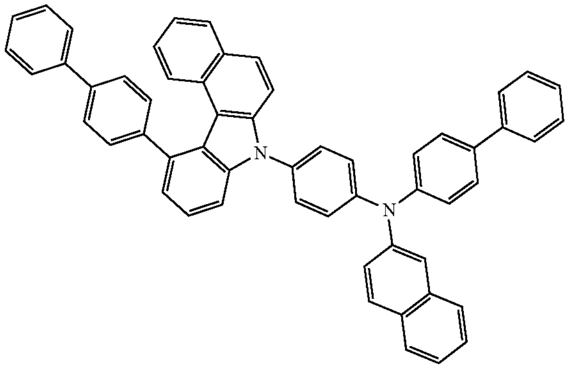
344
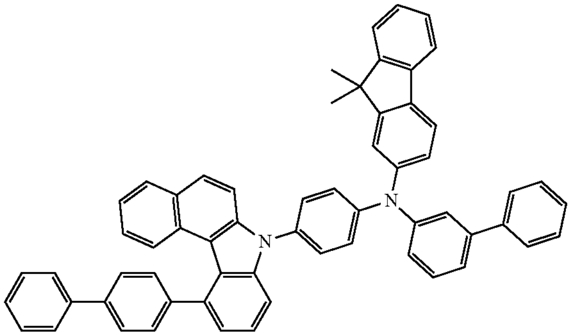

-continued
345
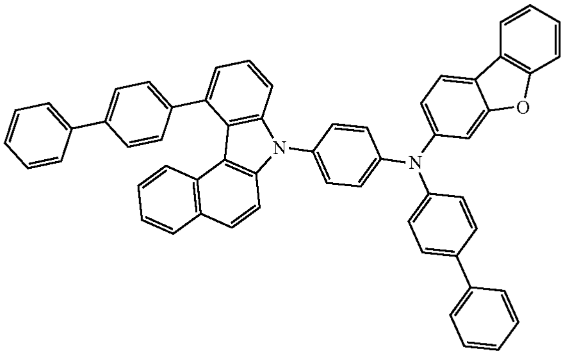
346
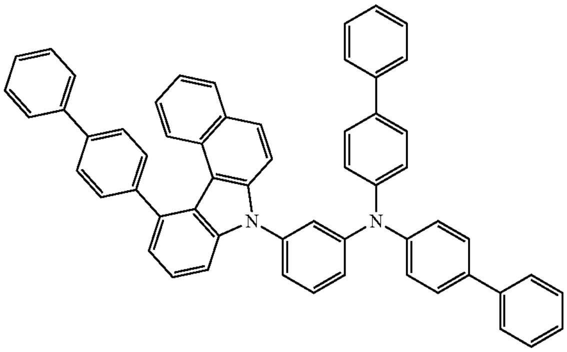
347
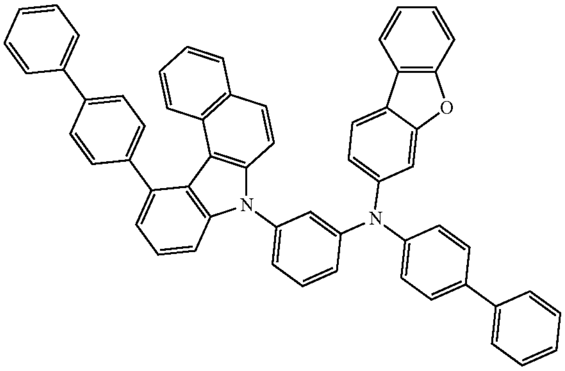
348
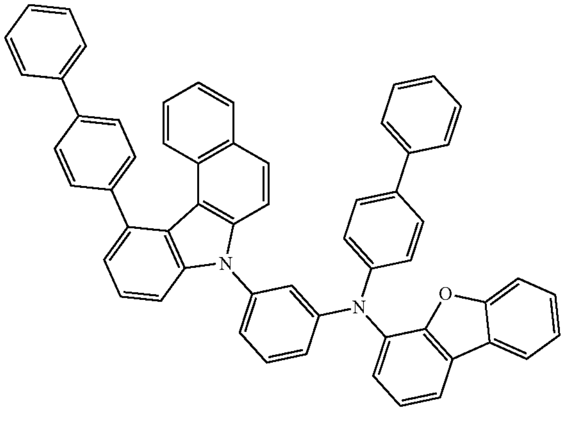
-continued
349
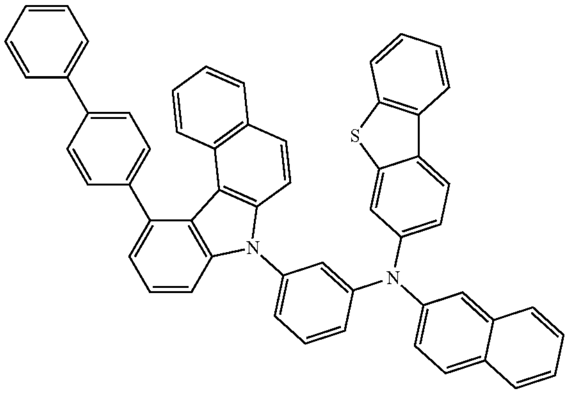
350
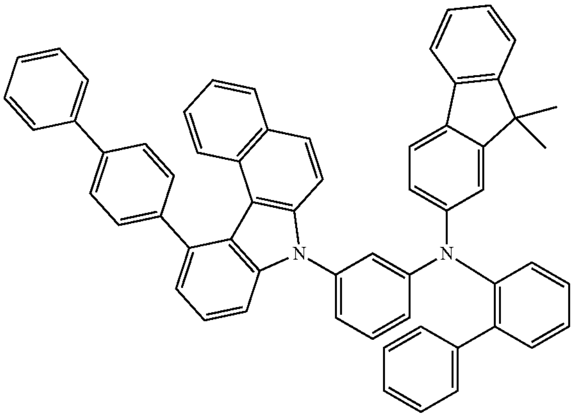
351
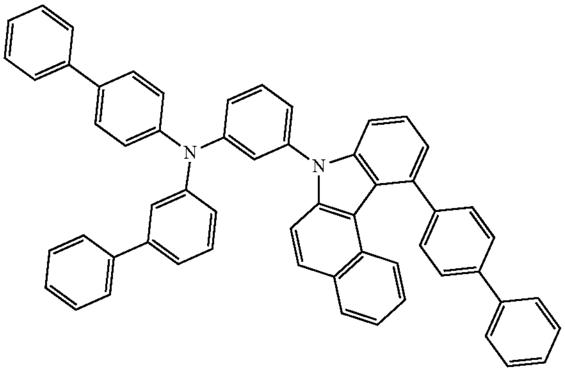

-continued
352
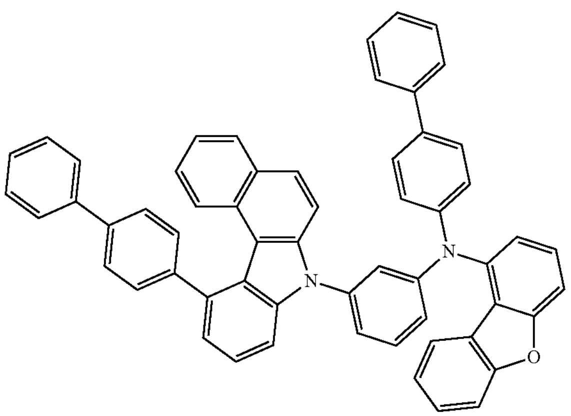
353
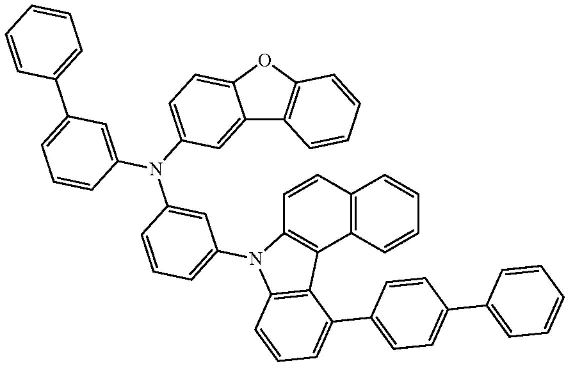
354
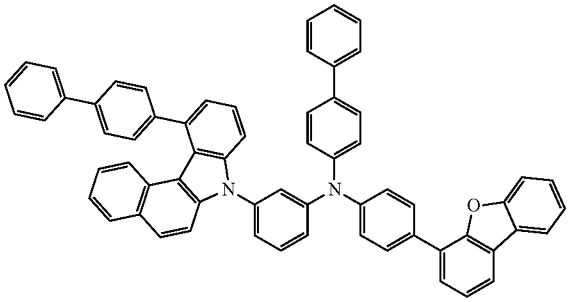
355
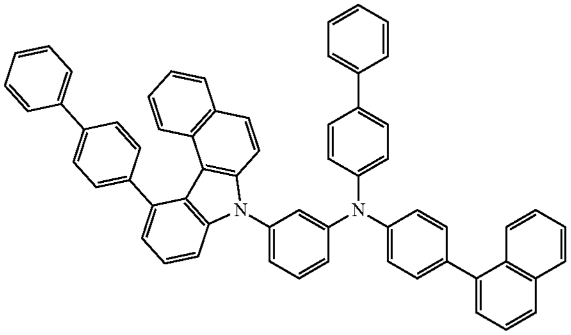
-continued
356
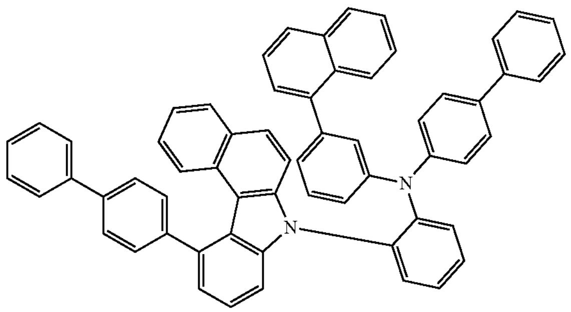
357
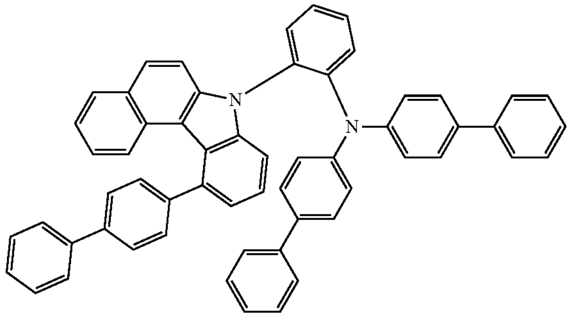
358
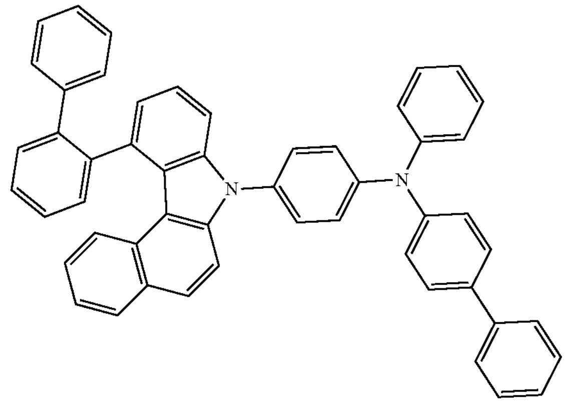
359
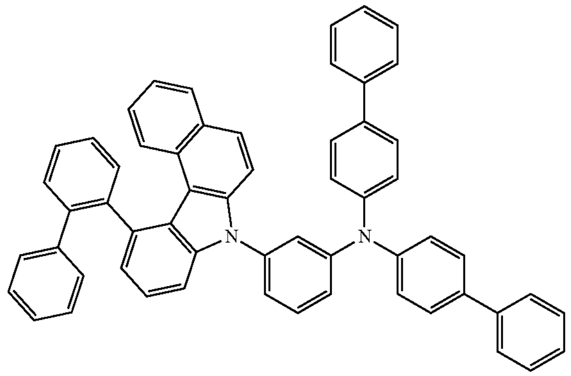

-continued
360
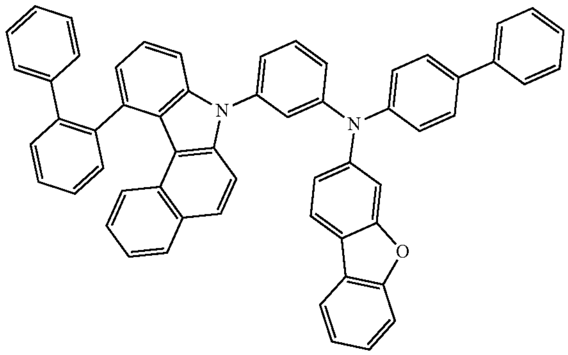
361
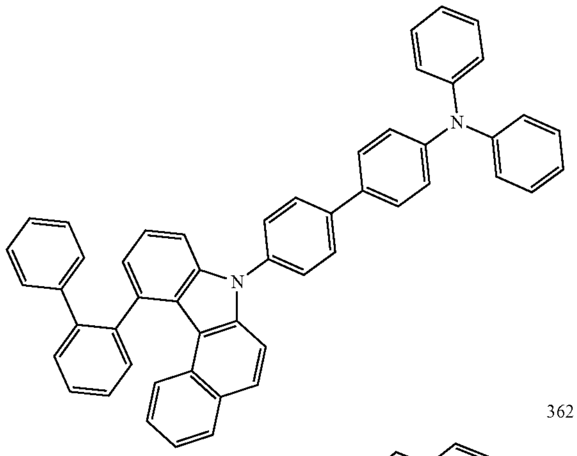
362
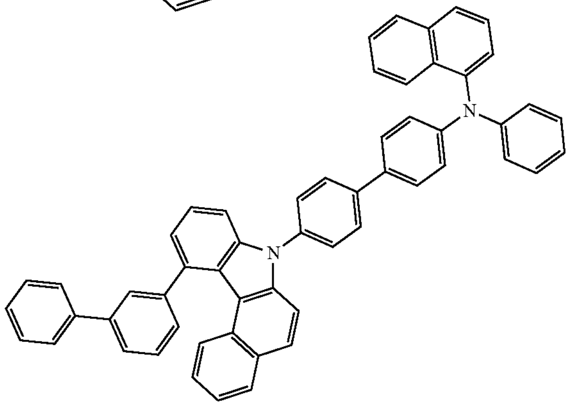
363
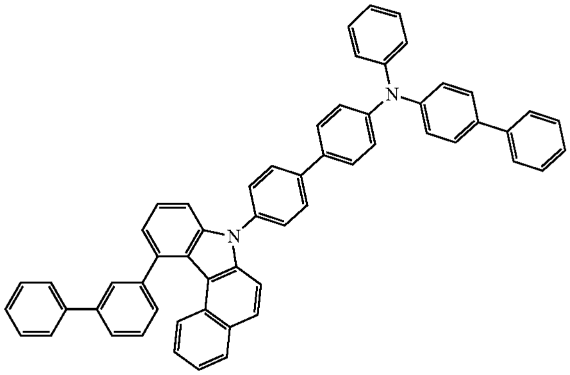
-continued
364
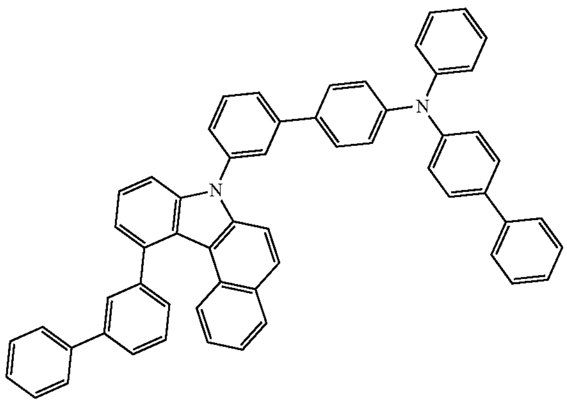
365
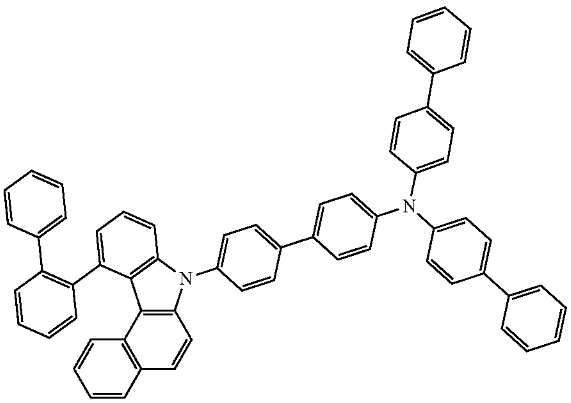
366
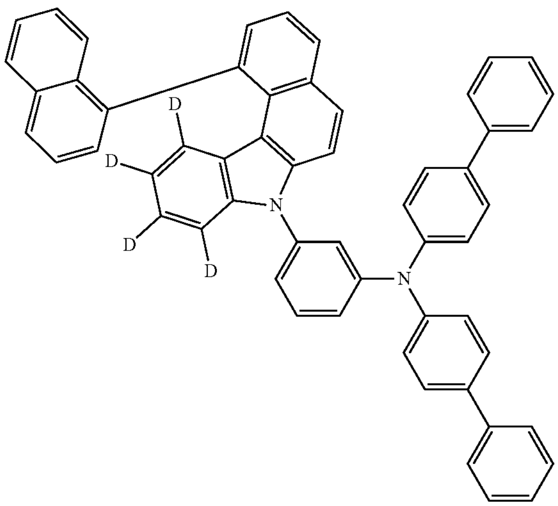

367
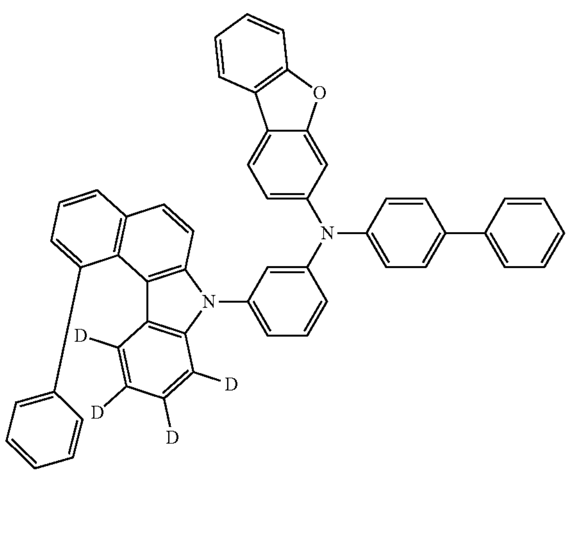
368
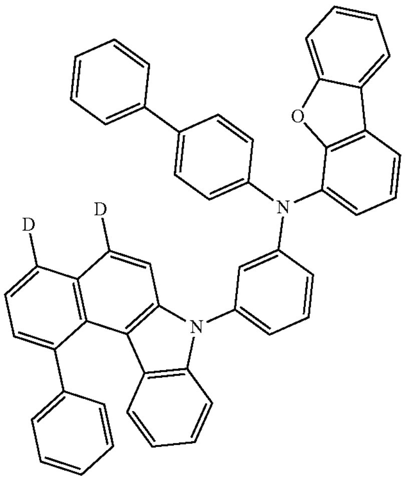
369
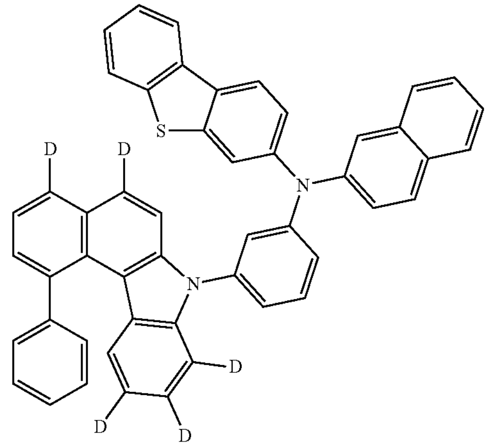
370
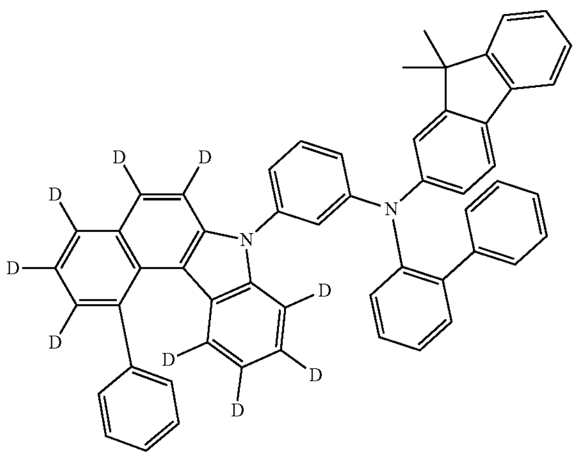
371
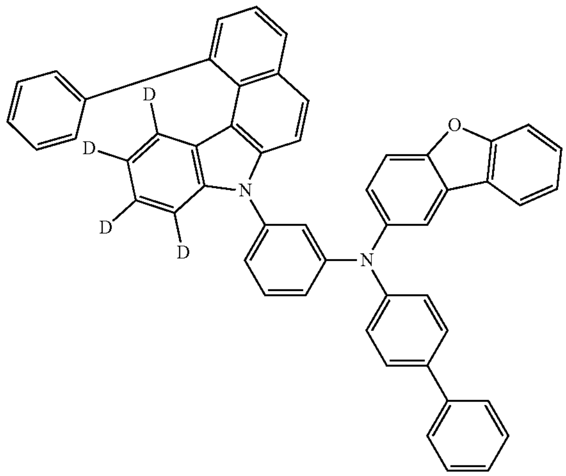
372
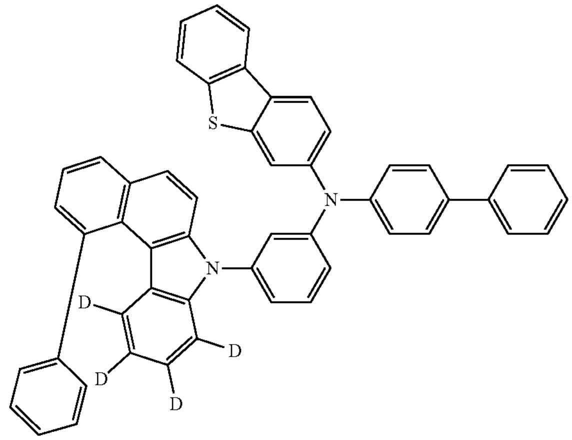

-continued
373
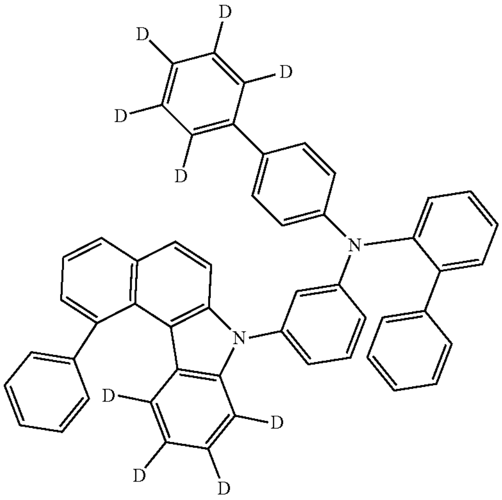
374
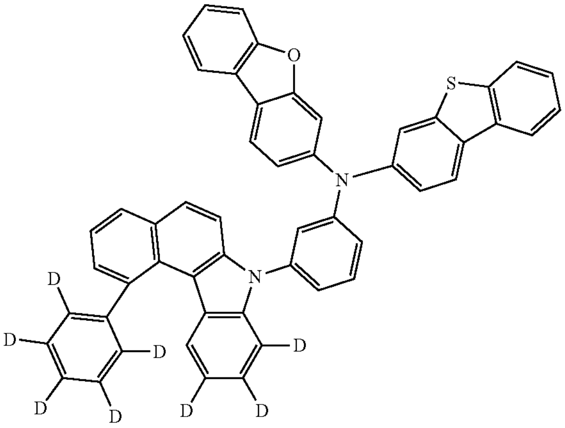
375
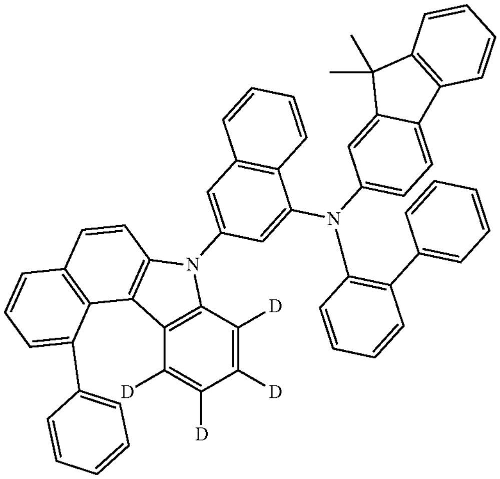
-continued
376
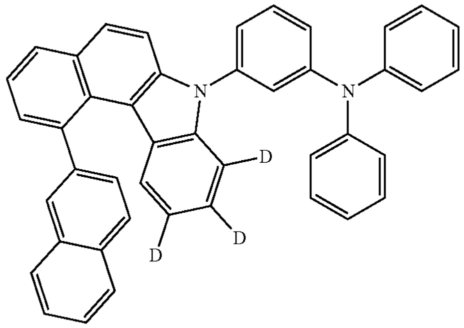
377
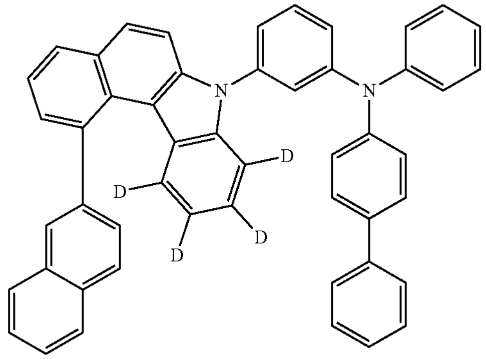
378
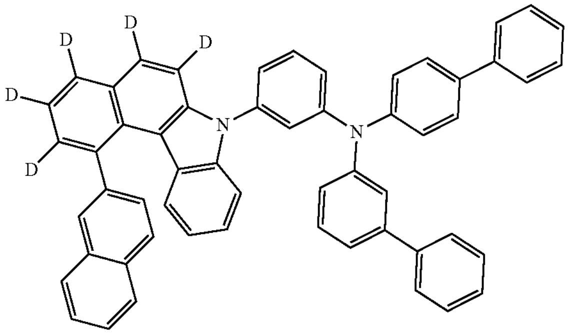
379
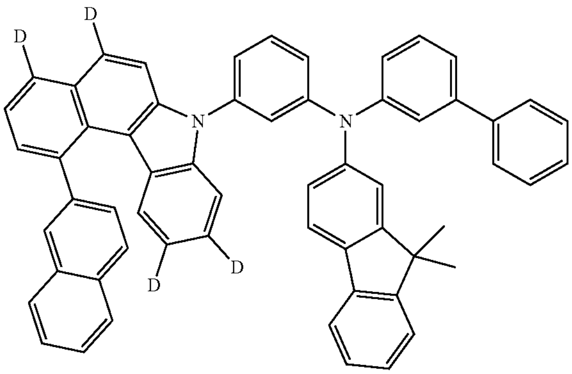

-continued
380
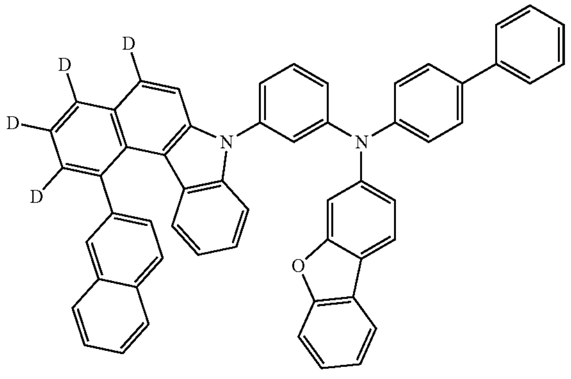
381
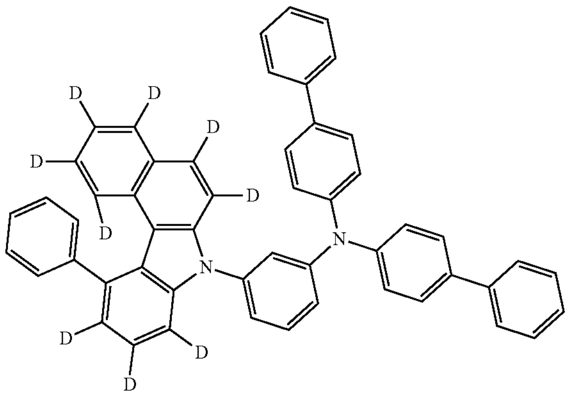
382
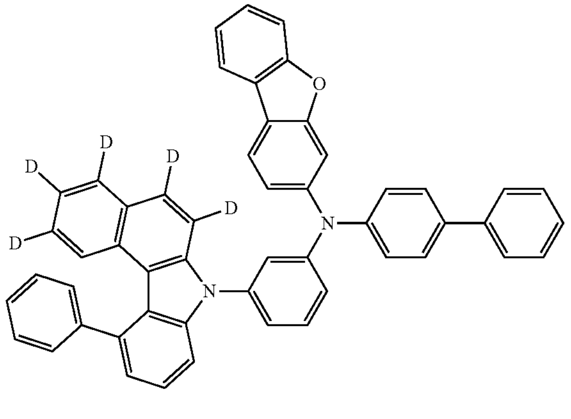
-continued
383
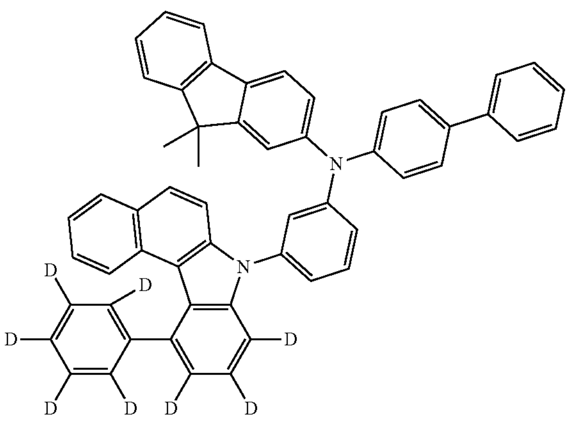
384
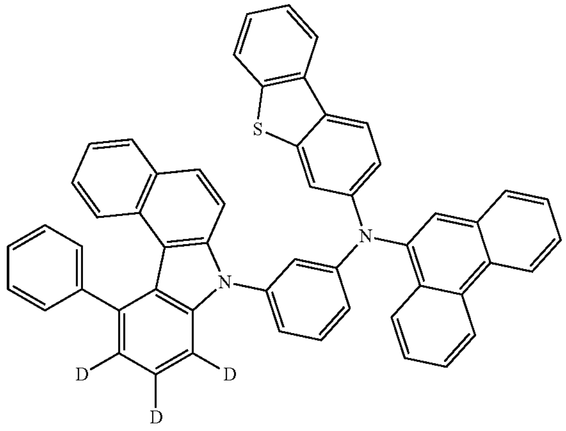
385
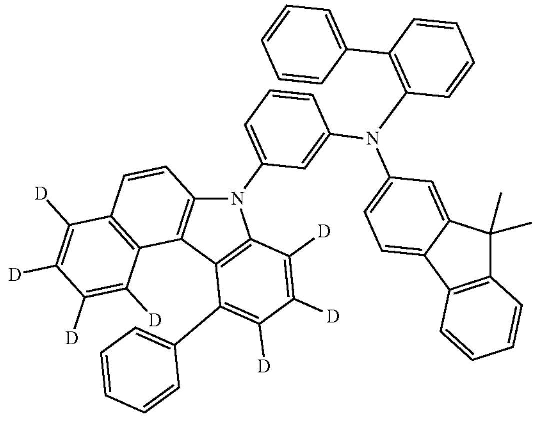

-continued
386
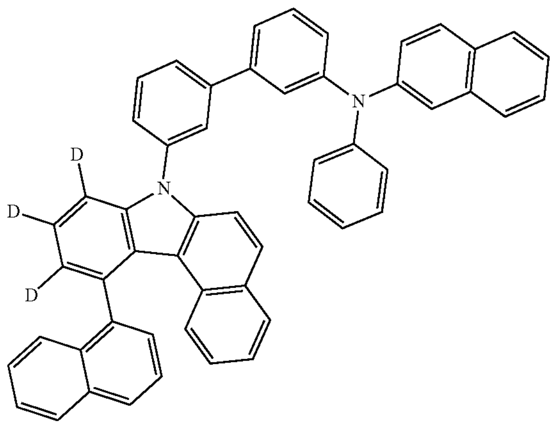
387
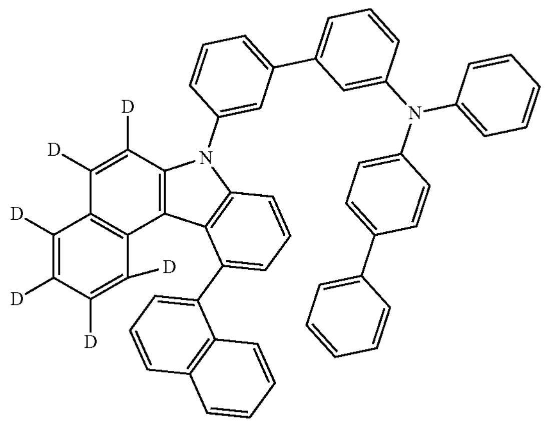
388
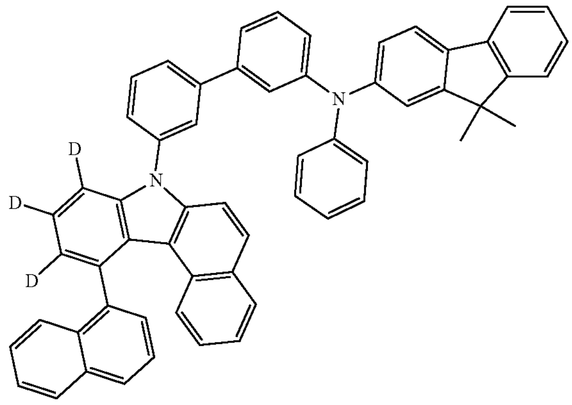
-continued
389
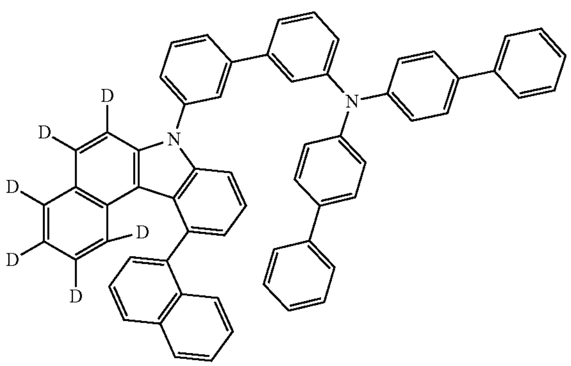
390
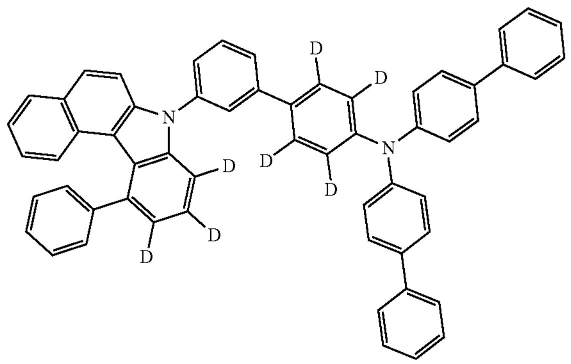
391
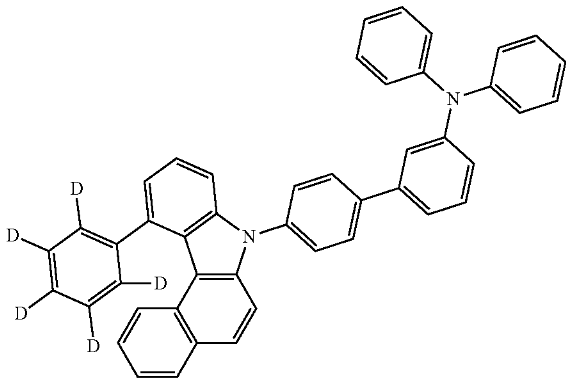
392
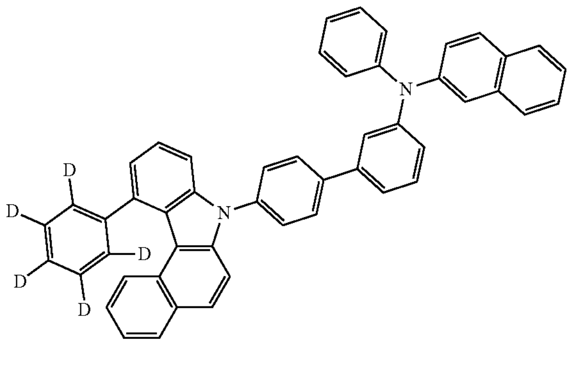

-continued

393

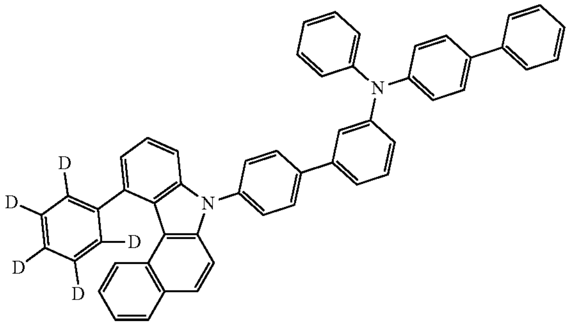

394

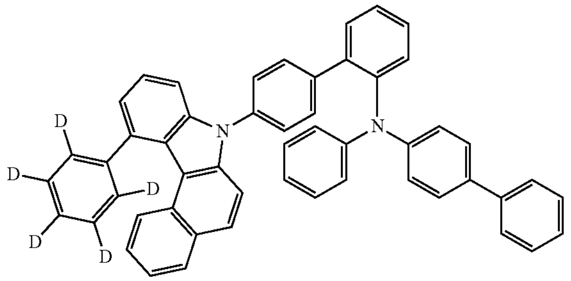

395

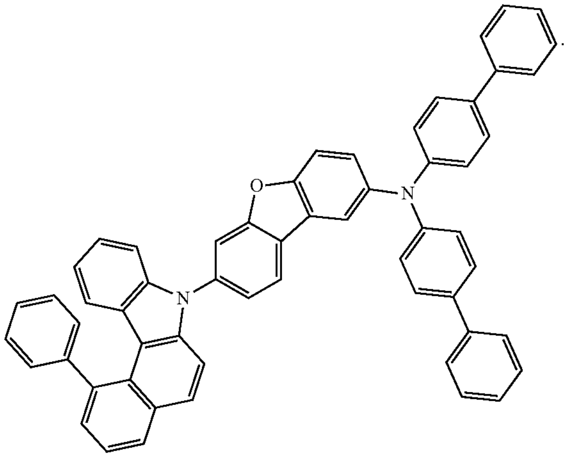

The synthesis method of the nitrogen-containing compound provided in this disclosure is not particularly limited. Those skilled in the art can determine the appropriate synthesis method based on the preparation method provided in the synthesis examples section of the nitrogen-containing compound in this disclosure. In other words, the synthesis examples of the present disclosure exemplarily provide methods for synthesizing nitrogen-containing compounds, and the raw materials used can be obtained through commercial purchases or methods well known in the art. Those skilled in the art can obtain all nitrogen-containing compounds provided in this disclosure based on these exemplary synthesis methods. All specific preparation methods for preparing the nitrogen-containing compounds will not be described in detail here. Those skilled in the art should understand that the present disclosure is not limited thereto.

A second aspect of the present disclosure provides an electronic element, comprising an anode and a cathode disposed opposite to each other, and a functional layer disposed between the anode and the cathode; wherein the functional layer comprises the nitrogen-containing compound described in the first aspect of the present disclosure.

Optionally, the functional layer comprises a hole transport layer, and the hole transport layer comprises the nitrogen-containing compound provided by the present disclosure.

Optionally, the electronic element is selected from an organic electroluminescent device and a photoelectric conversion device.

Optionally, the electronic element is an organic electroluminescent device, as shown in FIG. 1, the organic electroluminescent device comprises an anode 100, a hole transport layer 320, an organic light emitting layer 330, an electron transport layer 340, and a cathode 200 that are stacked in sequence.

Optionally, the anode 100 comprises an anode material, which is preferably a large work-function material contributing to injection of holes into the functional layer. Specific examples of the anode material include, but are not limited to: metals such as nickel, platinum, vanadium, chromium, copper, zinc, and gold, or alloys thereof; metal oxides such as zinc oxide, indium oxide, indium tin oxide (ITO), and indium zinc oxide (IZO); combinations of metals and oxides, such as ZnO:Al or $SnO_2$:Sb; and conductive polymers such as but not limited to poly(3-methylthiophene), poly[3,4-(ethylene-1,2-dioxy)thiophene](PEDT), polypyrrole, and polyaniline. Preferably, a transparent electrode comprising indium tin oxide (ITO) is included as the anode.

Optionally, the hole transport layer 320 comprises the nitrogen-containing compound of the present disclosure.

Optionally, the hole transport layer 320 comprises a first hole transport layer 321 and a second hole transport layer 322 which are stacked in sequence, and relative to the second hole transport layer 322, the first hole transport layer 321 is closer to the anode. The second hole transport layer is also called an electron blocking layer.

In the present disclosure, the material of the first hole transport layer 321 may be selected from phthalocyanine derivatives, naphthalocyanine derivatives, porphyrin derivatives, benzidine-type triarylamines, styrylamine-type triarylamines, diamine-type triarylamines, and other types of materials, which may be selected by those skilled in the art with reference to the prior arts. For example, the material of the first hole transport layer 321 is selected from the group consisting of the following compounds:

HT-1

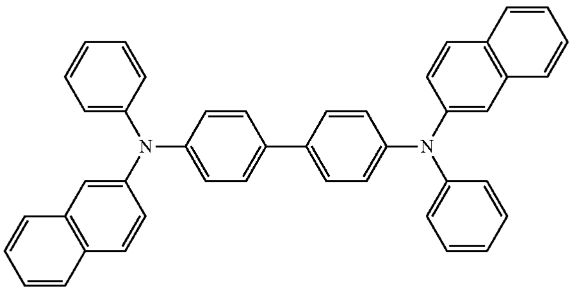

-continued

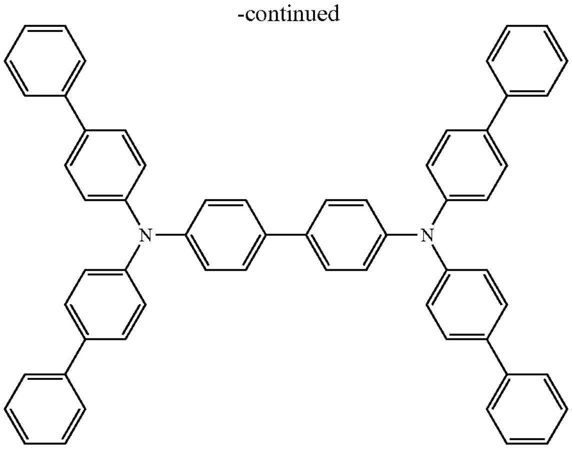

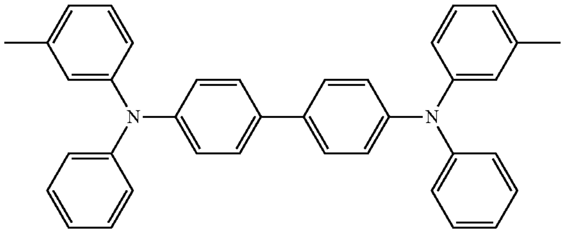

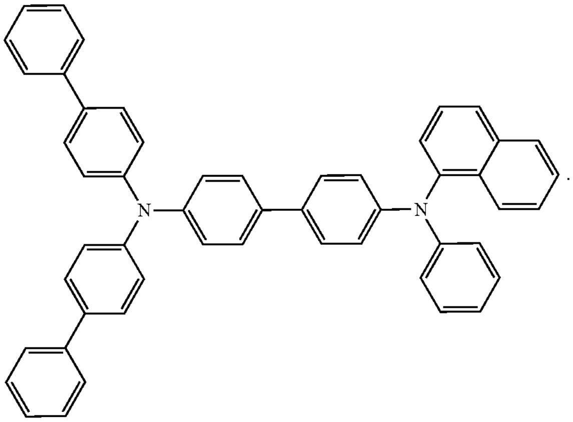

In a specific embodiment, the material of the first hole transport layer 321 is HT-1.

Optionally, the second hole transport layer 322 comprises the nitrogen-containing compound of the present disclosure.

Optionally, the organic light emitting layer 330 is composed of a host material and a guest material. Holes injected into the organic light emitting layer 330 and electrons injected into the organic light emitting layer 330 can recombine in the organic light emitting layer 330 to form excitons. The excitons transmit energy to the host material, and the host material transmits the energy to the guest material, thereby enabling the guest material to emit light.

The host material of the organic light emitting layer 330 may comprise metal chelating compounds, stilbene derivatives, aromatic amine derivatives, dibenzofuran derivatives, anthracene derivatives or other types of materials. For example, the host material is selected from one or more of the following compounds:

BH-1

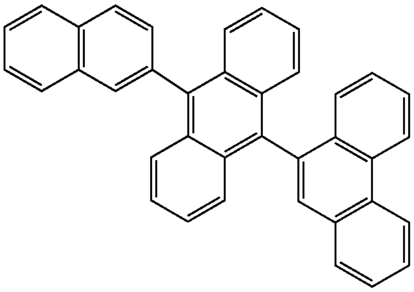

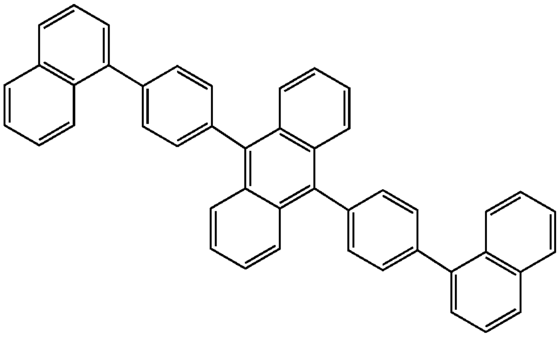

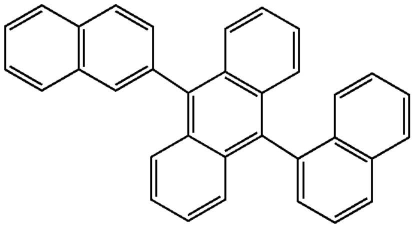

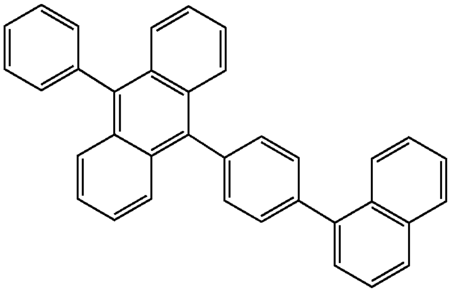

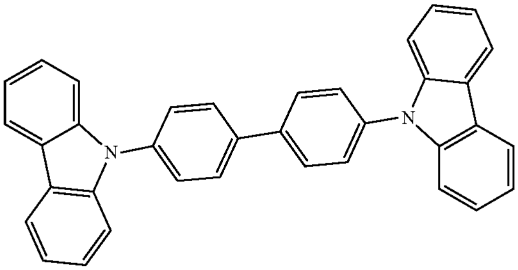

-continued
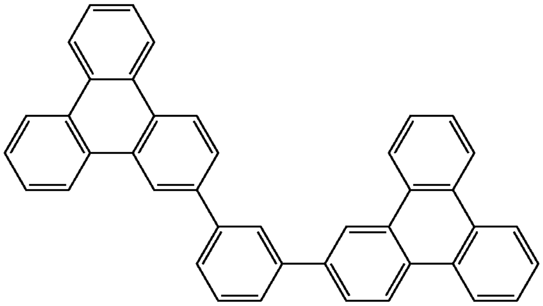
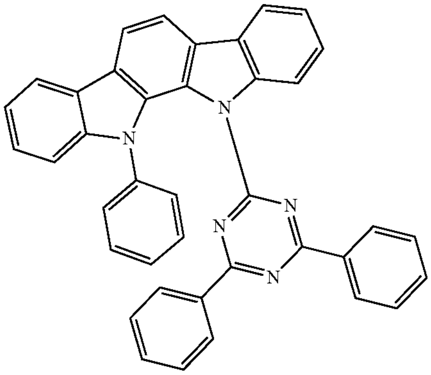
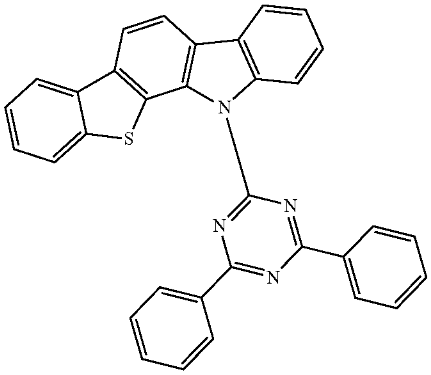
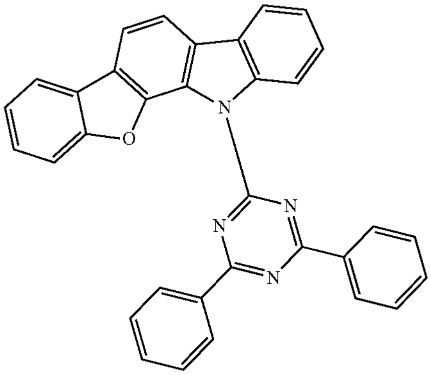
-continued
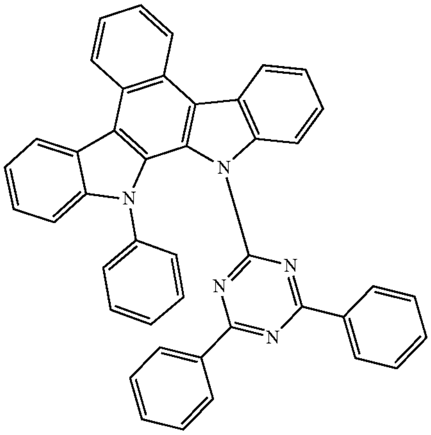
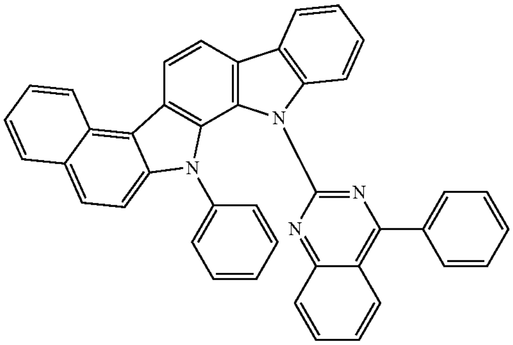
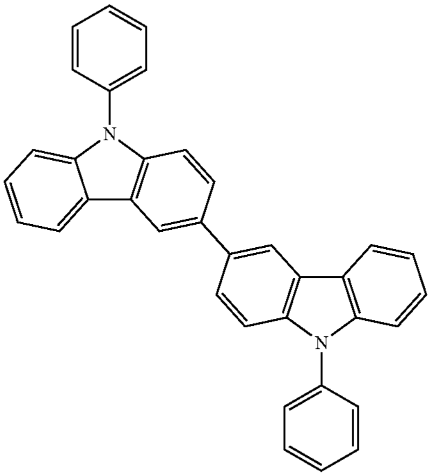

-continued

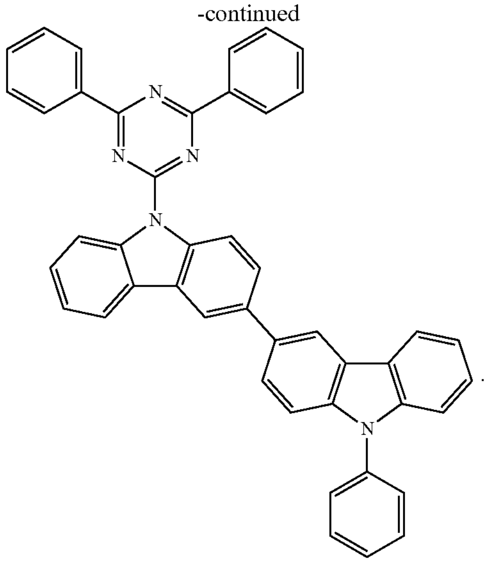

In a specific embodiment, the host material of the organic light emitting layer 330 is BH-1.

The guest material of the organic light emitting layer 330 may be a compound having a condensed aryl ring or a derivative thereof, a compound having a heteroaryl ring or a derivative thereof, a bisarylamine derivative with a condensed aromatic subunit, or other materials, and the present disclosure is not particularly restricted in this respect. For example, the guest material is selected from at least one of the following compounds:

BD-1

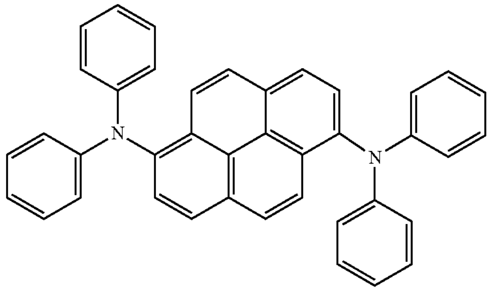

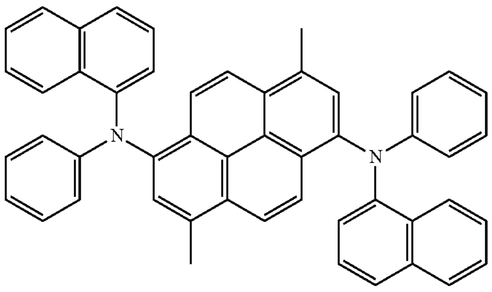

-continued

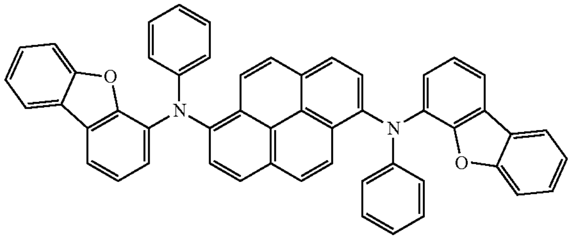

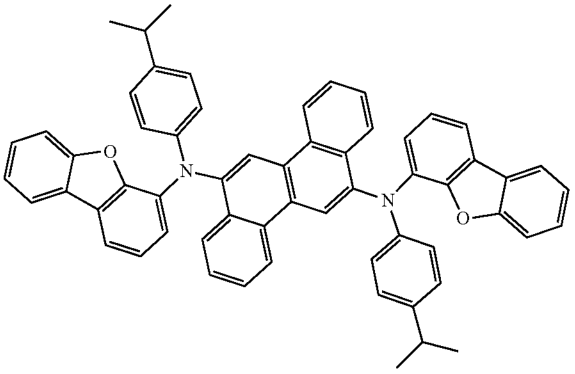

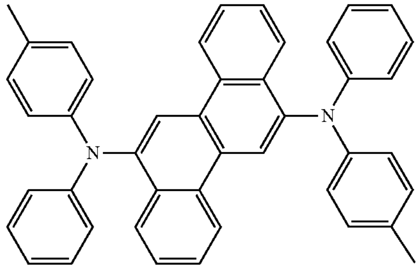

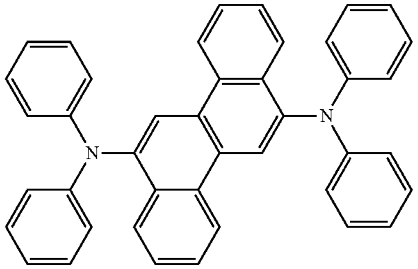

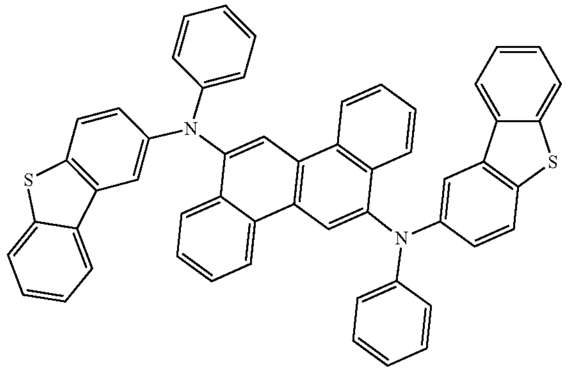

-continued

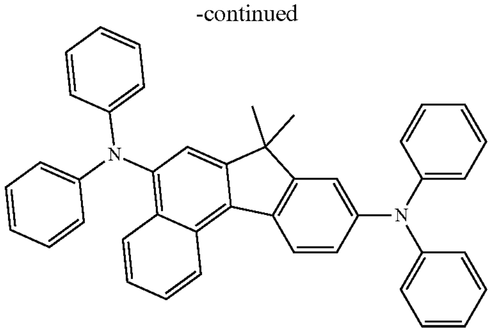

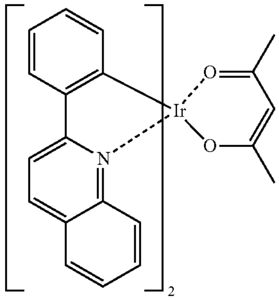

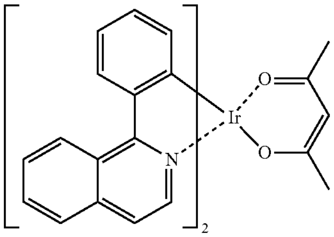

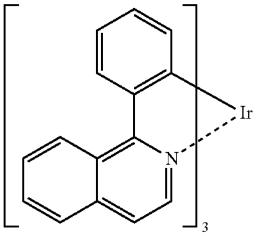

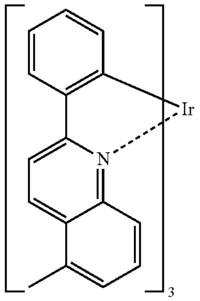

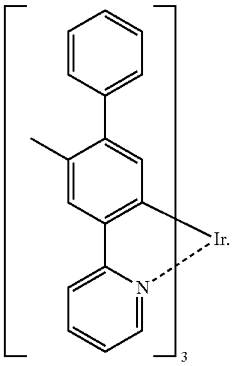

In a specific embodiment, the guest material of the organic light emitting layer 330 is BD-1.

The electron transport layer 340 may be a single-layer structure or a multi-layer structure, and may comprise one or more electron transport material(s). The electron transport materials may generally comprise metal complexes and/or nitrogen-containing heterocyclic derivatives, wherein, the metal complex material can be selected from, for example, LiQ, $Alq_3$, $Bepq_2$, etc.; the nitrogen-containing heterocyclic derivative can be an aromatic ring with a nitrogen-containing six-membered ring or a five-membered ring skeleton, fused aromatic ring compounds with a six-membered ring or a five-membered ring skeleton, etc. Specific examples include but are not limited to 1,10-phenanthroline compounds such as BCP, Bphen, NBphen, DBimiBphen, BimiBphen, etc., or at least one of the following compounds:

ET-1

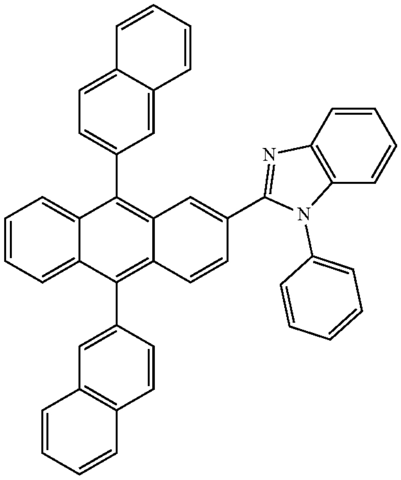

ET-2

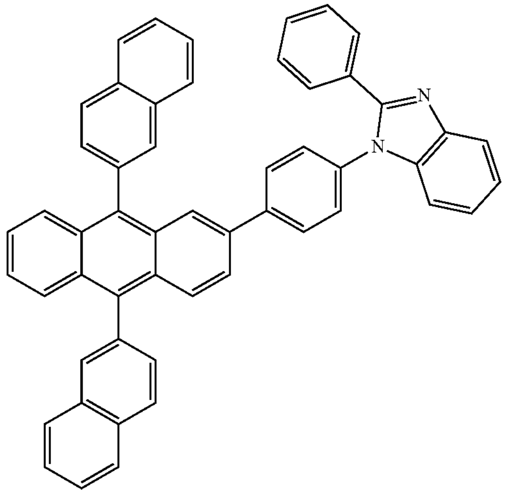

-continued

ET-3

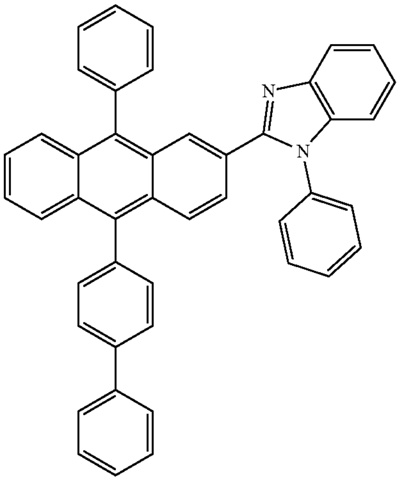

ET-4

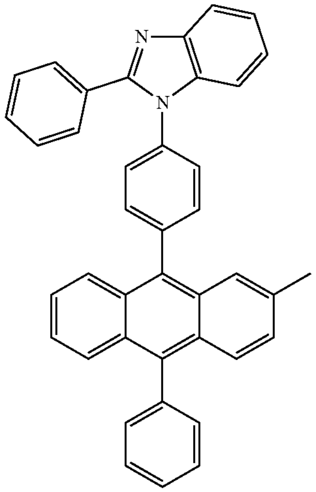

ET-5

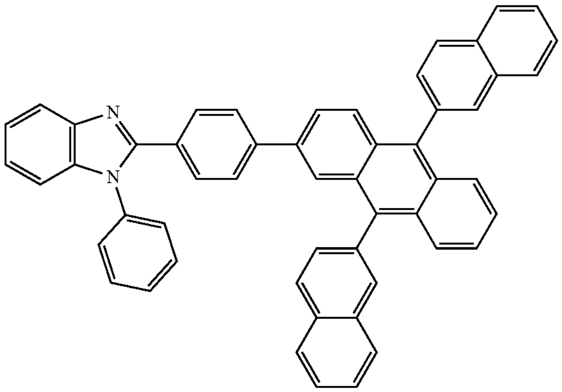

.

In a specific embodiment, the electron transport layer 340 is composed of ET-1 and LiQ.

In the present disclosure, the cathode 200 may comprise a cathode material, which is a low work-function material contributing to injection of electrons into the functional layer. Specific examples of the cathode material include, but are not limited to, metals such as magnesium, calcium, sodium, potassium, titanium, indium, yttrium, lithium, gadolinium, aluminum, silver, tin and plumbum, or alloys thereof; or multilayer materials such as LiF/Al, Liq/Al, $LiO_2$/Al, LiF/Ca, LiF/Al and $BaF_2$/Ca. Preferably, a metal electrode comprising magnesium and silver is included as the cathode.

Optionally, as shown in FIG. 1, a hole injection layer 310 is further disposed between the anode 100 and the first hole transport layer 321 so as to enhance the ability to inject holes into the first hole transport layer 321. The hole injection layer 310 may be selected from benzidine derivatives, starburst arylamine compounds, phthalocyanine derivatives, and other materials, and the present disclosure is not particularly restricted in this respect. The material of the hole injection layer 310 is, for example, selected from the following compounds and any combinations thereof:

F4-TCNQ

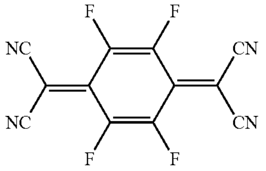

HAT-CN

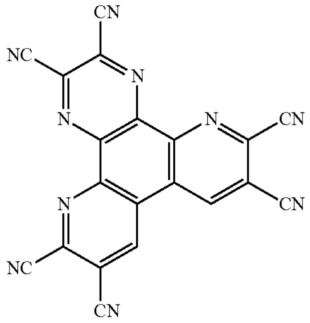

m-MTDATA

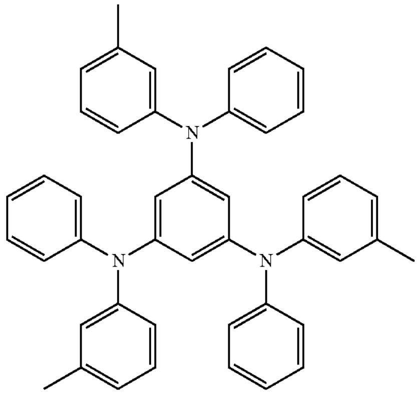

-continued

1T-NATA

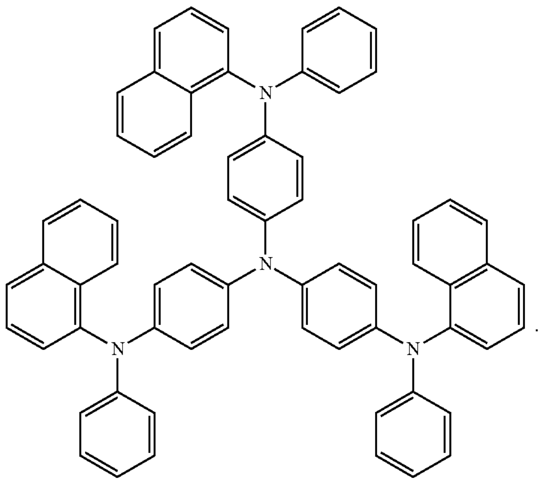

In a specific embodiment, the hole injection layer 310 is composed of F4-TCNQ.

Optionally, as shown in FIG. 1, an electron injection layer 350 is further disposed between the cathode 200 and the electron transport layer 340 so as to enhance the ability to inject electrons into the electron transport layer 340. The electron injection layer 350 may comprise an inorganic material such as an alkali metal sulfide, an alkali metal halide, and the like, or may comprise a complex of an alkali metal and an organic compound. For example, the electron injection layer 350 comprises LiQ or Yb, or the composition of Mg and LiF.

In the present disclosure, the organic electroluminescent device may be a blue organic electroluminescent device, a red organic electroluminescent device or a green organic electroluminescent device, preferably a blue organic electroluminescent device.

Figure 3:
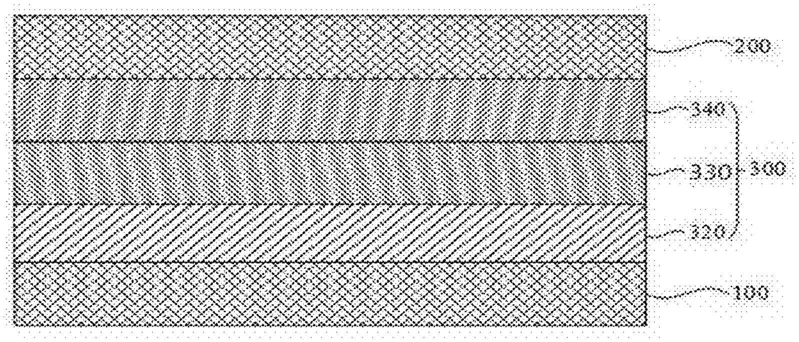
FIG. 3 is a schematic structural diagram of a photoelectric conversion device according to an embodiment of the present disclosure.

According to another embodiment, the electronic element is a photoelectric conversion device. As shown in FIG. 3, the photoelectric conversion device may comprise an anode 100 and a cathode 200 disposed opposite to each other, and a functional layer 300 disposed between the anode 100 and the cathode 200.

According to a specific embodiment, as shown in FIG. 3, the photoelectric conversion device may comprise an anode 100, a hole transport layer 320, an organic light emitting layer 330, an electron transport layer 340 and a cathode 200 that are stacked in sequence. Optionally, the hole transport layer 320 comprises the nitrogen-containing compound provided by the present disclosure.

Optionally, the photoelectric conversion device is a solar cell, especially an organic thin film solar cell.

A third aspect of the present disclosure provides an electronic device, comprising the electronic element described in the second aspect of the present disclosure.

Figure 2:
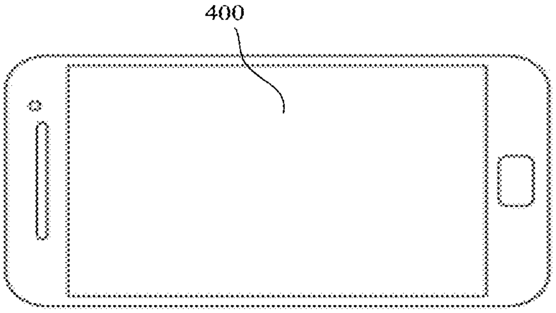
FIG. 2 is a schematic structural diagram of a first electronic device according to an embodiment of the present disclosure.

According to one embodiment, as shown in FIG. 2, the electronic device is a first electronic device 400, and the first electronic device 400 comprises the organic electroluminescent device described above. The first electronic device 400 is, for example, a display device, a lighting device, an optical communication device, or other types of electronic devices, including, but not limited to, for example, a computer screen, a mobile phone screen, a television, electronic paper, emergency lighting, an optical module, etc.

Figure 4:
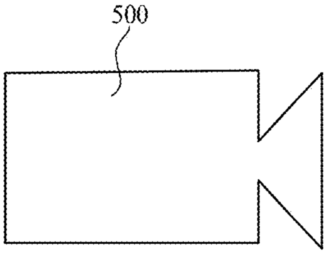
FIG. 4 is a schematic structural diagram of a second electronic device according to an embodiment of the present disclosure.

According to another embodiment, as shown in FIG. 4, the electronic device is a second electronic device 500, and the second electronic device 500 comprises the photoelectric conversion device described above. The second electronic device 500 is, for example, a solar power generation device, a light detector, a fingerprint identification device, an optical module, a CCD camera or another type of electronic device.

Hereinafter, the present disclosure will be further described in detail through examples. However, the following examples are only examples of the present disclosure but not limitations of the present disclosure.

Compounds for which a synthesis method is not mentioned in the present disclosure are all raw material products obtained commercially.

I. Synthesis of Intermediate IM I-X

1. IM I-A was Taken as an Example to Illustrate the Synthesis of IM I-X

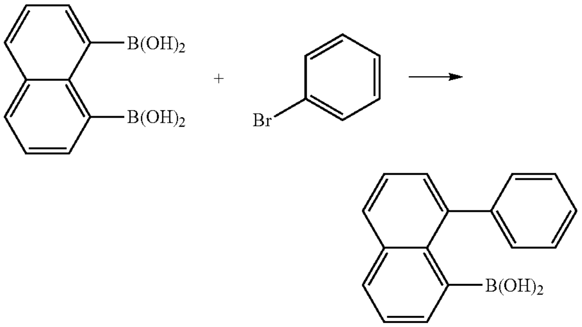

IM I-A-1

(1) Under the protection of $N_2$, 1,8-naphthalenediboric acid (40.00 g, 185.36 mmol), bromobenzene (29.1 g, 185.36 mmol), potassium carbonate (56.1 g, 405.93 mmol), tetrbutylammonium bromide (11.9 g, 37.06 mmol), toluene (300 mL), ethanol (120 mL) and deionized water (80 mL) were added to a three-necked flask. The resulting mixture was stirred for 15 minutes, followed by addition of tetrakis(triphenylphosphine) palladium (4.3 g, 3.71 mmol), and then was heated to 75° C.-80° C. and stirred for 8 hours. The resulting solution was cooled to room temperature and then extracted with toluene (200 mL). The resulting organic phases were combined and dried with anhydrous magnesium sulfate, and the organic phase was passed through a silica gel chromatography column to remove the catalyst and was proceeded twice with ethyl acetate/anhydrous ethanol for recrystallization; to obtain a white solid, which is the intermediate IM I-A-1 (38.2 g, yield 83.1%).

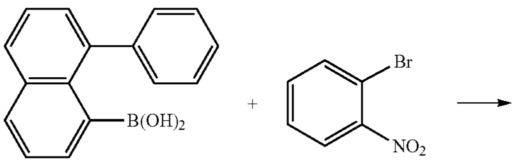

IM I-A-1

-continued

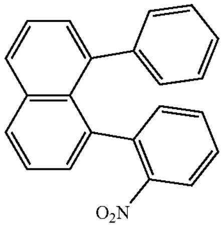

IM I-A-2

(2) Under the protection of $N_2$, IM I-A-1 (38.0 g, 153.17 mmol), o-bromonitrobenzene (30.9 g, 153.17 mmol), potassium carbonate (46.4 g, 335.75 mmol), tetrabutylammonium bromide (10.0 g, 31.09 mmol), toluene (300 mL), ethanol (120 mL) and deionized water (80 mL) were added to a three-necked flask. The resulting mixture was stirred for 15 minutes, followed by addition of tetrakis(triphenylphosphine)palladium (3.5 g, 3.05 mmol), and then was heated to 75° C.-80° C. and stirred for 40 hours. The resulting solution was cooled to room temperature and then extracted with toluene (200 mL). The resulting organic phases were combined and dried with anhydrous magnesium sulfate, and then the organic phase was passed through a silica gel chromatography column to remove the catalyst and was concentrated under reduced pressure to remove the solvent, to obtain a yellow oil, which is IM I-A-2 (32.8 g, yield 65.8%).

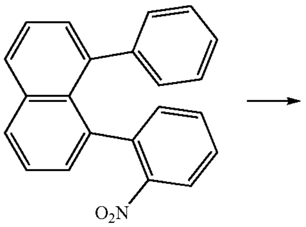

IM I-A-2

-continued

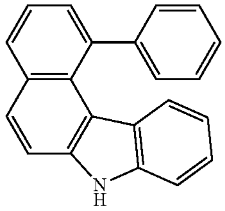

IM I-A (3) Under the protection of $N_2$, IM I-A-2 (32.0 g, 98.35 mmol), triphenylphosphine (59.3 g, 226.10 mmol) and 300 mL of o-dichlorobenzene were added to a three-necked flask. The resulting mixture was heated to 150° C. to react for 18 h under stirring. The resulting solution was concentrated under reduced pressure to remove the o-dichlorobenzene, and the resulting black residue was extracted with n-hexane for three times. The extract was collected and passed through a silica gel column, and then was concentrated under reduced pressure to remove the solvent, to obtain a silver-gray scale-like solid, which is IM I-A (17.1 g, yield 59.3%).

2. Other IM I-X were synthesized with reference to the method of synthesizing IM I-A, with difference that, bromobenzene was replaced by Raw Material 1, and o-bromonitrobenzene was replaced by Raw Material 2. The intermediates synthesized in each step and the yield of the last step are shown in Table 1.

TABLE 1
| Raw Material 1 | IM I-X-1 | Raw Material 2 | IM I-X-2 | IM I-X | Yield/% |
|---|---|---|---|---|---|
| 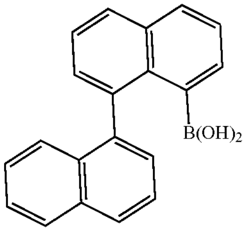 IM I-B-1 | 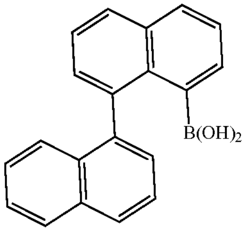 IM I-B-1 | 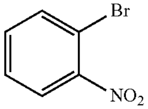 | 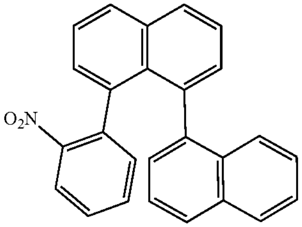 IM I-B-2 | 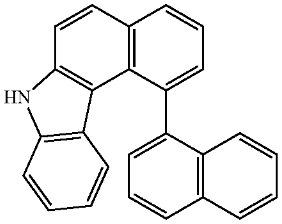 IM I-B | 42.3 |
| 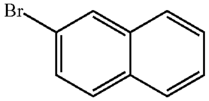 | 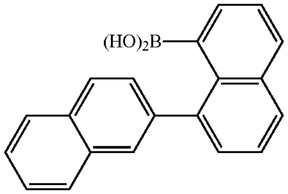 IM I-C-1 | 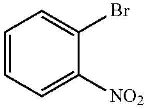 | 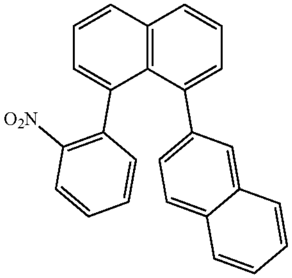 IM I-C-2 | 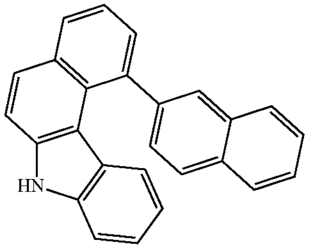 IM I-C | 46.7 |
| 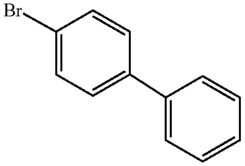 [SMILES: Brc1ccc(-c2ccccc2)cc1] | 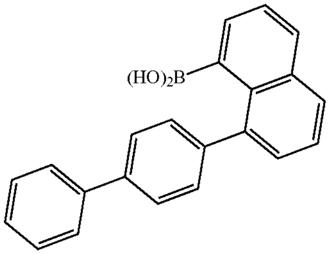 IM I-D-1 | 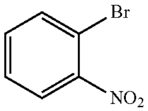 | 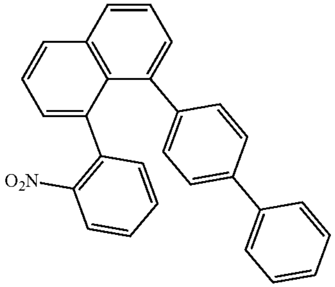 IM I-D-2 | 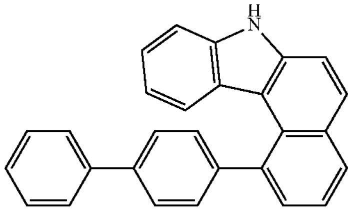 IM I-D | 47.9 |

TABLE 1-continued
| Raw Material 1 | IM I-X-1 | Raw Material 2 | IM I-X-2 | IM I-X | Yield/% |
|---|---|---|---|---|---|
| 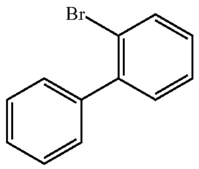 [SMILES: Brc1ccccc1-c1ccccc1] | 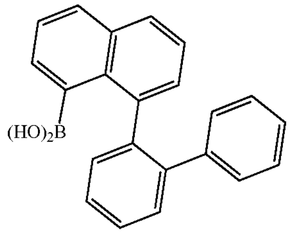 IM I-E-1 | 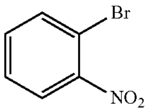 | 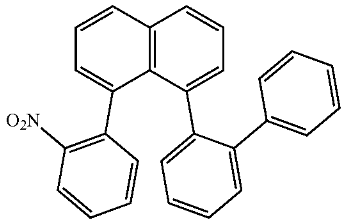 IM I-E-2 | 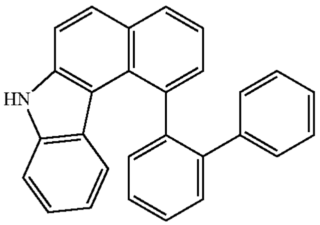 IM I-E | 39.8 |
| 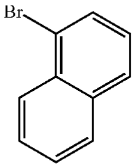 | 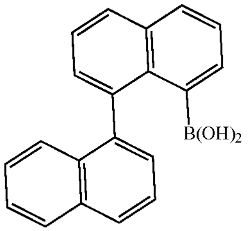 IM I-B-1 | 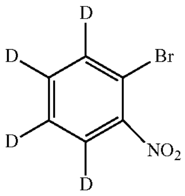 [SMILES: [2H]c1c([2H])c([2H])c([N+](=O)[O-])c(Br)c1[2H]] | 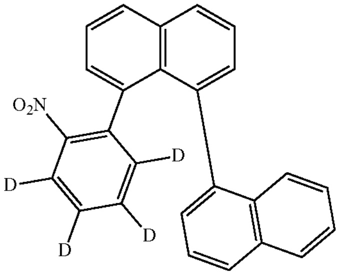 IM I-F-2 | 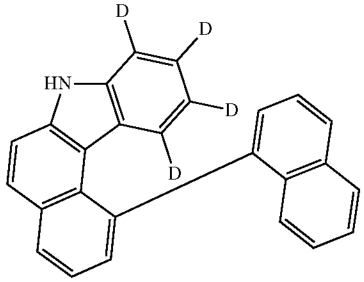 IM I-F | 26.3 |

II. Synthesis of Intermediates IM I-f to IM I-i:

1. Synthesis of IM I-f

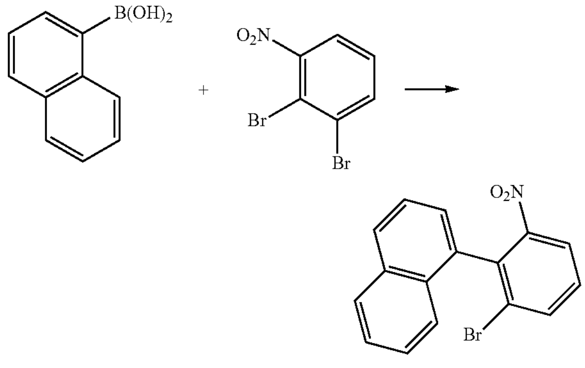

IM I-f-1

(1) IM I-f-1 was prepared using the same synthesis method as IM I-A-2, with the difference that IM I-A-1 was replaced by 1-naphthaleneboronic acid and o-bromonitrobenzene was replaced by 2,3-dibromonitrobenzene, respectively, and other conditions remained unchanged, to obtain IM I-f-1 (28.5 g, yield 72.4%).

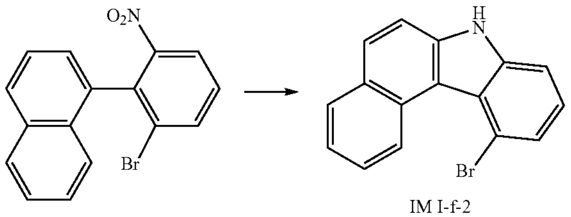

IM I-f-1

IM I-f-2

(2) IM I-f-2 was prepared using the same synthesis method as IM I-A, with the difference that IM I-A-2 was replaced by IM I-f-1, and other conditions remained unchanged, to obtain IM I-f-2 (15.7 g, yield 62.2%).

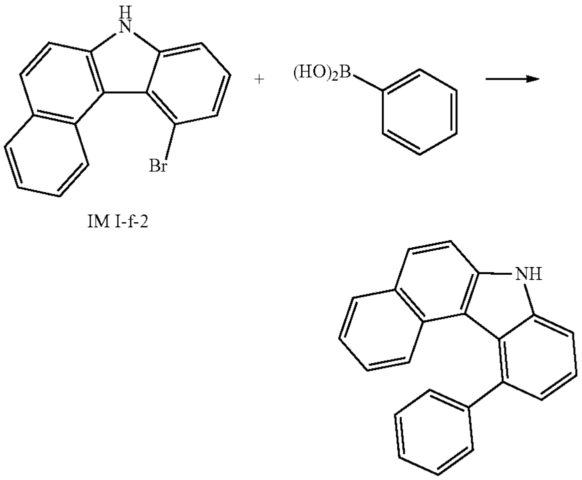

IM I-f-2

IM I-f (3) Under the protection of $N_2$, IM I-f-2 (15 g, 50.65 mmol), phenylboronic acid (6.48 g, 53.18 mmol), potassium carbonate (16.09 g, 116.49 mmol), tetrabutylammonium bromide (3.26 g, 10.13 mmol), toluene (90 mL), ethanol (45 mL), and deionized water (30 mL) were added to a three-necked flask. The resulting mixture was stirred for 15 minutes, followed by addition of tetrakis(triphenylphosphine)palladium (2.93 g, 2.53 mmol), and then was heated to 75° C.-80° C., and stirred for 16 hours; the resulting solution was cooled to room temperature and then extracted with toluene (200 mL). The resulting organic phases were combined and dried with anhydrous magnesium sulfate, and the organic phase was passed through a silica gel chromatography column to remove the catalyst and was concentrated under reduced pressure to remove the solvent; to obtain a yellow oil, which is IM I-f (10.8 g, yield 72.7%).

2. Synthesis of IM I-g to IM I-i

IM I-g to IM I-i were synthesized with reference to the synthesis method of IM I-f (the above step (3)), with the difference that phenylboronic acid was replaced by Raw Material 3 to react with IM I-f-2, and other conditions remained unchanged, the intermediates synthesized and yield thereof are shown in Table 2.

TABLE 2

| Raw Material 3 | Intermediate | Yield/ % |
|---|---|---|
| 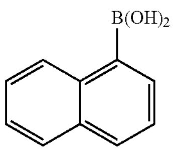 [SMILES: OB(O)c1cccc2ccccc12] | 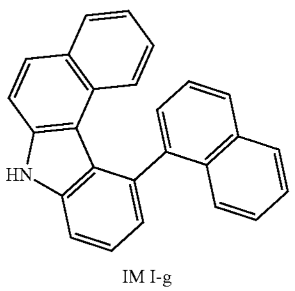 [SMILES: c1ccc2c(-c3cccc4[nH]c5ccc6ccccc6c5c34)cccc2c1] IM I-g | 71.6 |

TABLE 2-continued

| Raw Material 3 | Intermediate | Yield/ % |
| --- | --- | --- |
| 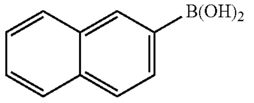 [SMILES: OB(O)c1ccc2ccccc2c1] | 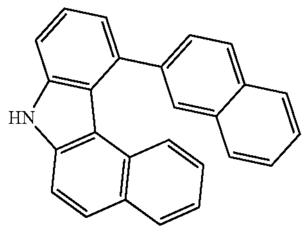<br>IM I-h | 69.8 |
| 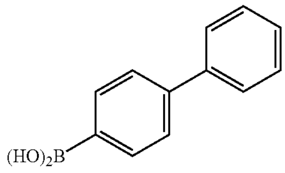 [SMILES: OB(O)c1ccc(-c2ccccc2)cc1] | 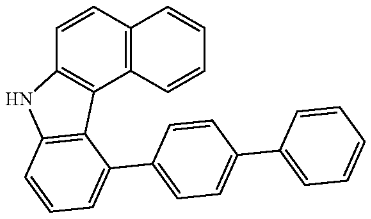<br>IM I-i | 66.9 |

III. Synthesis of IM I-j to IM I-k

1. Synthesis of IM I-j

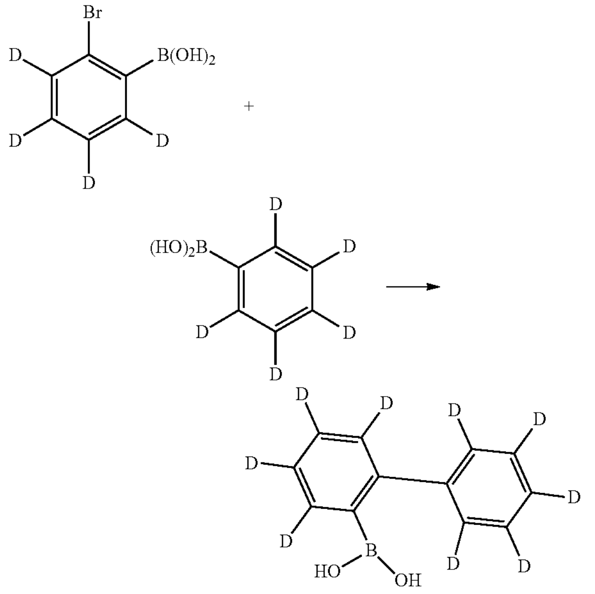

I-J-1

(1) Under the protection of $N_2$, (2-bromophenyl-3, 4, 5, 6-$d_4$)boronic acid (50 g, 244.02 mmol), deuterophenylboronic acid (46.49 g, 366.02 mmol), potassium carbonate (77.56 g, 561.25 mmol), tetrabutylammonium bromide (15.73 g, 48.80 mmol), toluene (400 mL), ethanol (150 mL) and deionized water (100 mL) were added to a three-necked flask. The resulting mixture was stirred for 15 minutes, followed by addition of tetrakis(triphenylphosphine)palladium (14.10 g, 12.20 mmol), and then heated to 75° C.-80° C. and stirred for 8 hours. Subsequently, the resulting solution was cooled to room temperature and washed with water to neutral. The resulting organic phases were combined and dried with anhydrous magnesium sulfate, and then the organic phase was passed through a silica gel column to remove the catalyst and was concentrated under reduced pressure to remove the solvent; to obtain a yellow oil, which is I-J-1 (24.23 g, yield 48.0%).

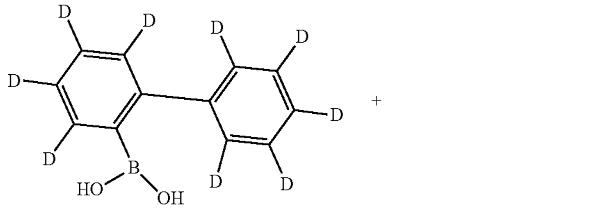

I-J-1

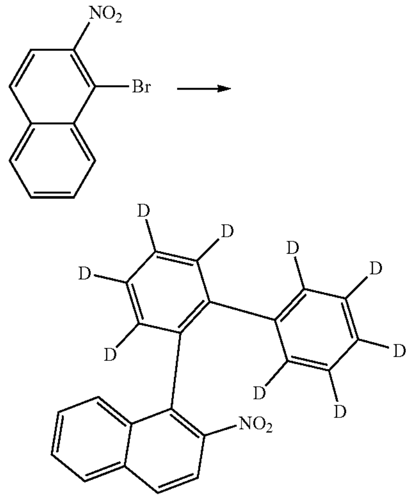

I-J-2

(2) Under the protection of $N_2$, I-J-1 (24 g, 115.87 mmol), 1-bromo-2-nitronaphthalene (43.82 g, 173.83 mmol), potassium carbonate (36.83 g, 266.54 mmol), tetrabutylammonium bromide (7.47 g, 23.18 mmol), toluene (280 mL), ethanol (80 mL) and deionized water (60 mL) were added to a three-necked flask. The resulting mixture was stirred for 30 minutes, followed by addition of tetrakis(triphenylphosphine)palladium (6.7 g, 5.79 mmol), and then was heated to 75° C.-80° C. and stirred for 36 hours. Subsequently, the resulting solution was cooled to room temperature and washed with water to neutral; and the resulting organic phases were combined and dried with anhydrous magnesium sulfate, and the organic phase was passed through a silica gel column (petroleum ether:dichloromethane=2:1, v/v), the eluent containing the product was collected, and concentrated under reduced pressure to remove the solvent, to obtain a white powdery solid, which is I-J-2 (22.15 g, yield 57.2%).

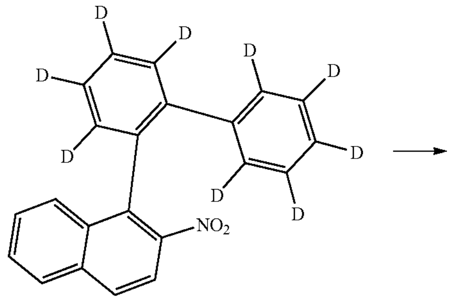

I-J-2

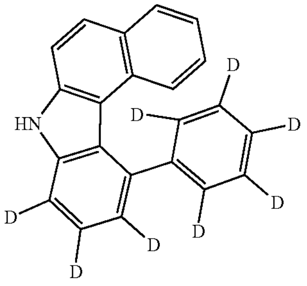

IM I-j (3) IM I-j was prepared using the same synthesis method as IM I-A, with the difference that IM I-A-2 was replaced by I-J-2, and other conditions remained unchanged, and IM I-j (12.31 g, yield 56.9%) was obtained.

2. Synthesis of IM I-k

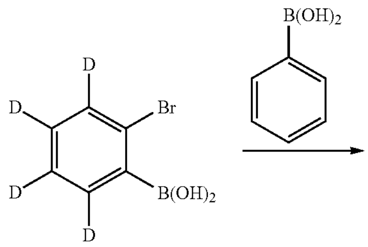

-continued

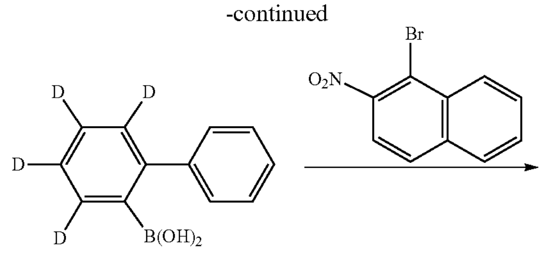

IM I-k-1

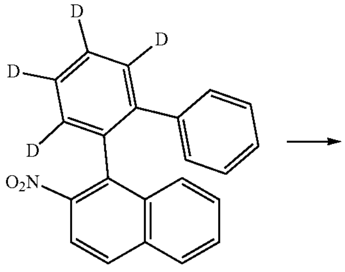

IM I-k-2

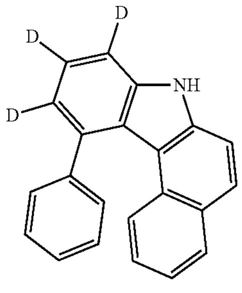

IM I-k

IM I-k was synthesized using the same synthesis method as IM I-j, with the difference that (2-bromophenyl-3,4,5,6-d4)boronic acid was replaced by phenylboronic acid, and other conditions remained unchanged, and IM I-k (13.17 g, yield in the last step 62.1%) was obtained.

IV. Synthesis of Intermediate IM I-X-Y

1. Synthesis of IM I-A-L1

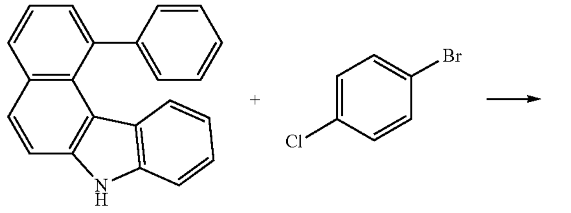

IM I-A

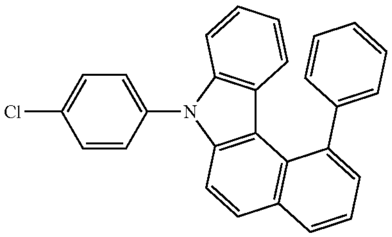

IM I-A-L1

Under the protection of $N_2$, IM I-A (15 g, 51.13 mmol), p-chlorobromobenzene (9.79 g, 51.13 mmol), copper iodide (0.19 g, 1.02 mmol), potassium carbonate (14.12 g, 102.26 mmol), 1,10-phenanthroline (5.07 g, 25.56 mmol) and 18-crown ether-6 (0.13 g, 0.51 mmol) were added to a 1 L three-necked flask, followed by addition of 150 mL of DMF; nitrogen was purged continuously for 20 minutes, and the resulting mixture was slowly heated to reflux and stirred for 24 h. The resulting solution was cooled to room temperature, and was added to 1 L of water to remove DMF, and extracted with dichloromethane and then dried with anhydrous magnesium sulfate for 30 minutes, and then concentrated under reduced pressure to remove the solvent, and passed through silica gel chromatography column with a mixture of dichloromethane/petroleum ether (volume ratio 1:2) as the eluent, to obtain an off-white solid, which is IM I-A-L1 (15.18 g, yield 73.5%).

2. Other IM I-X-Y were synthesized with reference to the synthesis method of IM I-A-L1, with the difference that IM I-A was replaced by Raw Material 4, and p-chlorobromobenzene was replaced by Raw Material 5, and the main raw materials used, intermediates synthesized and yields thereof are shown in Table 3.

TABLE 3
| Raw Material 4 | Raw Material 5 | IM I-X-Y | Yield/% |
|---|---|---|---|
| 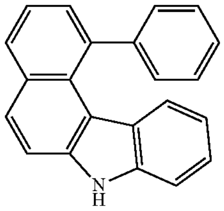 IM I-A | 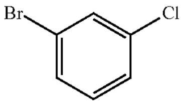 | 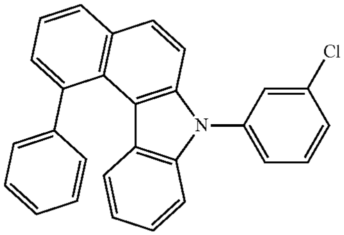 IM I-A-L2 | 42.3 |
| 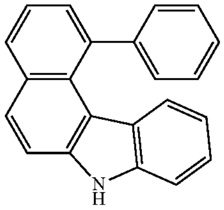 IM I-A | 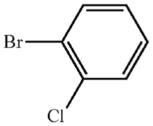 | 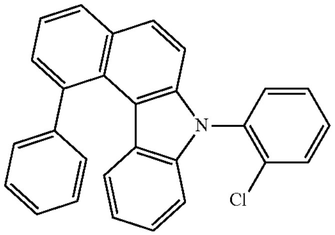 IM I-A-L3 | 46.7 |
| 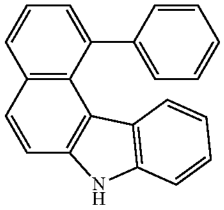 IM I-A | 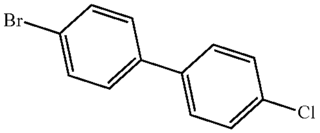 [SMILES: Clc1ccc(-c2ccc(Br)cc2)cc1] | 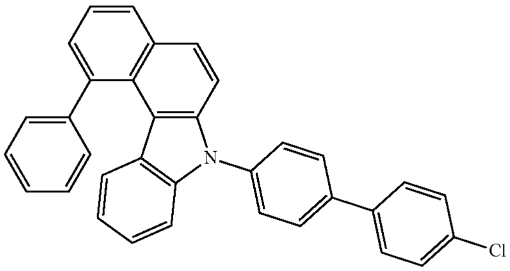 IM I-A-L4 | 47.9 |

TABLE 3-continued
| Raw Material 4 | Raw Material 5 | IM I-X-Y | Yield/% |
|---|---|---|---|
| 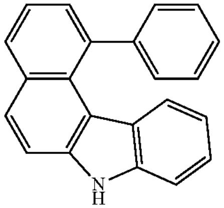 IM I-A | 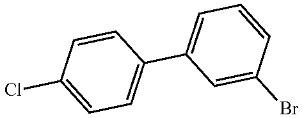 [SMILES: Clc1ccc(-c2cccc(Br)c2)cc1] | 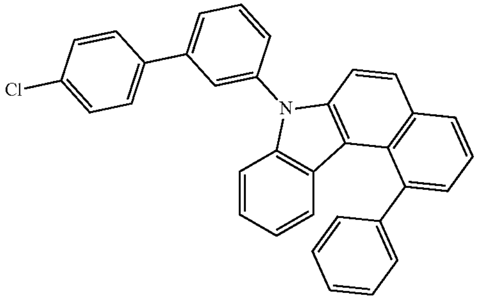 IM I-A-L5 | 50.2 |
| 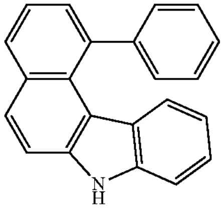 IM I-A | 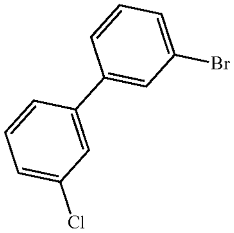 [SMILES: Clc1cccc(-c2cccc(Br)c2)c1] | 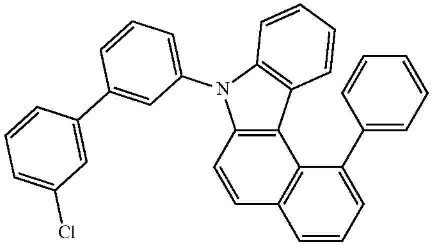 IM I-A-L6 | 39.8 |
| 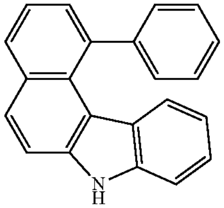 IM I-A | 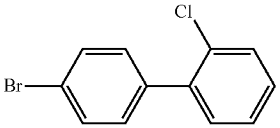 [SMILES: Clc1ccccc1-c1ccc(Br)cc1] | 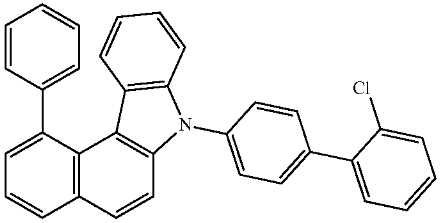 IM I-A-L7 | 44.5 |

TABLE 3-continued
| Raw Material 4 | Raw Material 5 | IM I-X-Y | Yield/% |
|---|---|---|---|
| 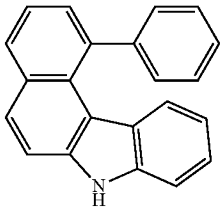 IM I-A | 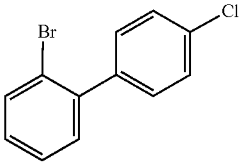 [SMILES: Clc1ccc(-c2ccccc2Br)cc1] | 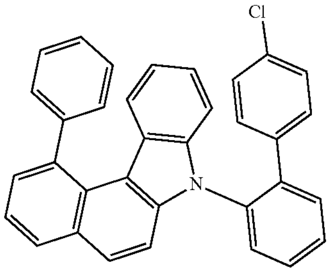 IM I-A-L8 | 47.1 |
| 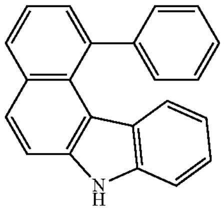 IM I-A | 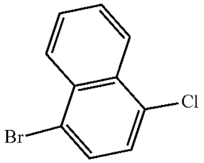 [SMILES: Clc1ccc(Br)c2ccccc12] | 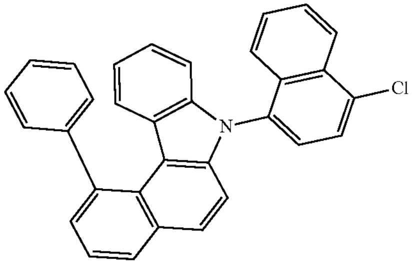 IM I-A-L9 | 55.2 |
| 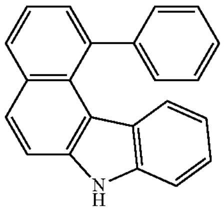 IM I-A | 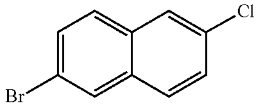 [SMILES: Clc1ccc2cc(Br)ccc2c1] | 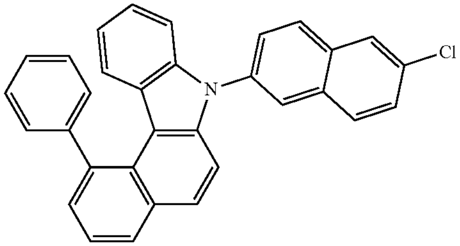 IM I-A-L10 | 49.6 |

TABLE 3-continued
| Raw Material 4 | Raw Material 5 | IM I-X-Y | Yield/% |
|---|---|---|---|
| 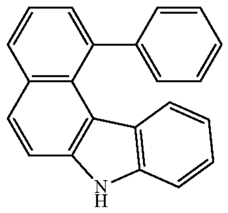 IM I-A | 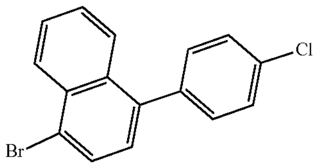 [SMILES: Clc1ccc(-c2ccc(Br)c3ccccc23)cc1] | 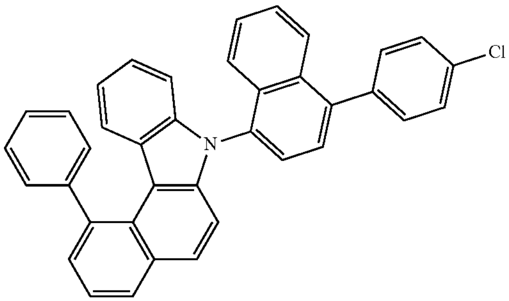 IM I-A-L11 | 44.7 |
| 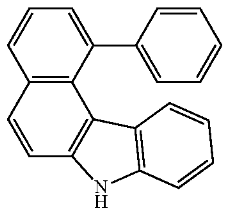 IM I-A | 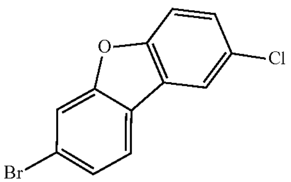 [SMILES: Clc1ccc2oc3cc(Br)ccc3c2c1] | 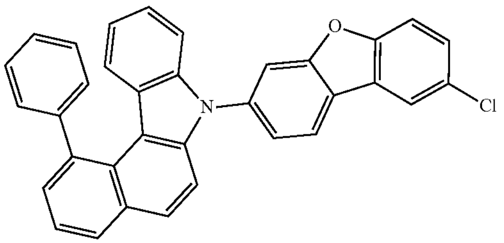 IM I-A-L12 | 41.4 |
| 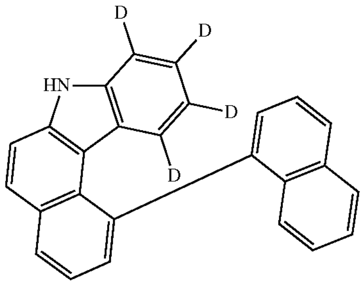 IM I-F | 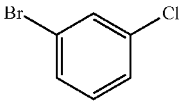 | 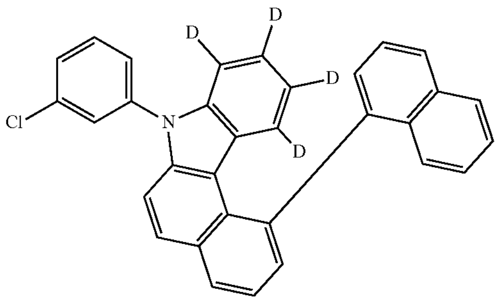 IM I-F-L1 | 38.6 |

TABLE 3-continued
| Raw Material 4 | Raw Material 5 | IM I-X-Y | Yield/% |
|---|---|---|---|
| 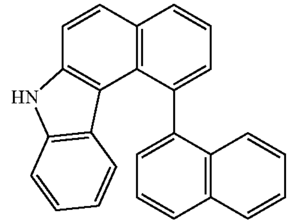 IM I-B | 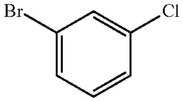 | 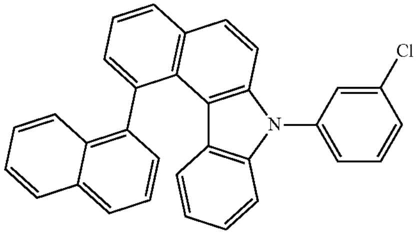 IM I-B-L1 | 49.1 |
| 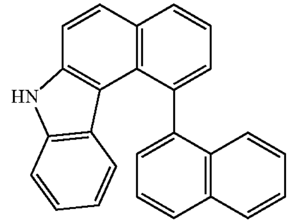 IM I-B | 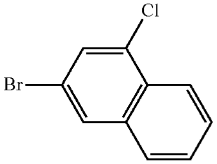 [SMILES: Clc1cc(Br)cc2ccccc12] | 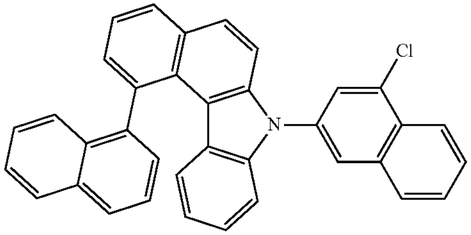 IM I-B-L2 | 47.3 |
| 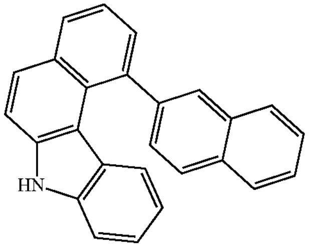 IM I-C | 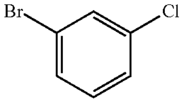 | 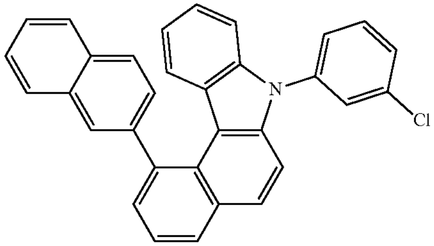 IM I-C-L1 | 44.3 |

TABLE 3-continued
| Raw Material 4 | Raw Material 5 | IM I-X-Y | Yield/% |
| --- | --- | --- | --- |
| 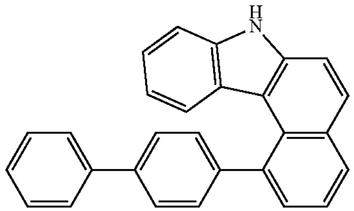 IM I-D | 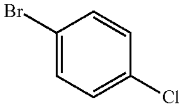 | 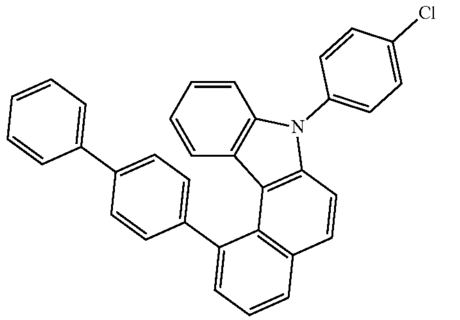 IM I-D-L1 | 47.8 |
| 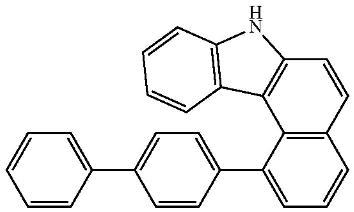 IM I-D | 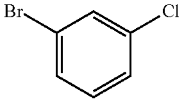 | 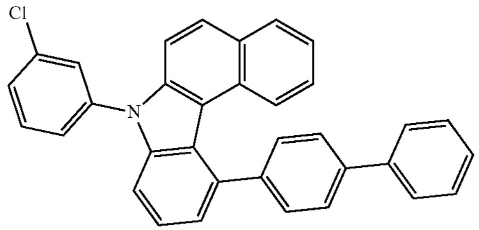 IM I-D-L2 | 41.1 |
| 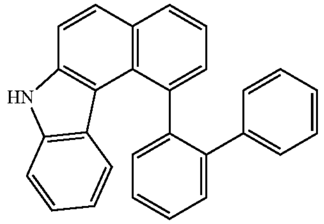 IM I-E | 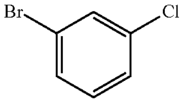 | 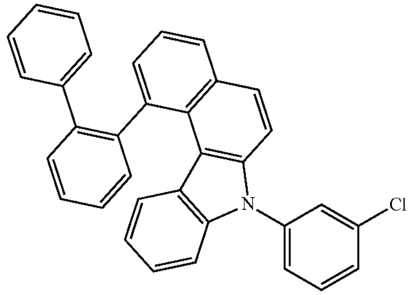 IM I-E-L1 | 45.4 |

TABLE 3-continued
| Raw Material 4 | Raw Material 5 | IM I-X-Y | Yield/% |
|---|---|---|---|
| 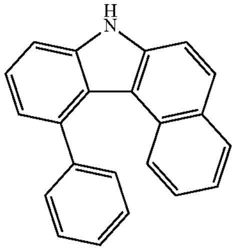 IM I-f | 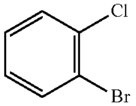 | 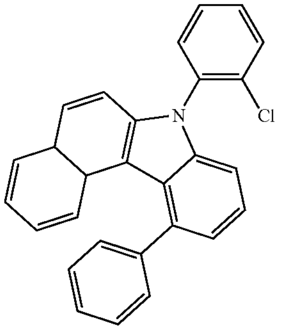 IM I-f-L1 | 37.6 |
| 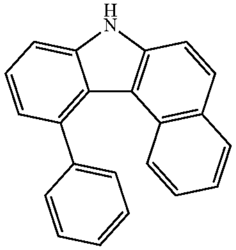 IM I-f | 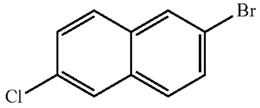 [SMILES: Clc1ccc2cc(Br)ccc2c1] | 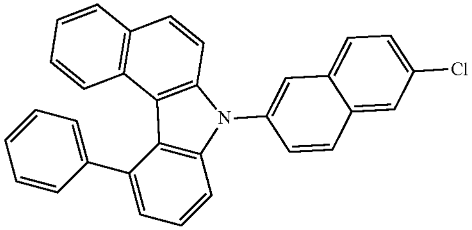 IM I-f-L2 | 46.4 |
| 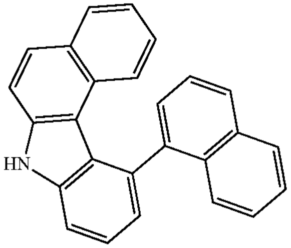 IM I-g | 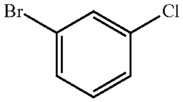 | 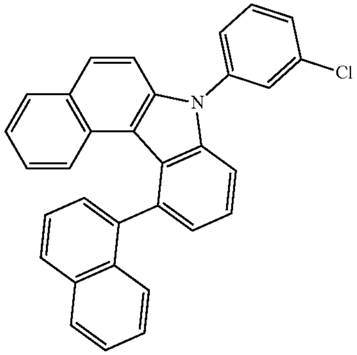 IM I-g-L1 | 45.8 |

TABLE 3-continued
| Raw Material 4 | Raw Material 5 | IM I-X-Y | Yield/% |
|---|---|---|---|
| 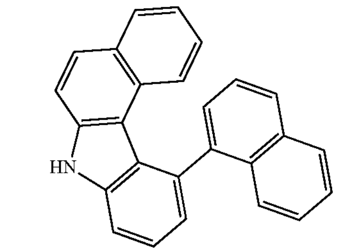 IM I-g | 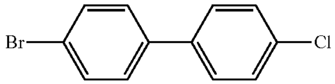 [SMILES: Clc1ccc(-c2ccc(Br)cc2)cc1] | 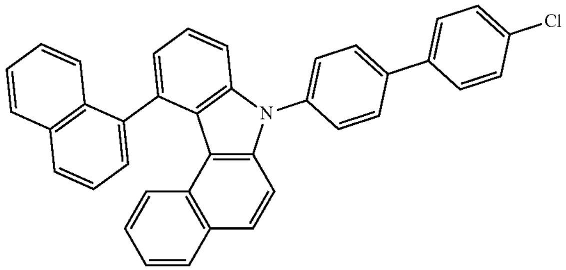 IM I-g-L2 | 52.9 |
| 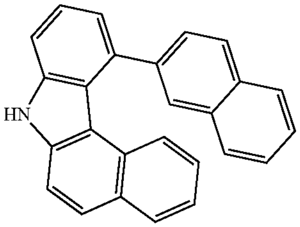 IM I-h | 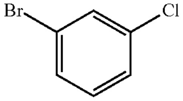 | 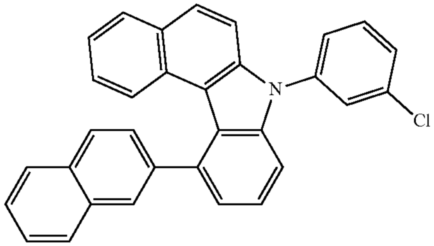 IM I-h-L1 | 49.1 |
| 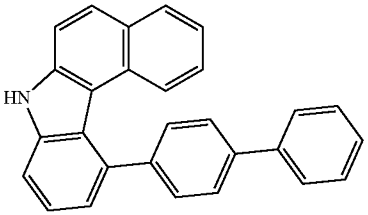 IM I-i | 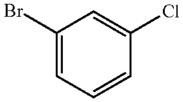 | 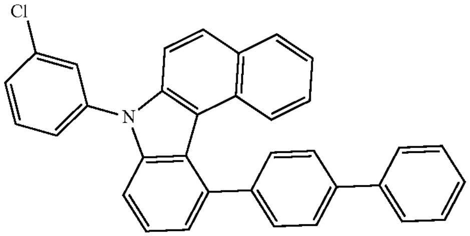 IM I-i-L1 | 46.7 |

TABLE 3-continued
| Raw Material 4 | Raw Material 5 | IM I-X-Y | Yield/% |
|---|---|---|---|
| 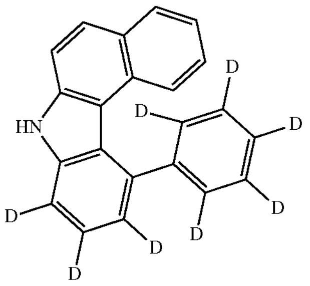 IM I-j | 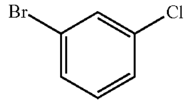 | 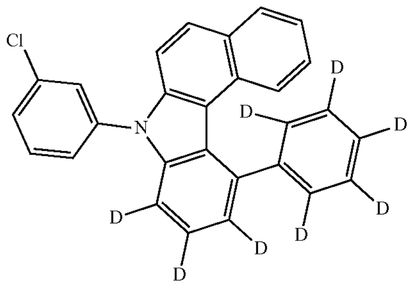 IM I-j-L1 | 47.2 |
| 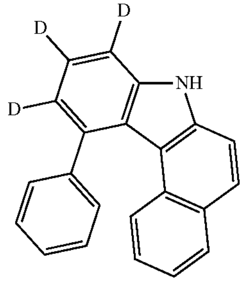 IM I-k | 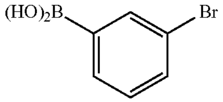 | 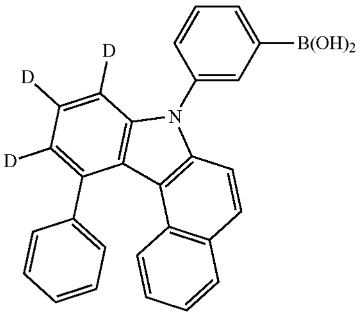 IM I-k-L | 41.7 |

V. Synthesis of Intermediate IM I-k-L1

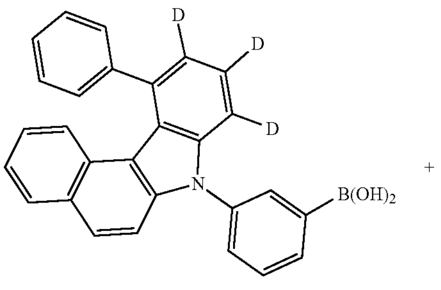

IM I-k-L

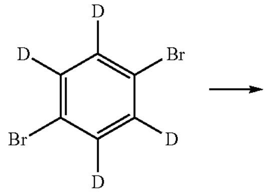

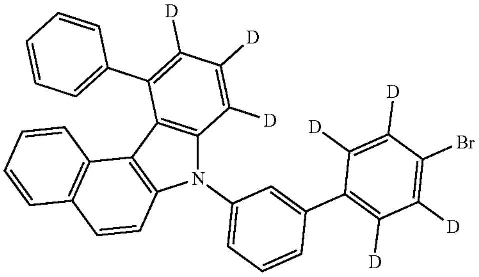

IM I-k-L1

Under the protection of $N_2$, IM I-k-L (20 g, 48.04 mmol), 1-bromo-2-nitronaphthalene (13.79 g, 57.65 mmol), potassium carbonate (15.27 g, 110.50 mmol), tetrabutylammonium bromide (3.1 g, 9.61 mmol), toluene (160 mL), ethanol (60 mL) and deionized water (40 mL) were added to a three-necked flask. The resulting mixture was stirred for 30 minutes, followed by addition of tetrakis(triphenylphosphine)palladium (2.78 g, 2.40 mmol), and then was heated to 75° C.-80° C., and stirred for 36 hours; and subsequently, the resulting solution was cooled to room temperature, and washed with water to neutral, and the resulting organic phases were combined and dried with anhydrous magnesium sulfate, and the organic phase was passed through a silica gel column (petroleum ether:dichloromethane=2:1, v/v), the eluent containing the product was collected, and concentrated under reduced pressure to remove the solvent, to obtain a white powdery solid, which is IM I-k-L1 (15.23 g, yield 59.6%).

Synthesis Example 1: Synthesis of Compound 6

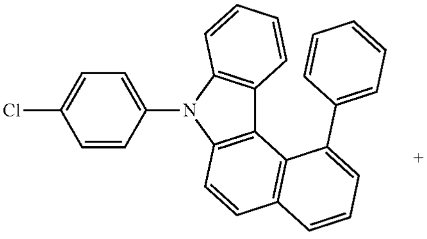

IM I-A-L1

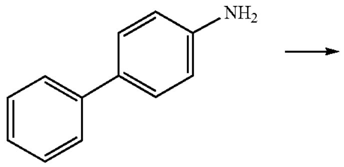

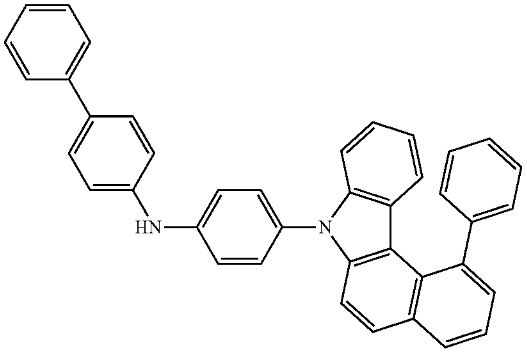

IM I-A-N (1) IM I-A-L1 (15 g, 37.14 mmol), 4-aminobiphenyl (6.16 g, 36.3 mmol), tris(dibenzylideneacetone)dipalladium (0.34 g, 0.37 mmol), 2-bicyclo hexylphosphine-2',4',6'-triisopropylbiphenyl (0.35 g, 0.74 mmol) and sodium tert-butoxide (5.35 g, 55.71 mmol) were added to toluene (150 mL), and the resulting mixture was heated to 108° C. and stirred for 4 hours under the protection of nitrogen; then the resulting solution was cooled to room temperature, and was washed with water and then dried by adding magnesium sulfate and filtered. The resulting filtrate was concentrated under reduced pressure to remove the solvent, obtaining a yellow solid crude product; the crude product was then purified by re-crystallization form a toluene system to obtain IM I-A-N (12.69 g, 64.6% yield).

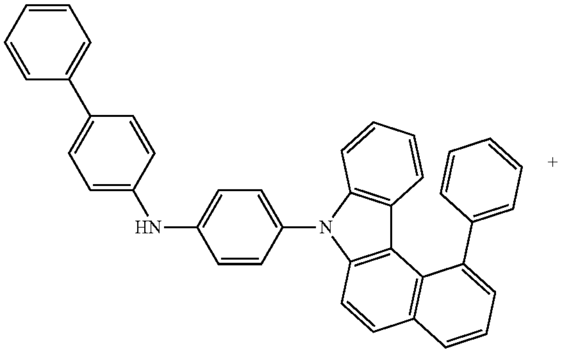

IM I-A-N

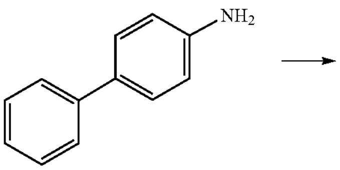

-continued

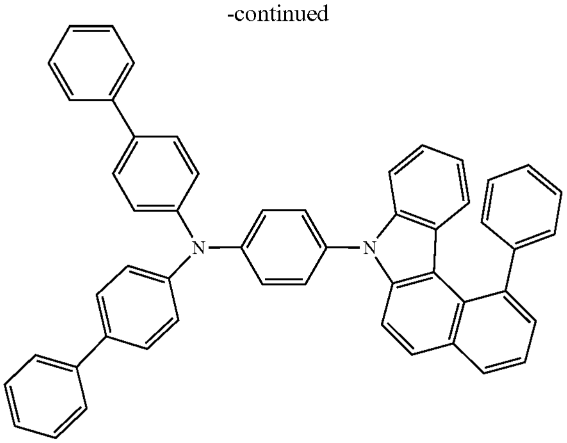

6

(2) IM I-A-N (10 g, 18.63 mmol), 4-bromobiphenyl (4.56 g, 19.56 mmol), tris(dibenzylideneacetone)dipalladium (0.17 g, 0.19 mmol), 2-dicyclohexylphosphine-2',6'-dimethoxybiphenyl (0.15 g, 0.38 mmol) and sodium tert-butoxide (2.69 g, 27.95 mmol) were added to toluene (100 mL), and the resulting mixture was heated to 108° C. and stirred for 1 hour under the protection of nitrogen; then the resulting solution was cooled to room temperature, and washed with water and dried by adding magnesium sulfate and filtered. The resulting filtrate was concentrated under reduced pressure to remove the solvent; the crude product was purified by re-crystallization from a toluene system to obtain a white solid compound 6 (6.96 g, yield 54.2%), mass spectrum: m/z=689.3[M+H]$^+$.

Synthesis Examples 2 to 35

Other compounds were synthesize with reference to the method for synthesizing compound 6, with the difference that IM I-A-L1 was replaced by raw material 6, 4-aminobiphenyl was replaced by Raw Material 7, and 4-bromobiphenyl was replaced by Raw Material 8, and the main raw materials used, the compounds synthesized, the yield of the last step, and the mass spectrometry characterization results are shown in Table 4.

TABLE 4
| Synthesis Example | Raw Material 6 | Raw Material 7 | Raw Material 8 |
| --- | --- | --- | --- |
| 2 | 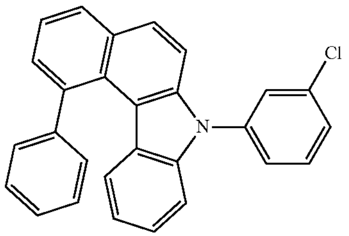 IM I-A-L2 | 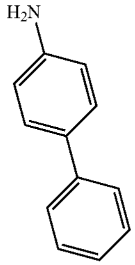 [SMILES: Nc1ccc(-c2ccccc2)cc1] | 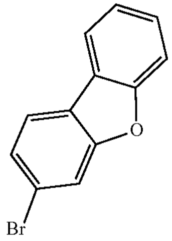 [SMILES: Brc1ccc2c(c1)oc1ccccc12] |
| 3 | 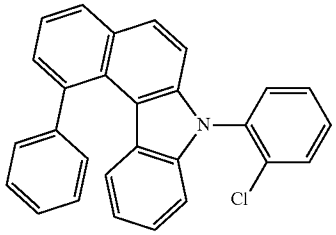 IM I-A-L3 | 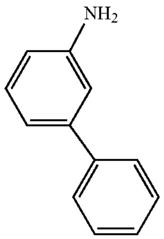 [SMILES: Nc1cccc(-c2ccccc2)c1] | 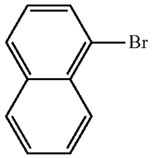 [SMILES: Brc1cccc2ccccc12] |
| 4 | 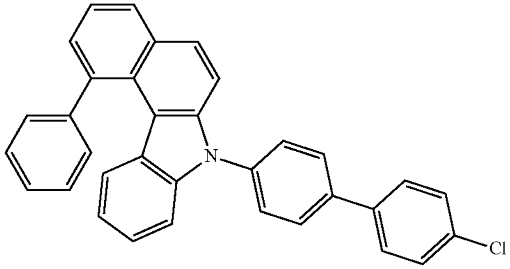 IM I-A-L4 | 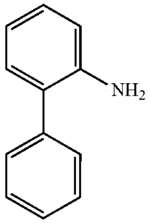 [SMILES: Nc1ccccc1-c1ccccc1] | 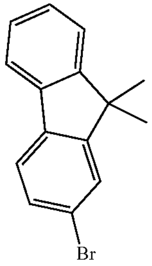 [SMILES: CC1(C)c2ccccc2-c2ccc(Br)cc21] |

TABLE 4-continued
| | | | |
|---|---|---|---|
| 5 | 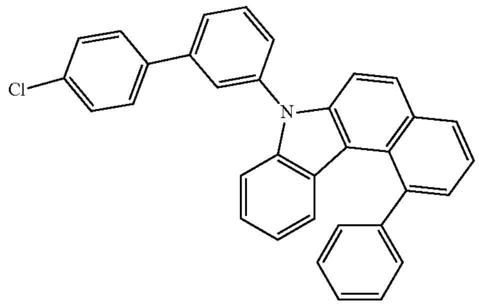 IM I-A-L5 | 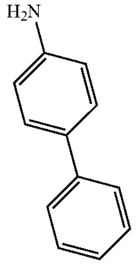 [SMILES: Nc1ccc(-c2ccccc2)cc1] | 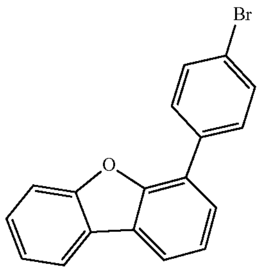 [SMILES: Brc1ccc(-c2cccc3c2oc2ccccc23)cc1] |
| 6 | 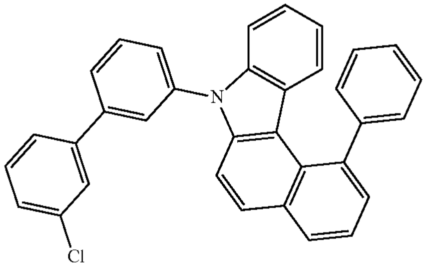 IM I-A-L6 | 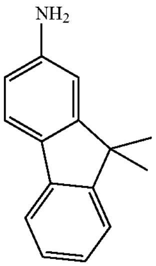 [SMILES: CC1(C)c2ccccc2-c2ccc(N)cc21] | 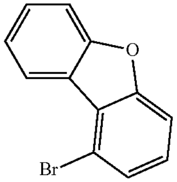 [SMILES: Brc1cccc2oc3ccccc3c12] |
| 7 | 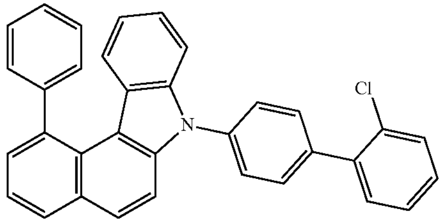 IM I-A-L7 | 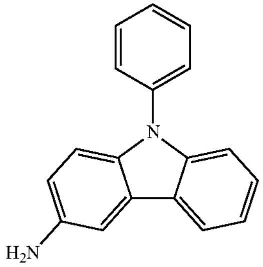 [SMILES: Nc1ccc2c(c1)c1ccccc1n2-c1ccccc1] | 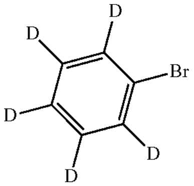 |

TABLE 4-continued
| | | | |
|---|---|---|---|
| 8 | 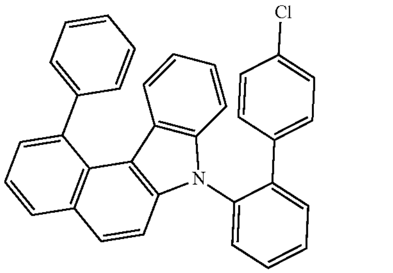<br>IM I-A-L8 | 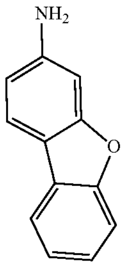 [SMILES: Nc1ccc2c(c1)oc1ccccc12] | 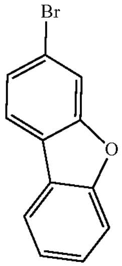 |
| 9 | 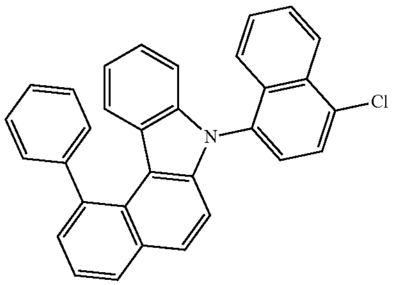<br>IM I-A-L9 | 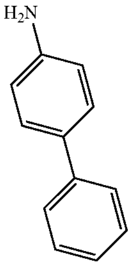 [SMILES: Nc1ccc(-c2ccccc2)cc1] | 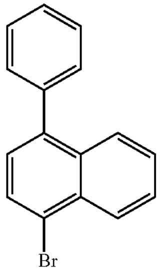 [SMILES: Brc1ccc(-c2ccccc2)c2ccccc12] |
| 10 | 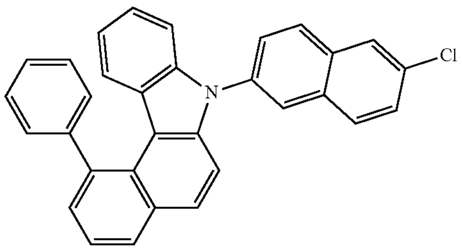<br>IM I-A-L10 | 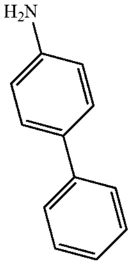 | 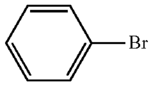 |

TABLE 4-continued
| | | | |
|---|---|---|---|
| 11 | 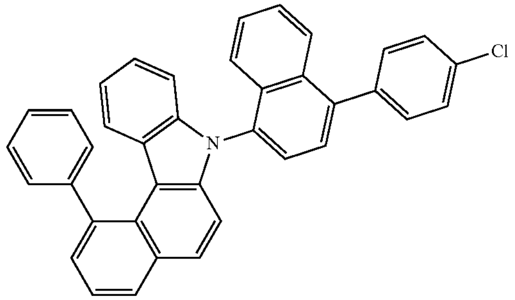<br>IM I-A-L11 | 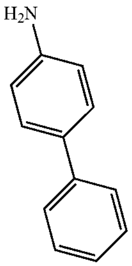 [SMILES: Nc1ccc(-c2ccccc2)cc1] | 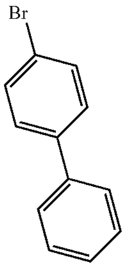 [SMILES: Brc1ccc(-c2ccccc2)cc1] |
| 12 | 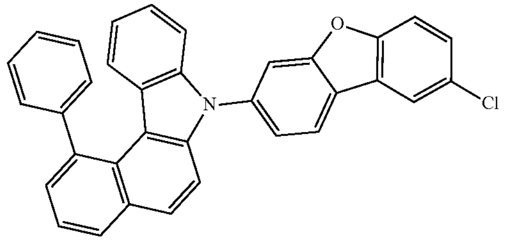<br>IM I-A-L12 | 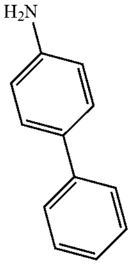 [SMILES: Nc1ccc(-c2ccccc2)cc1] | 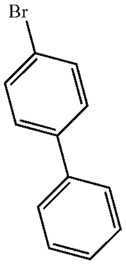 [SMILES: Brc1ccc(-c2ccccc2)cc1] |
| 13 | 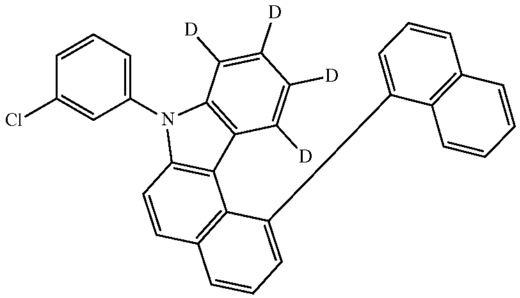<br>IM I-F-L1 | 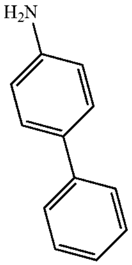 [SMILES: Nc1ccc(-c2ccccc2)cc1] | 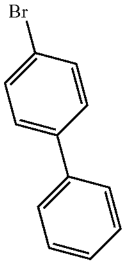 [SMILES: Brc1ccc(-c2ccccc2)cc1] |

TABLE 4-continued
| | | | |
|---|---|---|---|
| 14 | 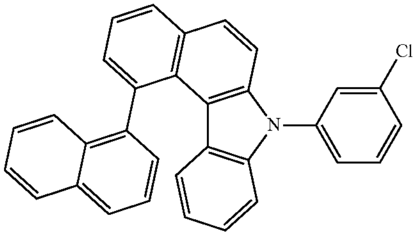 IM I-B-L1 | 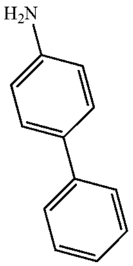 | 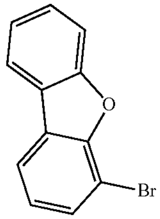 [SMILES: Brc1cccc2c1oc1ccccc12] |
| 15 | 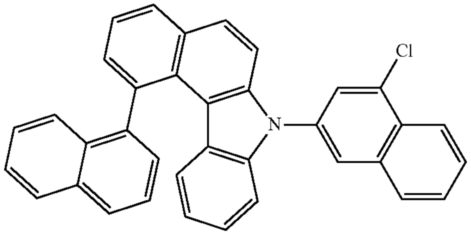 IM I-B-L2 | 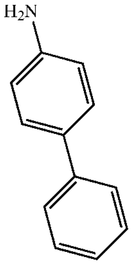 [SMILES: Nc1ccc(-c2ccccc2)cc1] | 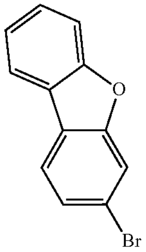 |
| 16 | 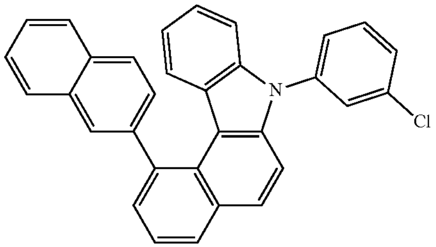 IM I-C-L1 | 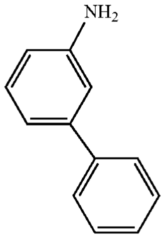 [SMILES: Nc1cccc(-c2ccccc2)c1] | 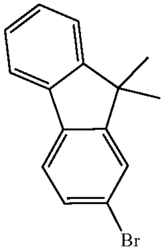 [SMILES: CC1(C)c2ccccc2-c2ccc(Br)cc21] |

TABLE 4-continued
| | | | |
|---|---|---|---|
| 17 | 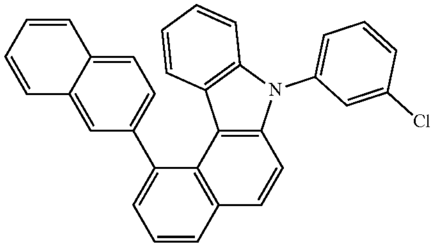<br>IM I-C-L1 | 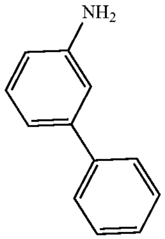 [SMILES: Nc1cccc(-c2ccccc2)c1] | 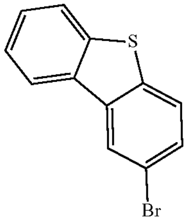 [SMILES: Brc1ccc2sc3ccccc3c2c1] |
| 18 | 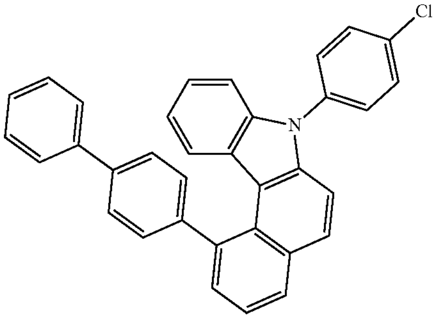<br>IM I-D-L1 | 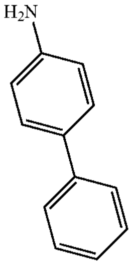 [SMILES: Nc1ccc(-c2ccccc2)cc1] | 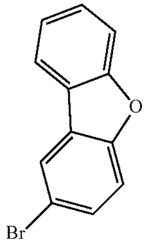 |
| 19 | 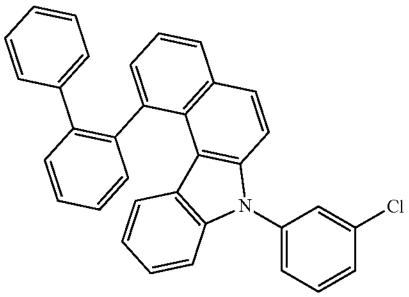<br>IM I-E-L1 | 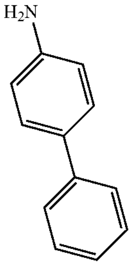 | 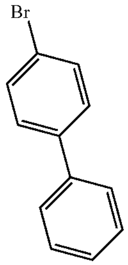 [SMILES: Brc1ccc(-c2ccccc2)cc1] |

TABLE 4-continued
| | | | |
|---|---|---|---|
| 20 | 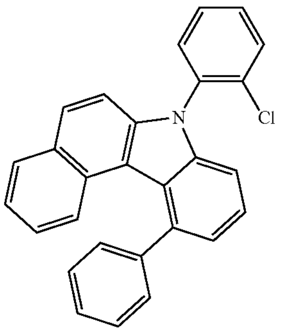<br>IM I-f-L1 | 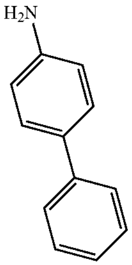 [SMILES: Nc1ccc(-c2ccccc2)cc1] | 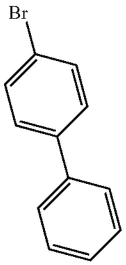 [SMILES: Brc1ccc(-c2ccccc2)cc1] |
| 21 | 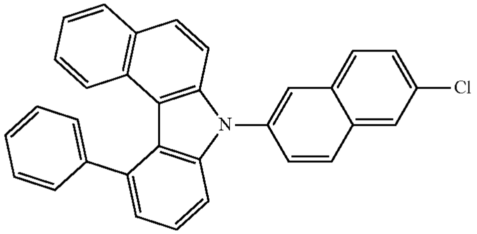<br>IM I-f-L2 | 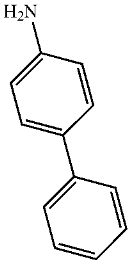 [SMILES: Nc1ccc(-c2ccccc2)cc1] | 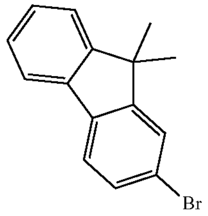 [SMILES: CC1(C)c2ccccc2-c2ccc(Br)cc21] |
| 22 | 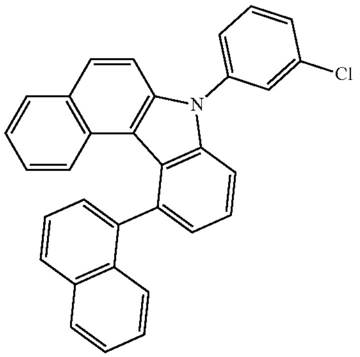<br>IM I-g-L1 | 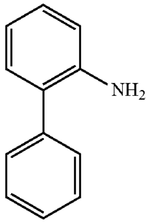 [SMILES: Nc1ccccc1-c1ccccc1] | 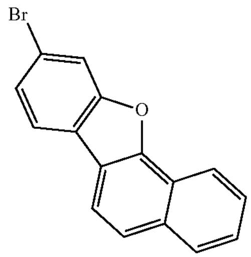 [SMILES: Brc1ccc2c(c1)oc1c3ccccc3ccc21] |

TABLE 4-continued
| | | | |
|---|---|---|---|
| 23 | 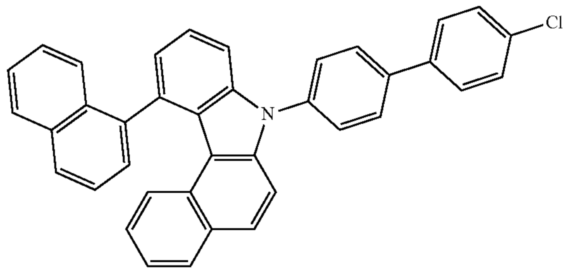<br>IM I-g-L2 | 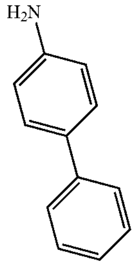 [SMILES: Nc1ccc(-c2ccccc2)cc1] | 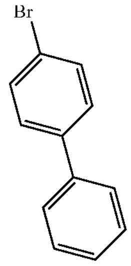 [SMILES: Brc1ccc(-c2ccccc2)cc1] |
| 24 | 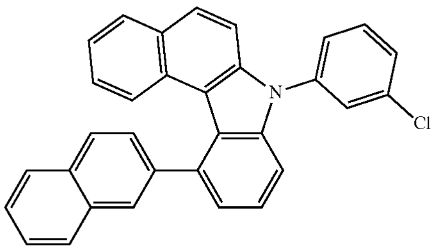<br>IM I-h-L1 | 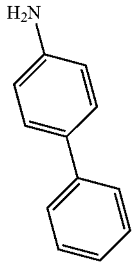 [SMILES: Nc1ccc(-c2ccccc2)cc1] | 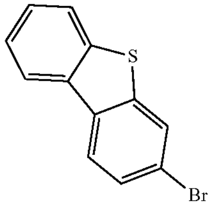 [SMILES: Brc1ccc2c(c1)sc1ccccc12] |
| 25 | 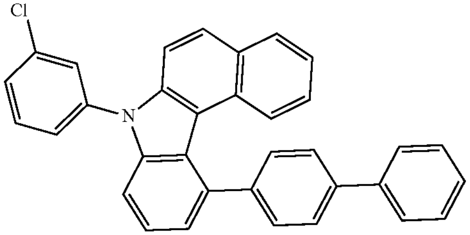<br>IM I-i-L1 | 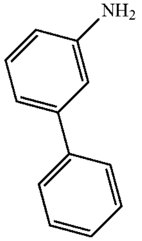 [SMILES: Nc1cccc(-c2ccccc2)c1] | 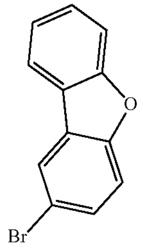 |

TABLE 4-continued
| | | | |
|---|---|---|---|
| 26 | 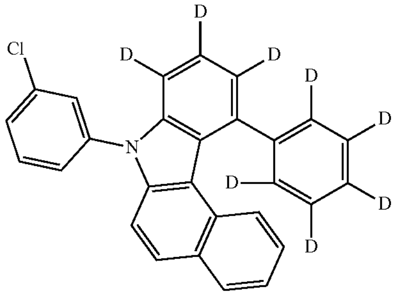<br>IM I-j-L1 | 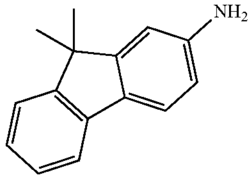 [SMILES: CC1(C)c2ccccc2-c2ccc(N)cc21] | 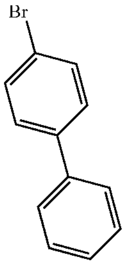 [SMILES: Brc1ccc(-c2ccccc2)cc1] |
| 27 | 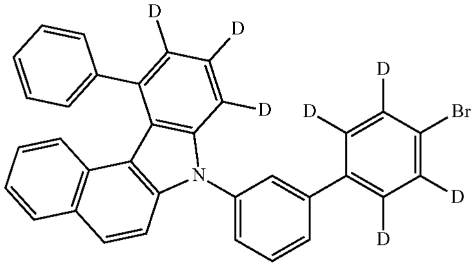<br>IM I-k-L1 | 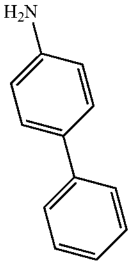 [SMILES: Nc1ccc(-c2ccccc2)cc1] | 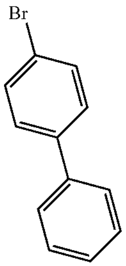 [SMILES: Brc1ccc(-c2ccccc2)cc1] |
| 28 | 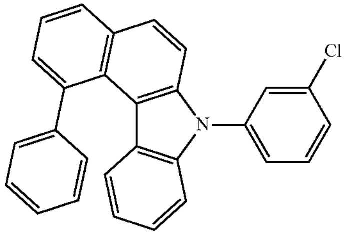<br>IM I-A-L2 | 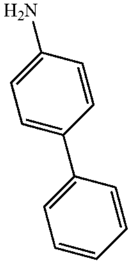 [SMILES: Nc1ccc(-c2ccccc2)cc1] | 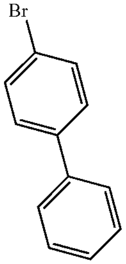 [SMILES: Brc1ccc(-c2ccccc2)cc1] |

TABLE 4-continued
| | | | |
|---|---|---|---|
| 29 | 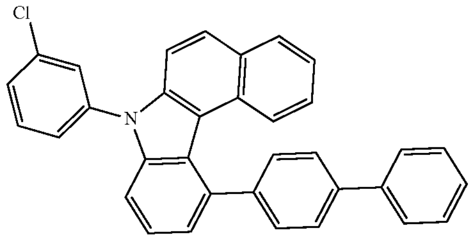 IM I-D-L2 | 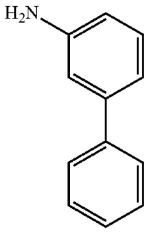 [SMILES: Nc1cccc(-c2ccccc2)c1] | 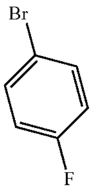 |
| 30 | 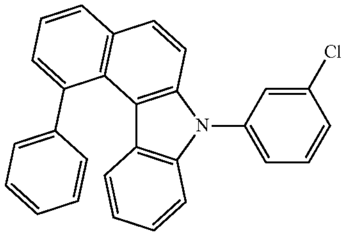 IM I-A-L2 | 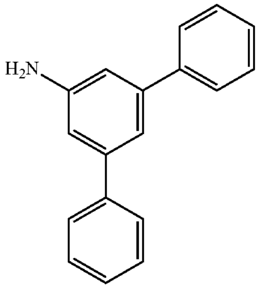 [SMILES: Nc1cc(-c2ccccc2)cc(-c2ccccc2)c1] | 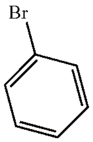 |
| 31 | 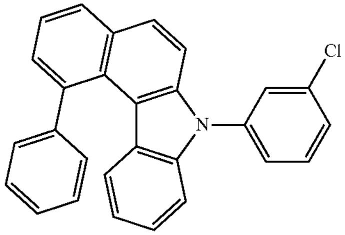 IM I-A-L2 | 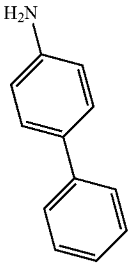 [SMILES: Nc1ccc(-c2ccccc2)cc1] | 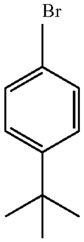 |

TABLE 4-continued
| | | | |
|---|---|---|---|
| 32 | 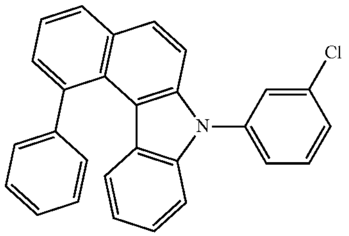 IM I-A-L2 | 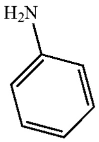 | 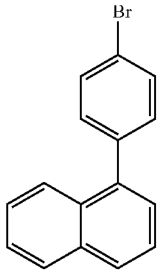 [SMILES: Brc1ccc(-c2cccc3ccccc23)cc1] |
| 33 | 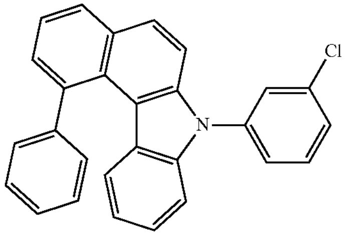 IM I-A-L2 | 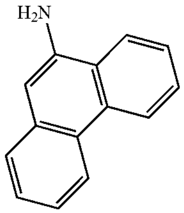 [SMILES: Nc1cc2ccccc2c2ccccc12] | 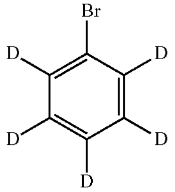 [SMILES: [2H]c1c([2H])c([2H])c(Br)c([2H])c1[2H]] |
| 34 | 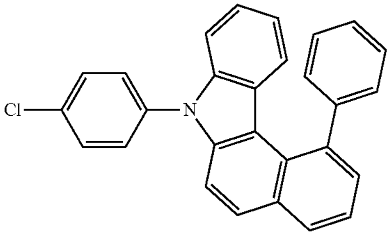 IM I-A-L1 | 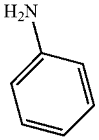 | 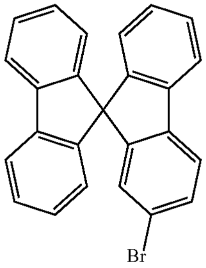 [SMILES: Brc1ccc2c(c1)C1(c3ccccc3-c3ccccc31)c1ccccc1-2] |

TABLE 4-continued
| | | | |
|---|---|---|---|
| 35 | 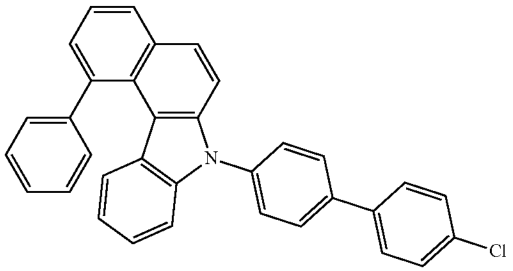<br>IM I-A-L4 | 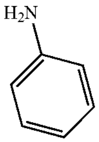 | 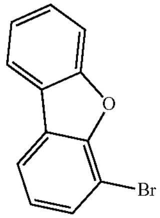 [SMILES: Brc1cccc2c1oc1ccccc12] |
| Synthesis Example | Compound | Yield/% | Mass Spectrometry m/z $[M + H]^+$ |
| 2 | 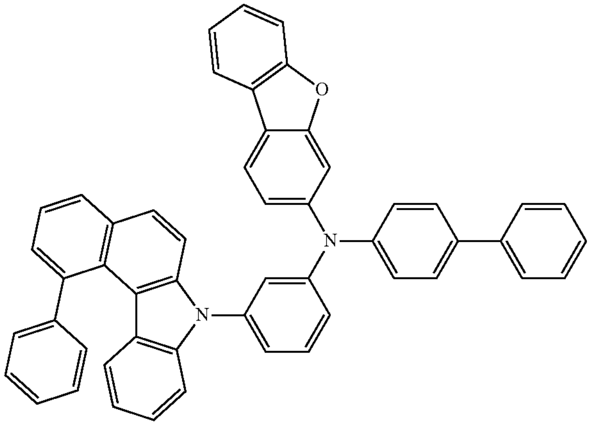<br>27 | 42.3 | 703.3 |

TABLE 4-continued
| | | | |
|---|---|---|---|
| 3 | 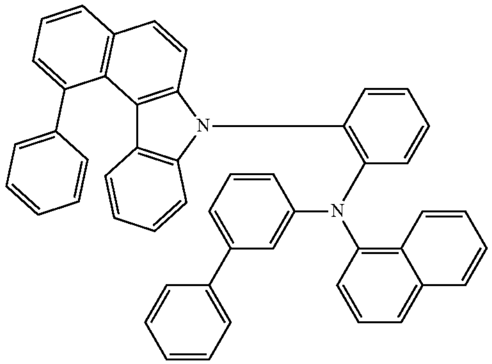 44 | 46.7 | 663.3 |
| 4 | 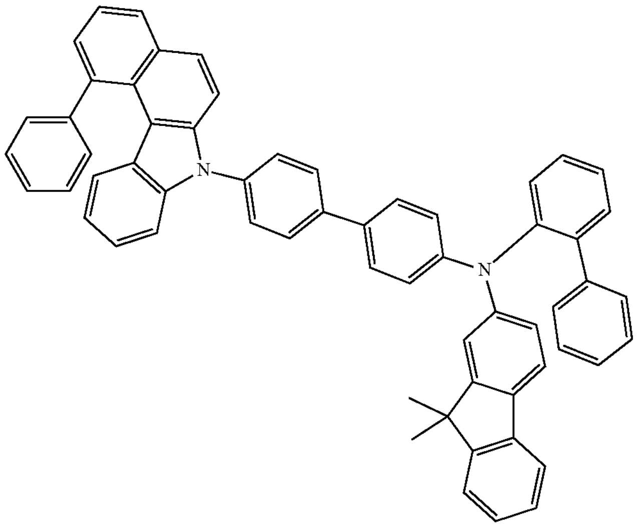 64 | 47.9 | 805.4 |

TABLE 4-continued
| | | | |
|---|---|---|---|
| 5 | 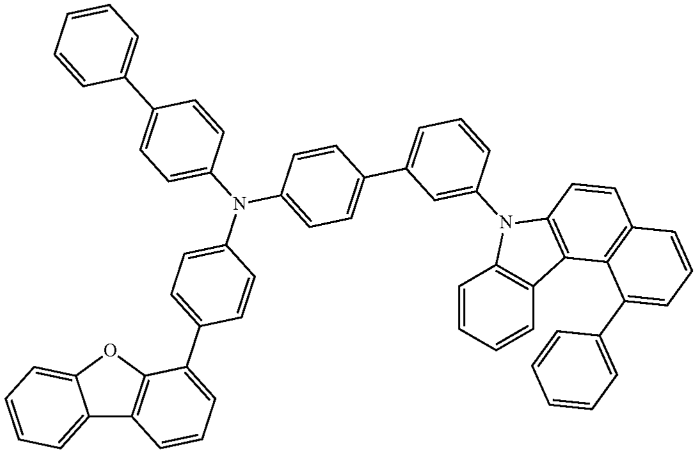<br>80 | 50.2 | 855.3 |
| 6 | 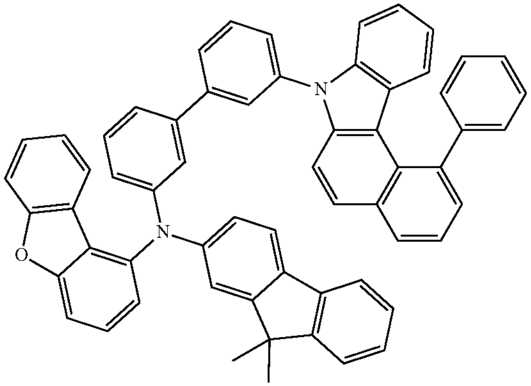<br>94 | 39.8 | 819.3 |

TABLE 4-continued
| | | | |
|---|---|---|---|
| 7 | 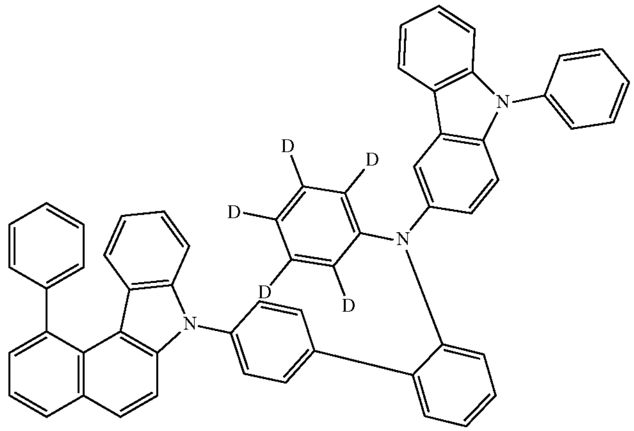<br>99 | 42.7 | 783.4 |
| 8 | 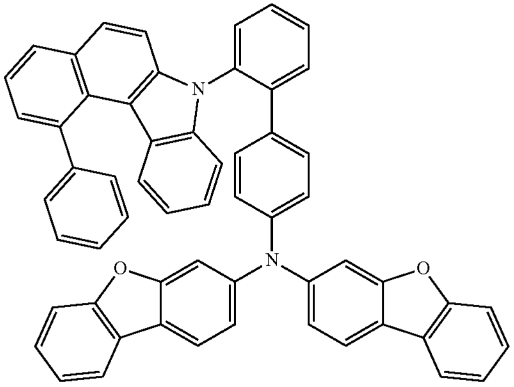<br>101 | 56.1 | 793.4 |

TABLE 4-continued
| | | | |
|---|---|---|---|
| 9 | 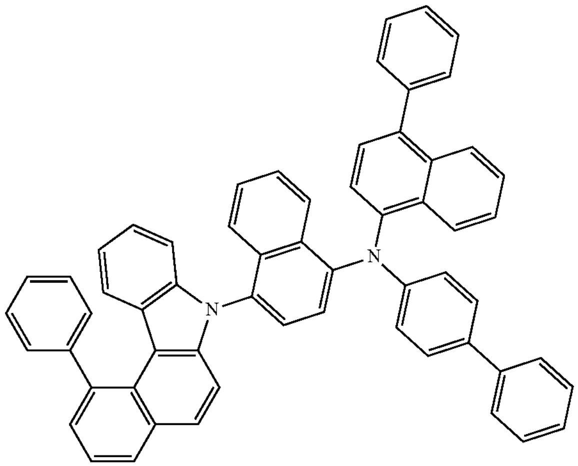 123 | 49.4 | 789.3 |
| 10 | | 52.8 | 663.3 |
| 11 | | 51.6 | 815.3 |
| 12 | | 43.9 | 779.3 |
| 13 | | 46.7 | 743.3 |
| 14 | | 55.6 | 753.3 |
| 15 | | 51.9 | 803.3 |
| 16 | | 59.5 | 779.3 |
| 17 | | 56.8 | 769.3 |

TABLE 4-continued
| | | | |
|---|---|---|---|
| 18 | 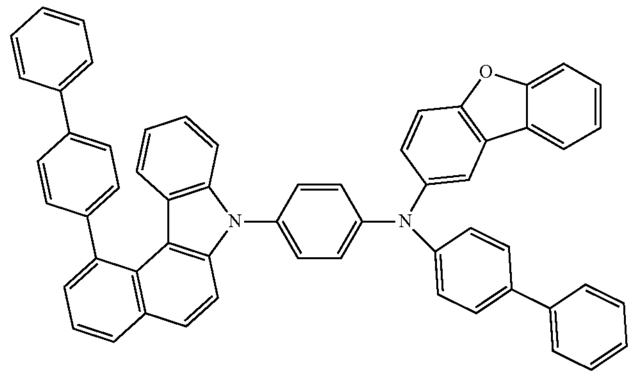 210 | 60.1 | 779.3 |
| 19 | 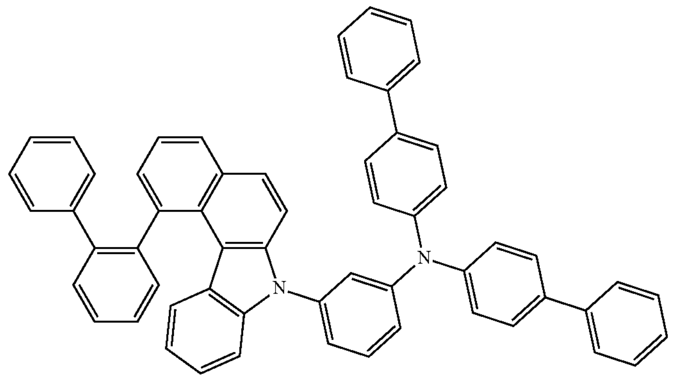 224 | 59.2 | 765.3 |

TABLE 4-continued
| | | | |
|---|---|---|---|
| 20 | 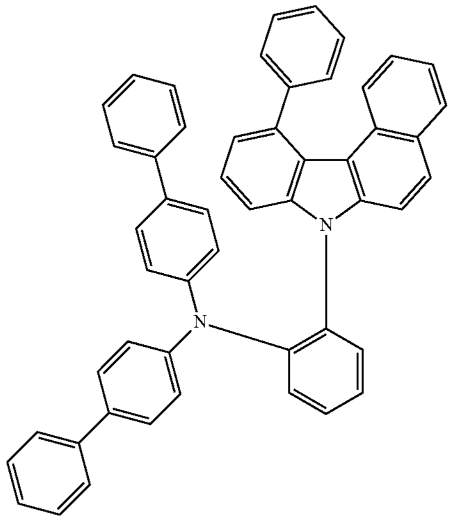 [SMILES: c1ccc(-c2ccc(N(c3ccc(-c4ccccc4)cc3)c3ccccc3-n3c4cccc(-c5ccccc5)c4c4c5ccccc5ccc43)cc2)cc1] | 42.0 | 689.3 |
| 21 | 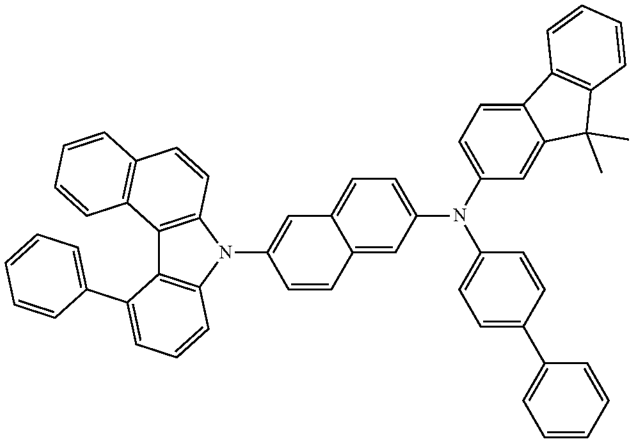 | 42.3 | 779.3 |
275

TABLE 4-continued
| | | | |
|---|---|---|---|
| 22 | 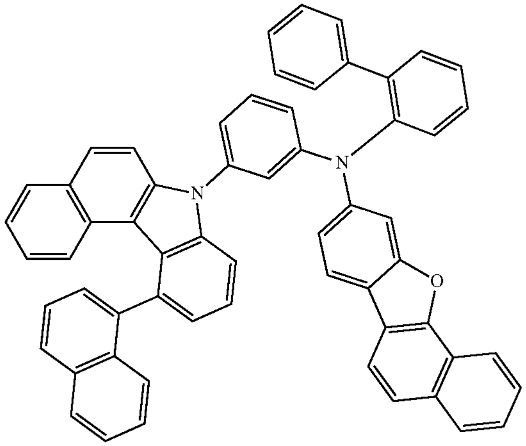<br>285 | 46.7 | 803.3 |
| 23 | 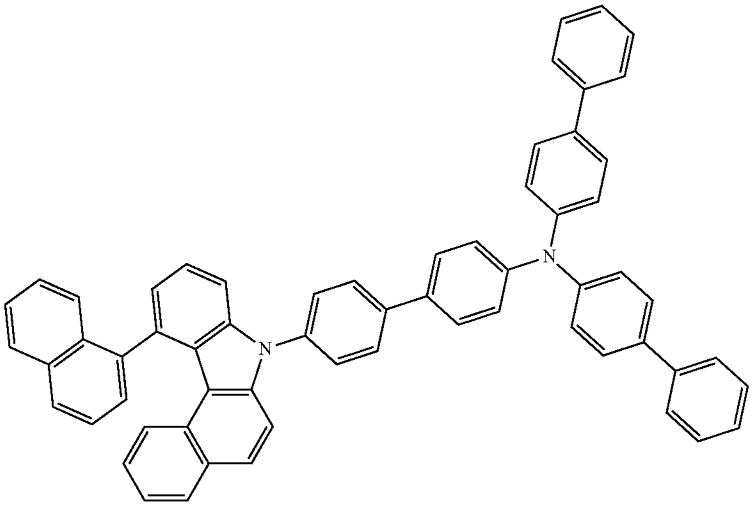<br>300 | 47.9 | 815.3 |

TABLE 4-continued
| | | | |
|---|---|---|---|
| 24 | 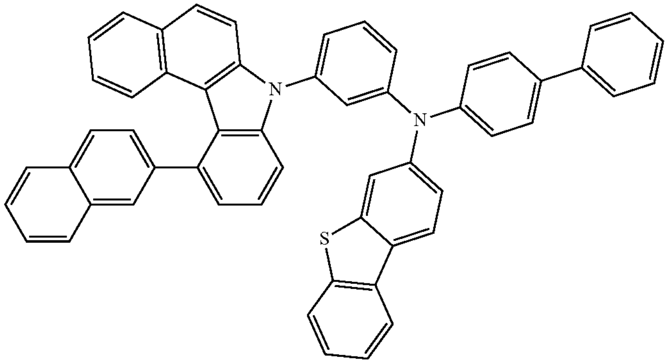 320 | 50.2 | 769.3 |
| 25 | 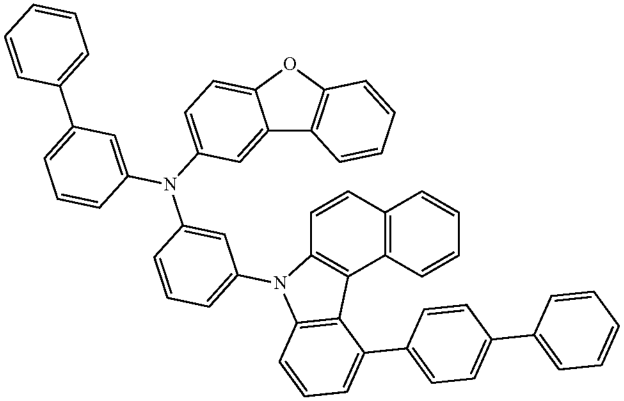 353 | 39.8 | 779.3 |

TABLE 4-continued
| | | | |
|---|---|---|---|
| 26 | 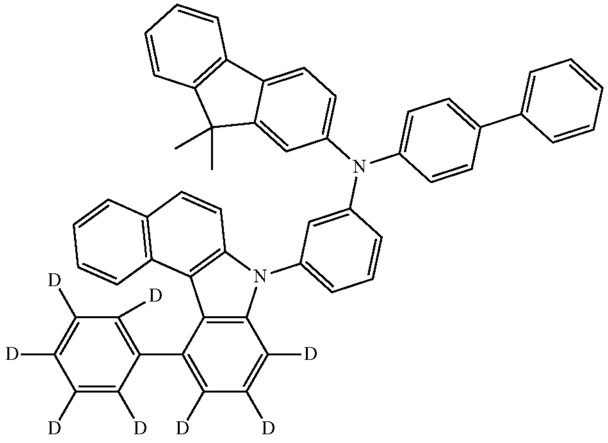<br>383 | 63.5 | 737.4 |
| 27 | 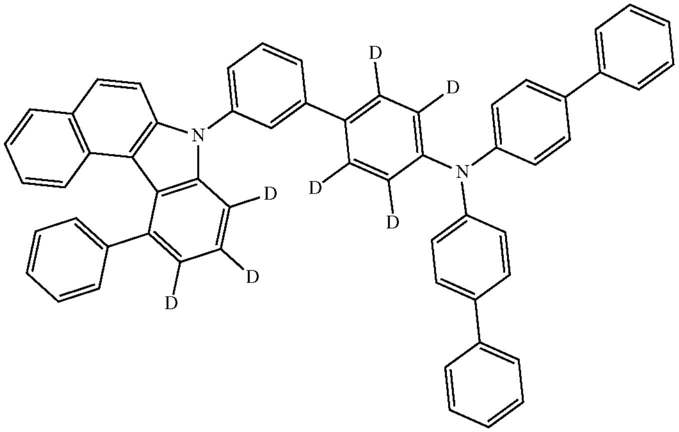<br>390 | 46.3 | 772.4 |

TABLE 4-continued
| | | | |
|---|---|---|---|
| 28 | 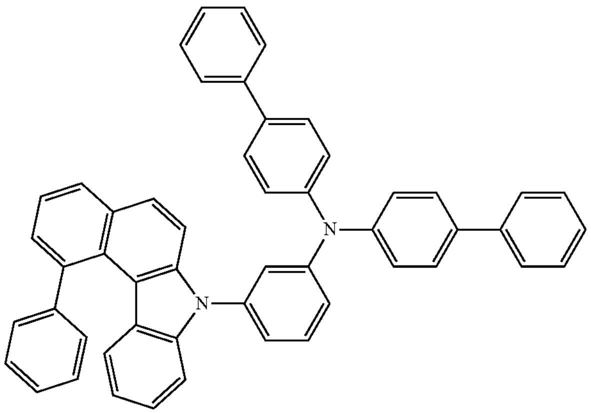 26 | 44.9 | 689.3 |
| 29 | 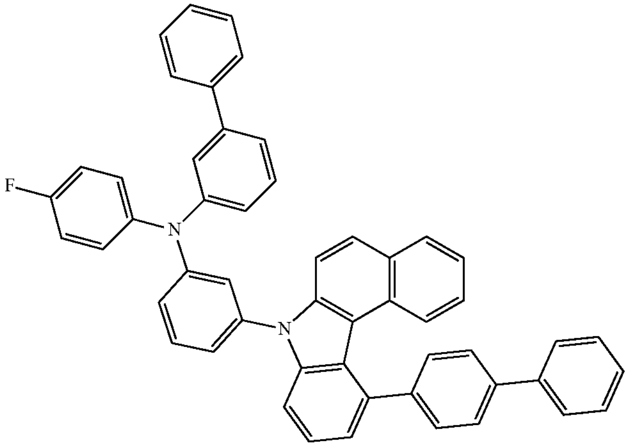 11 | 51.1 | 707.3 |

TABLE 4-continued
| | | | |
|---|---|---|---|
| 30 | 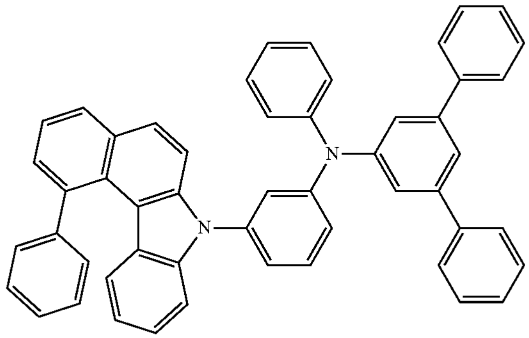 12 | 41.8 | 689.3 |
| 31 | 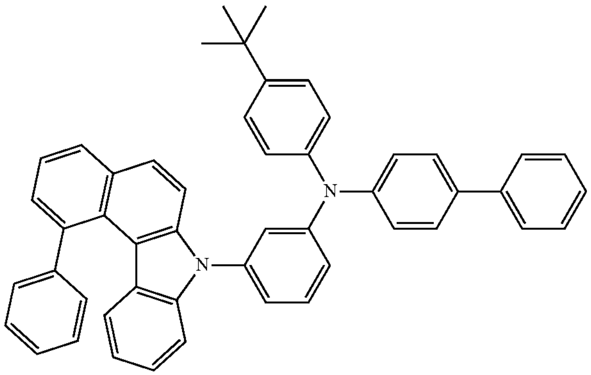 13 | 43.2 | 669.3 |

TABLE 4-continued
| | | | |
|---|---|---|---|
| 32 | 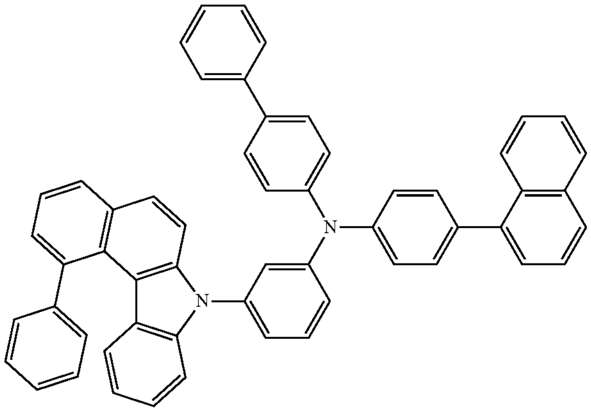<br>35 | 42.0 | 739.3 |
| 33 | 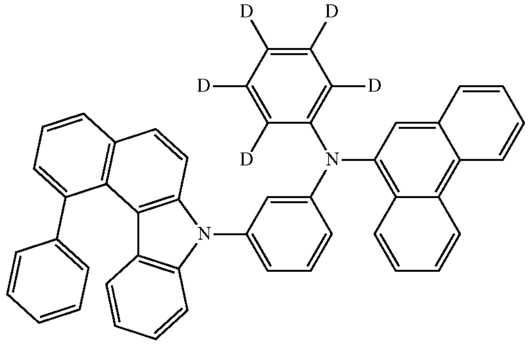<br>14 | 39.7 | 642.3 |

TABLE 4-continued
| | | | |
|---|---|---|---|
| 34 | 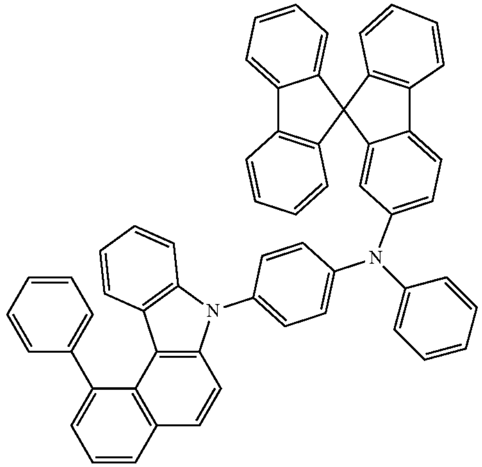 9 | 44.8 | 775.3 |
| 35 | 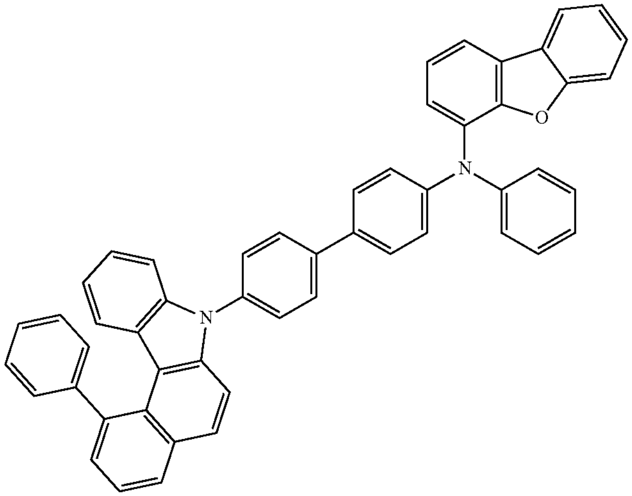 66 | 43.6 | 703.3 |

The NMR data of some compounds are shown in Table 5.

TABLE 5

| Compound | NMR data $^1$H-NMR (400 MHZ, $CD_2Cl_2$) δ ppm |
|---|---|
| Compound 6 | 8.28 (d, 1H),7.92 (d, 1H), 7.78 (d, 1H), 7.68-7.64 (m, 2H), 7.62 (d, 2H), 7.69-7.58 (m, 8H), 7.52 (d, 1H), 7.49-7.45 (m, 2H), 7.43-7.39 (m, 7H), 7.37-7.3 4 (m, 2H), 7.24 (t, 1H), 7.12 (d, 2H), 7.04 (d, 2H), 6.92 (d, 4H). |
| Compound 80 | 8.16 (d, 1H), 8.02 (d, 1H), 7.98 (d, 1H), 7.88 (d, 1H), 7.79-7.75 (m, 2H), 7.72 (d, 1H), 7.69-7.64 (m, 4H), 7.62-7.58 (m, 5H), 7.55-7.47 (m, 9H), 7.46-7.42 (m, 4H), 7.39-7.34 (m, 5H), 7.30 (d, 1H), 7.21 (t, 1H), 7.08-7.04 (m, 4H), 6.94 (d, 2H). |
| Compound 320 | 8.21 (d, 1H), 8.07-8.02 (m, 3H), 7.98-7.92 (m, 5H), 7.89-7.85 (m, 2H), 7.68 (s, 1H), 7.65-7.62 (m, 1H), 7.58-7.50 (m, 9H), 7.46-7.42 (m, 4H), 7.39-7.32 (m, 5H), 7.09 (d, 1H), 6.98 (d, 2H), 6.95 (d, 1H), 6.93 (s, 1H). |

Examples of Fabrication and Evaluation of Organic Electroluminescent Devices

Example 1: Blue Organic Electroluminescent Device

Preparing anode of the device: A glass substrate coated with ITO/Ag/ITO three-layer materials (with a thicknesses of 70 Å, 1000 Å, and 100 Å, respectively) was cut to dimensions of 40 mm×40 mm×0.7 mm, and then fabricated, by a photoetching process, into an experimental substrate with a cathode, an anode, and patterns of an insulation layer, and the surface was first cleaned by using ultrapure water and isopropanol to clean the pollutants on the surface of the substrate; then 02: $N_2$ plasma gas was used to treat the surface of the substrate.

Compound F4-TCNQ was deposited on the experimental substrate (anode) to form a hole injection layer (HIL) with a thickness of 100 Å, and HT-1 was deposited on the surface of the hole injection layer to form a first hole transport layer (HTL-1) with a thickness of 950 Å.

Compound 6 was deposited by vacuum evaporation on the first hole transport layer to form a second hole transport layer (HTL-2) with a thickness of 50 Å.

On the second hole transport layer, the compounds BD-1 and BH-1 were deposited at a weight ratio of 2%:98% to form an organic light emitting layer (EML) with a thickness of 200 Å.

On the organic light emitting layer, the compounds ET-1 and LiQ were co-deposited at a weight ratio of 1:1 to form an electron transport layer (ETL) with a thickness of 350 Å.

Ytterbium (Yb) was deposited on the electron transport layer to form an electron injection layer (EIL) with a thickness of 20 Å.

On the electron injection layer, magnesium (Mg) and silver (Ag) were co-deposited at a weight ratio of 1:9 to form a cathode with a thickness of 130 Å.

Finally, CP-05 was deposited on the above cathode to form an organic coating layer (CPL) with a thickness of 750 Å, thereby completing the preparation of the organic light emitting device.

Examples 2 to 35

Organic electroluminescent devices were fabricated by the same method as used in Example 1, except that Compound 6 in Example 1 was replaced by the Compounds shown in Table 6 (column "HTL-2") when a second hole transport layer was formed.

Comparative Examples 1 to 4

Organic electroluminescent devices were fabricated respectively by the same method as used in Example 1, except that Compound 6 in Example 1 was replaced by Compound A, Compound B, Compound C and Compound D respectively when a second hole transport layer was formed.

Structures of the main materials used in the Examples and Comparative Examples are as follows:

F4-TCNQ

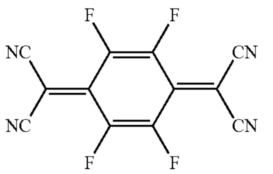

HT-1

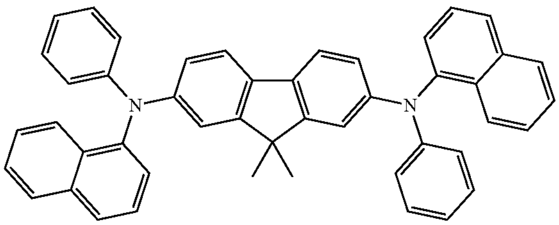

BH-1

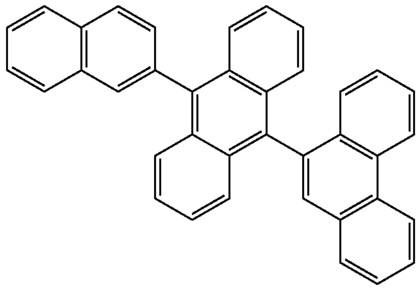

BD-1

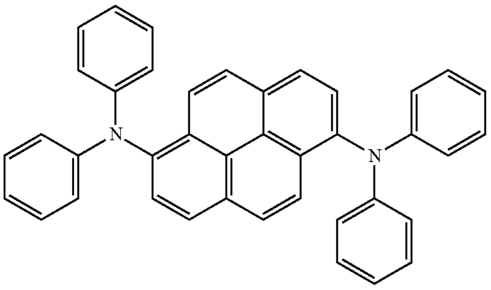

LiQ

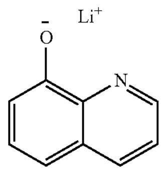

-continued

ET-1

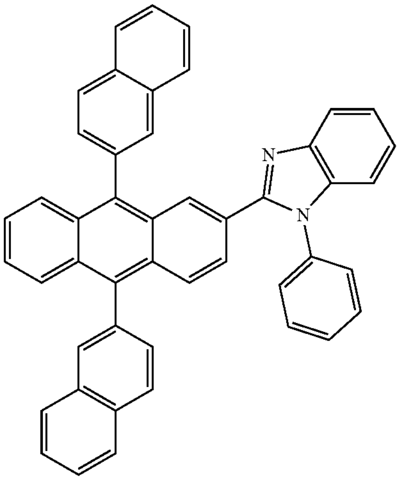

CP-05

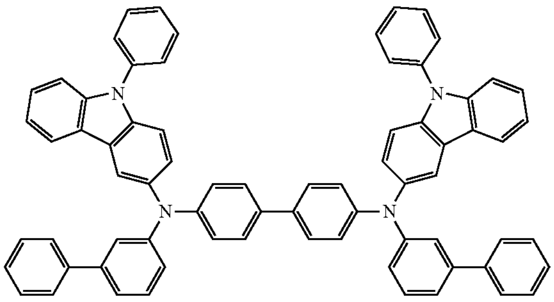

Compound A

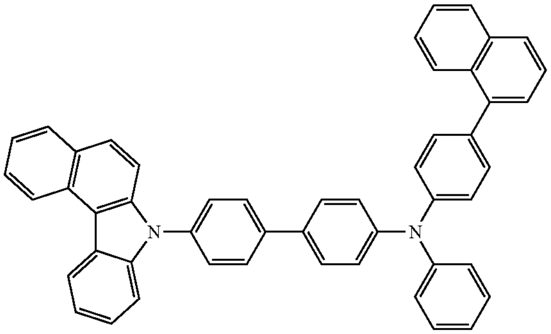

-continued

Compound B

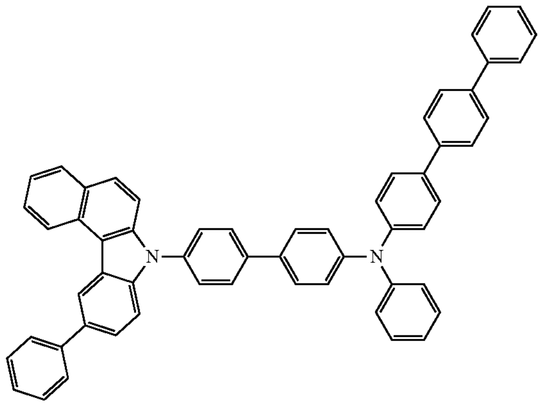

Compound C

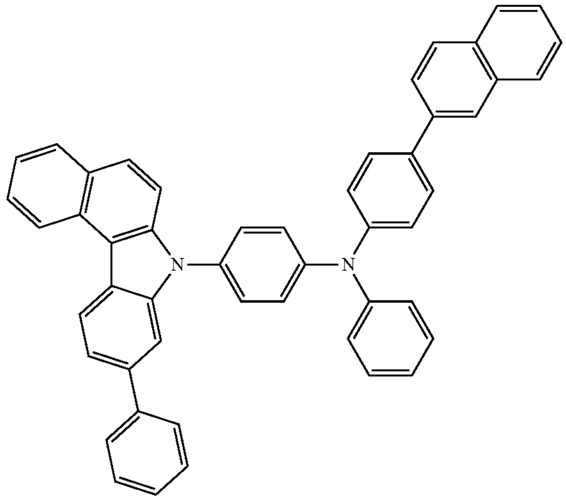

Compound D

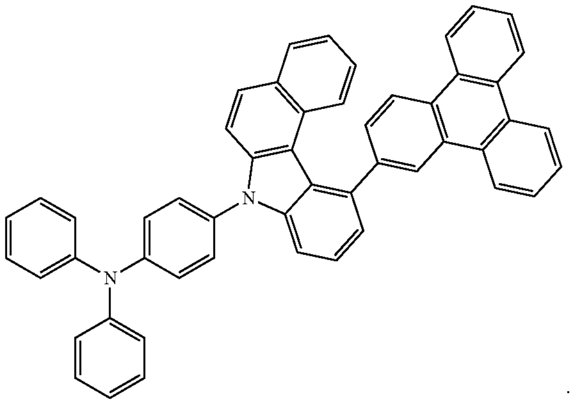

.

The organic electroluminescent devices fabricated in Examples 1 to 35 and Comparative Examples 1 to 4 were tested for their performance. Specifically, the IVL characteristics of the devices were tested under the condition of 10 $mA/cm^2$, and the $T_{95}$ lifetime of the devices was tested under the condition of 15 $mA/cm^2$. Test results are shown in Table 6.

TABLE 6

| NO. | HTL-2 | Operating Voltage (V) | Luminescence Efficiency Cd/A | Color Coordinate CIEy | $T_{95}$ Lifetime (h) |
|---|---|---|---|---|---|
| Example 1 | Compound 6 | 4.00 | 5.97 | 0.05 | 178 |
| Example 2 | Compound 27 | 3.97 | 6.21 | 0.05 | 182 |
| Example 3 | Compound 44 | 3.95 | 6.19 | 0.05 | 174 |
| Example 4 | Compound 64 | 3.97 | 6.23 | 0.05 | 181 |
| Example 5 | Compound 80 | 4.01 | 6.11 | 0.05 | 166 |
| Example 6 | Compound 66 | 3.98 | 6.23 | 0.05 | 171 |
| Example 7 | Compound 94 | 3.79 | 6.10 | 0.05 | 178 |
| Example 8 | Compound 99 | 3.93 | 6.04 | 0.05 | 168 |
| Example 9 | Compound 101 | 3.93 | 6.13 | 0.05 | 174 |
| Example 10 | Compound 123 | 4.00 | 6.18 | 0.05 | 184 |
| Example 11 | Compound 129 | 3.96 | 6.04 | 0.05 | 175 |
| Example 12 | Compound 131 | 4.00 | 6.07 | 0.05 | 187 |
| Example 13 | Compound 395 | 4.06 | 5.89 | 0.05 | 177 |
| Example 14 | Compound 366 | 3.92 | 6.12 | 0.05 | 182 |
| Example 15 | Compound 148 | 4.01 | 6.03 | 0.05 | 184 |
| Example 16 | Compound 173 | 3.92 | 6.30 | 0.05 | 173 |
| Example 17 | Compound 184 | 3.91 | 6.11 | 0.05 | 176 |
| Example 18 | Compound 193 | 3.99 | 5.99 | 0.05 | 172 |
| Example 19 | Compound 210 | 3.93 | 6.20 | 0.05 | 167 |
| Example 20 | Compound 224 | 3.94 | 6.04 | 0.05 | 172 |
| Example 21 | Compound 12 | 3.91 | 6.06 | 0.05 | 167 |
| Example 22 | Compound 13 | 3.95 | 5.98 | 0.05 | 170 |
| Example 23 | Compound 35 | 3.86 | 6.12 | 0.05 | 176 |
| Example 24 | Compound 14 | 3.89 | 5.97 | 0.05 | 182 |
| Example 25 | Compound 9 | 3.86 | 5.98 | 0.05 | 174 |
| Example 26 | Compound 26 | 3.85 | 6.19 | 0.05 | 173 |
| Example 27 | Compound 258 | 3.92 | 5.99 | 0.05 | 184 |
| Example 28 | Compound 275 | 3.81 | 5.87 | 0.05 | 176 |
| Example 29 | Compound 285 | 3.87 | 5.94 | 0.05 | 172 |
| Example 20 | Compound 300 | 3.89 | 5.79 | 0.05 | 176 |
| Example 31 | Compound 320 | 3.83 | 6.01 | 0.05 | 175 |
| Example 32 | Compound 353 | 3.86 | 5.68 | 0.05 | 179 |
| Example 33 | Compound 383 | 3.88 | 5.76 | 0.05 | 172 |
| Example 34 | Compound 390 | 3.89 | 5.88 | 0.05 | 182 |
| Example 35 | Compound 11 | 3.87 | 5.93 | 0.05 | 177 |
| Comparative Example 1 | Compound A | 4.10 | 4.42 | 0.05 | 107 |
| Comparative Example 2 | Compound B | 4.11 | 4.35 | 0.05 | 132 |
| Comparative Example 3 | Compound C | 4.13 | 4.61 | 0.05 | 128 |
| Comparative Example 4 | Compound D | 4.08 | 4.29 | 0.05 | 116 |

As can be seen from Table 6 above, compared with the organic electroluminescent devices prepared in Comparative Examples 1 to 4, performance of the organic electroluminescent devices prepared in Examples 1 to 35 using the nitrogen-containing compound of the present disclosure as the second hole transport layer material are improved, mainly as the luminescence efficiency of the device is increased by at least 23.2%, and the $T_{95}$ lifetime is prolonged by at least 25.8%.

According to the test results of Comparative Example 4, it can be seen that compared to the triphenylene aryl with a large conjugation plane, the small structure aryl is connected at the position a or position b of

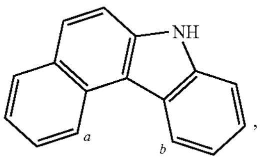 [SMILES: c1ccc2c(c1)ccc1[nH]c3ccccc3c12]

which increases the distortion of molecule in the spatial structure. Therefore, the material can maintain a high degree of amorphousness during the device manufacturing process, thereby improving the lifetime of the OLED device.

In summary, when the compound of the present disclosure is used as a second hole transport layer material to prepare an organic electroluminescent device, it can effectively prolong the lifetime of the organic electroluminescent device and improve the luminescence efficiency of the organic electroluminescent device.

The preferred embodiments of the present disclosure have been described in detail above with reference to the accompanying drawings. However, the present disclosure is not limited to the specific details of the above-mentioned embodiments. Within the scope of the technical concept of the present disclosure, various simple modifications can be made to the technical solution of the present disclosure. These simple modifications all belong to the protection scope of this disclosure. In addition, it should be noted that each of the specific technical features described in the above-mentioned specific embodiments can be combined in any suitable manner without conflict. In order to avoid unnecessary repetition, this disclosure describes various possible combinations. The combination method will not be further explained.

What is claimed is:

1. A nitrogen-containing compound having a structure shown in the following Formula 1:

Formula 1

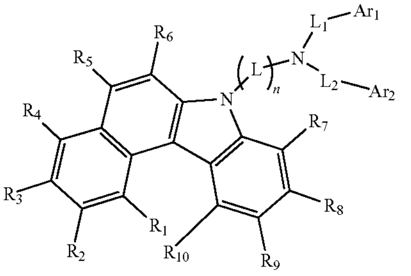

wherein, $R_2$ to $R_9$ are identical or different, and each is independently hydrogen or deuterium;

$R_1$ and $R_{10}$ are identical or different, and each is independently selected from hydrogen, deuterium, and group A, and only one of $R_1$ and $R_{10}$ is selected from group A, and the group A is selected from an aryl having 6 to 12 carbon atoms, and a deuterated aryl having 6 to 12 carbon atoms;

$Ar_1$ and $Ar_2$ are identical or different, and each is independently selected from a substituted or unsubstituted phenyl, a substituted or unsubstituted naphthyl, a substituted or unsubstituted biphenyl, a substituted or unsubstituted terphenyl, a substituted or unsubstituted phenanthryl, a substituted or unsubstituted anthryl, a substituted or unsubstituted fluorenyl, a substituted or unsubstituted dibenzofuranyl, a substituted or substituted dibenzothienyl, and a substituted or unsubstituted carbazolyl;

substituent(s) in $Ar_1$ and $Ar_2$ are each independently selected from deuterium, fluorine, cyano, methyl, ethyl, n-propyl, isopropyl, tert-butyl, phenyl, naphthyl, trideuteromethyl, trifluoromethyl, and trimethylsilyl; optionally, any two adjacent substituents form a benzene ring, or a fluorene ring;

each L is independently selected from a substituted or unsubstituted phenylene, a substituted or unsubstituted naphthylene, a substituted or unsubstituted biphenylene, a substituted or unsubstituted fluorenylene, a substituted or unsubstituted dibenzothienylene, a substituted or unsubstituted dibenzofuranylene, and a substituted or unsubstituted carbazolylene, n represents 1 or 2, and when n is 2, each L is identical or different;

substituent(s) in L are identical or different, and each is independently selected from deuterium, fluorine, cyano, methyl, ethyl, isopropyl, and tert-butyl;

$L_1$ and $L_2$ are identical or different, and each is independently selected from a single bond, a substituted or unsubstituted phenylene, and a substituted or unsubstituted naphthylene;

substituent(s) in $L_1$ and $L_2$ are identical or different, and each is independently selected from deuterium, fluorine, cyano, methyl, ethyl, isopropyl, tert-butyl, and phenyl.

2. The nitrogen-containing compound according to claim 1, wherein group A is selected from a deuterium-substituted or unsubstituted phenyl, a deuterium-substituted or unsubstituted naphthyl, and a deuterium-substituted or unsubstituted biphenyl.

3. The nitrogen-containing compound according to claim 1, wherein $Ar_1$ and $Ar_2$ are each independently selected from a substituted or unsubstituted group V, and the unsubstituted group V is selected from the following groups:

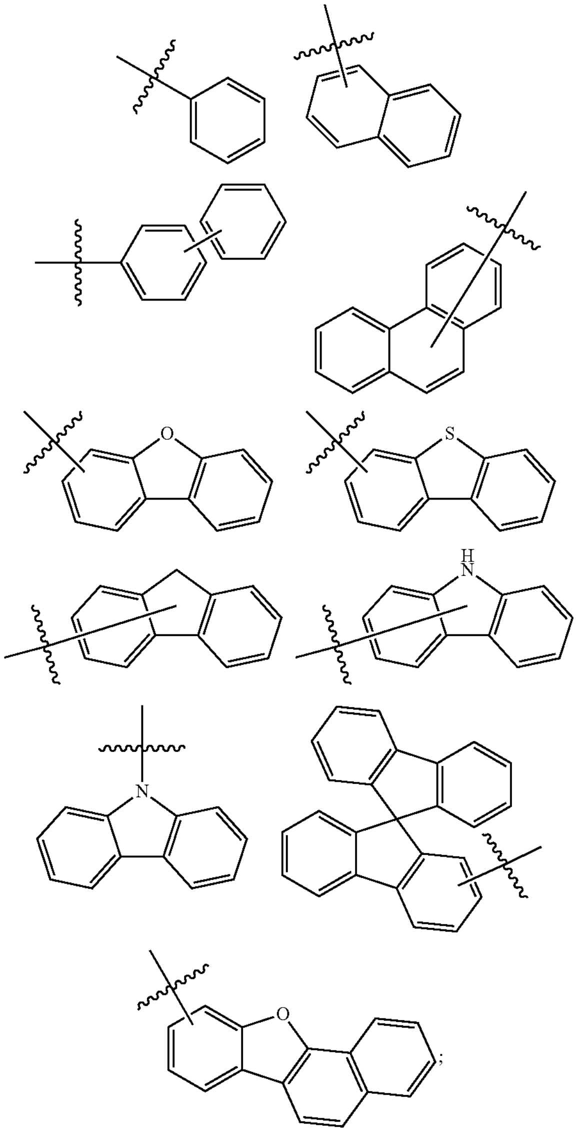

the substituted group V has one or more substituent(s), and each substituent is independently selected from deuterium, fluorine, cyano, methyl, ethyl, isopropyl, tert-butyl, trimethylsilyl, trideuteromethyl, trifluoromethyl, phenyl, and naphthyl.

4. The nitrogen-containing compound according to claim 1, wherein $Ar_1$ and $Ar_2$ are each independently selected from the group consisting of the following groups:

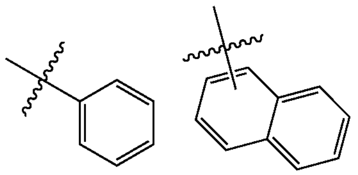

-continued

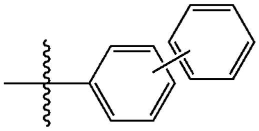

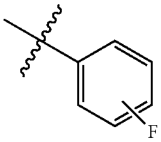

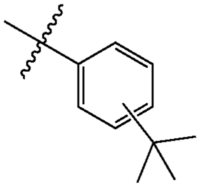

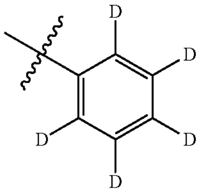

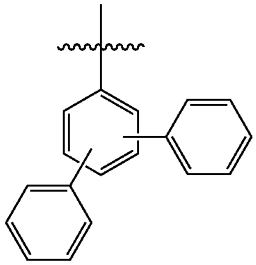

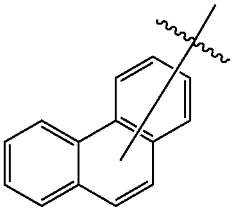

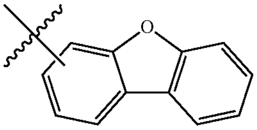

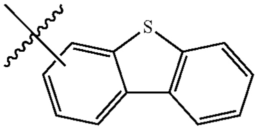

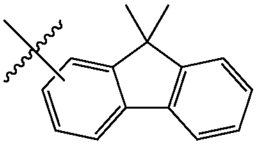

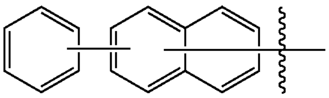

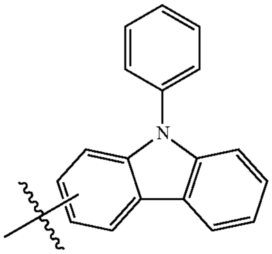

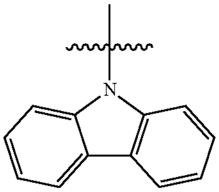

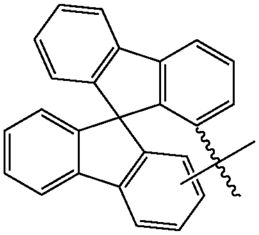

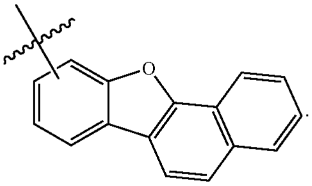

.

5. The nitrogen-containing compound according to claim 1, wherein each L is independently selected from the group consisting of the following groups:

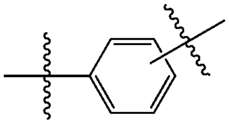

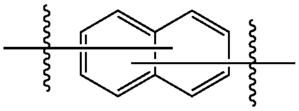

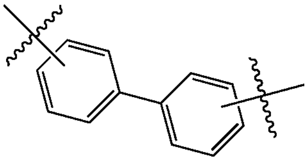

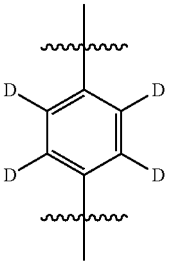

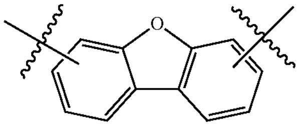

;

$L_1$ and $L_2$ are each independently selected from the group consisting of a single bond and the following groups:

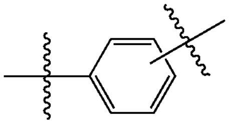

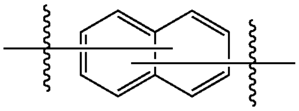

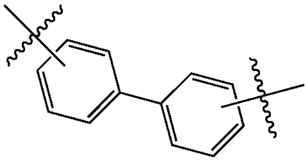

.

6. The nitrogen-containing compound according to claim 1, wherein the nitrogen-containing compound is selected from the group consisting of the following compounds:

1

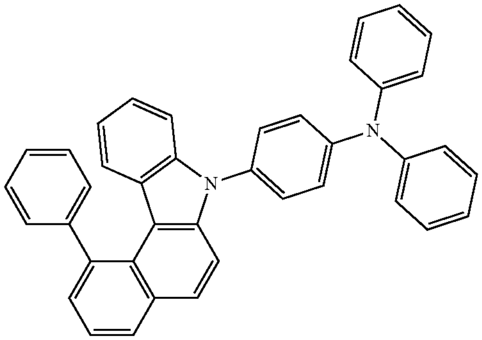

-continued
2
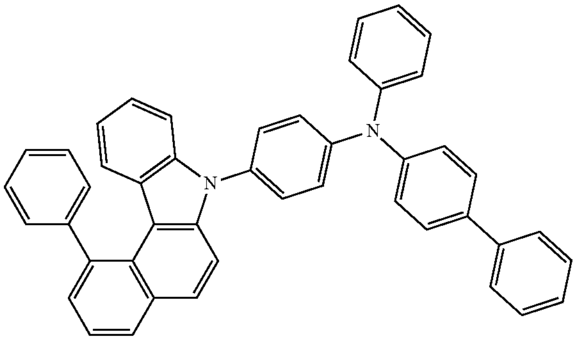
3
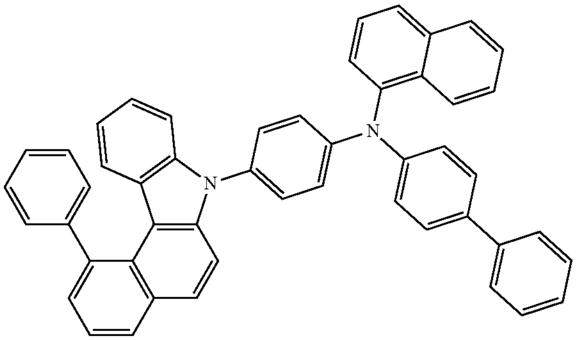
4
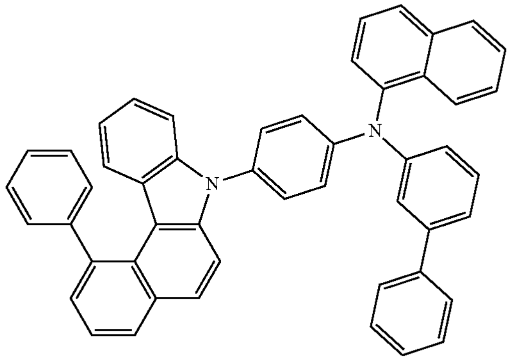
5
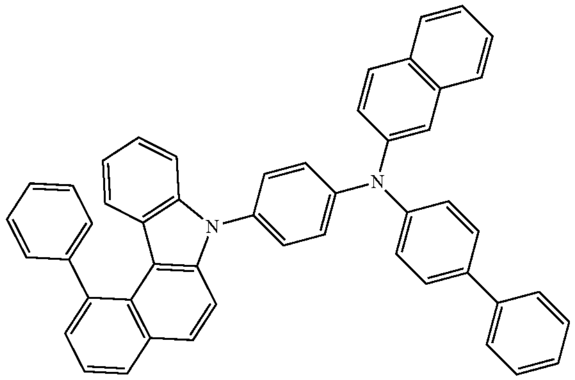
-continued
6
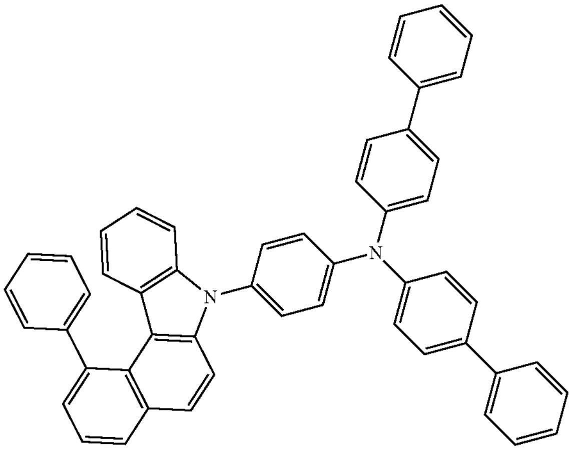
7
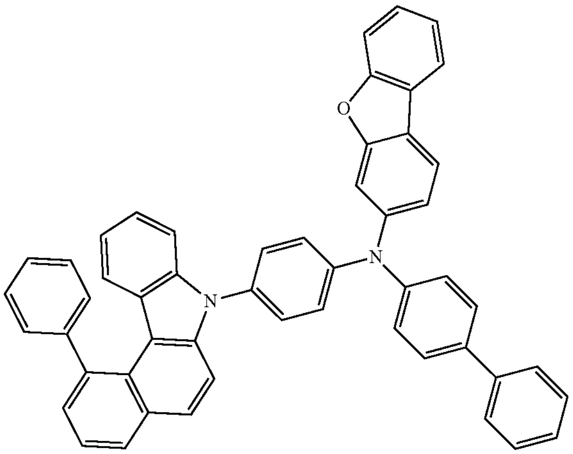
8
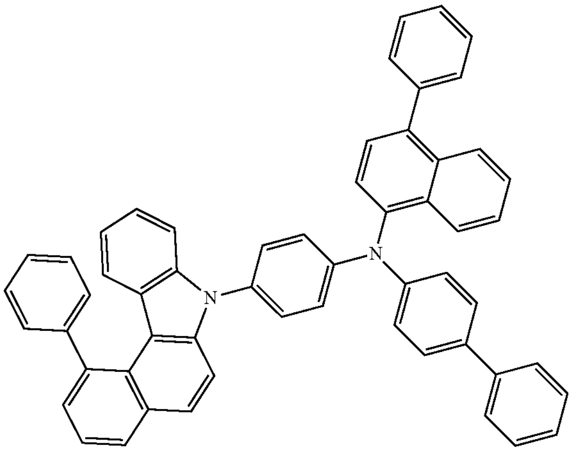

-continued
9
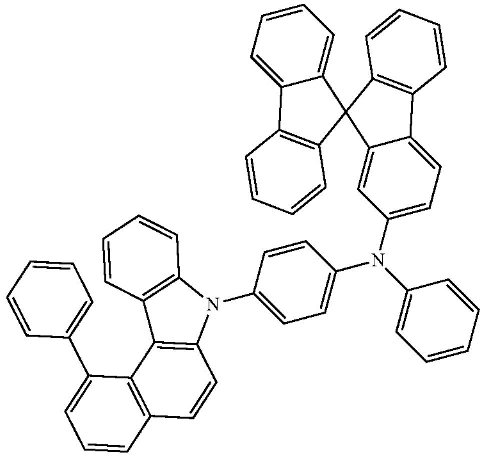
10
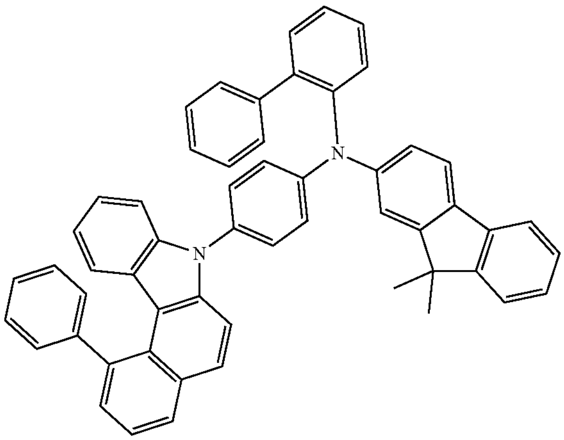
11
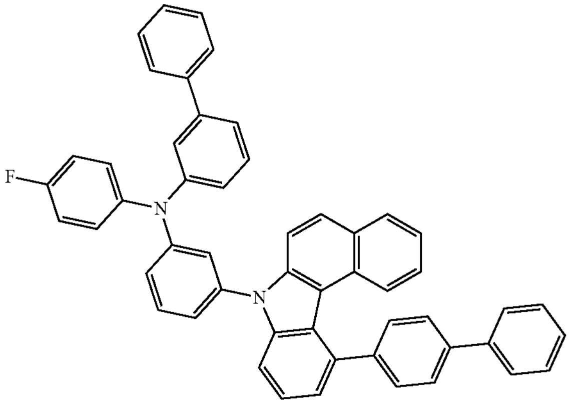
-continued
12
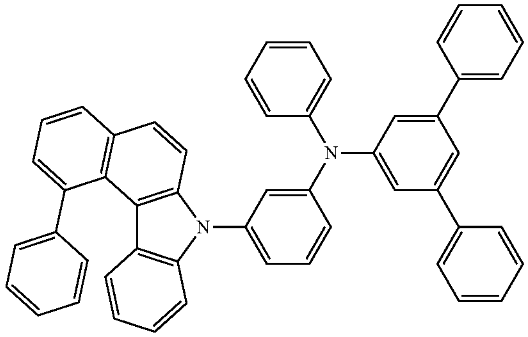
13
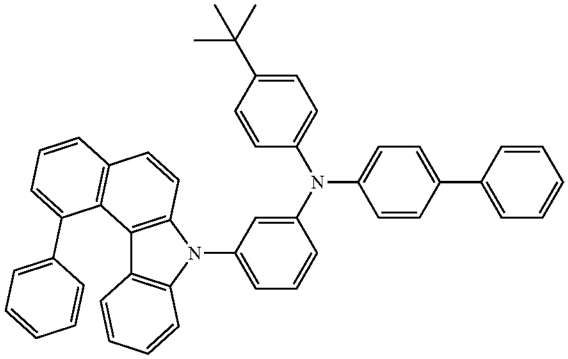
14
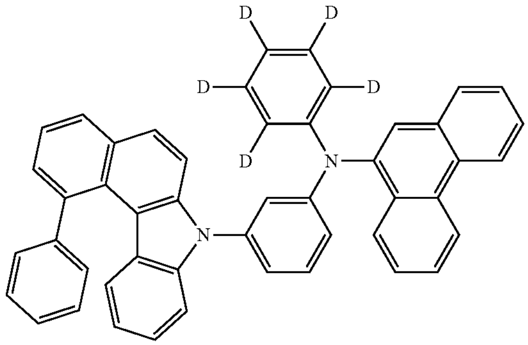
15
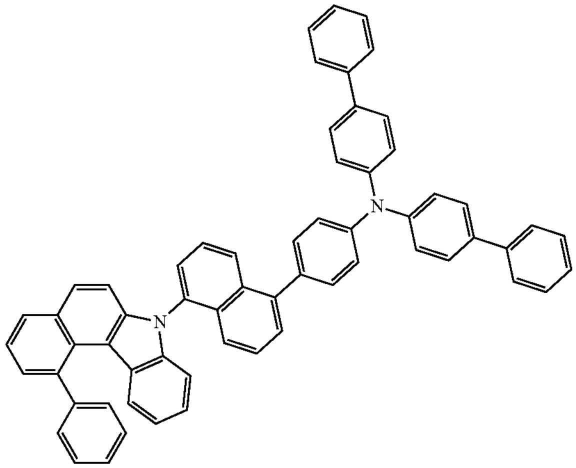

16
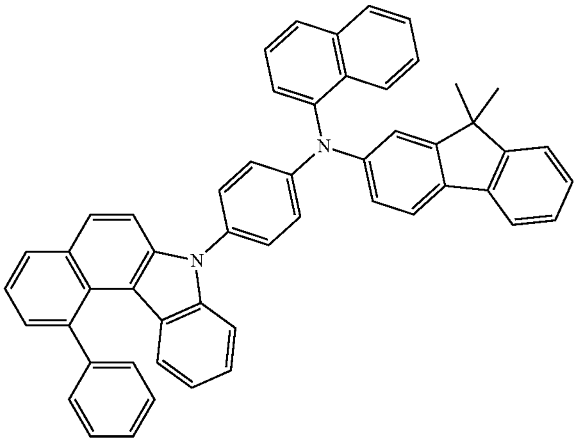
17
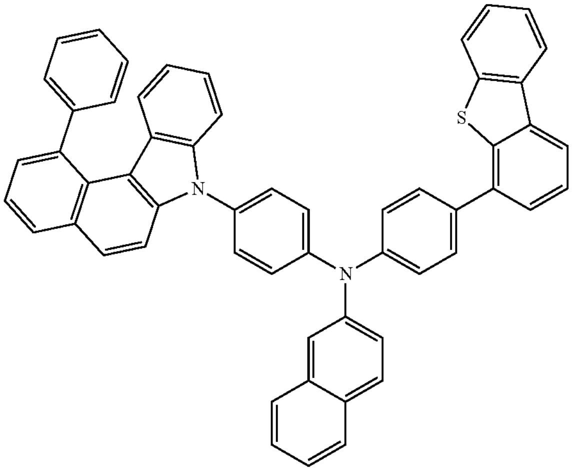
18
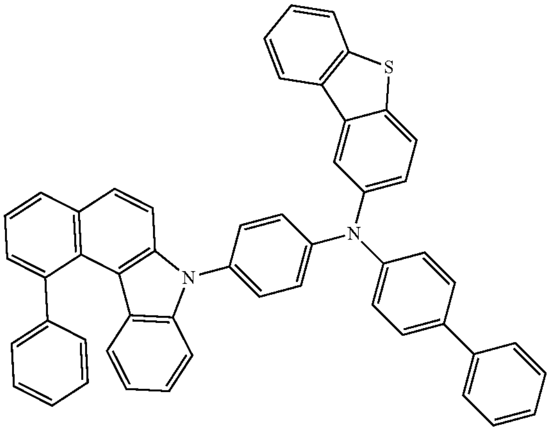
19
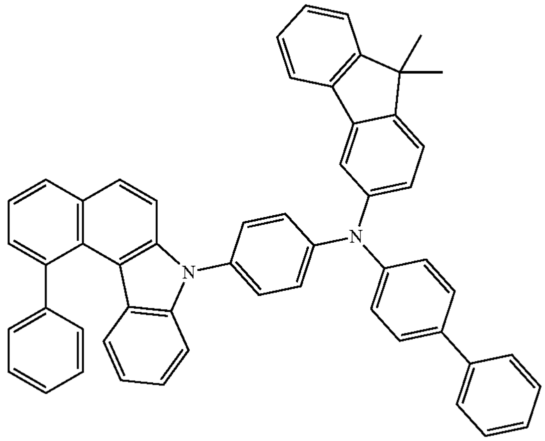
20
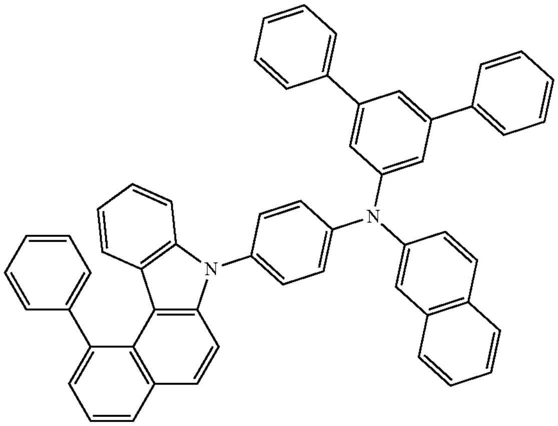
21
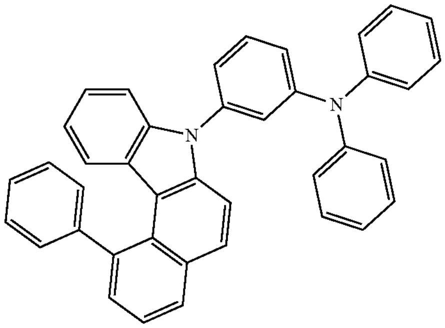
22
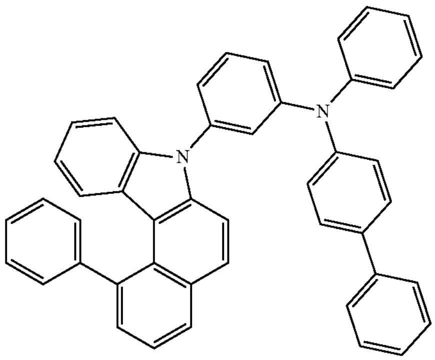

-continued
23
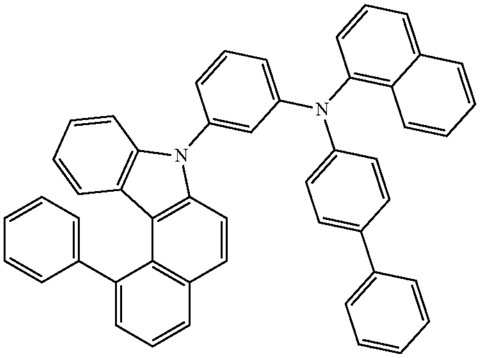
24
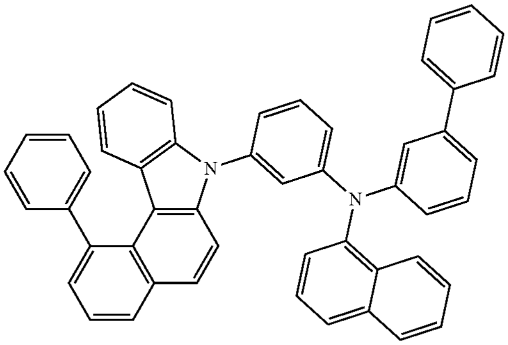
25
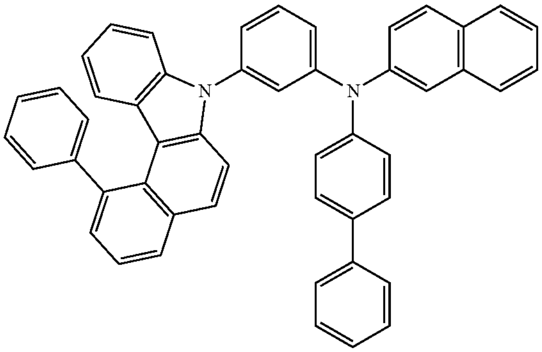
26
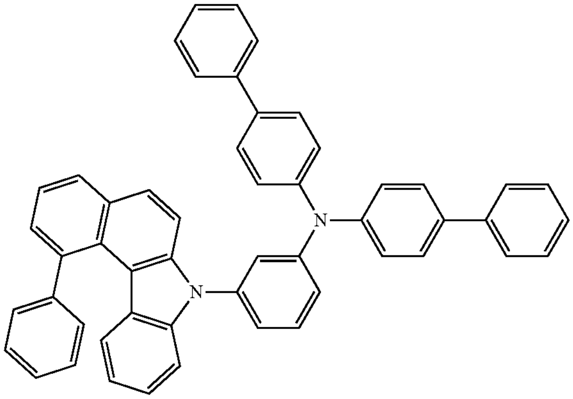
-continued
27
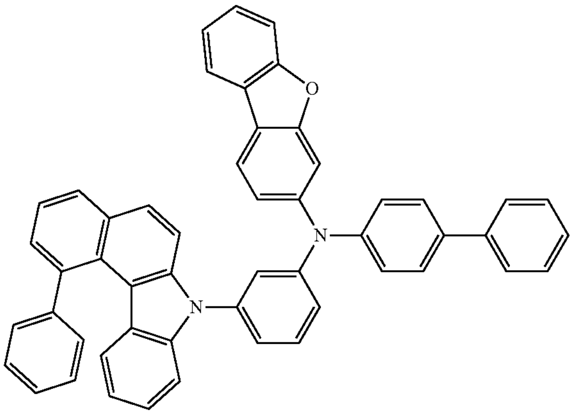
28
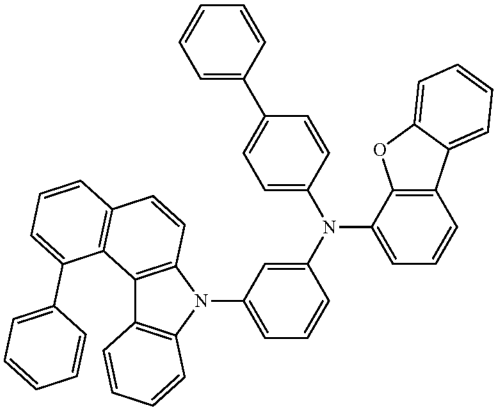
29
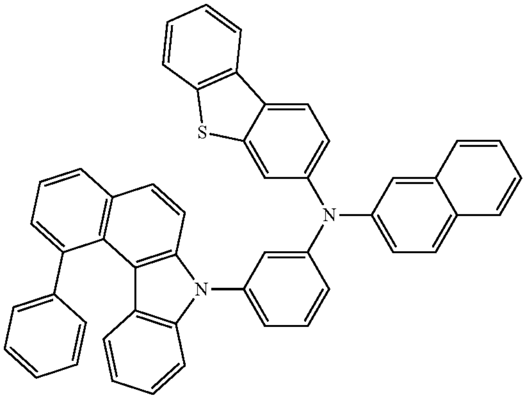

-continued
30
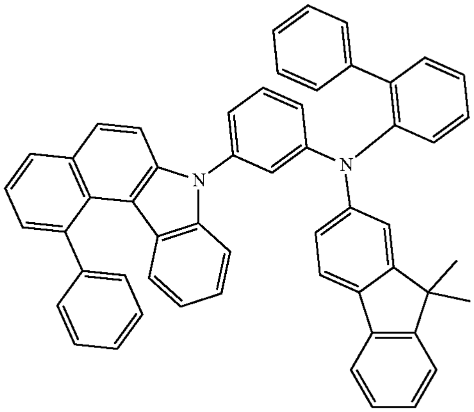
31
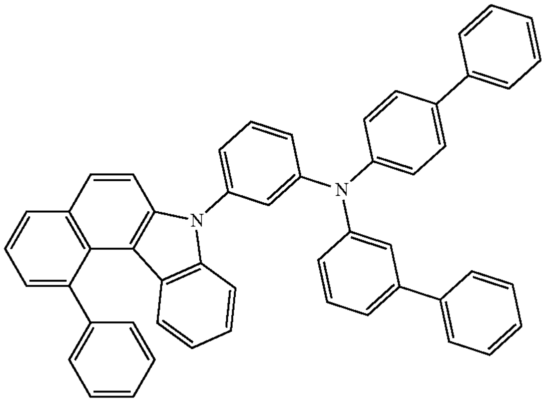
32
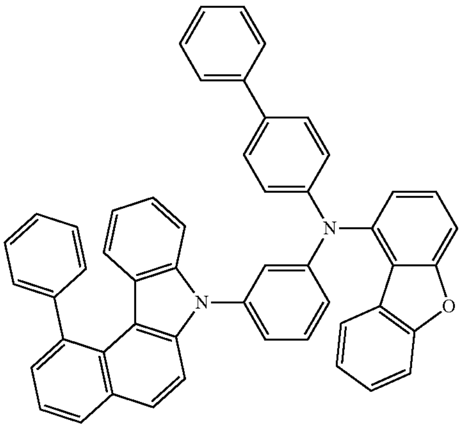
-continued
33
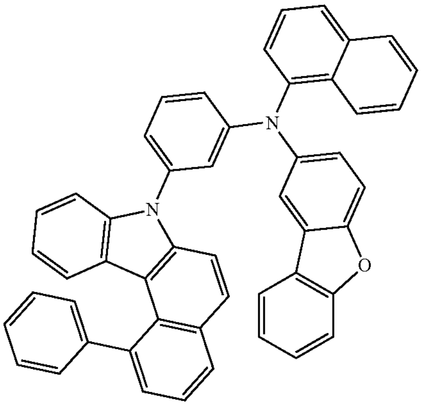
34
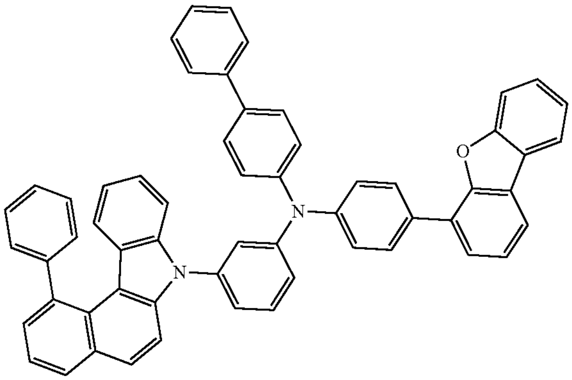
35
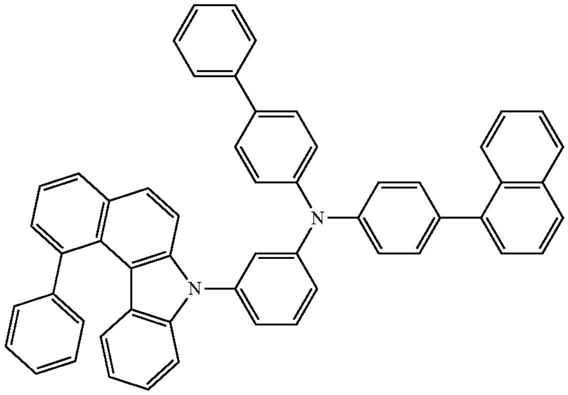
36
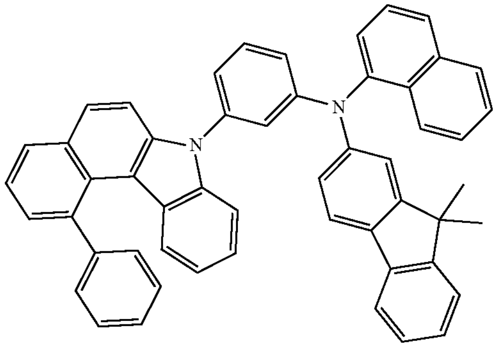

37
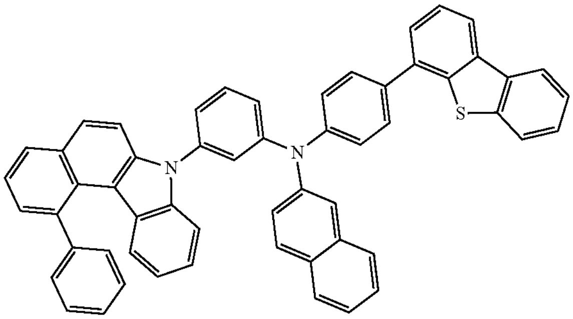
38
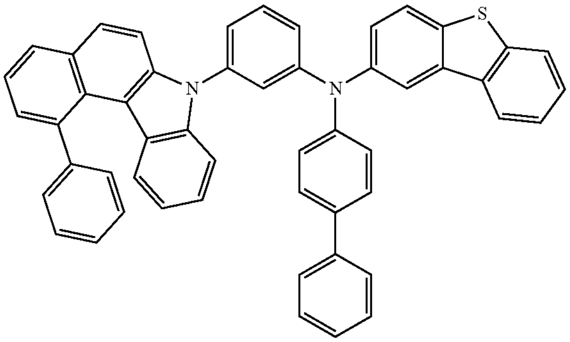
39
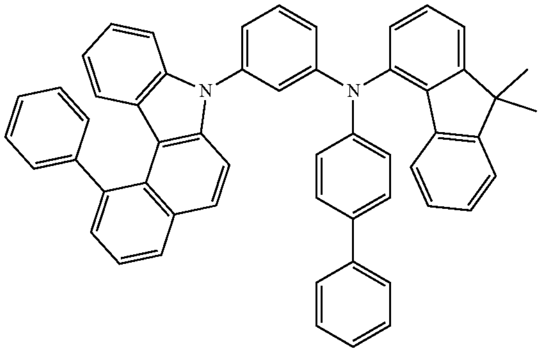
40
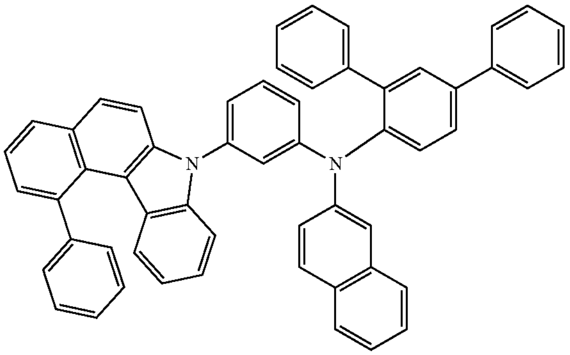
41
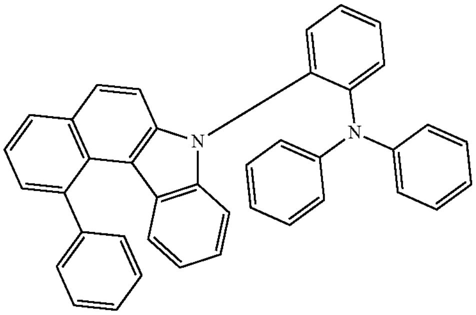
42
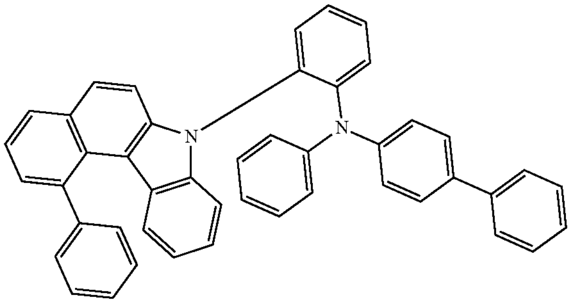
43
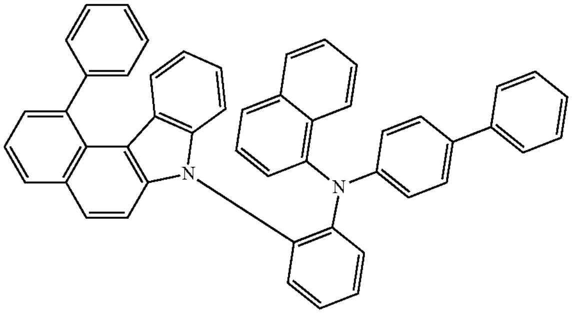
44
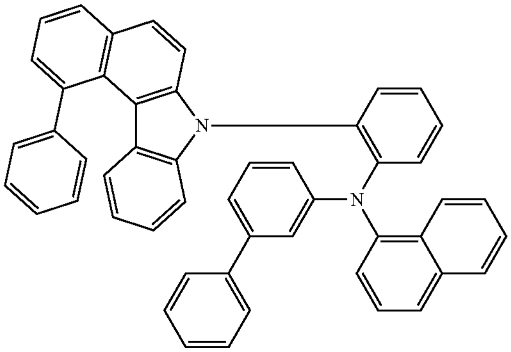

55
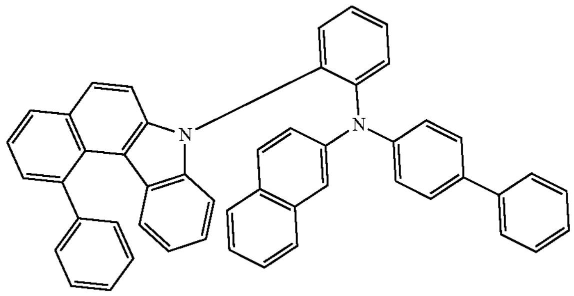
56
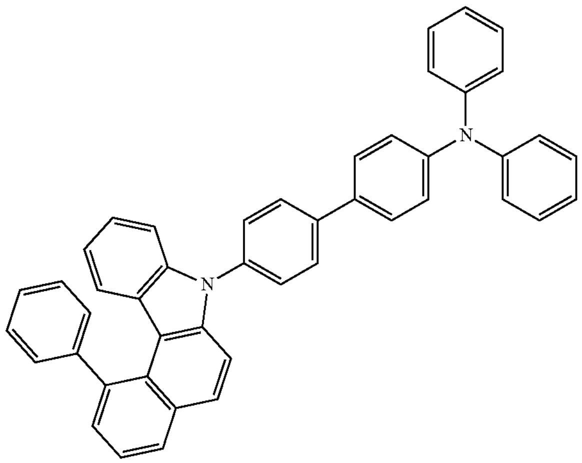
57
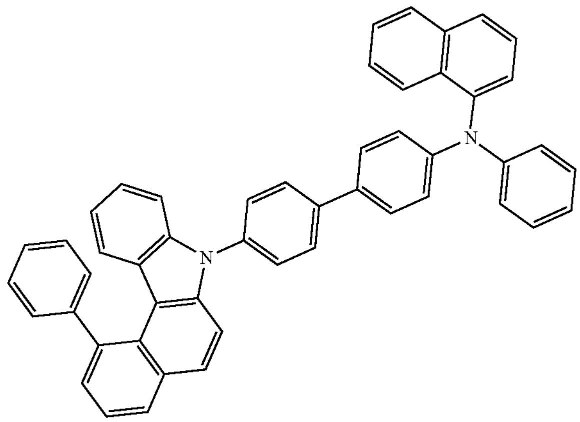
58
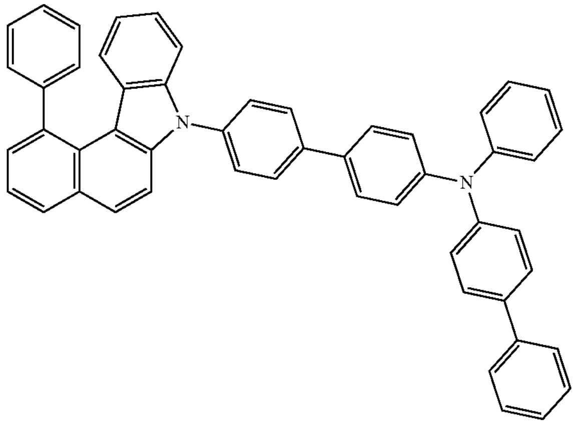
59
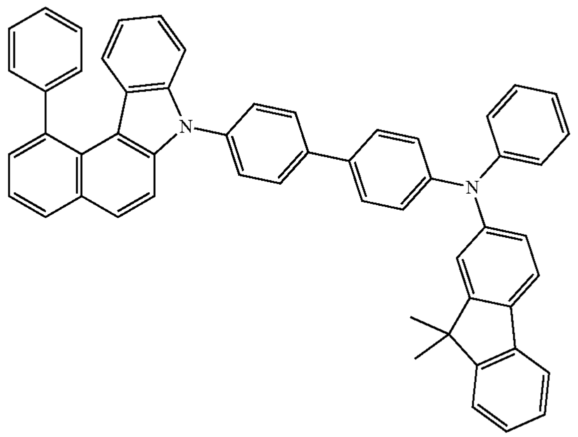
60
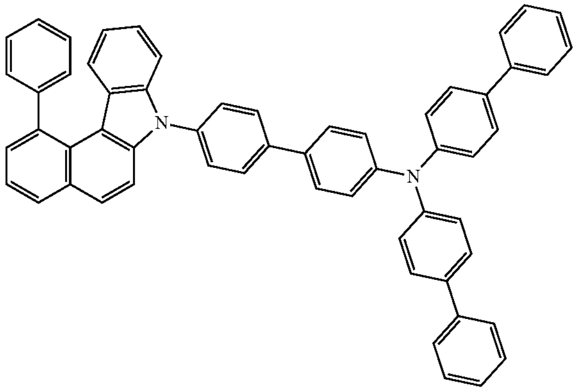

-continued
61
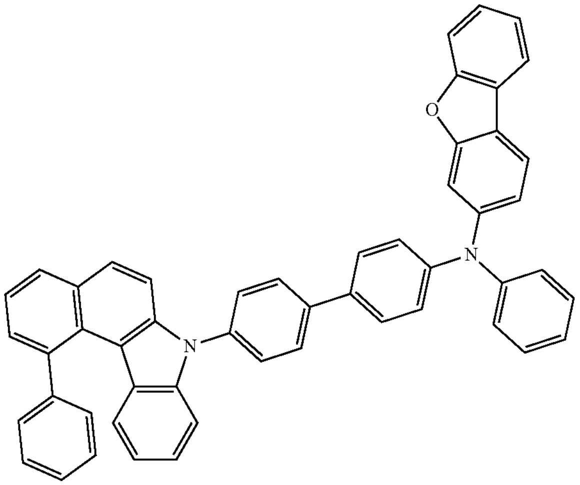
62
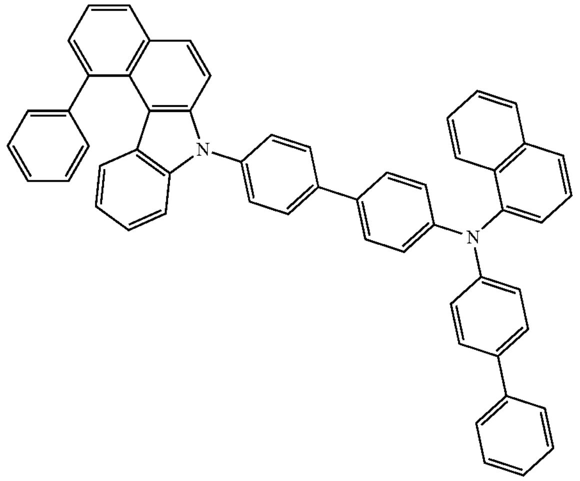
63
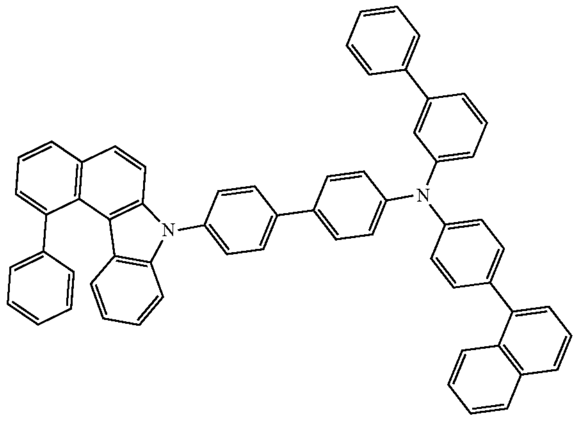
-continued
64
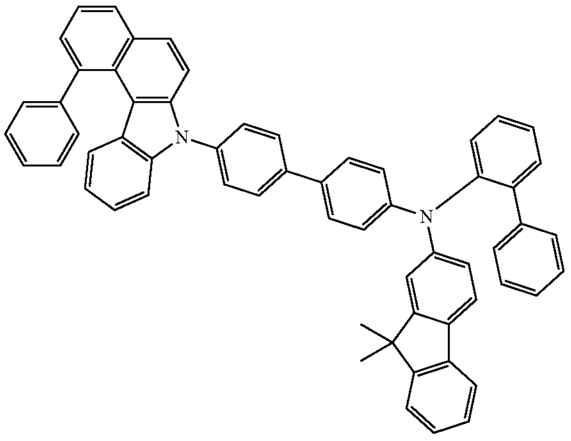
65
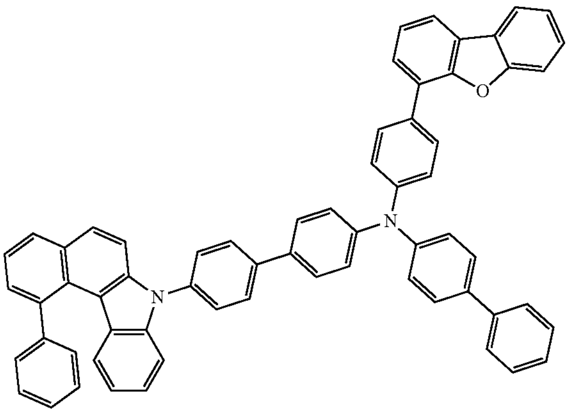
66
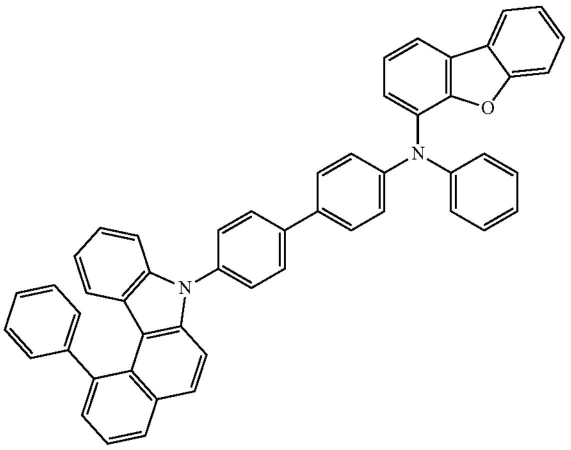

-continued
67
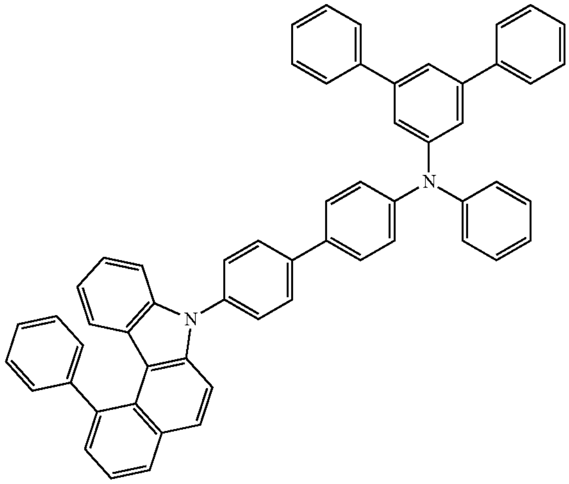
68
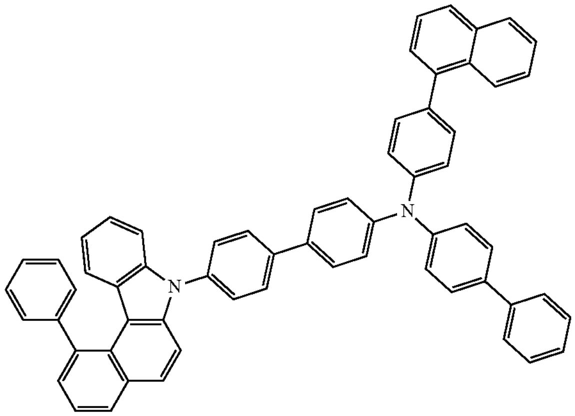
69
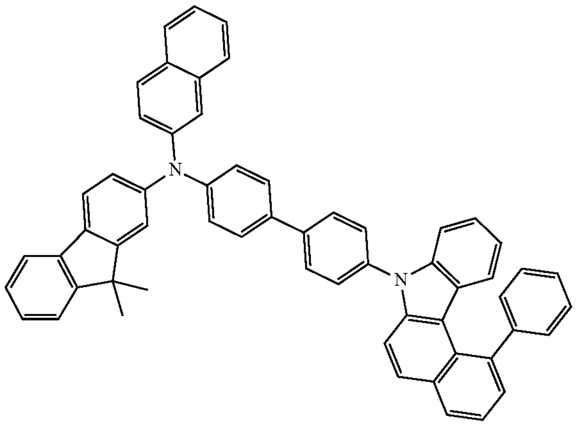
-continued
70
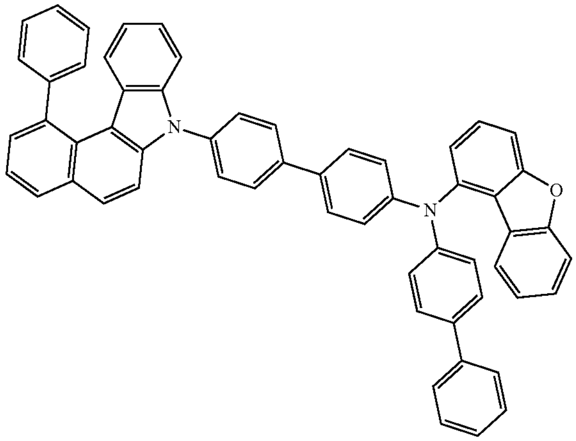
71
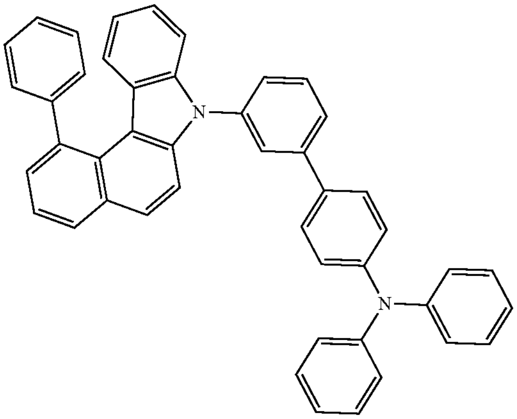
72
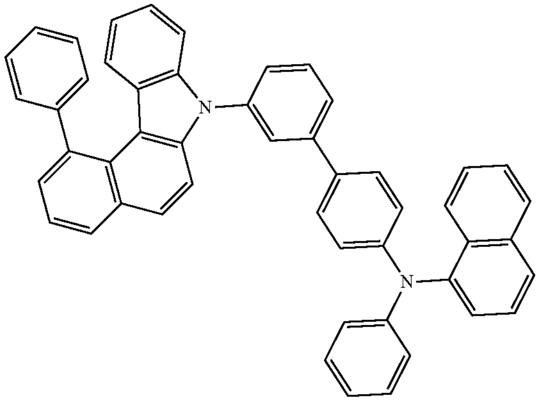

-continued
73
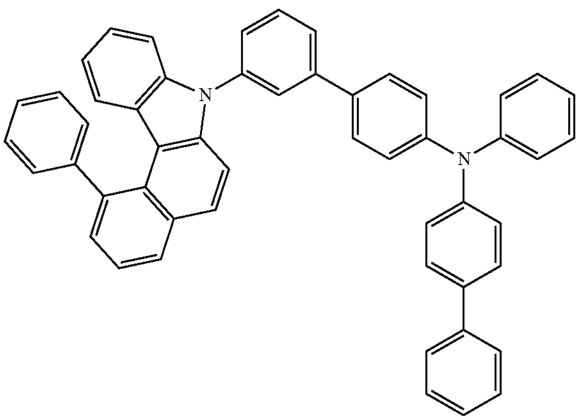
74
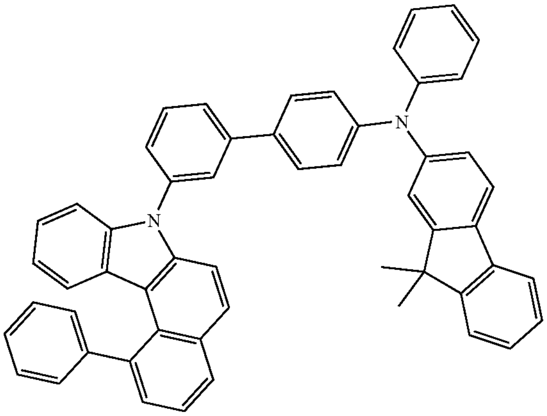
75
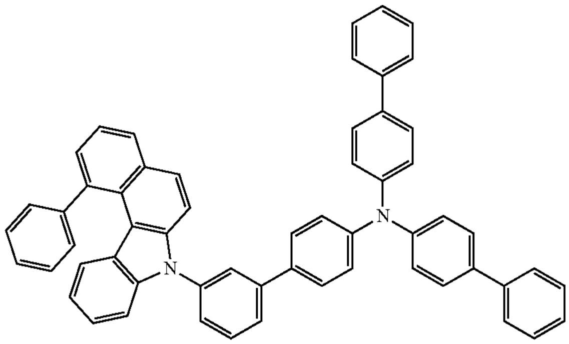
-continued
76
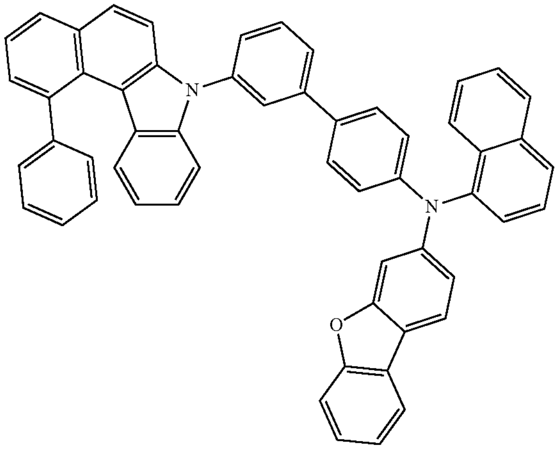
77
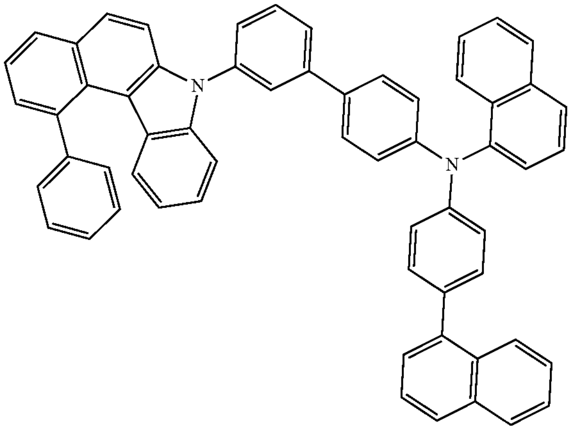
78
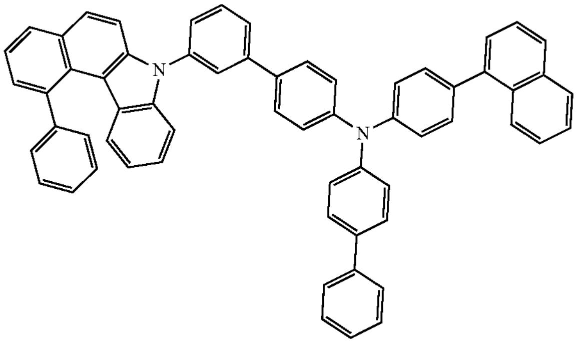

-continued
79
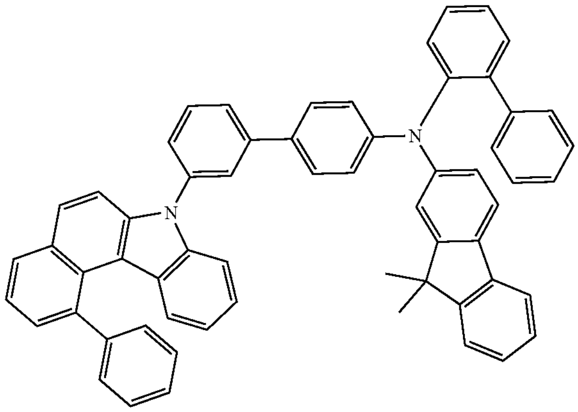
80
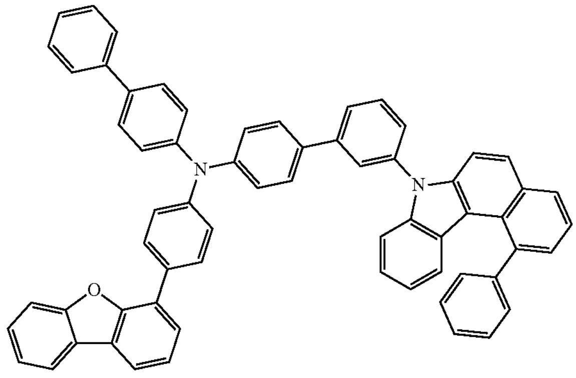
81
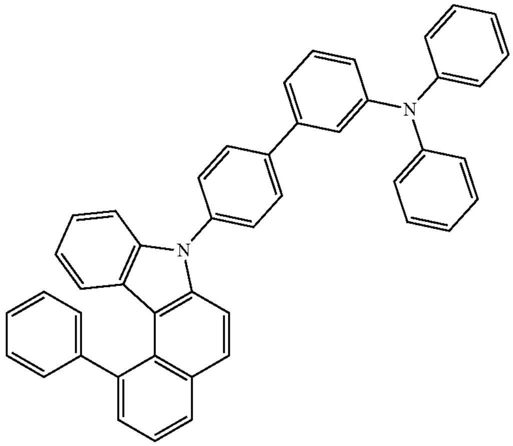
-continued
82
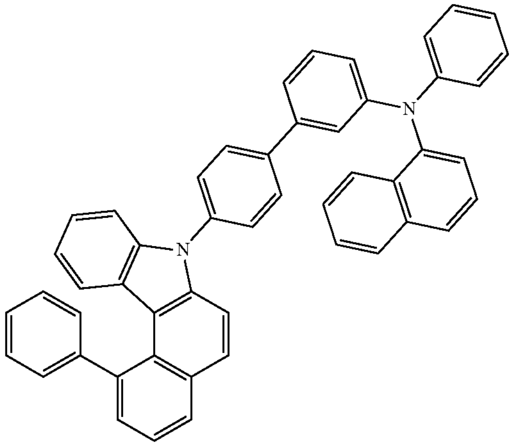
83
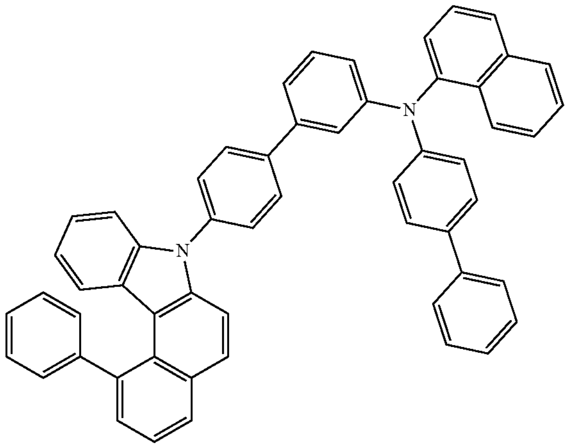
84
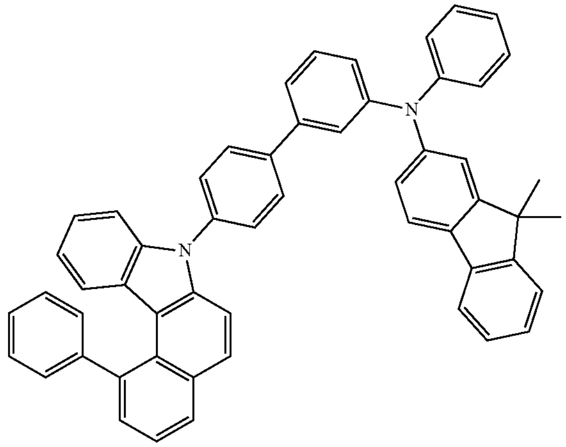

-continued
85
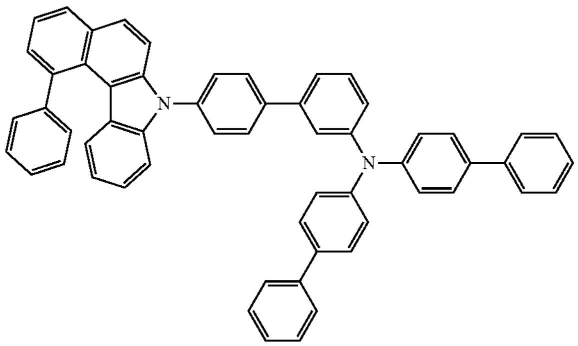
86
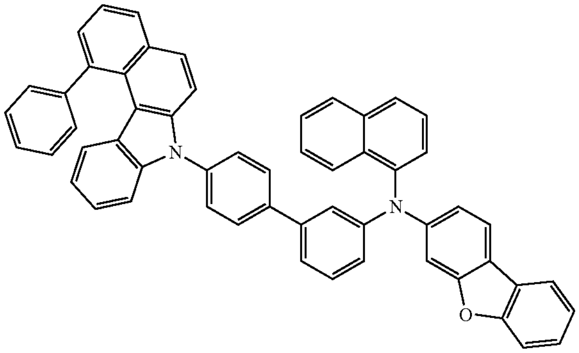
87
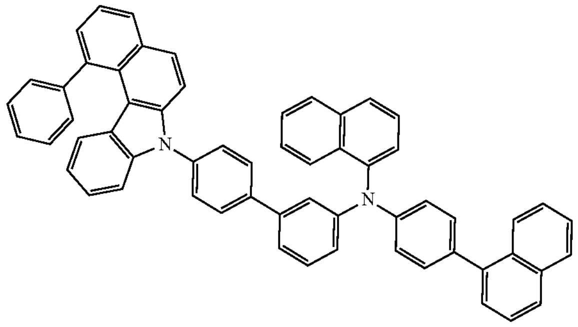
88
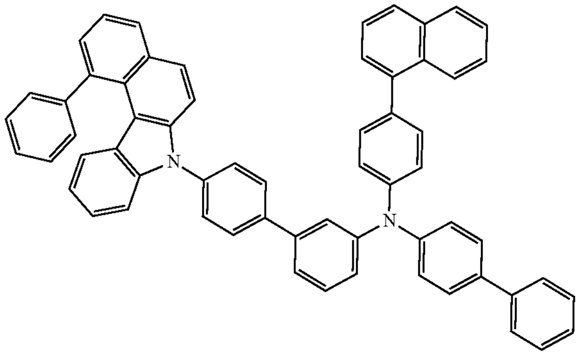
-continued
89
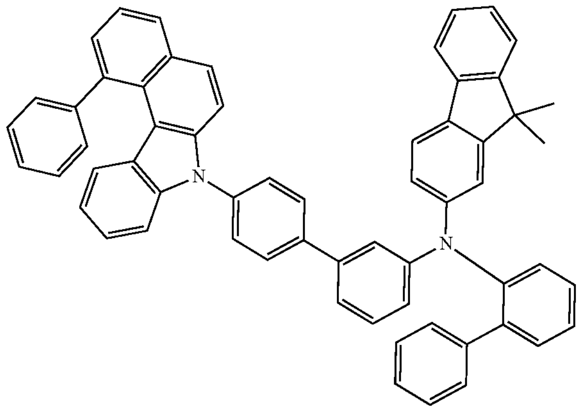
90
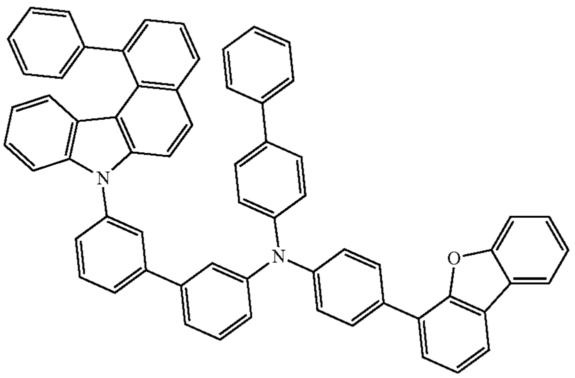
91
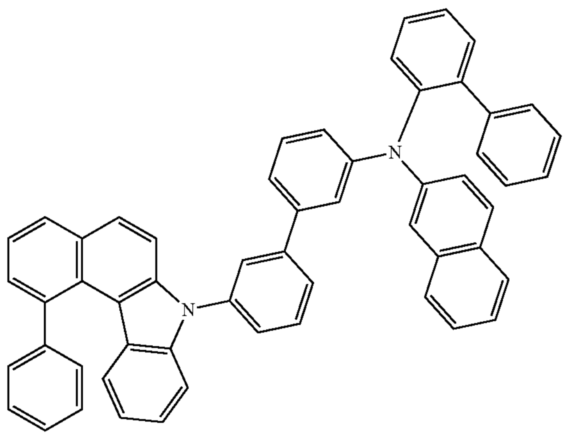

-continued
92
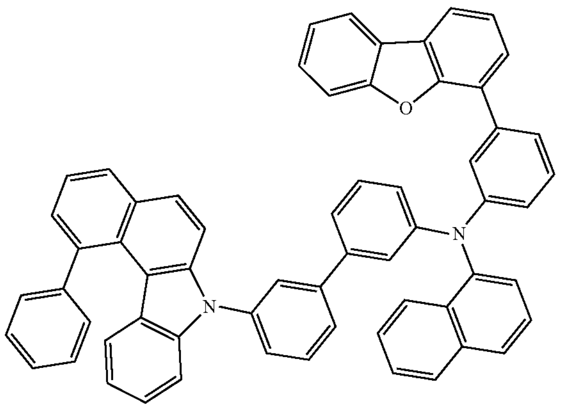
93
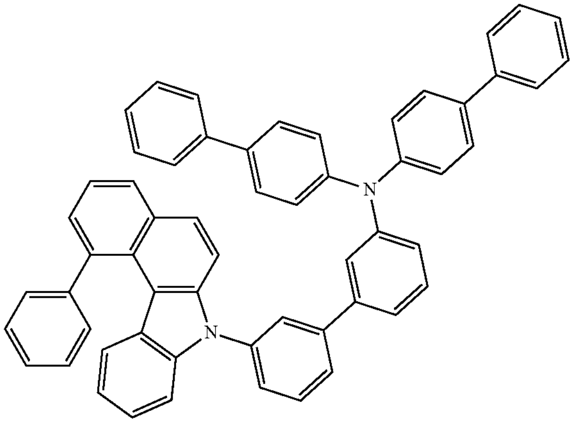
94
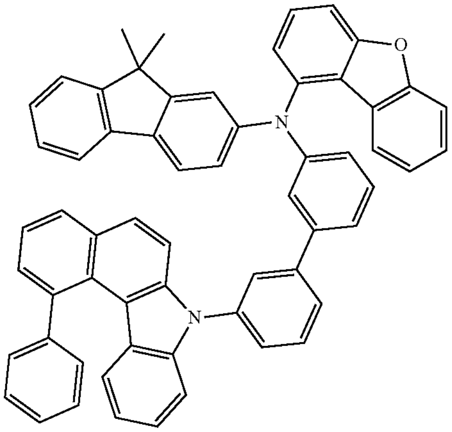
-continued
95
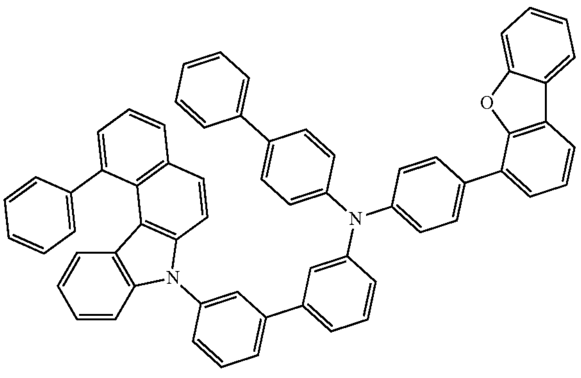
96
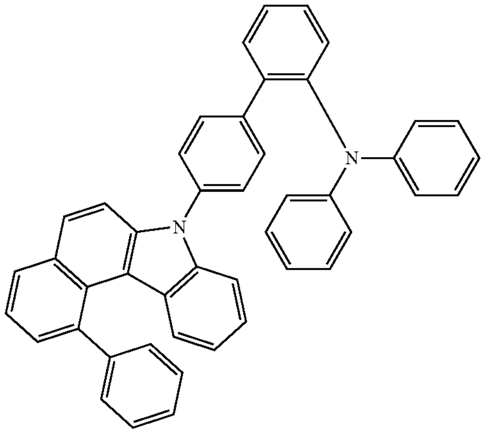
97
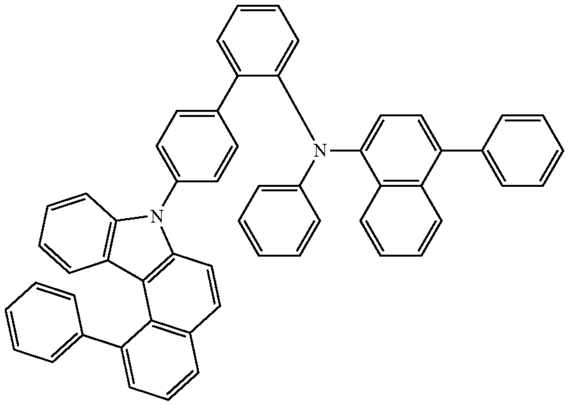
98
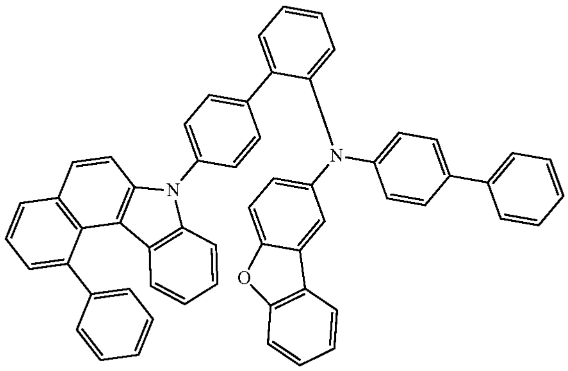

-continued
99
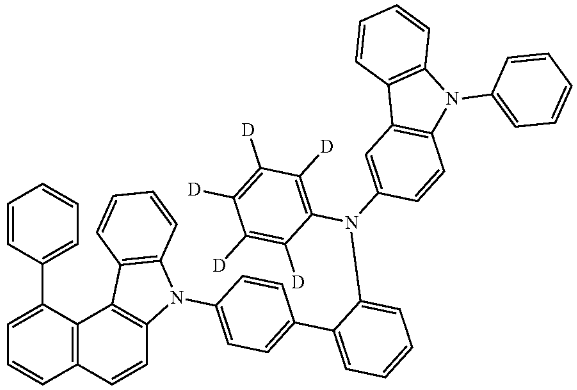
100
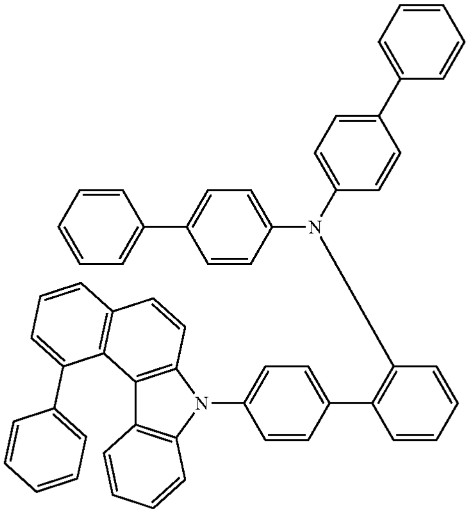
101
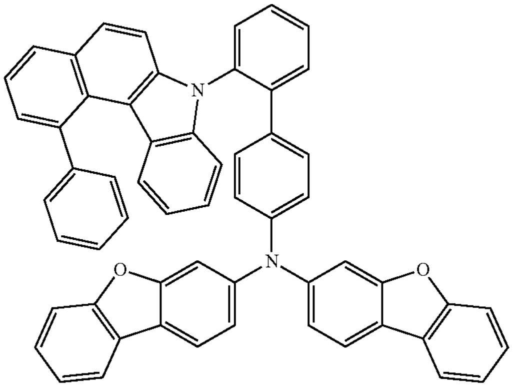
-continued
102
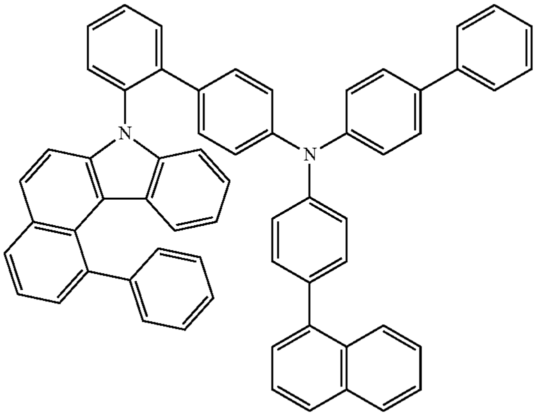
103
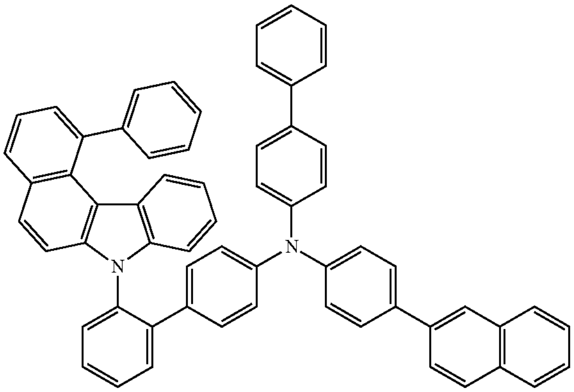
104
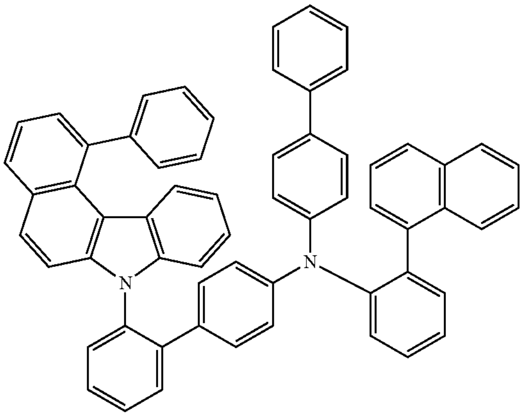

105
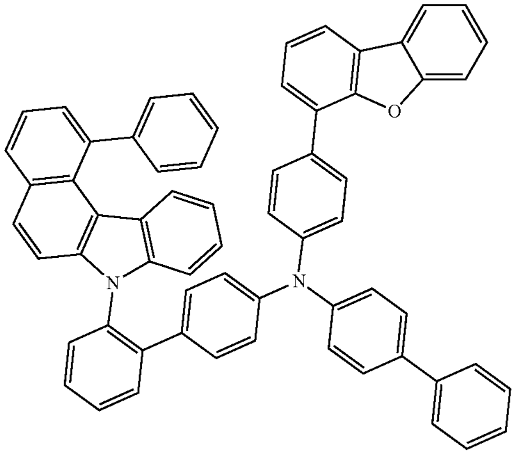
106
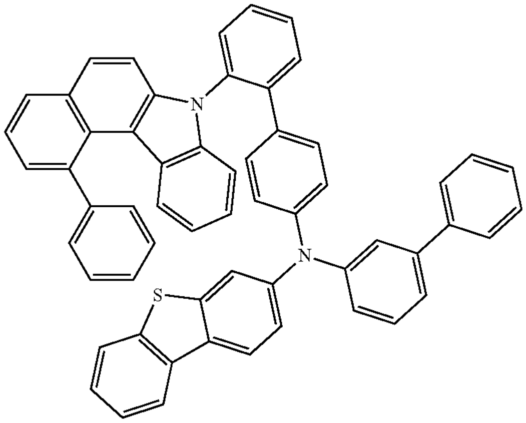
107
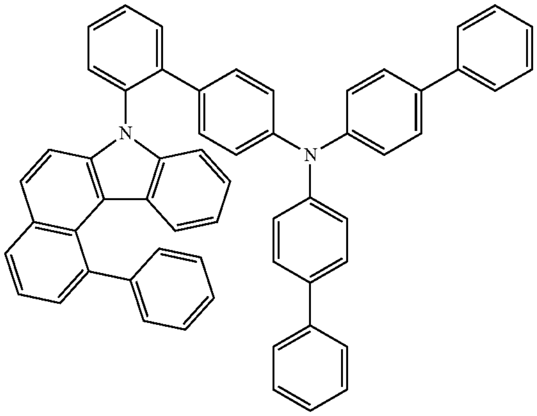
108
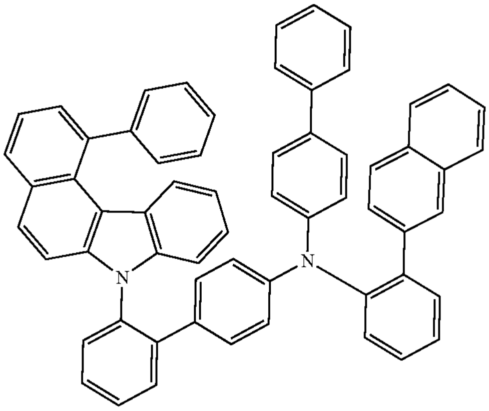
109
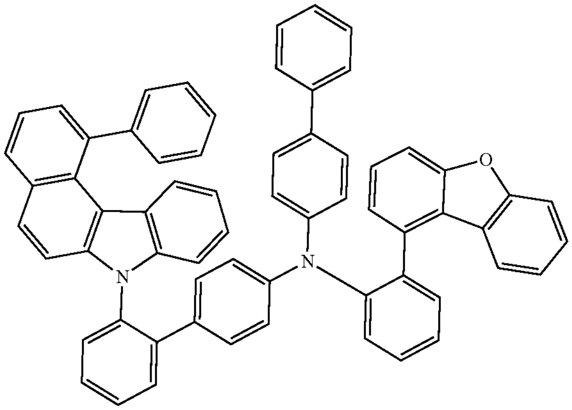
110
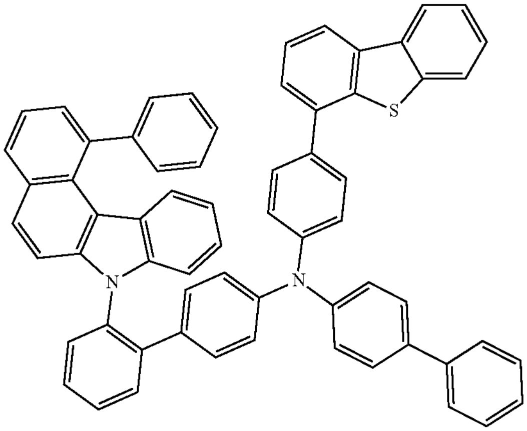

-continued
111
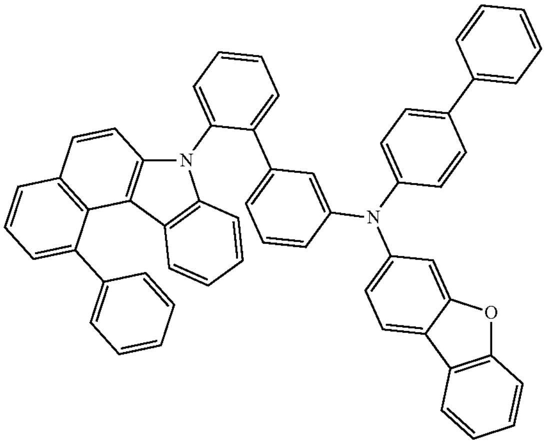
112
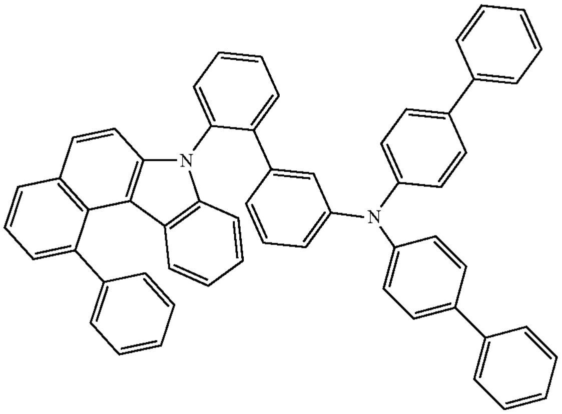
113
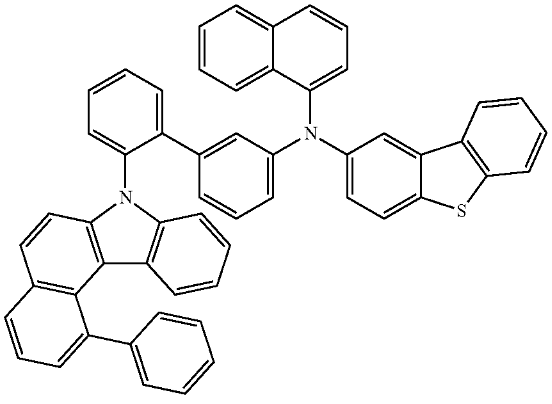
-continued
114
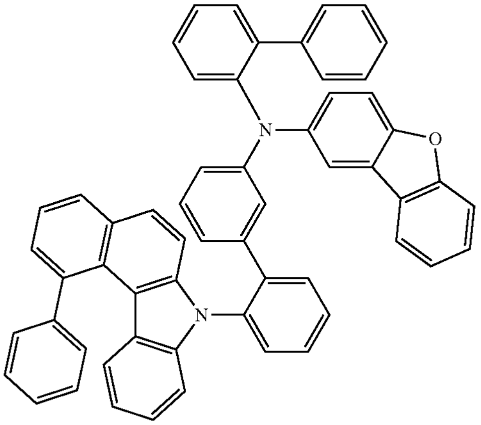
115
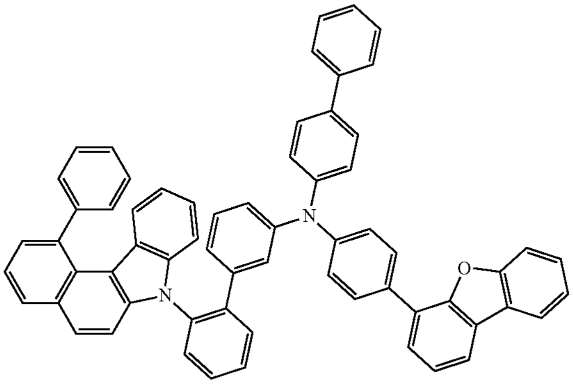
116
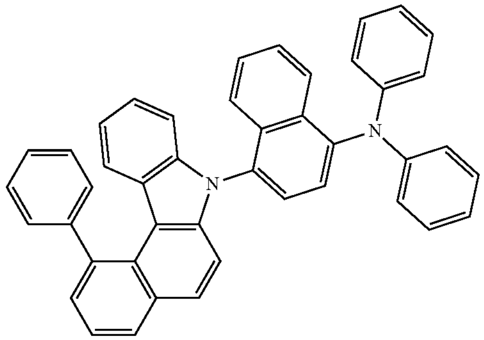
117
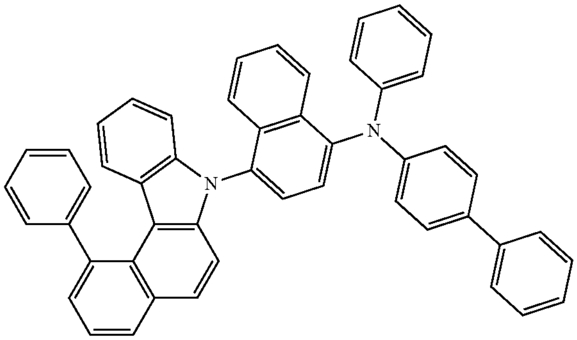

-continued
118
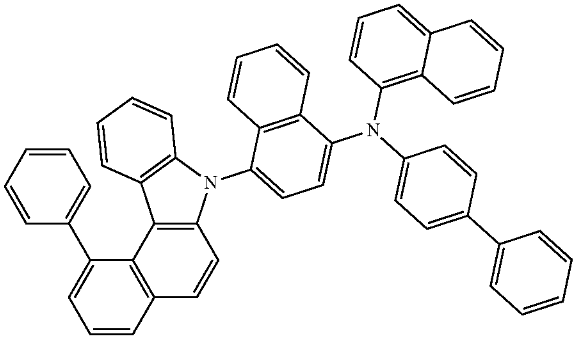
119
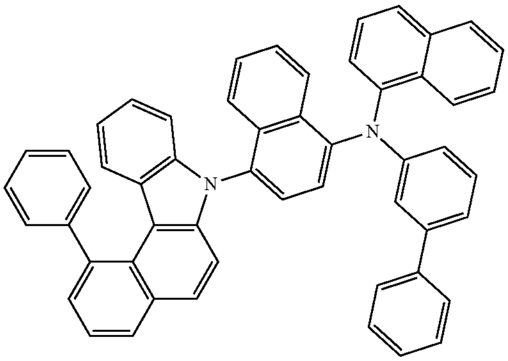
120
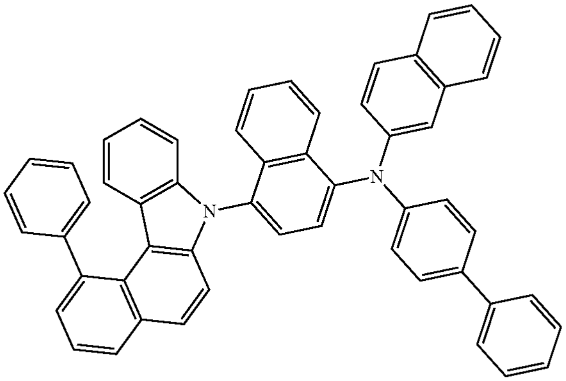
121
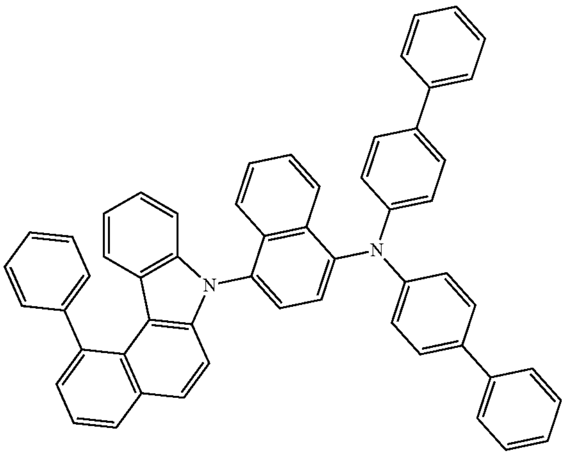
-continued
122
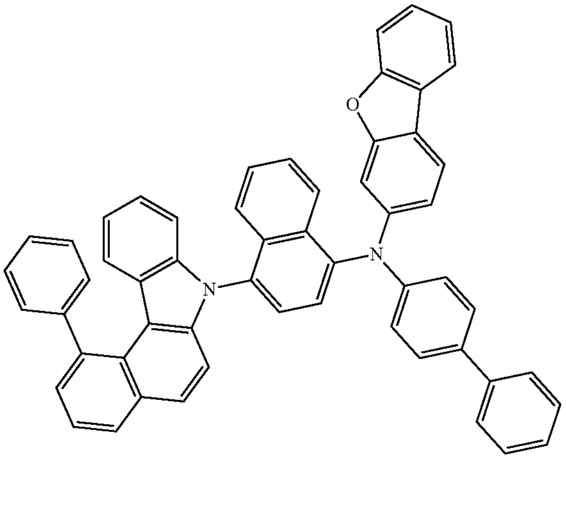
123
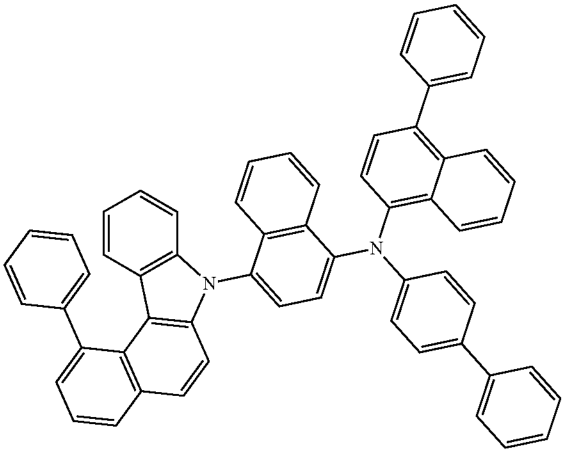
124
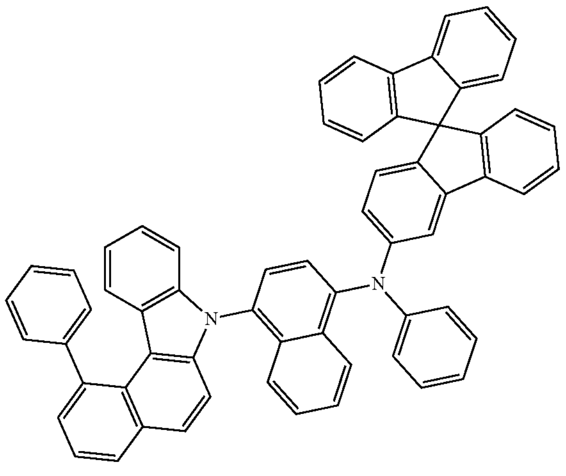

-continued
125
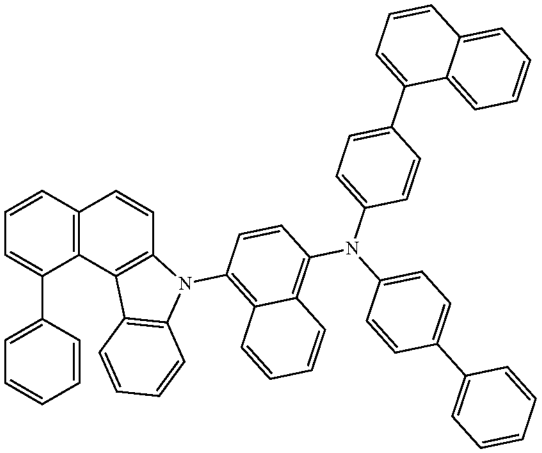
126
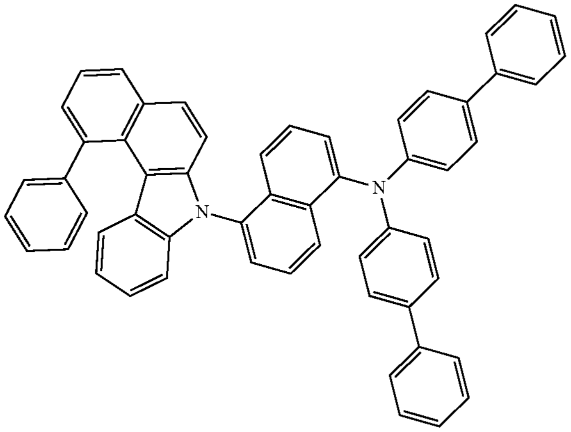
127
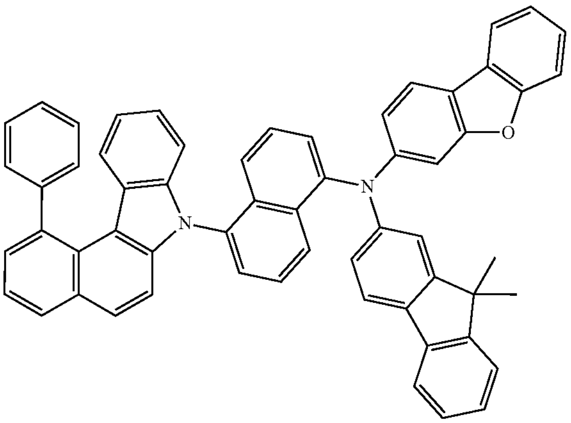
-continued
128
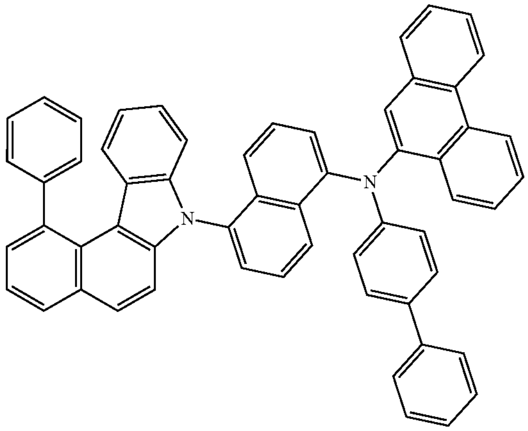
129
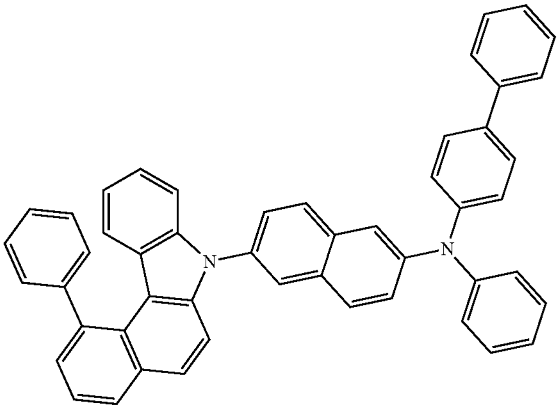
130
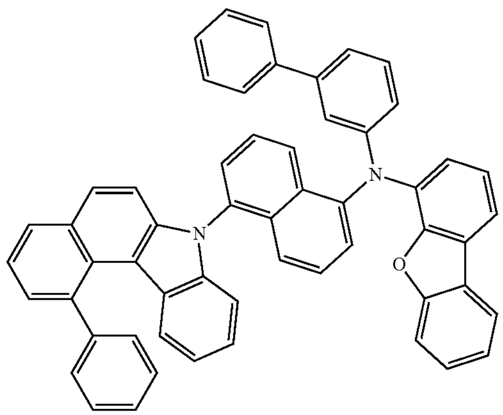

-continued
131
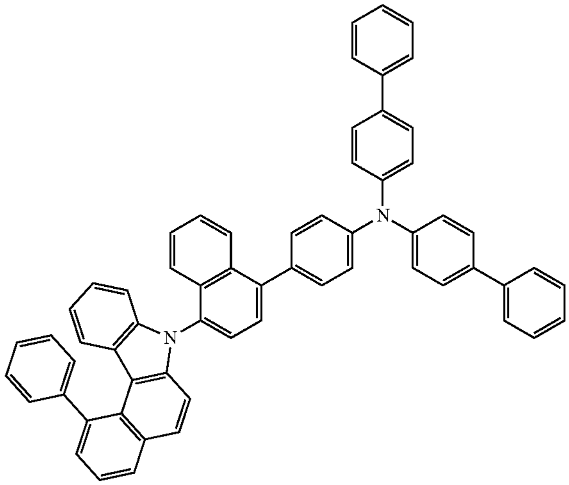
132
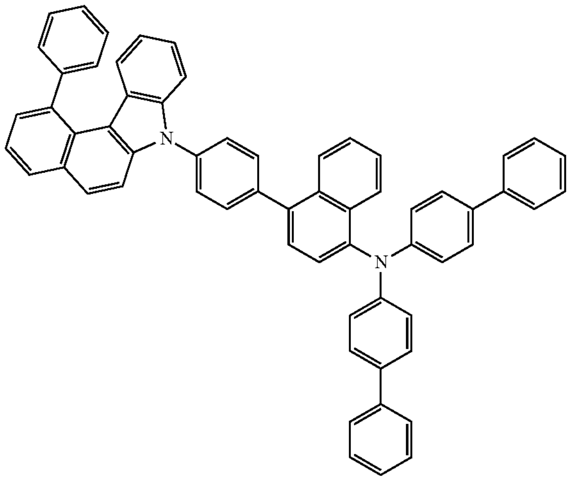
133
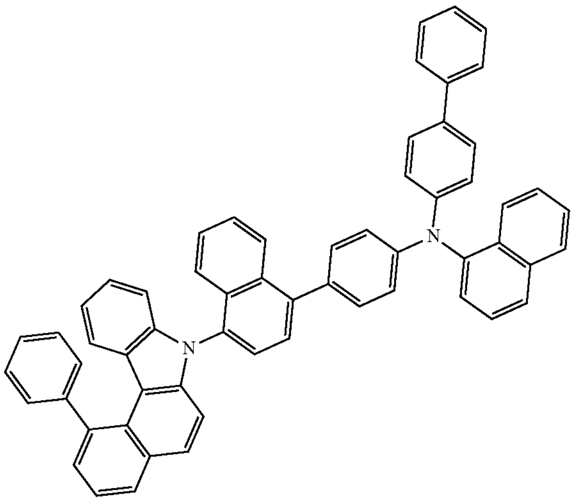
-continued
134
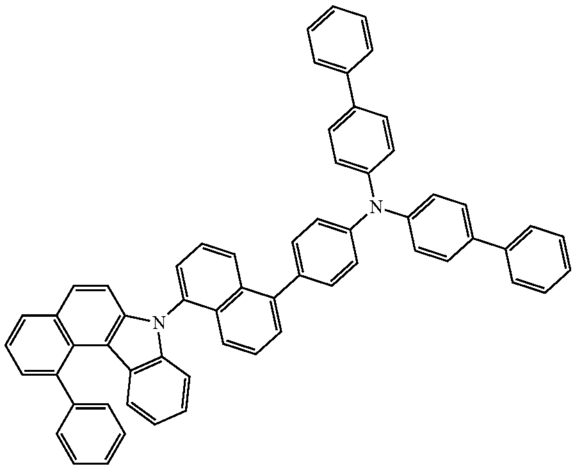
135
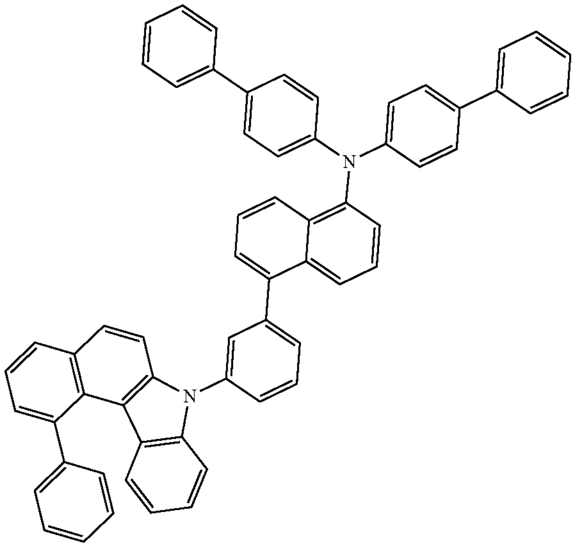
136
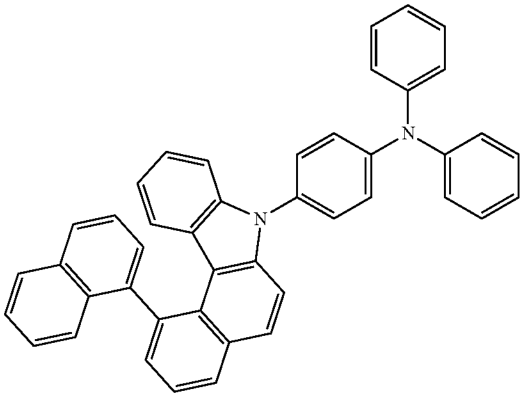

-continued
137
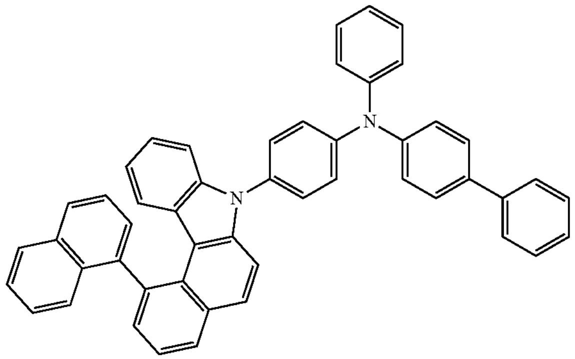
138
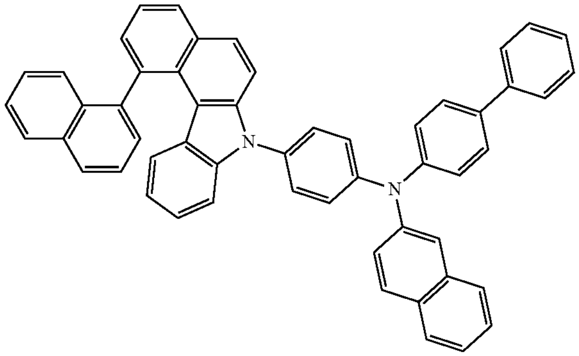
139
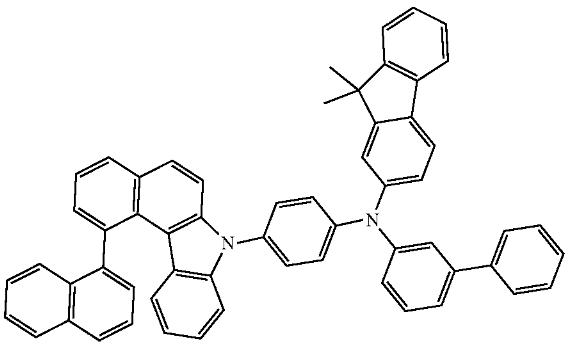
140
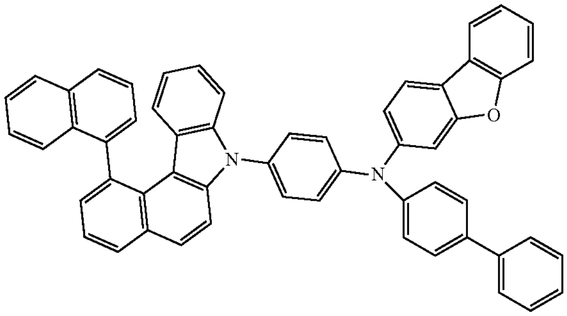
-continued
141
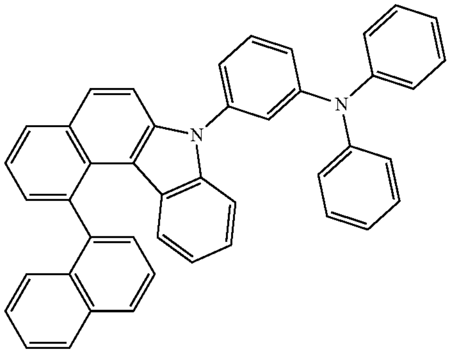
142
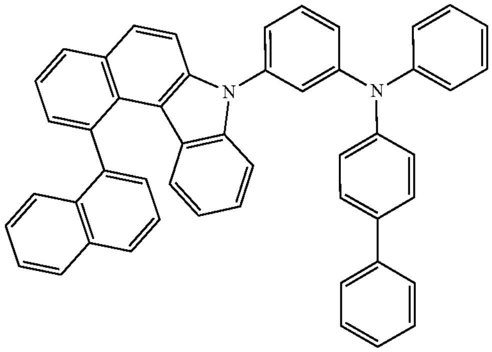
143
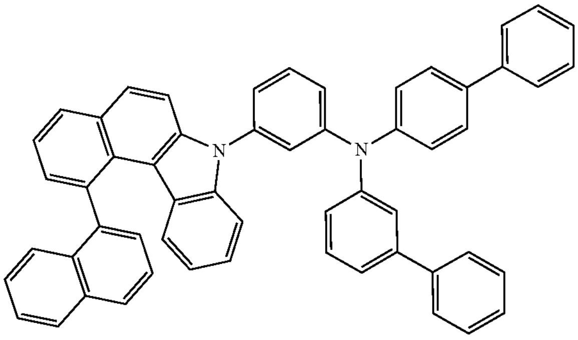
144
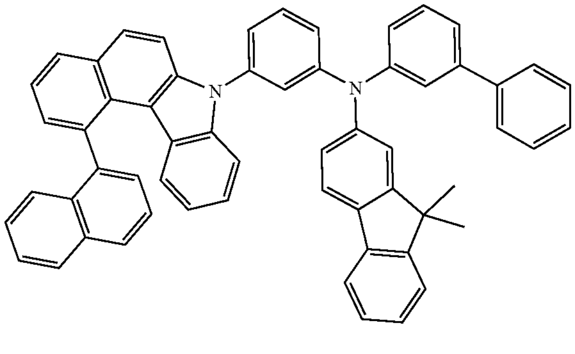

-continued
145
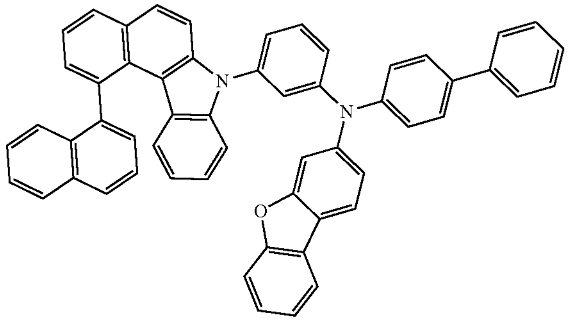
146
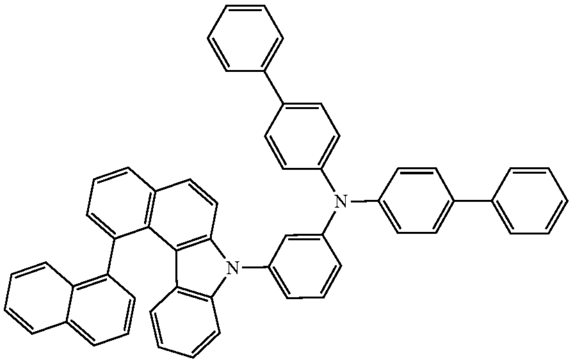
147
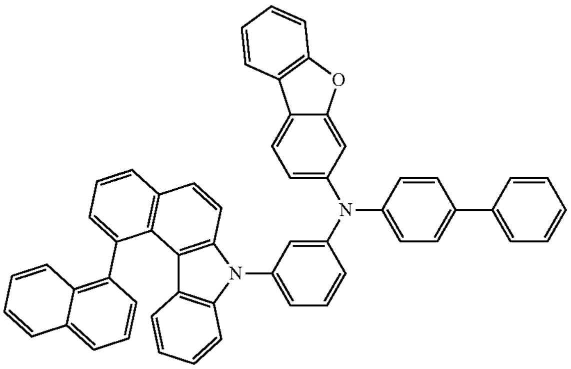
148
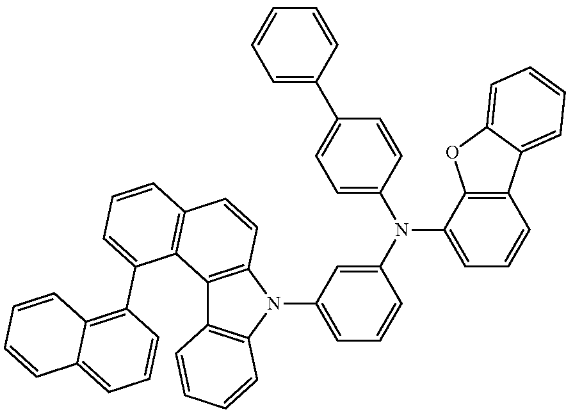
-continued
149
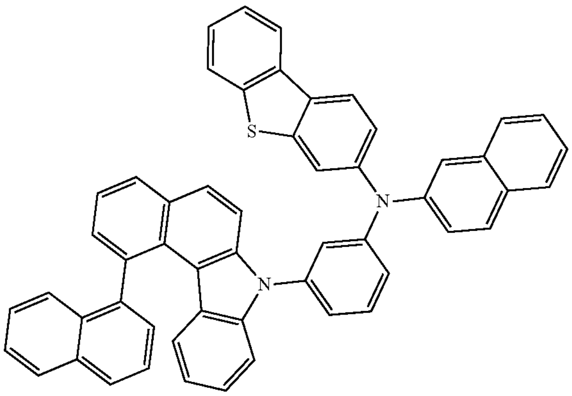
150
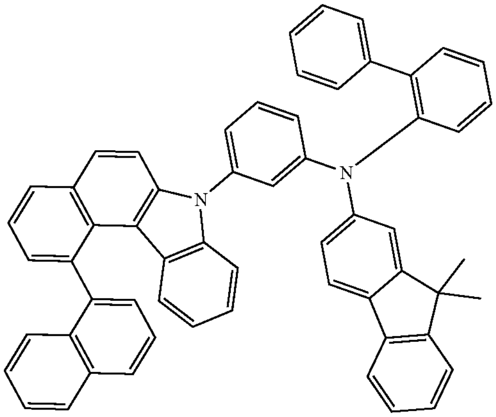
151
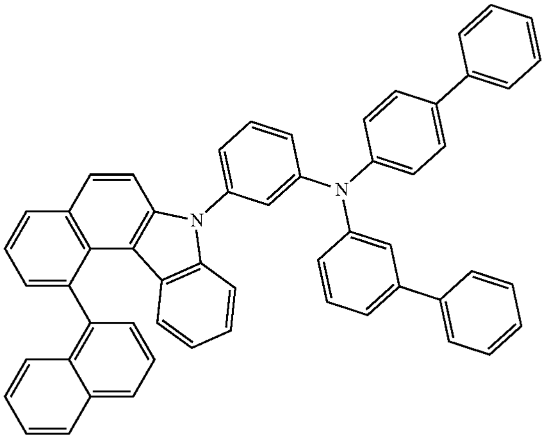

-continued
152
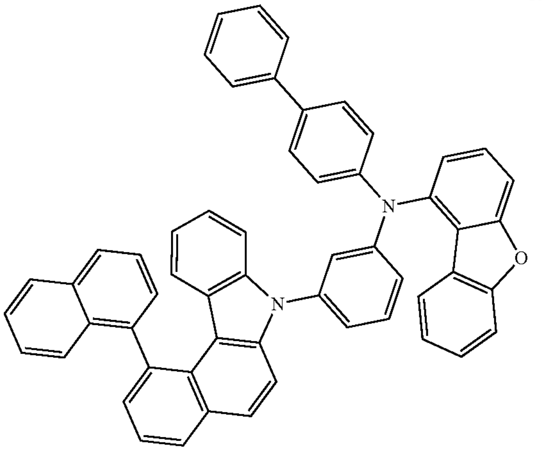
153
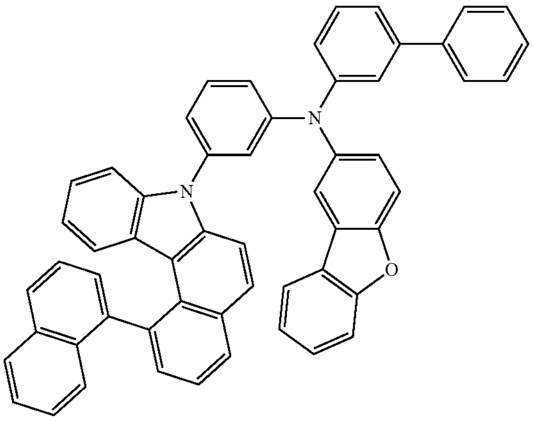
154
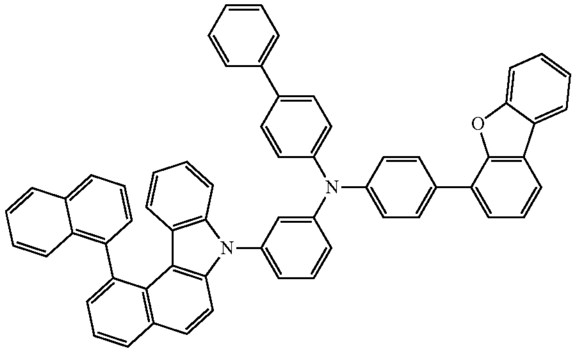
155
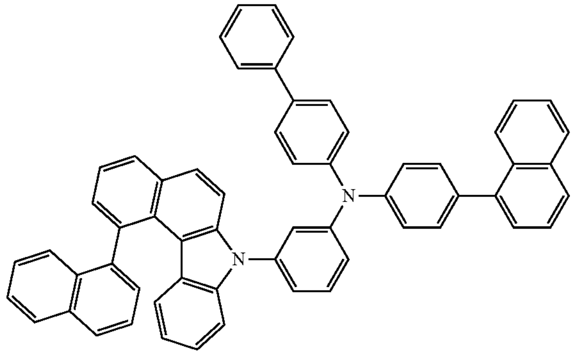
-continued
156
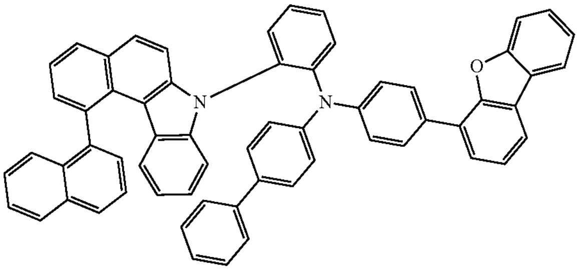
157
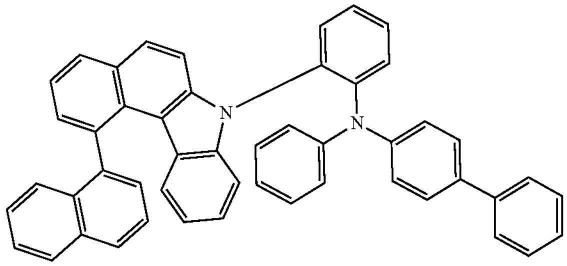
158
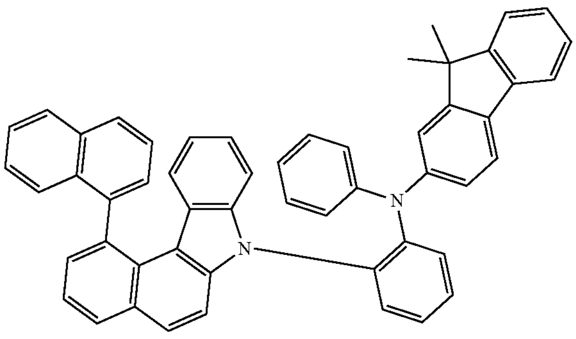
159
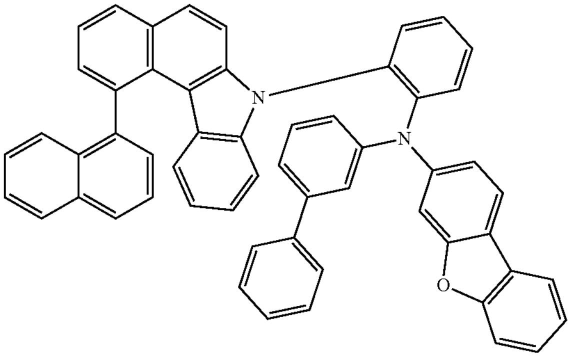

-continued
160
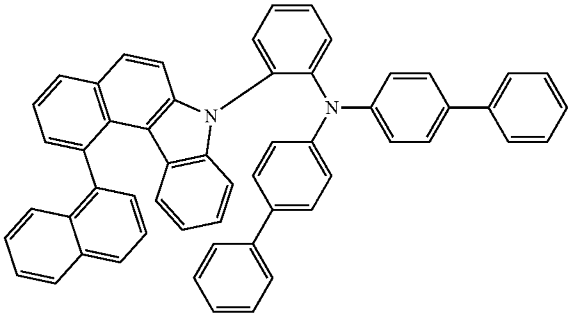
161
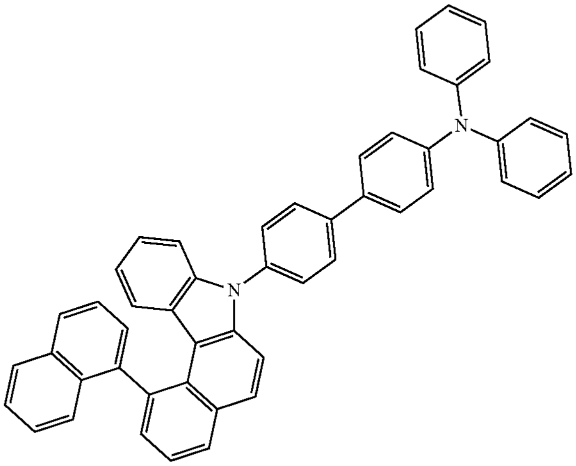
162
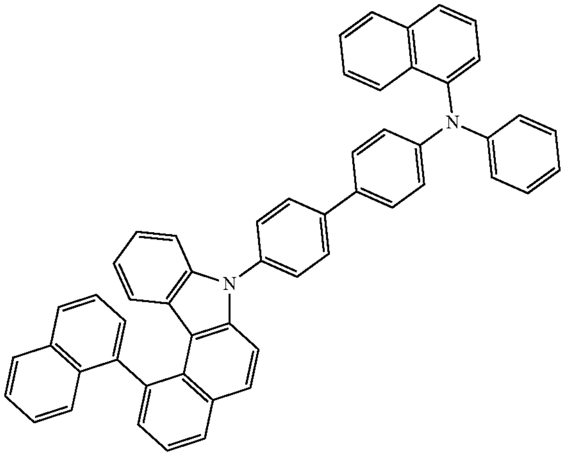
-continued
163
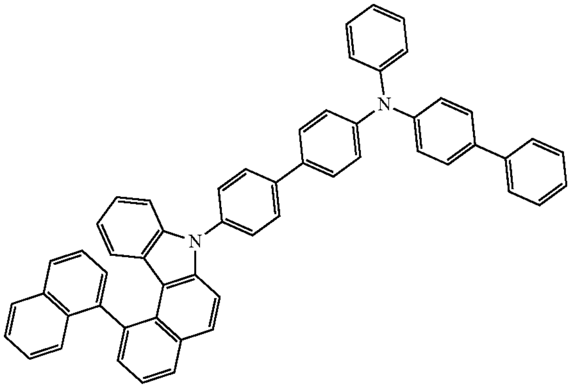
164
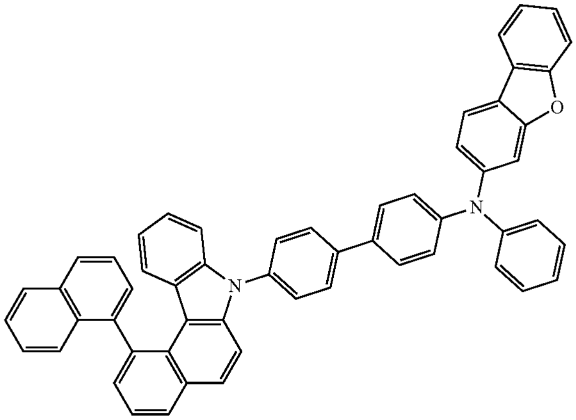
165
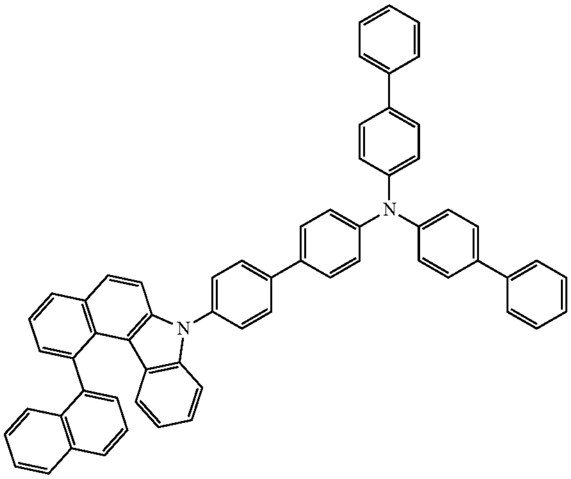

-continued
166
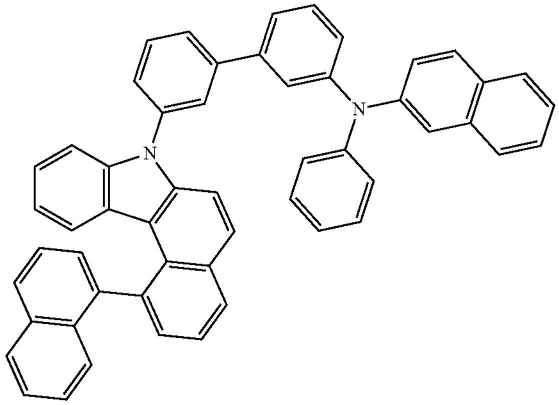
167
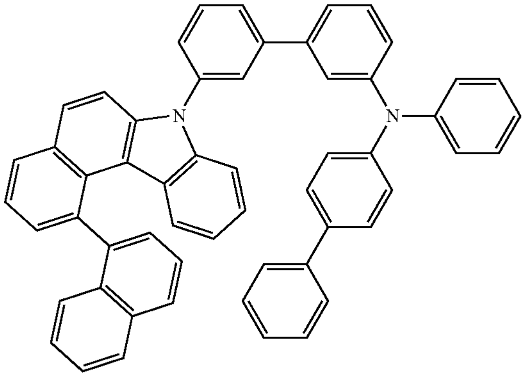
168
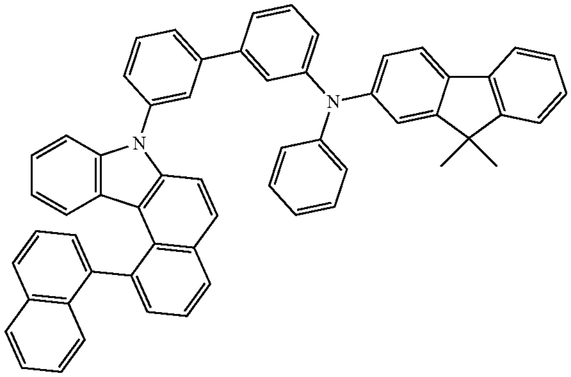
169
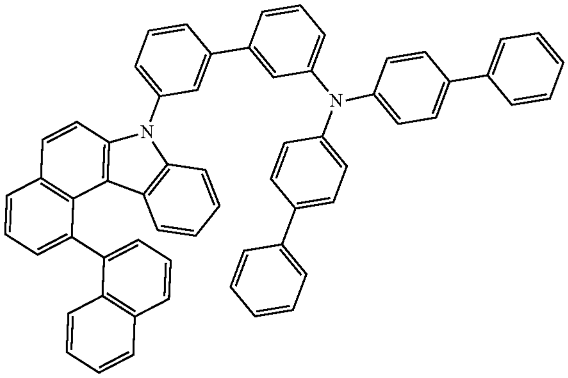
-continued
170
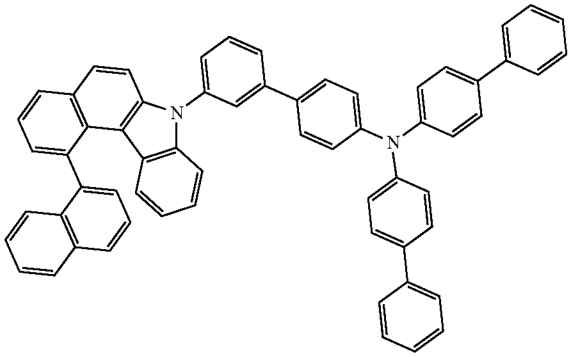
171
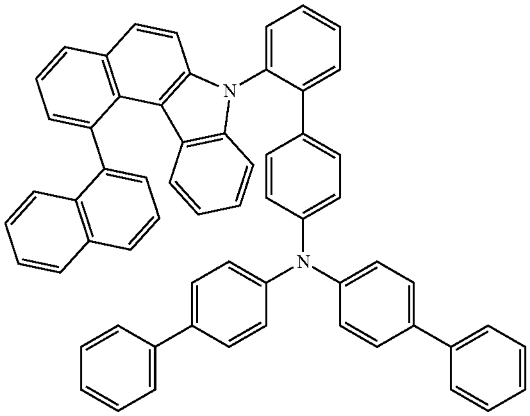
172
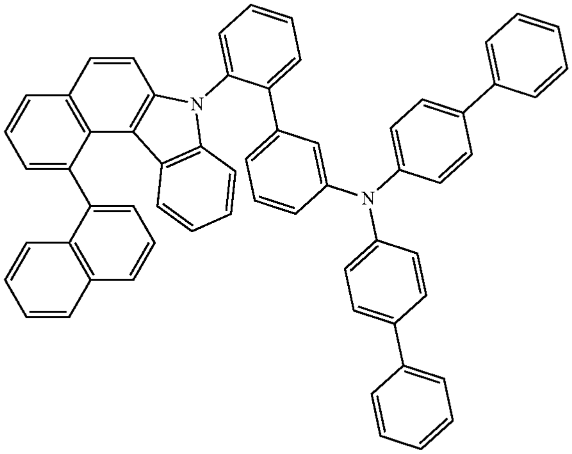

-continued
173
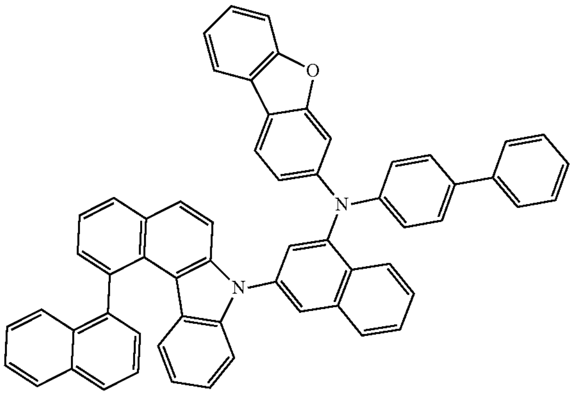
174
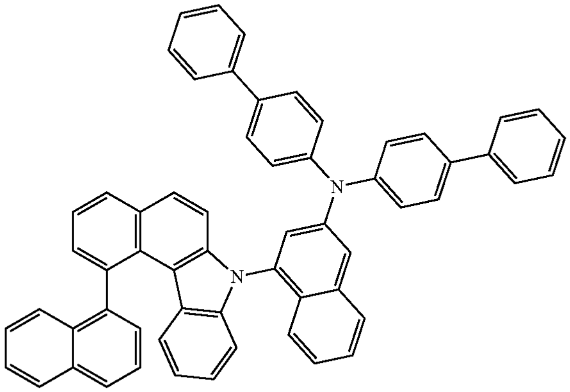
175
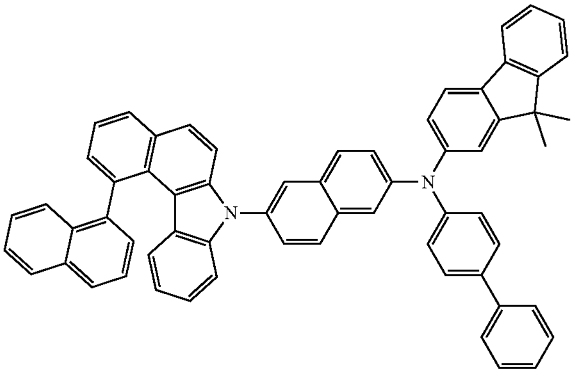
176
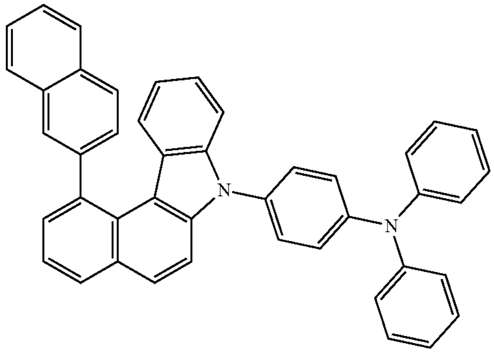
-continued
177
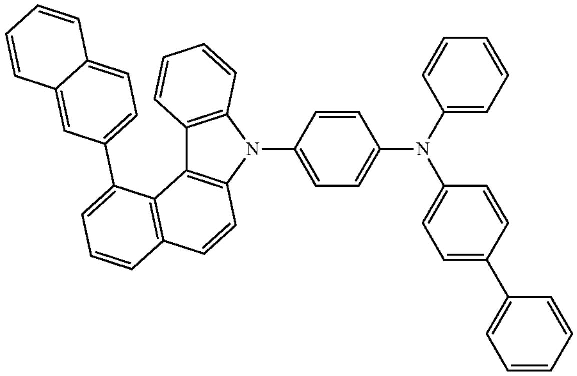
178
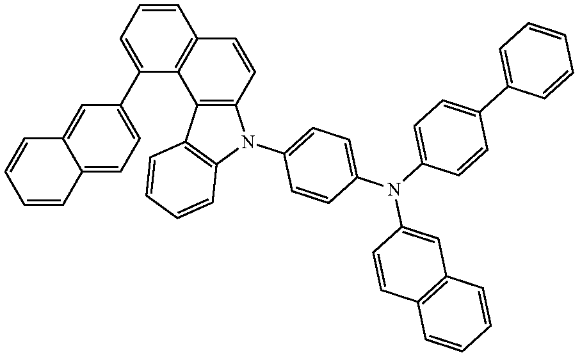
179
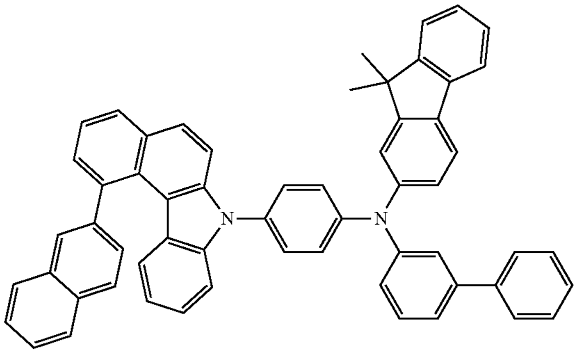
180
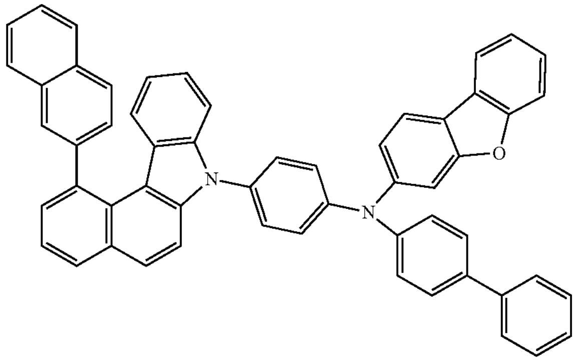

181
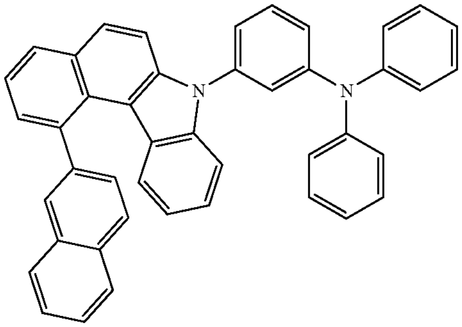
182
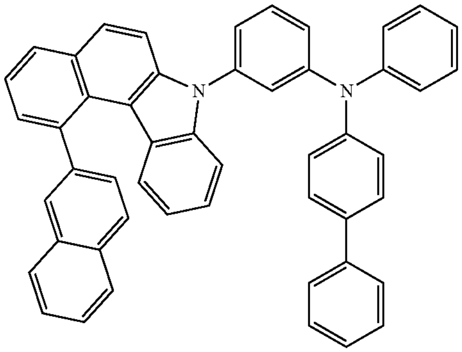
183
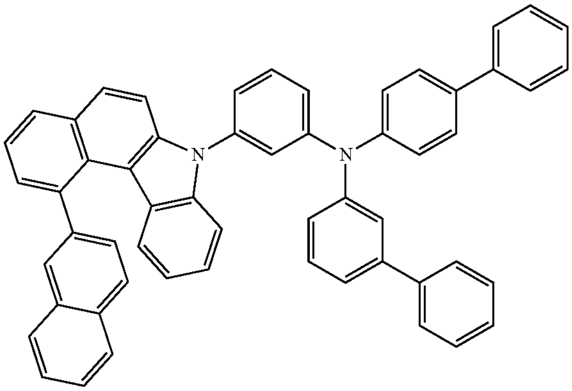
184
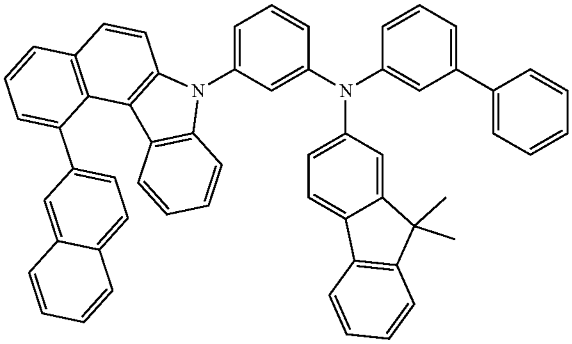
185
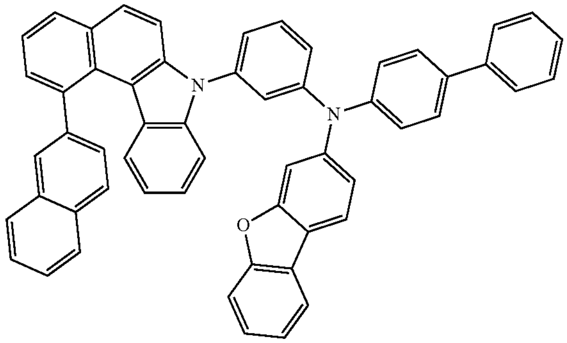
186
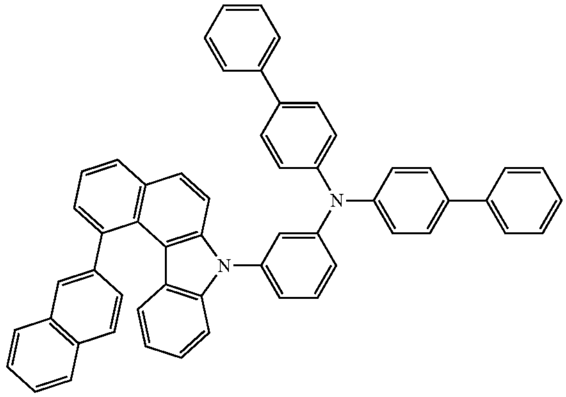
187
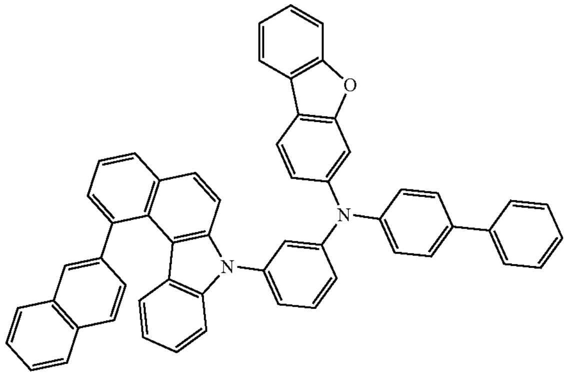
188
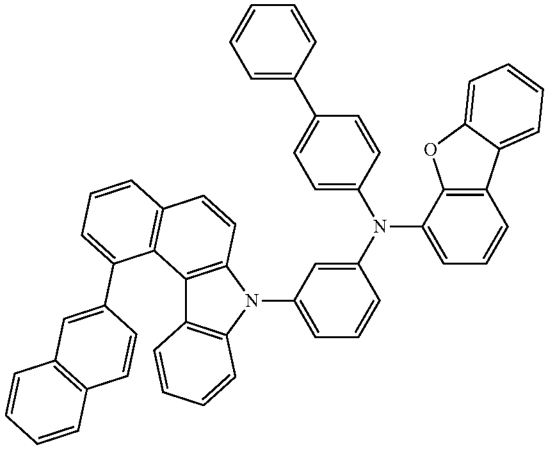

-continued
189
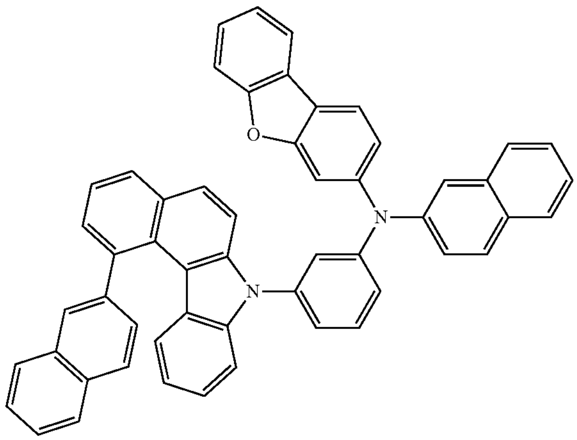
190
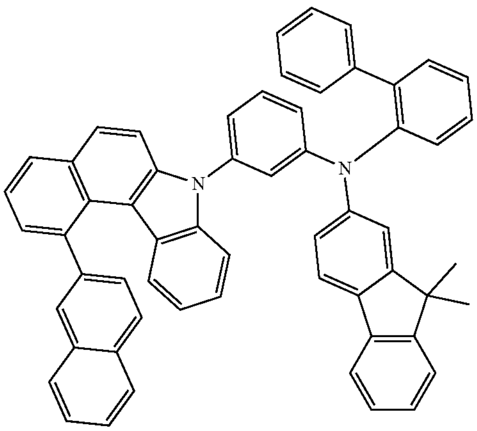
191
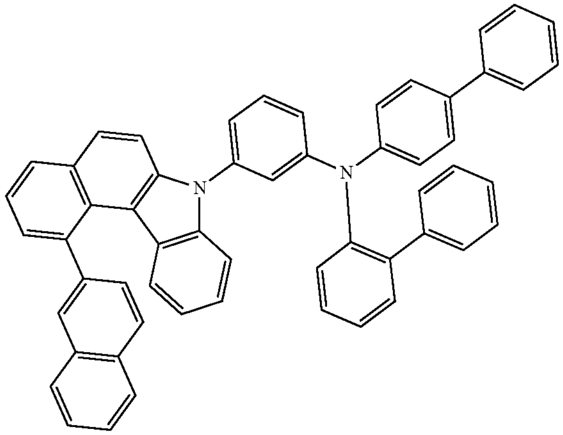
-continued
192
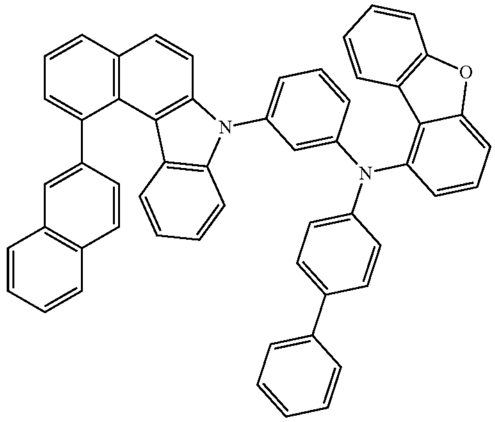
193
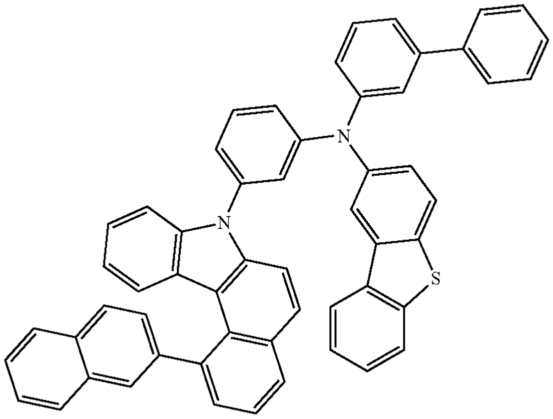
194
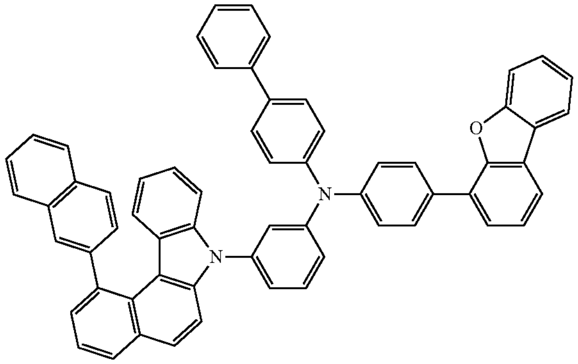
195
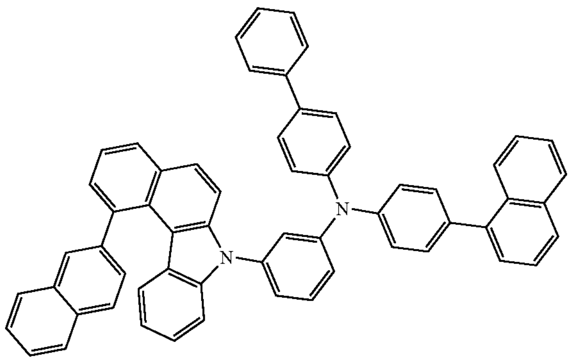

-continued
196
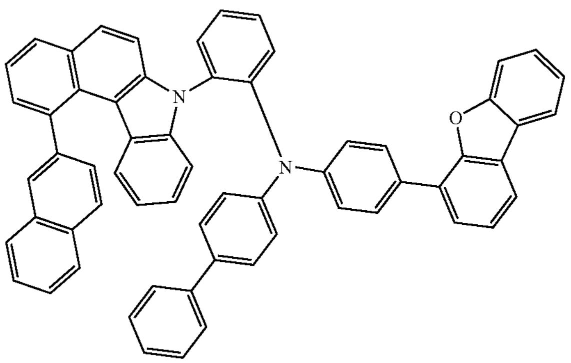
197
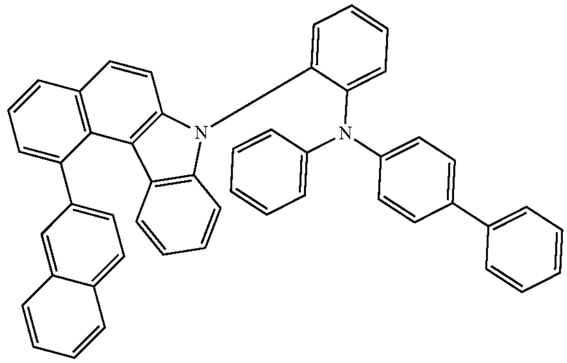
198
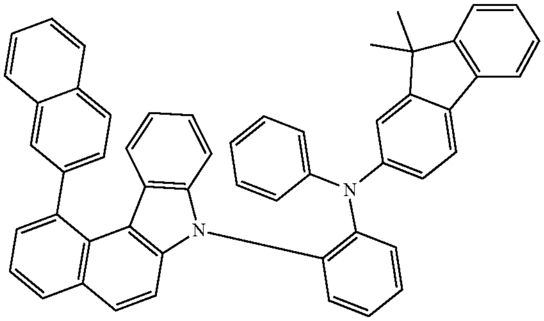
199
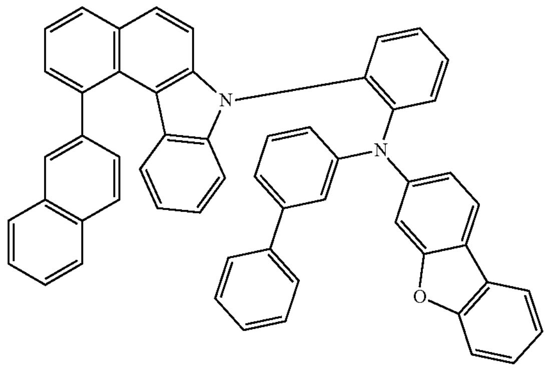
-continued
200
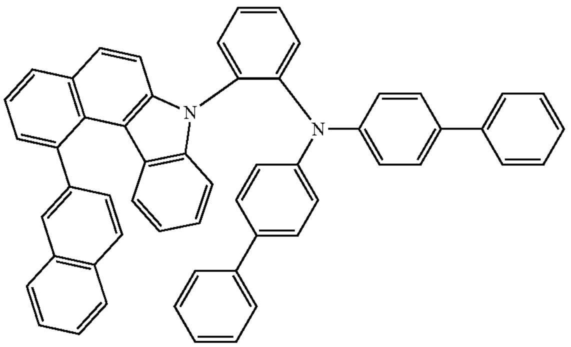
201
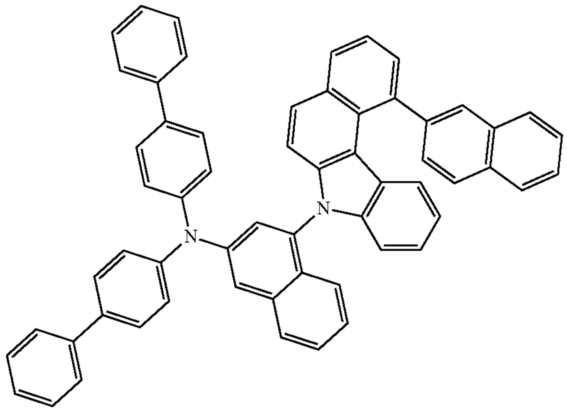
202
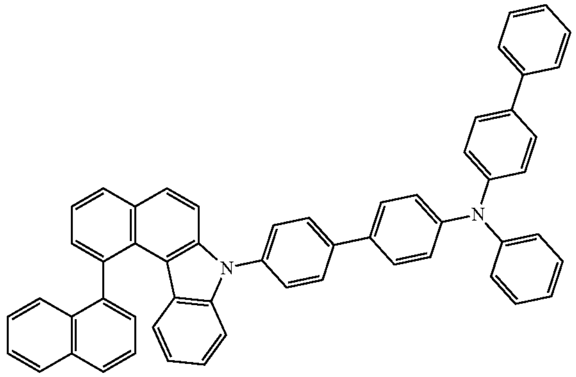
203
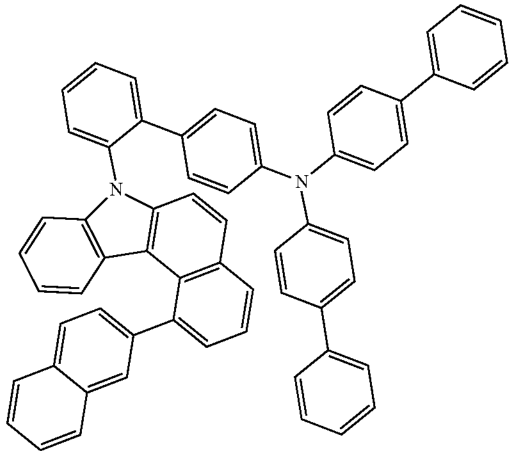

-continued
204
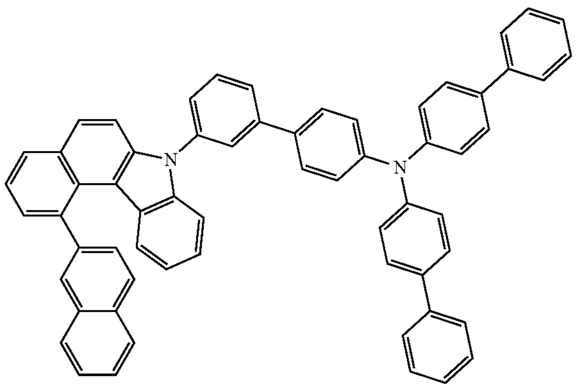
205
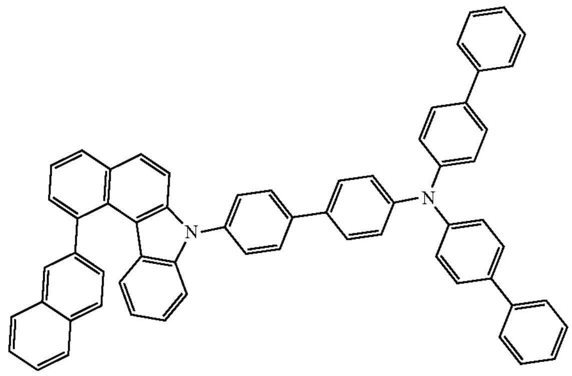
206
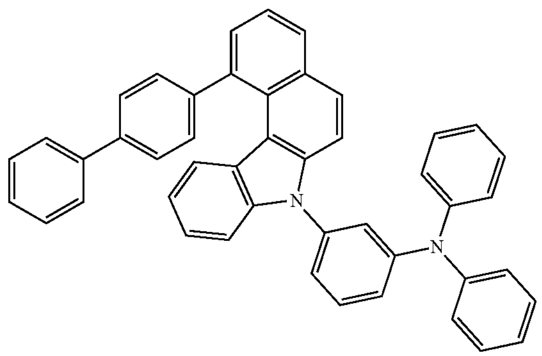
207
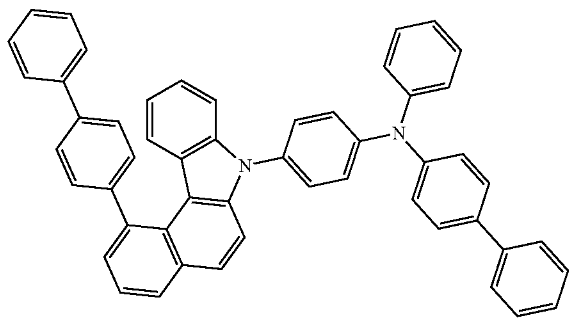
-continued
208
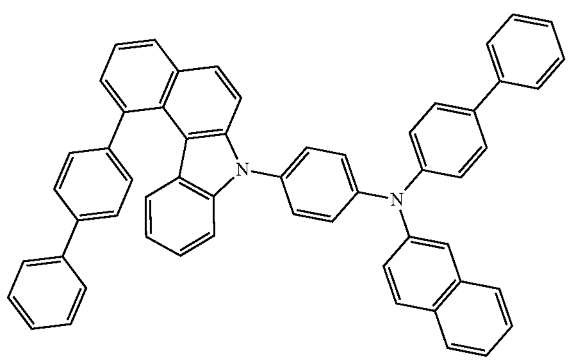
209
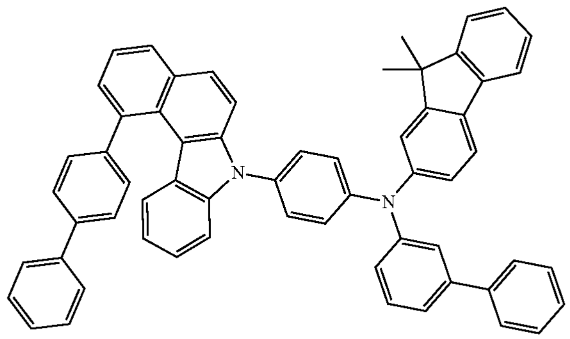
210
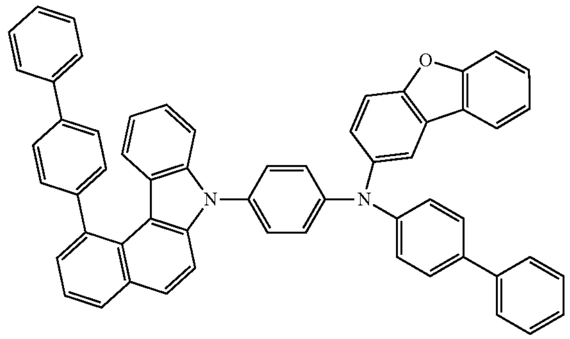
211
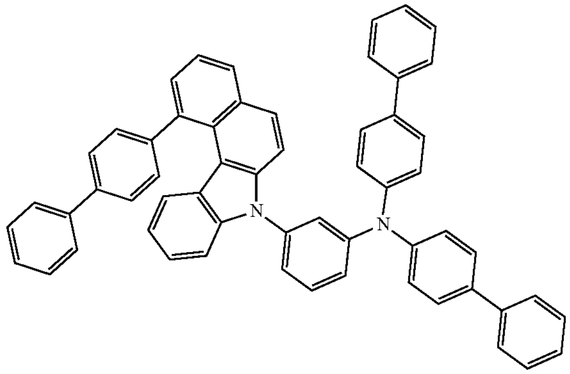

-continued
212
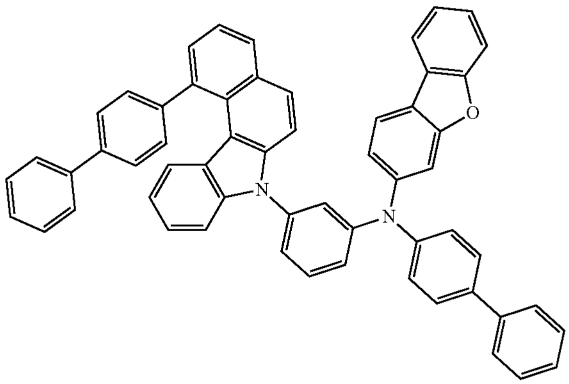
213
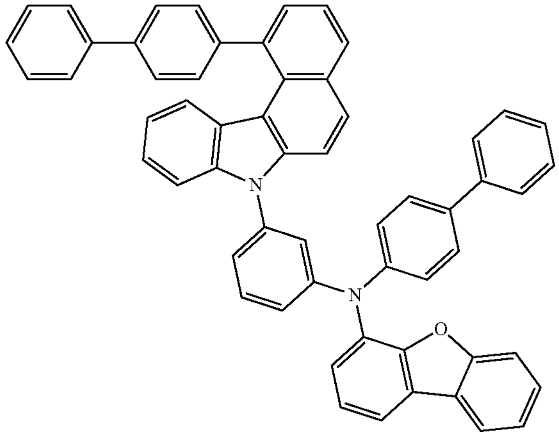
214
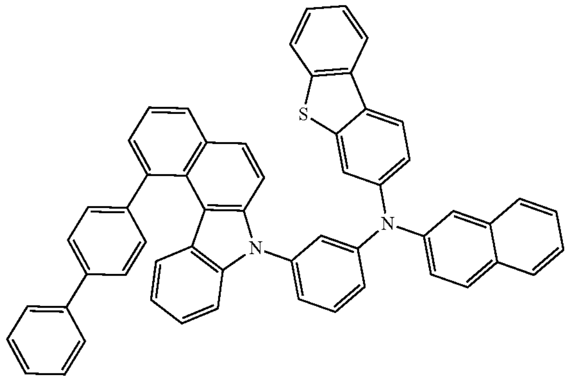
-continued
215
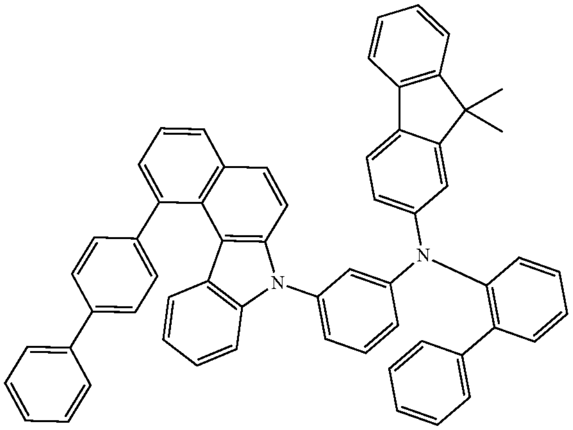
216
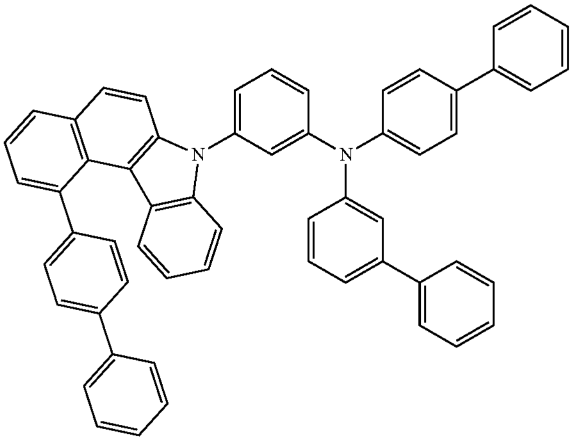
217
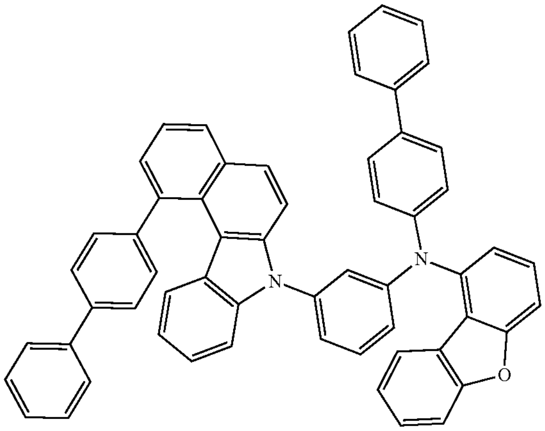

-continued
218
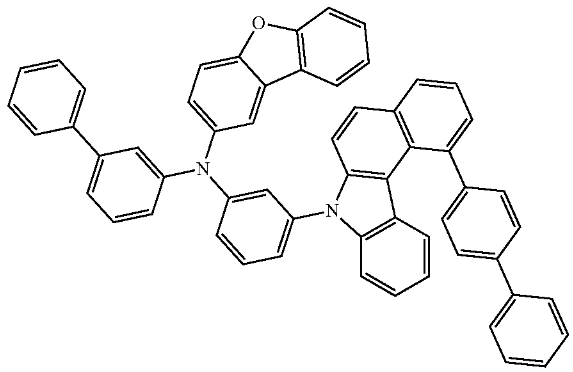
219
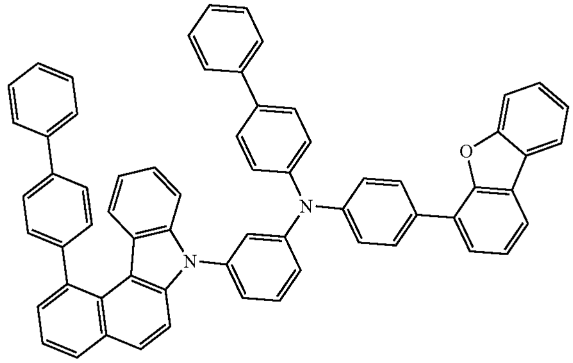
220
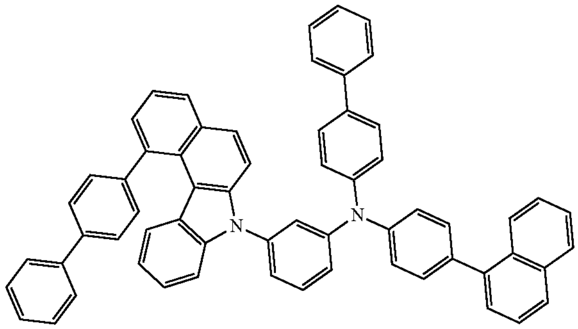
221
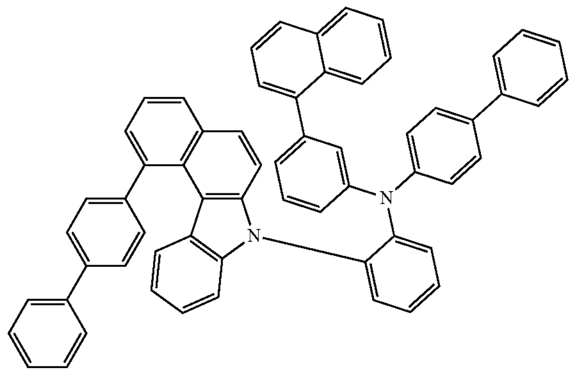
-continued
222
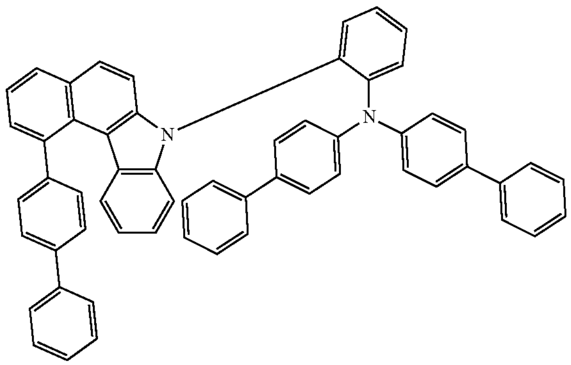
223
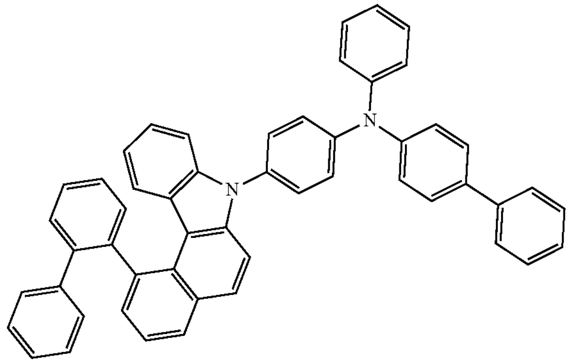
224
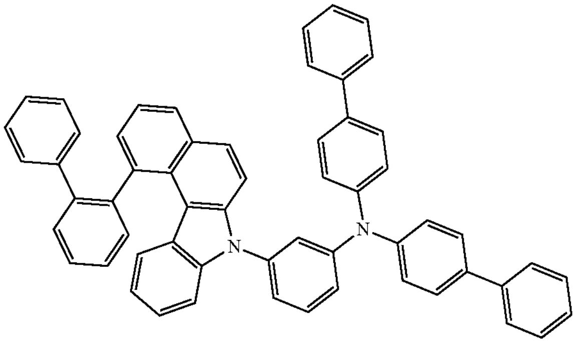
225
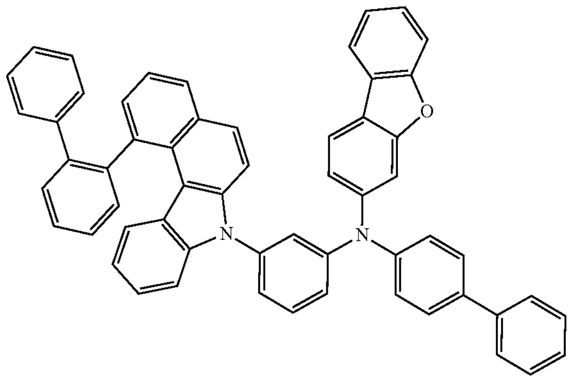

-continued
226
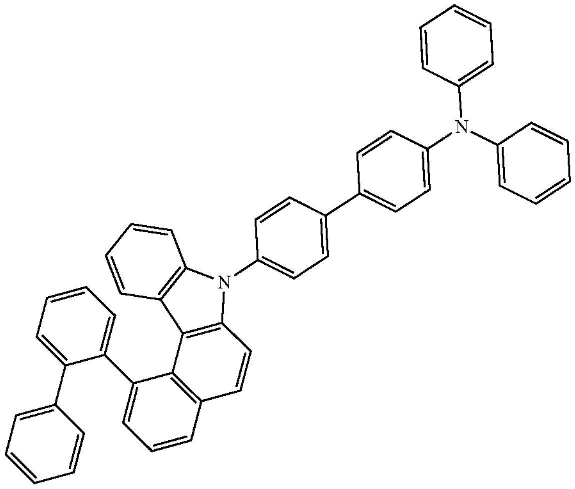
227
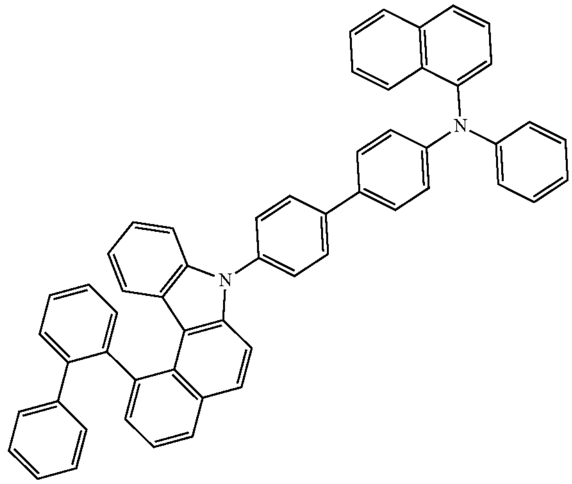
228
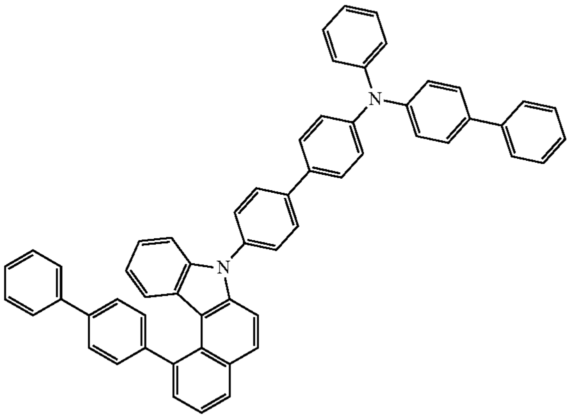
-continued
229
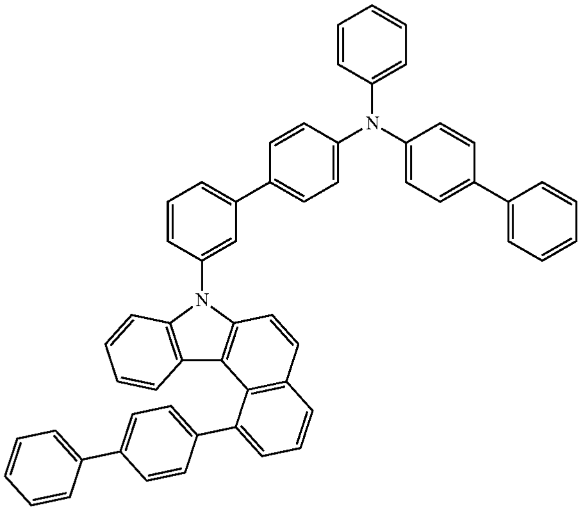
230
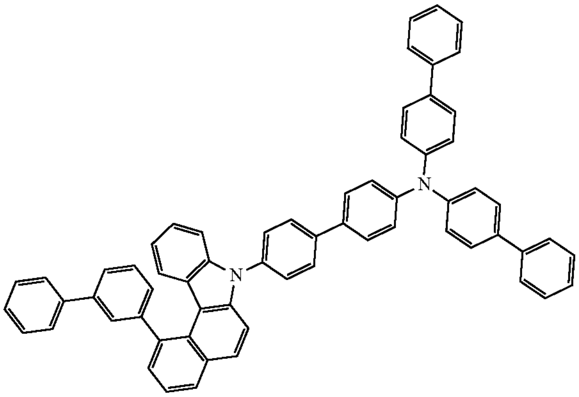
231
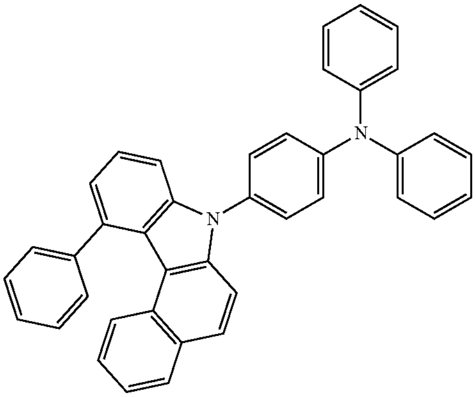

-continued
232
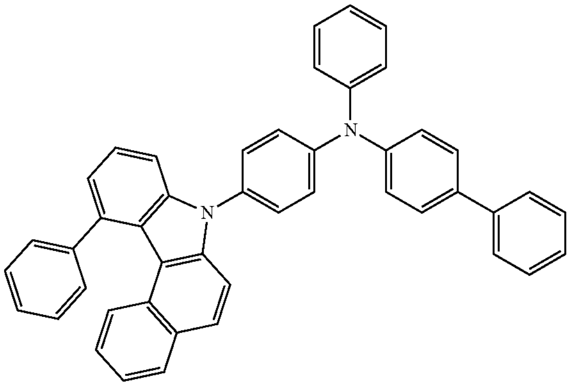
233
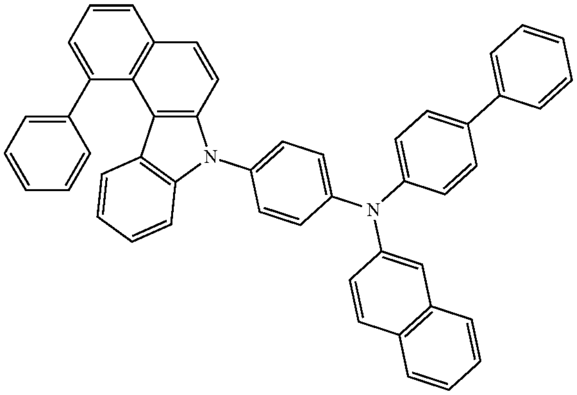
234
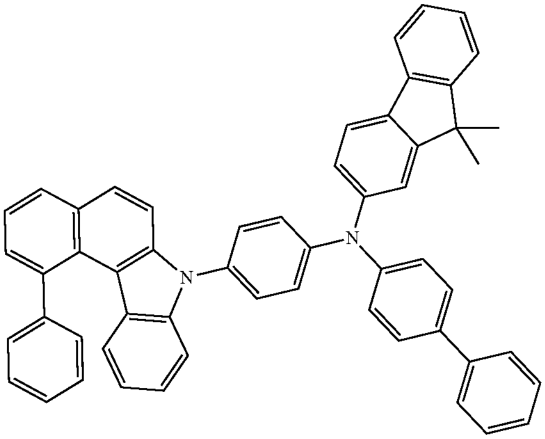
-continued
235
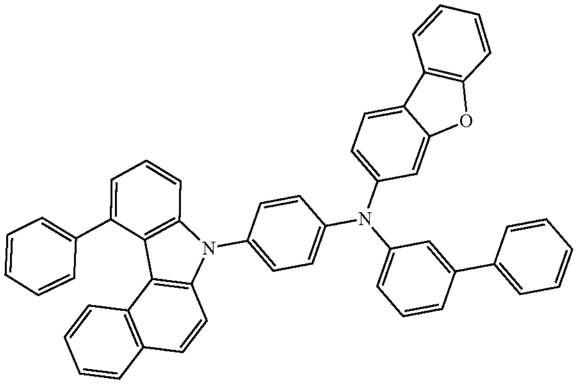
236
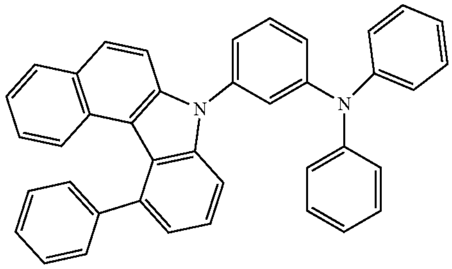
237
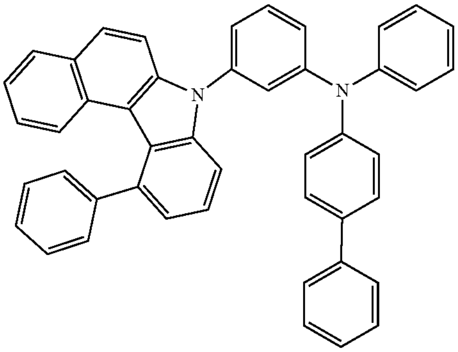
238
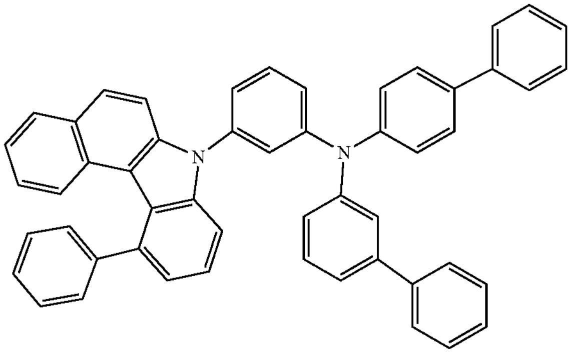

-continued
239
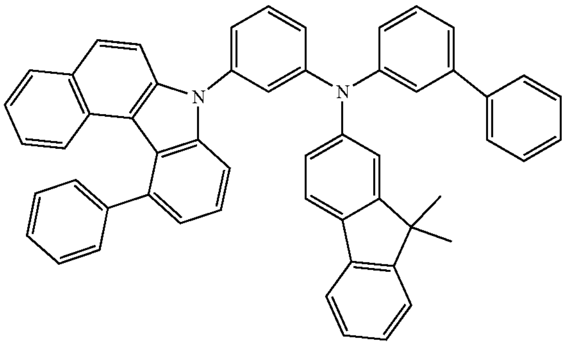
240
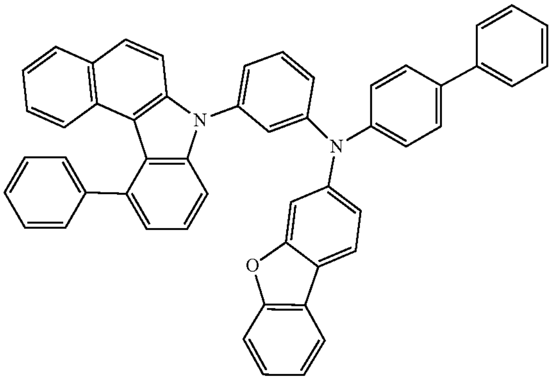
246
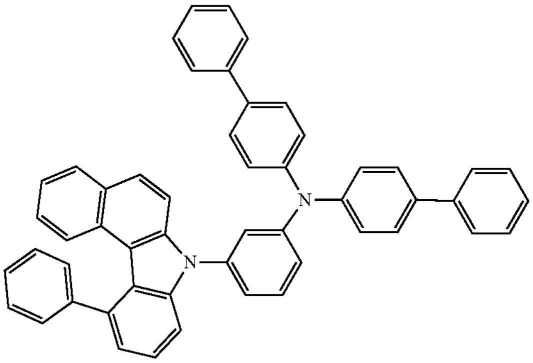
247
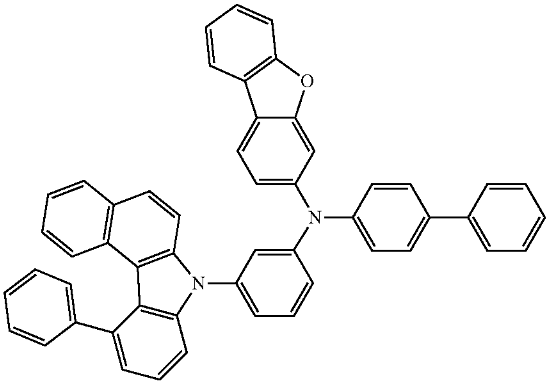
-continued
248
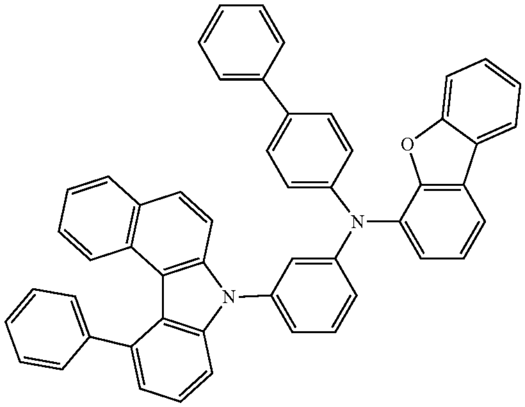
249
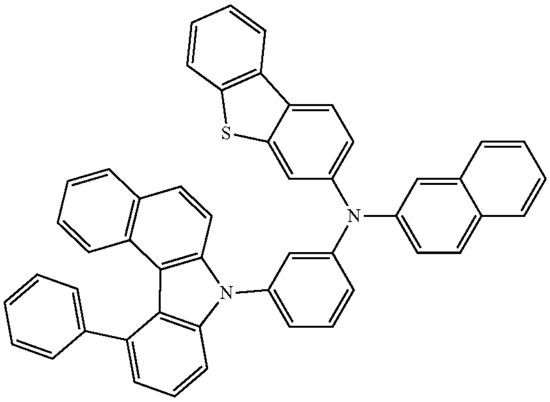
250
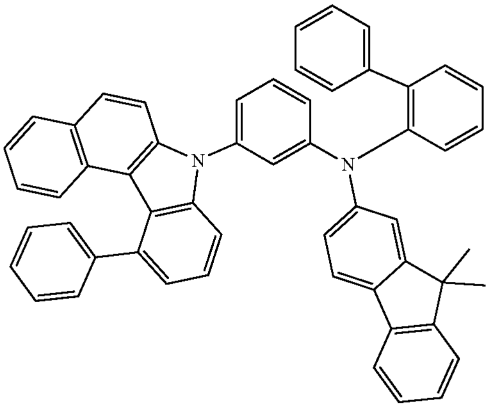
251
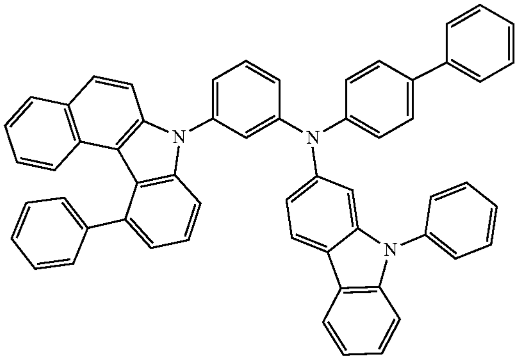

-continued
252
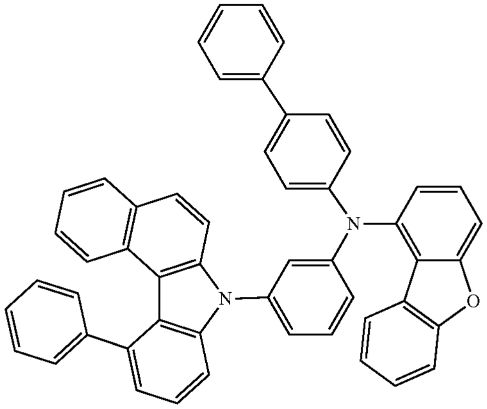
253
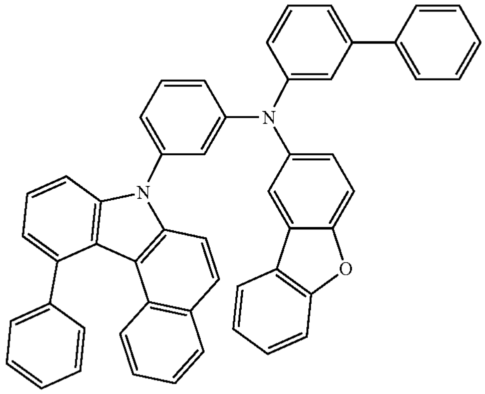
254
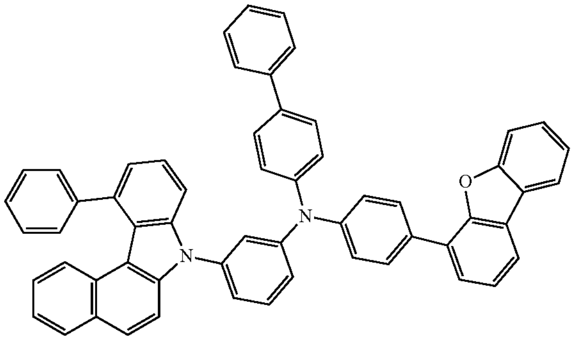
255
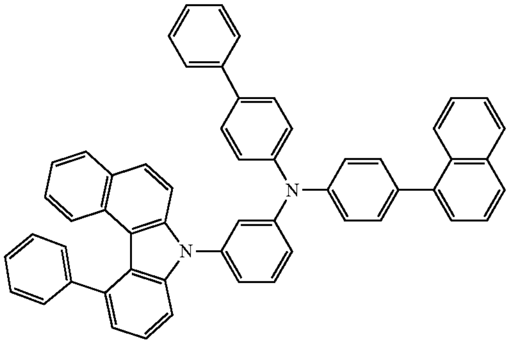
-continued
256
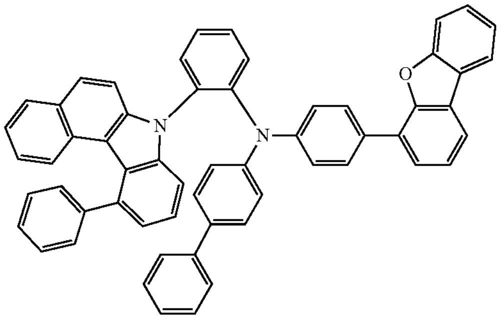
257
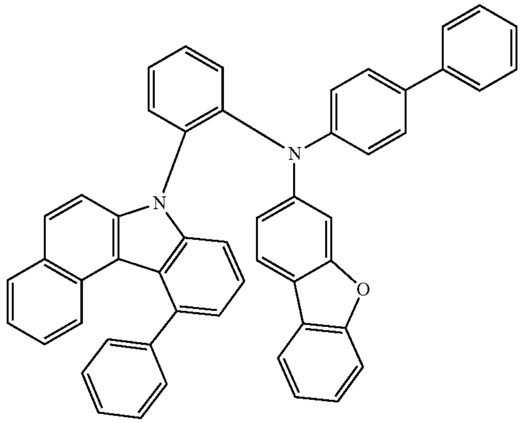
258
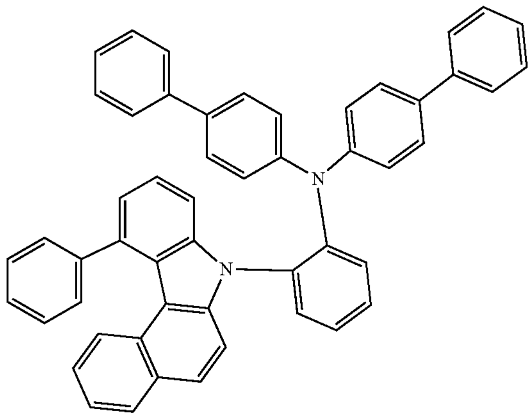
259
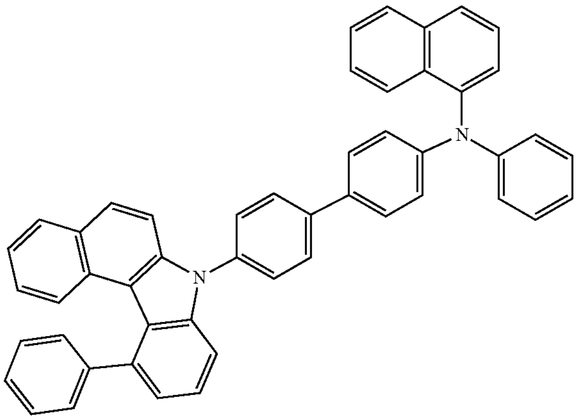

-continued
260
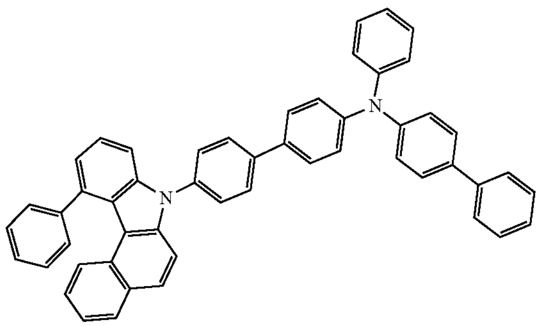
261
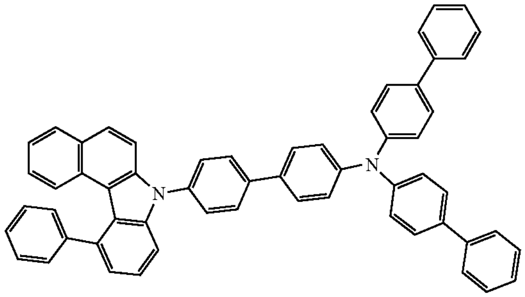
262
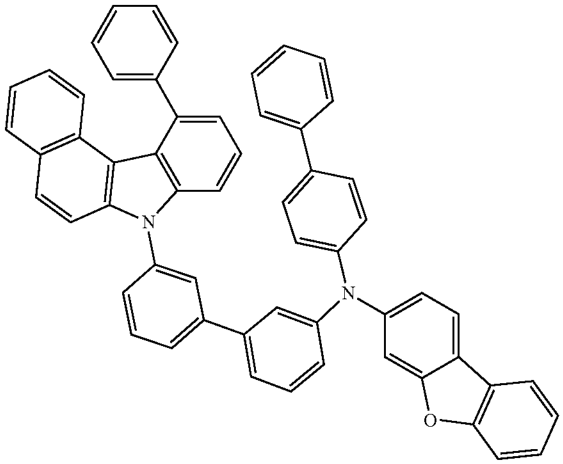
263
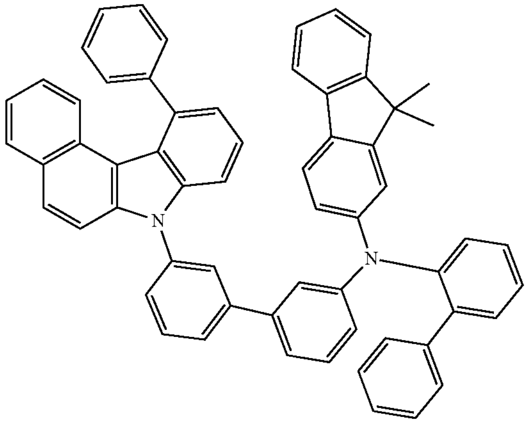
-continued
264
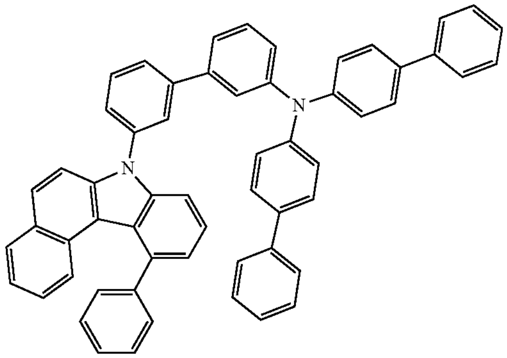
265
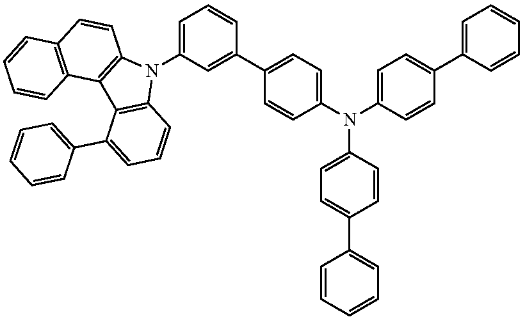
266
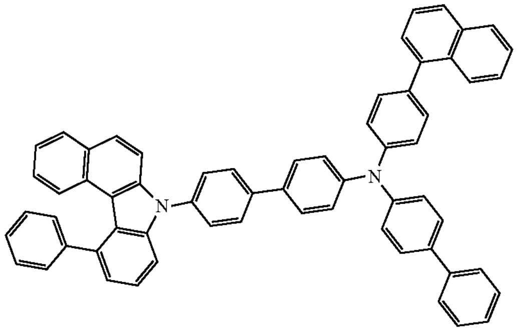
267
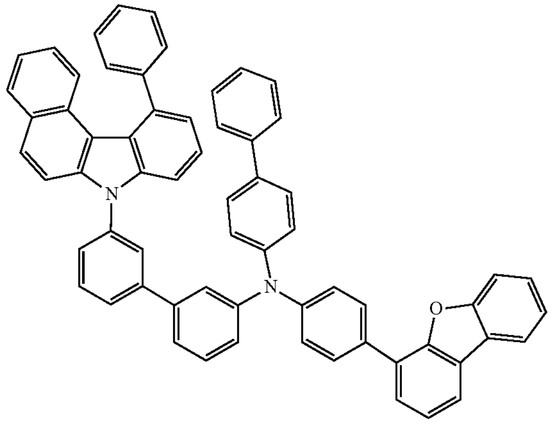

-continued
268
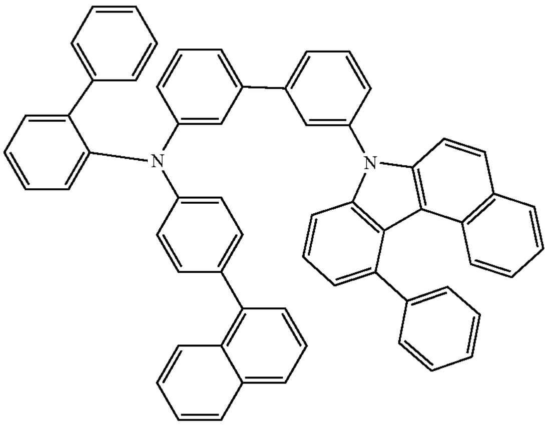
269
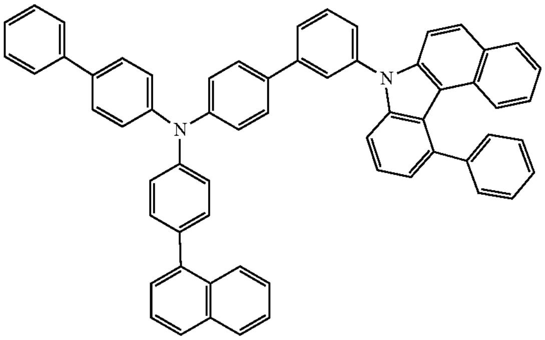
270
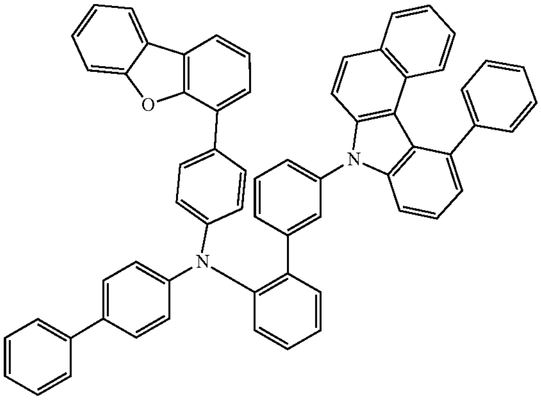
-continued
271
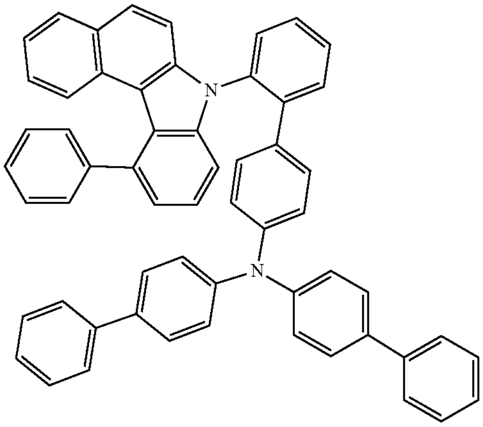
272
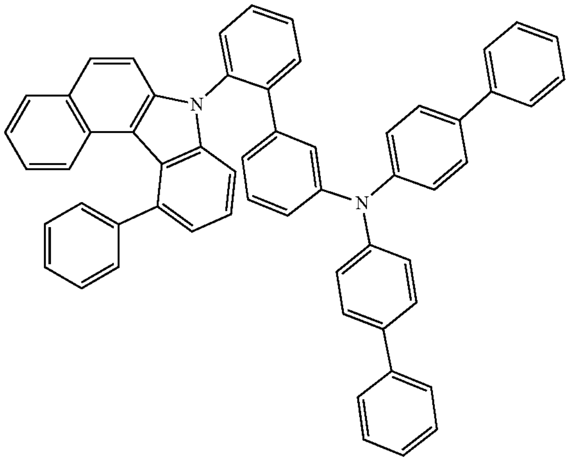
273
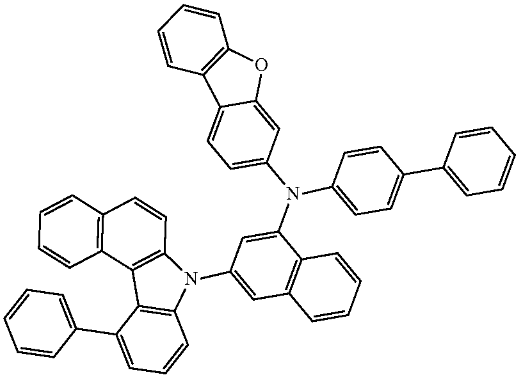

-continued
274
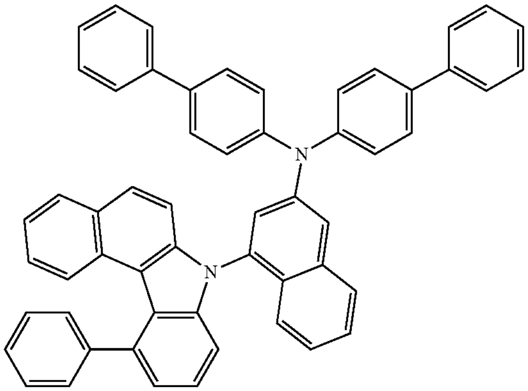
275
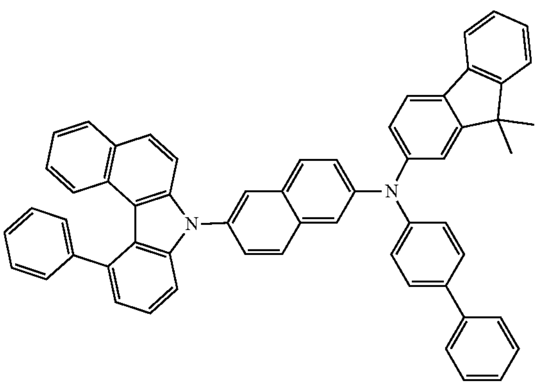
276
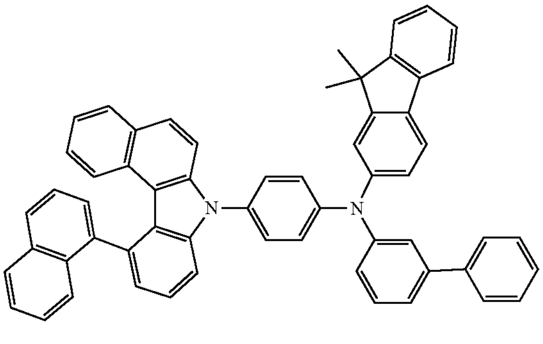
277
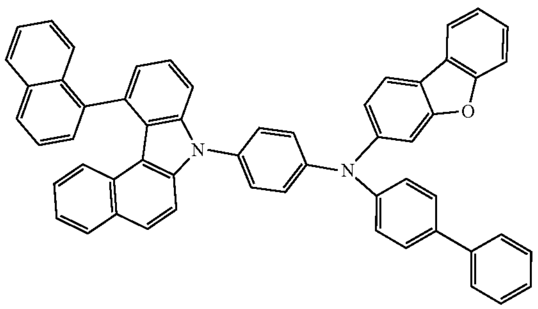
-continued
278
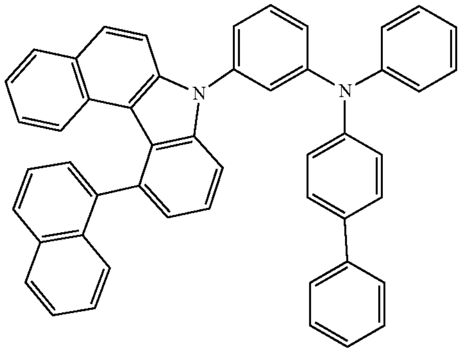
279
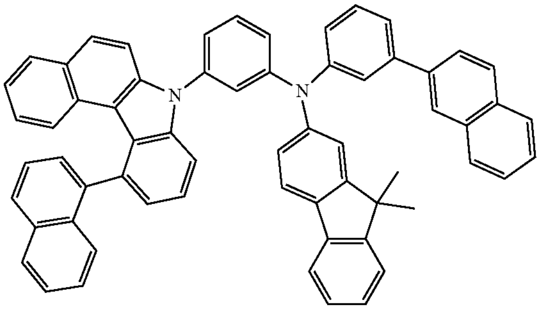
280
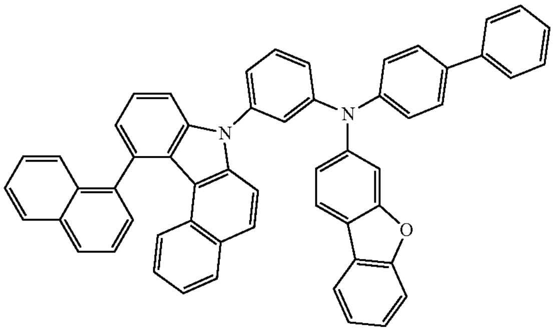
281
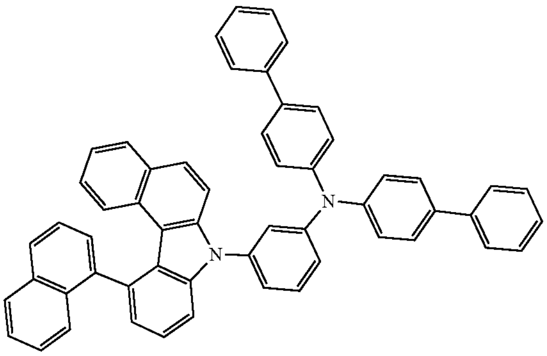

-continued
282
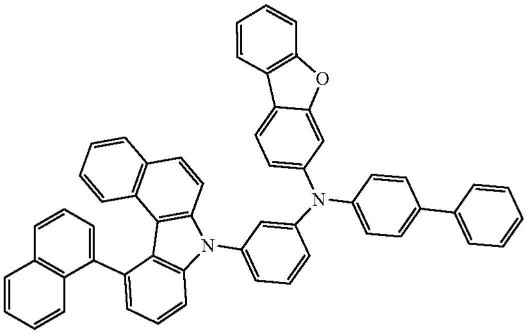
283
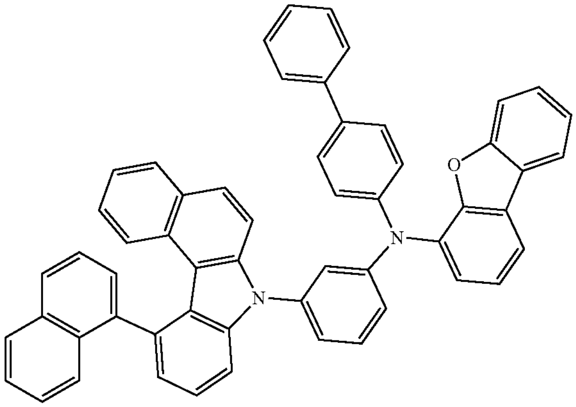
284
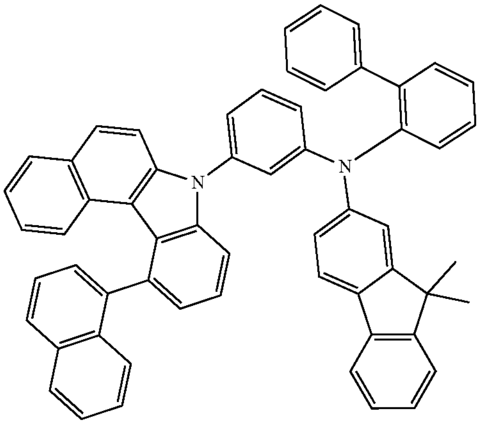
-continued
285
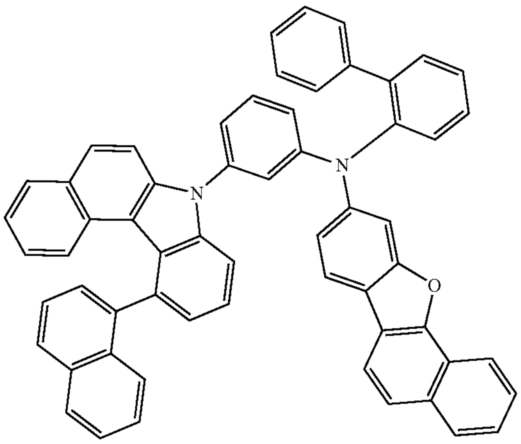
286
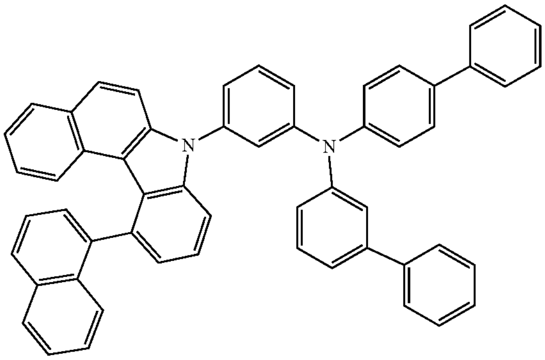
287
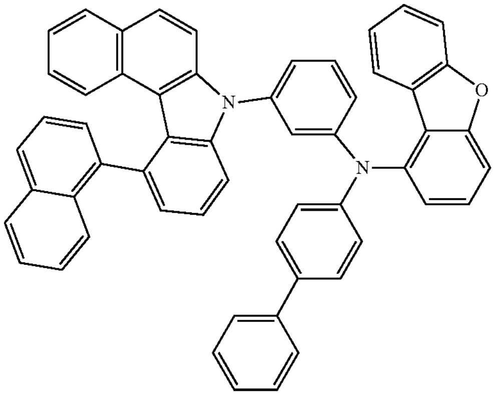

-continued
288
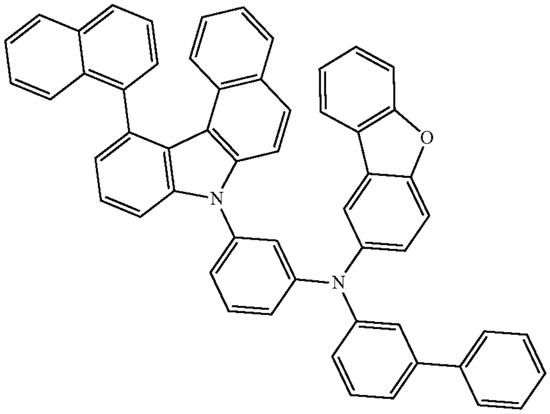
289
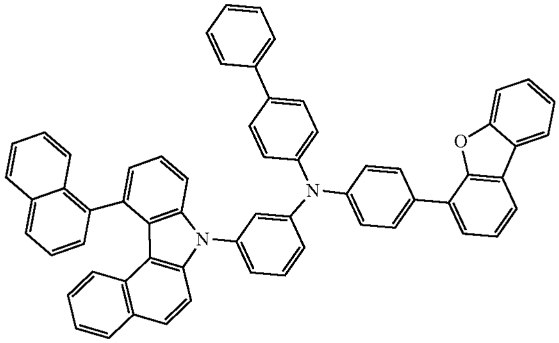
290
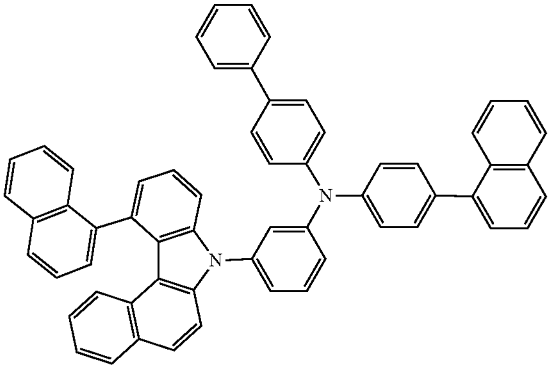
291
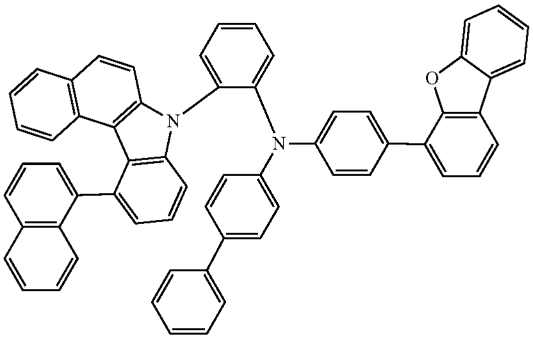
-continued
292
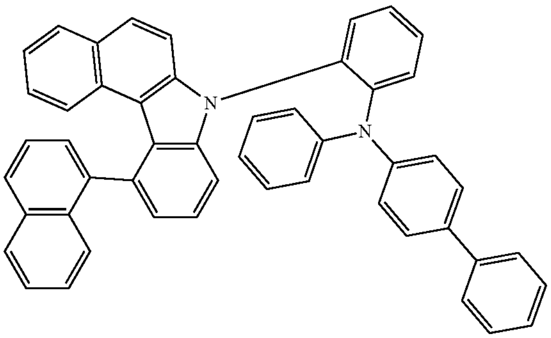
293
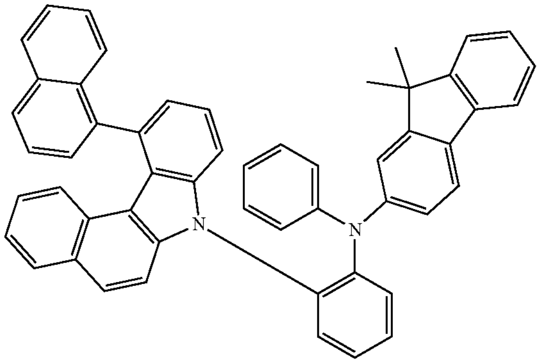
294
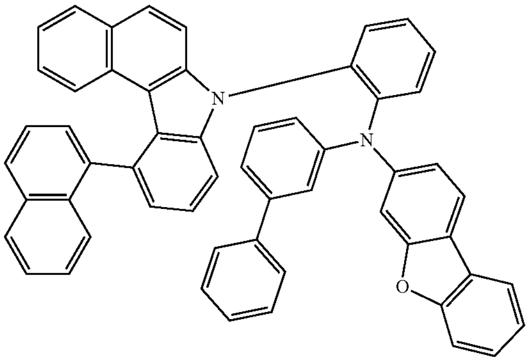
295
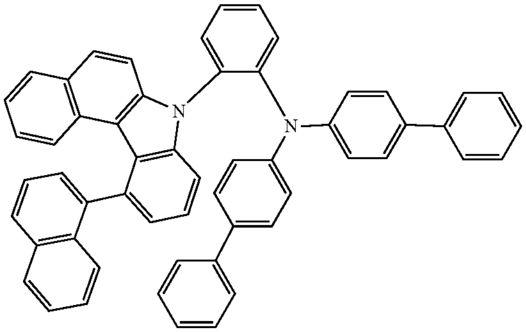

-continued
296
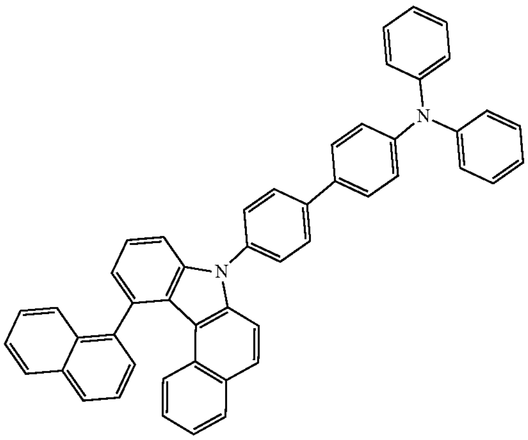
297
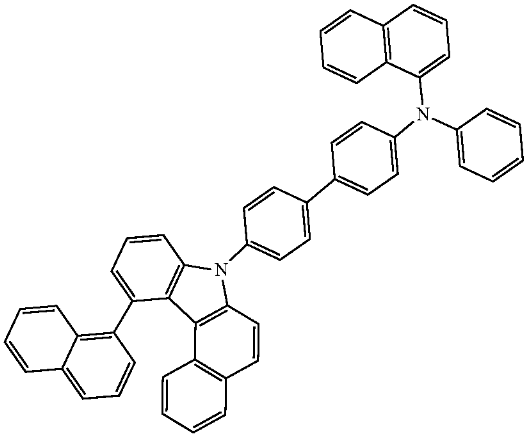
298
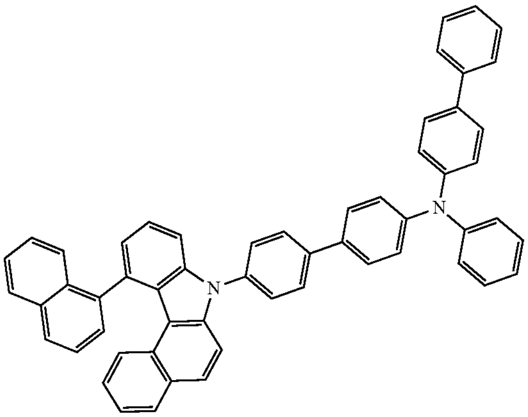
-continued
299
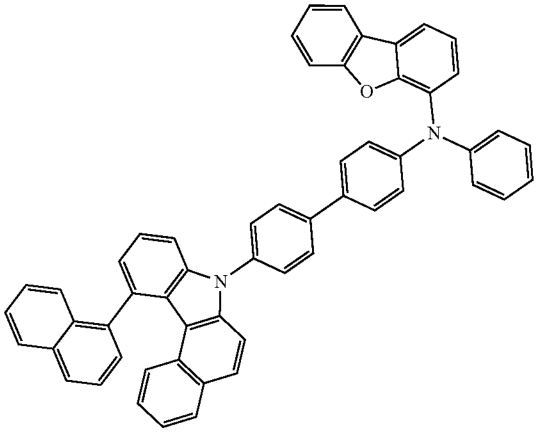
300
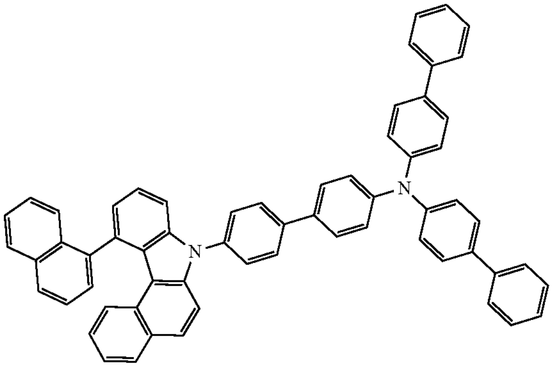
301
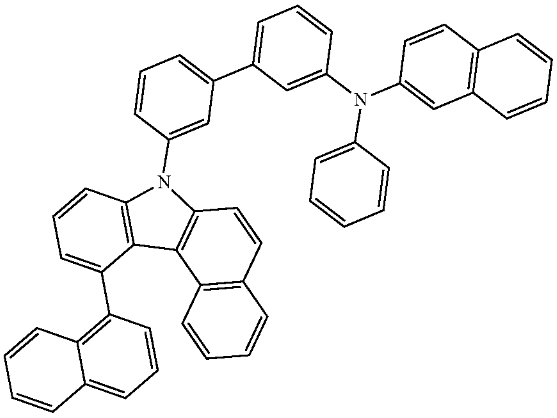

-continued
302
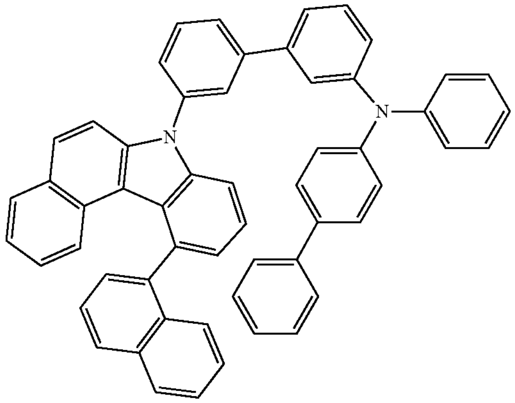
303
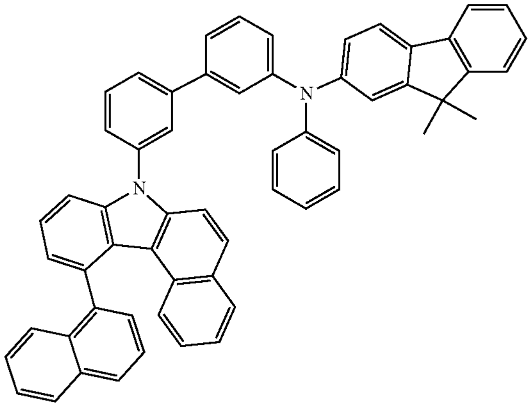
304
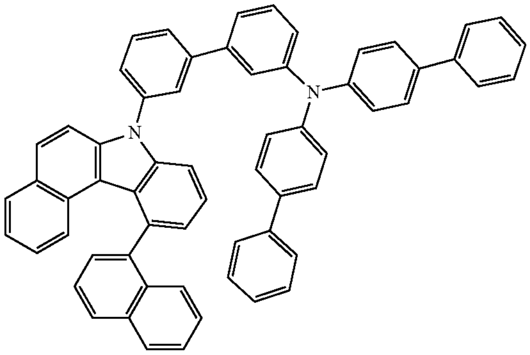
305
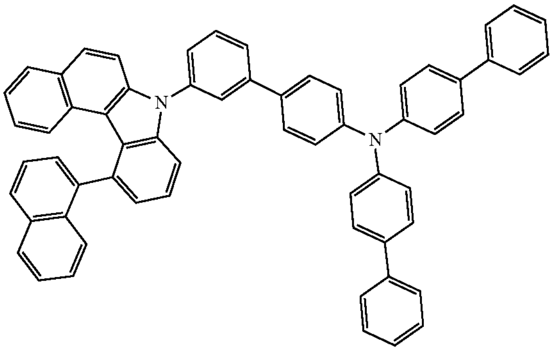
-continued
306
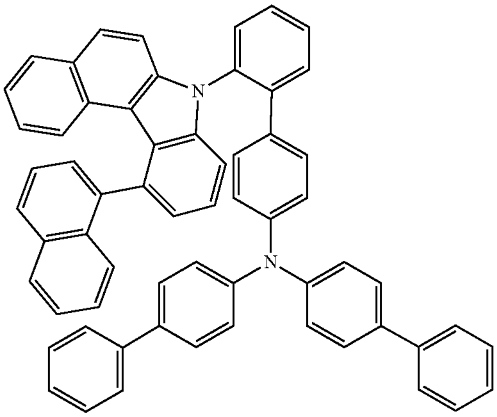
307
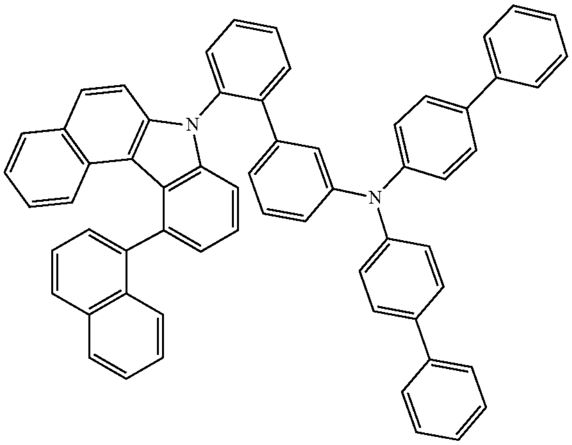
308
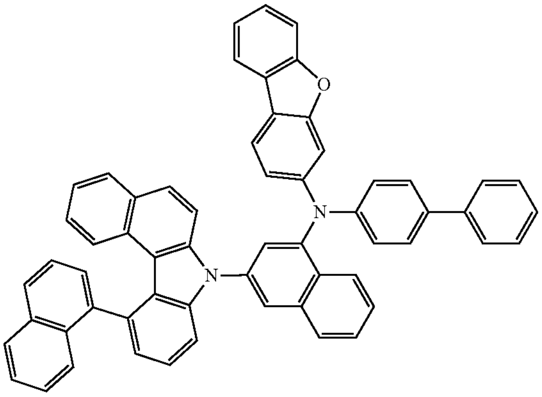

-continued
309
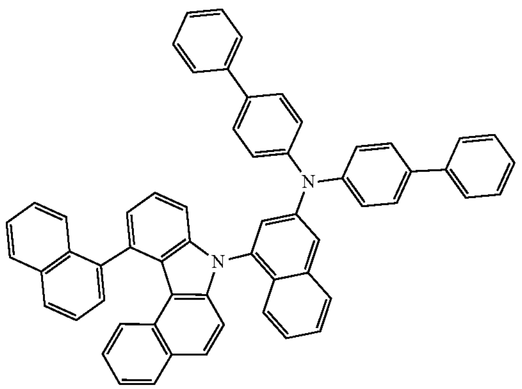
310
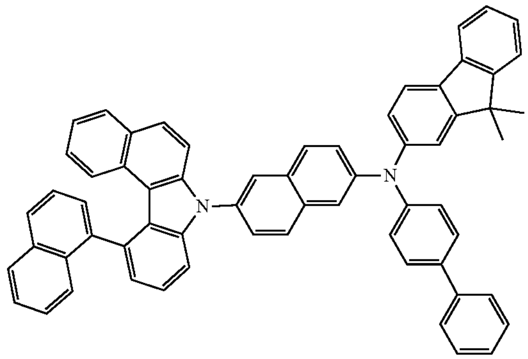
311
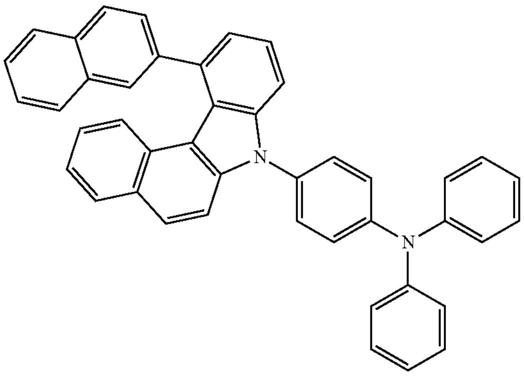
312
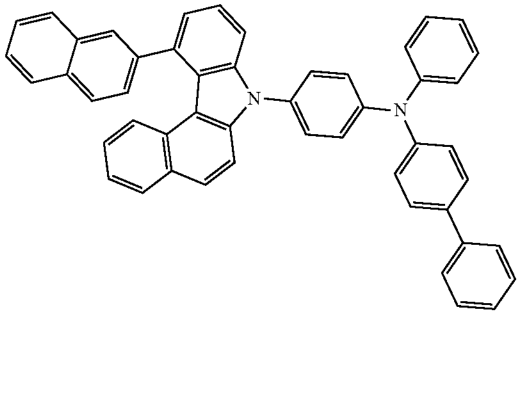
-continued
313
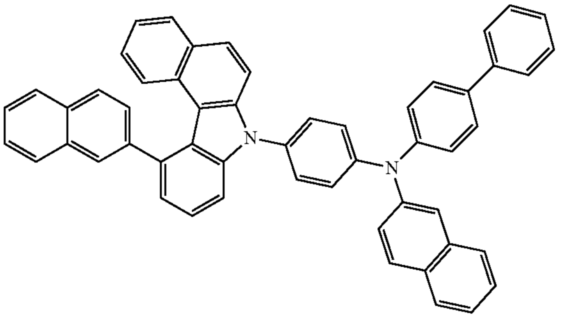
314
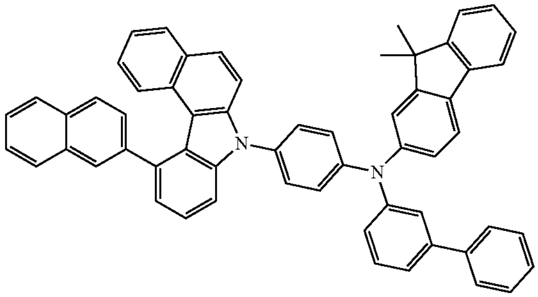
315
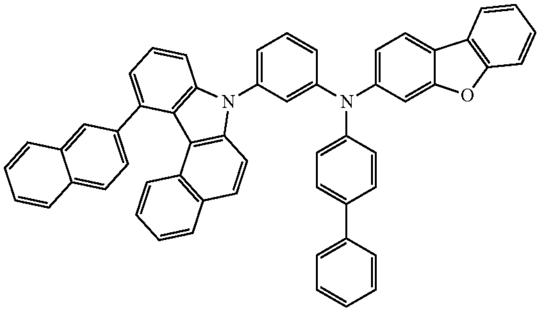
316
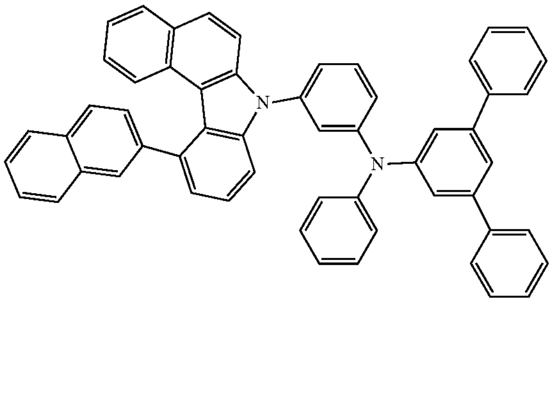

-continued
317
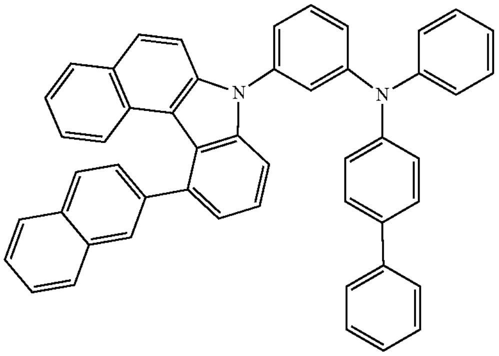
318
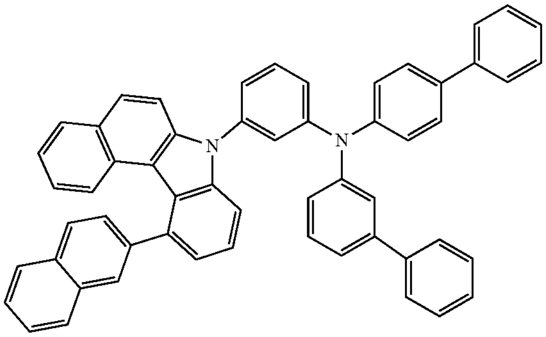
319
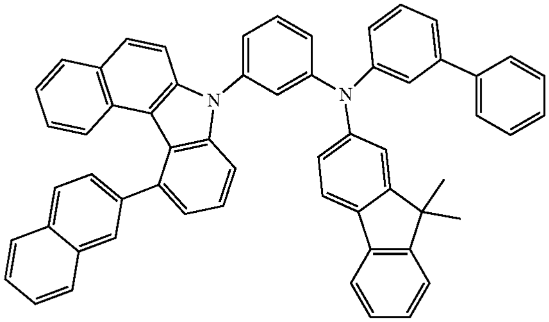
320
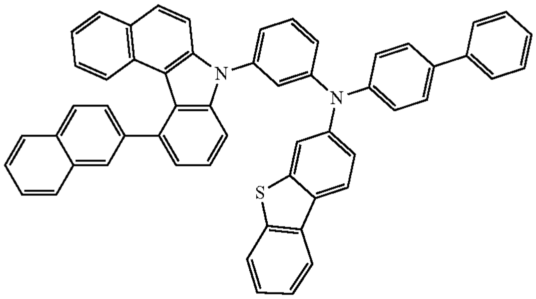
-continued
321
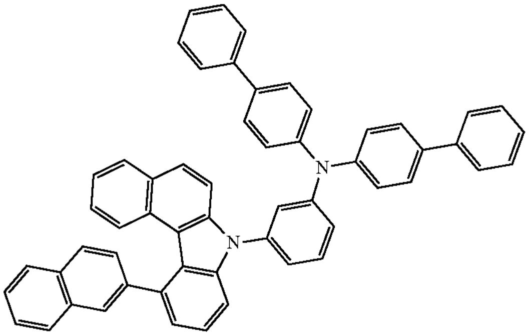
322
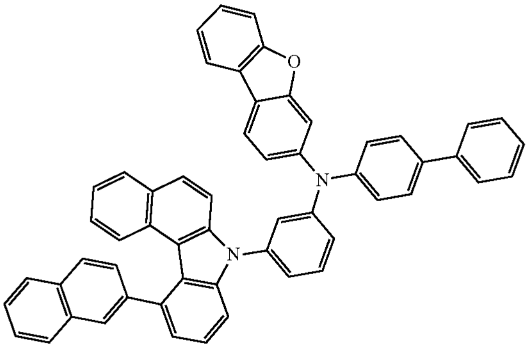
323
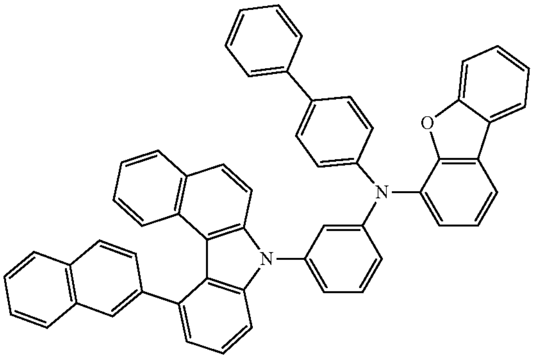
324
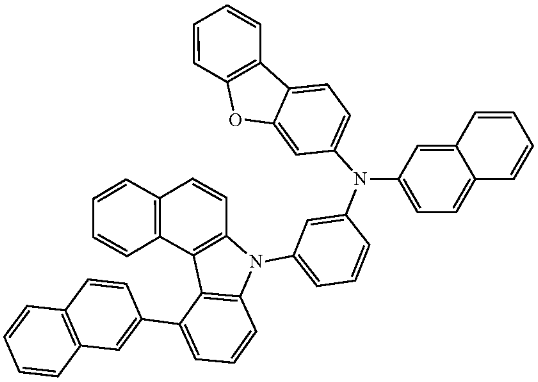

-continued
325
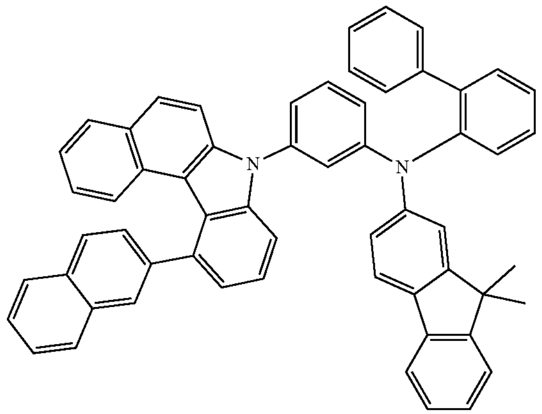
326
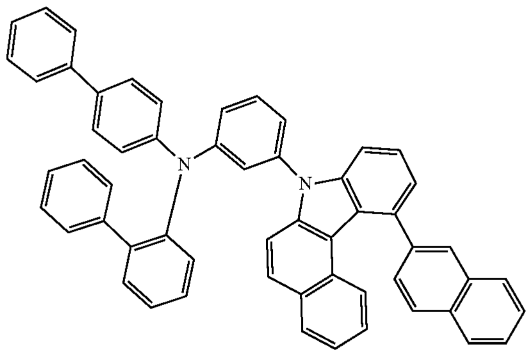
327
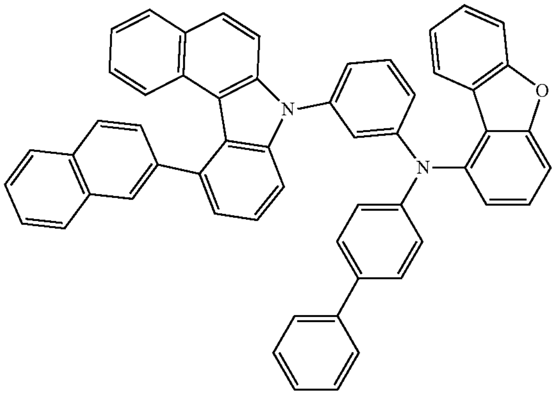
-continued
328
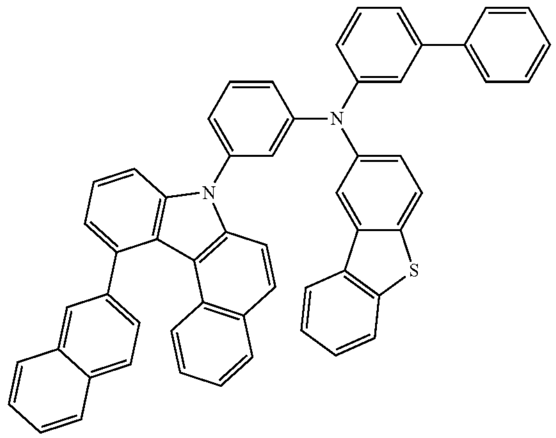
329
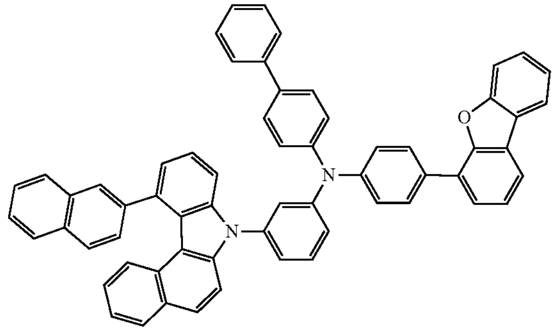
330
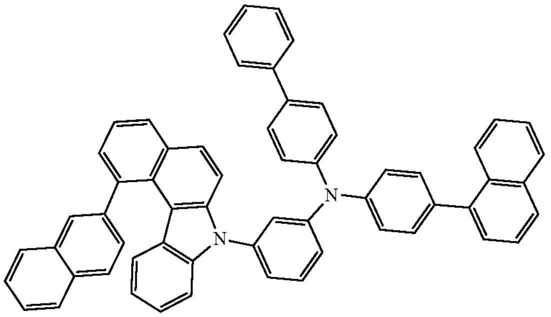
331
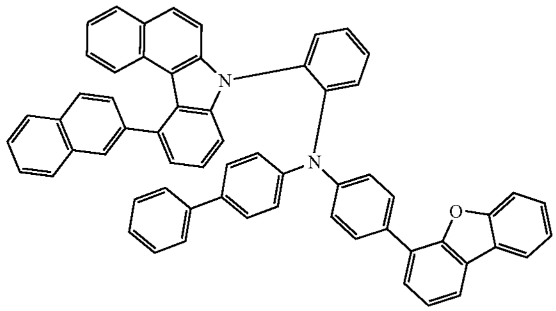

-continued
332
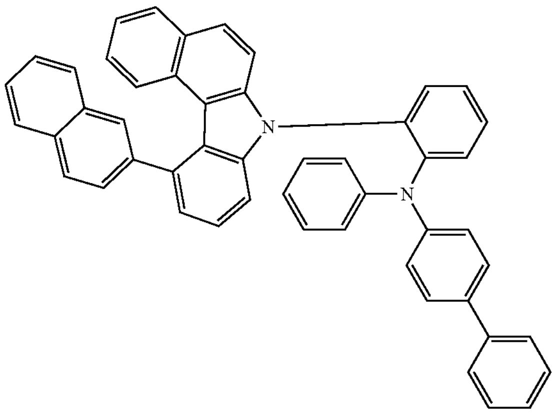
333
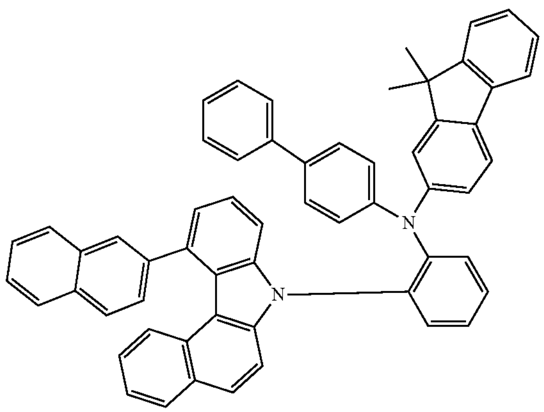
334
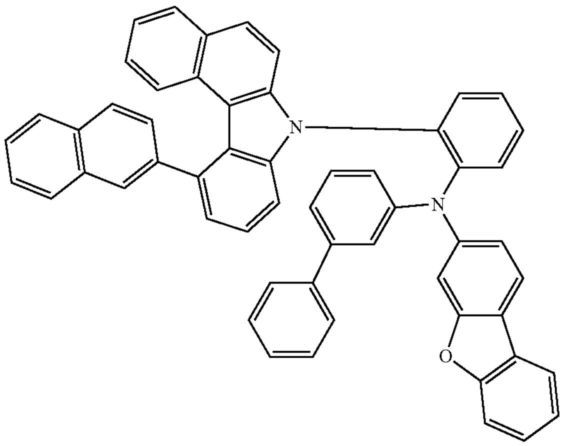
-continued
335
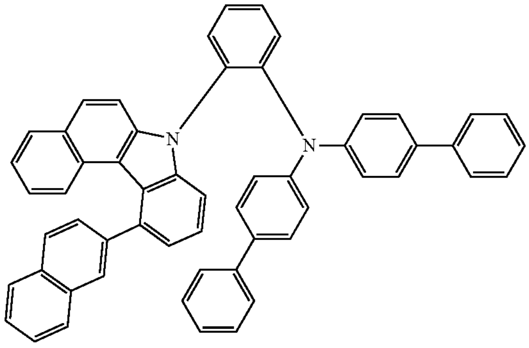
336
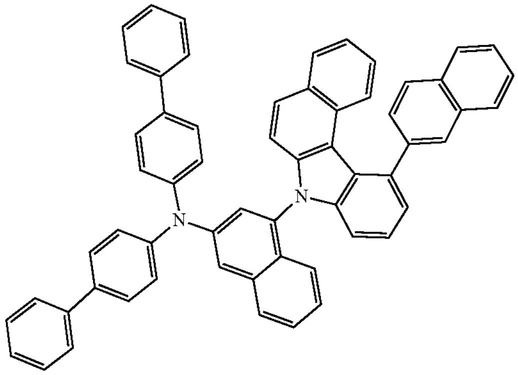
337
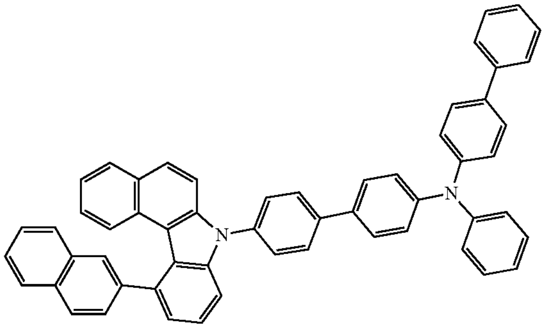
338
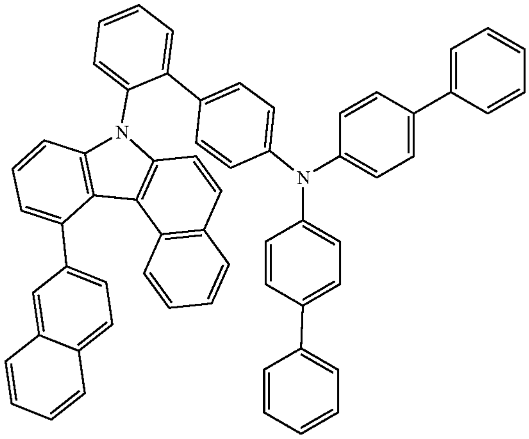

-continued
339
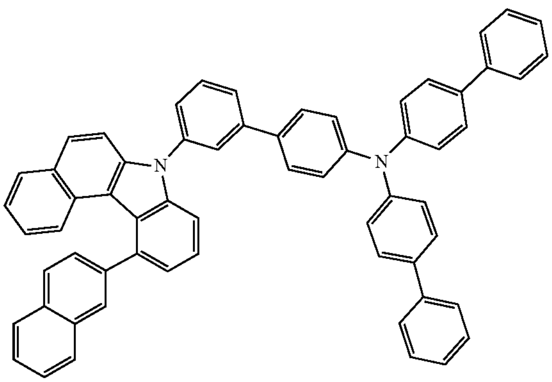
340
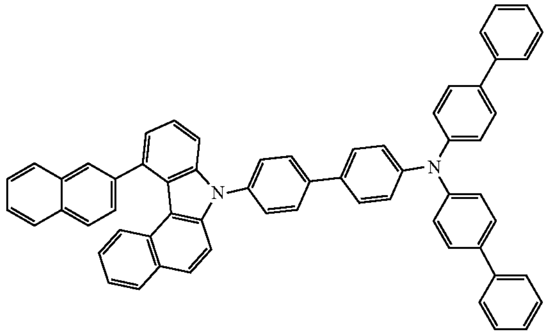
341
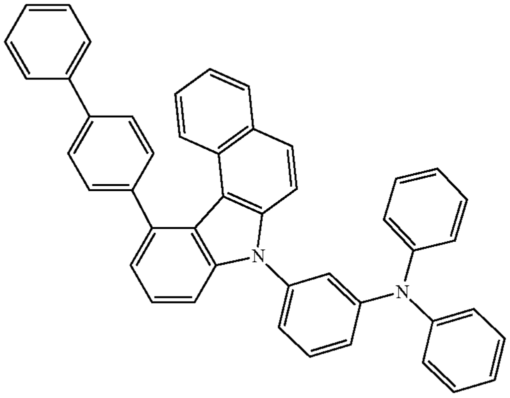
342
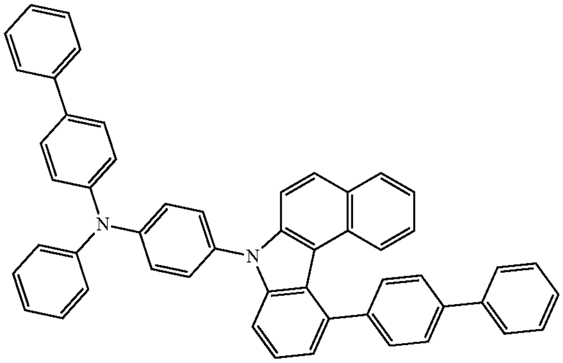
-continued
343
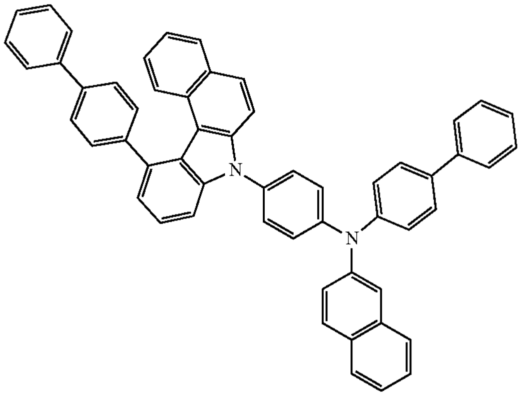
344
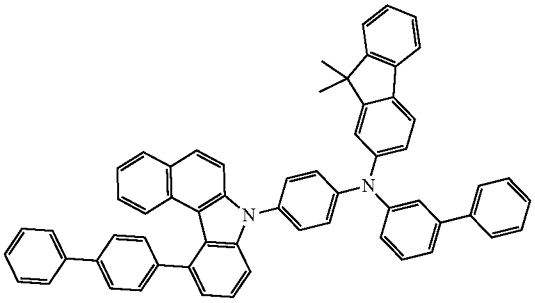
345
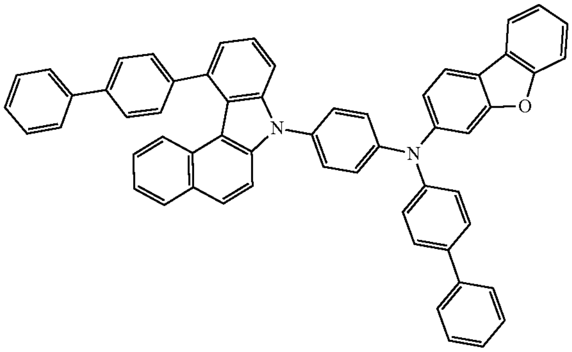
346
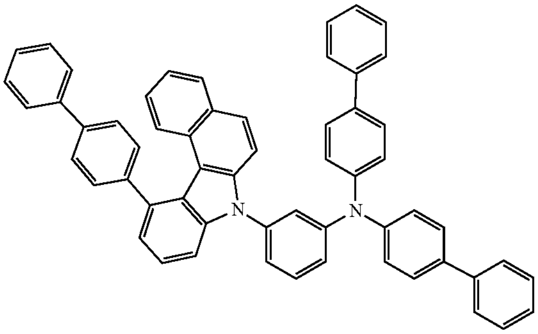

-continued
347
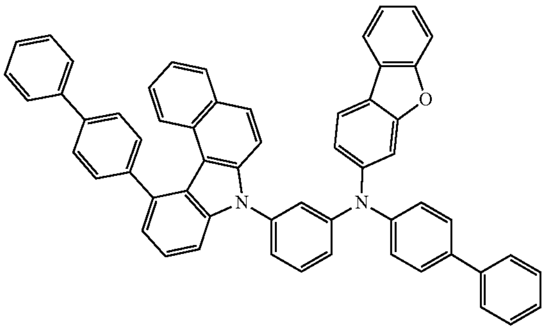
348
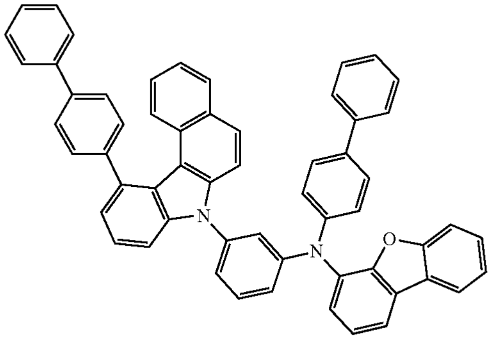
349
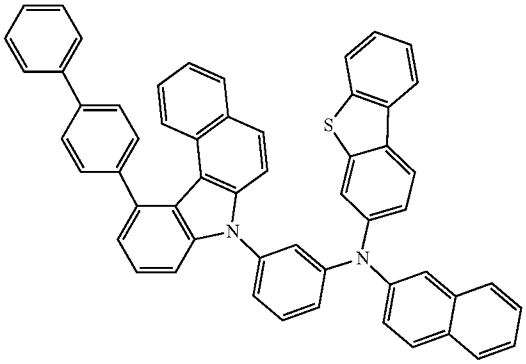
350
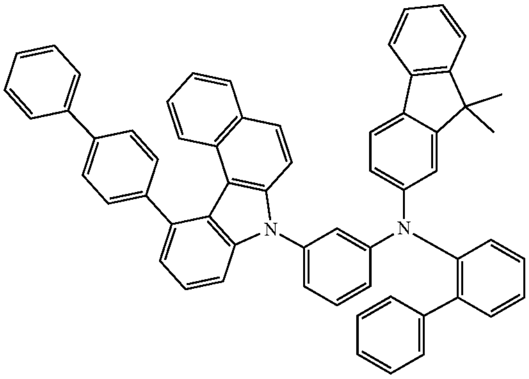
-continued
351
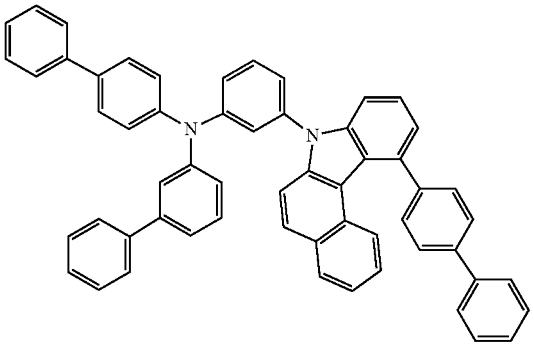
352
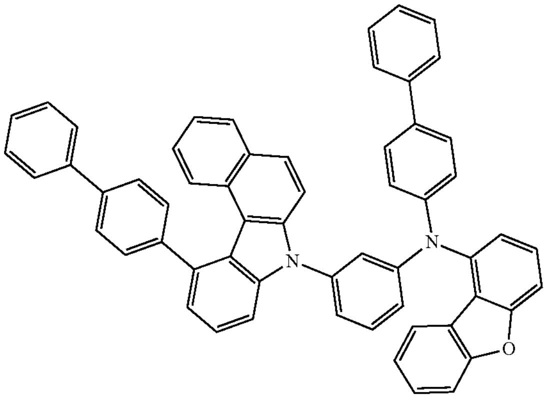
353
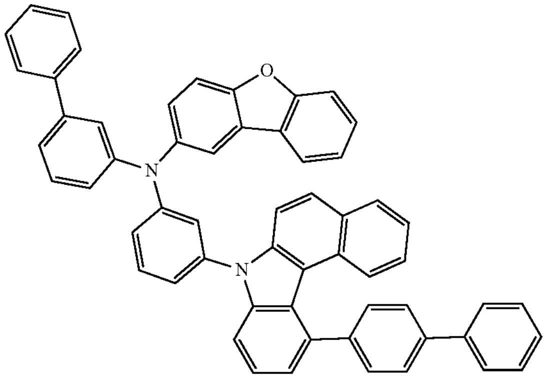
354
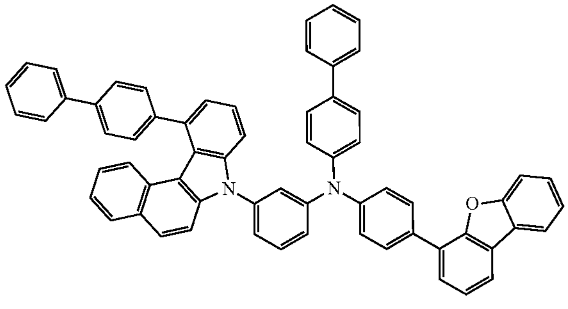

-continued
355
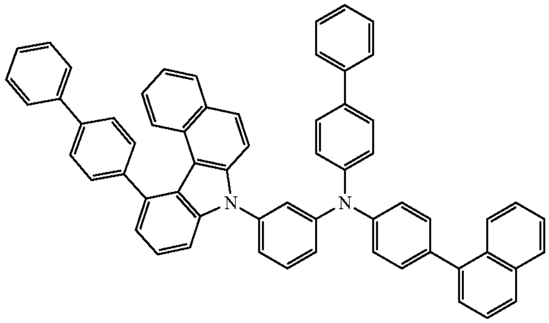
356
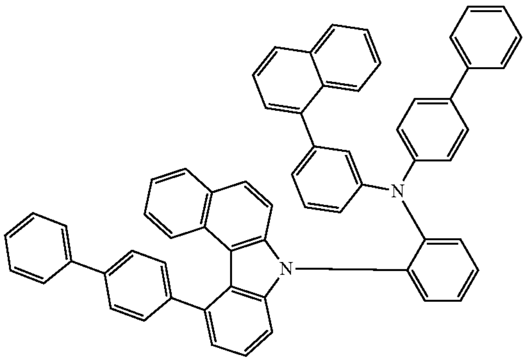
357
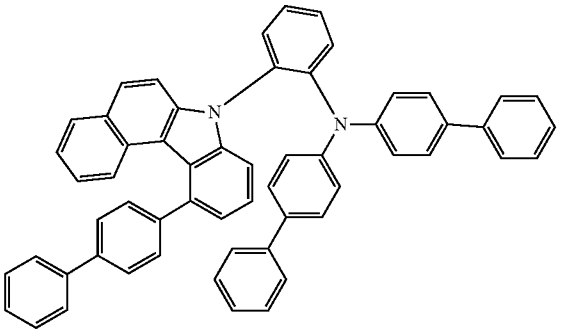
358
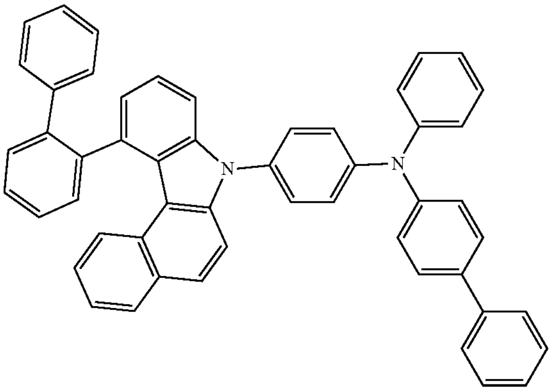
-continued
359
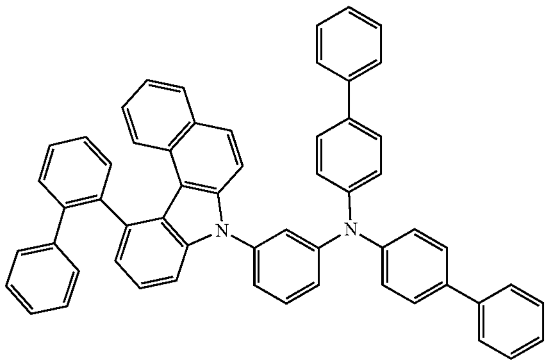
360
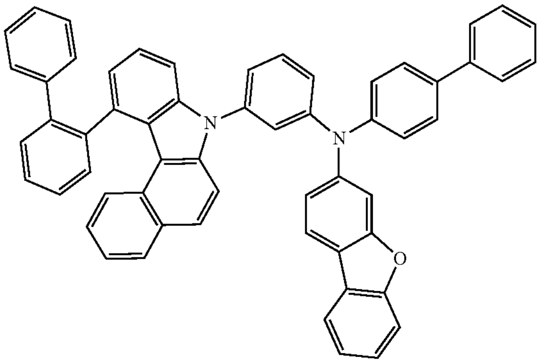
361
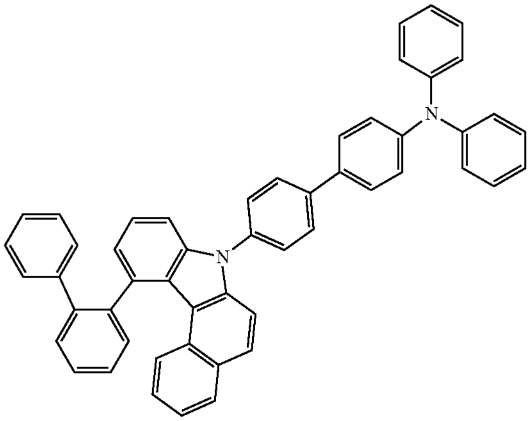
362
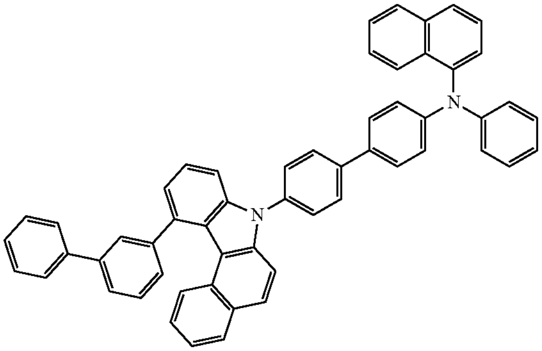

-continued
363
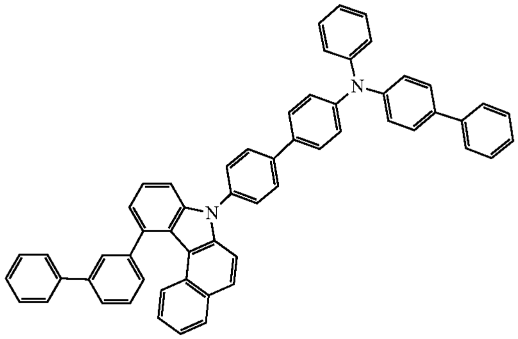
364
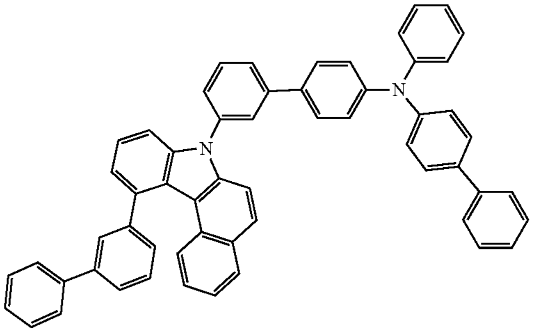
365
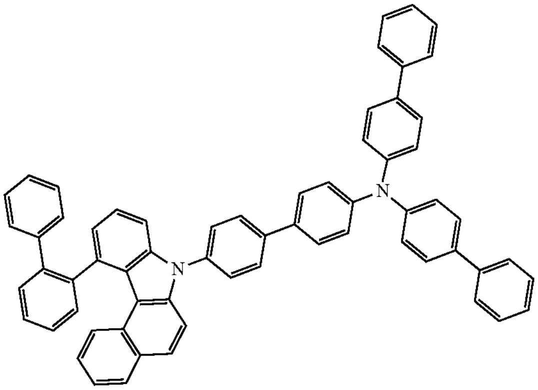
366
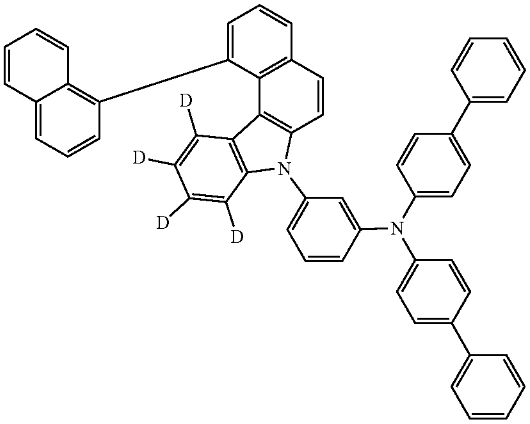
-continued
367
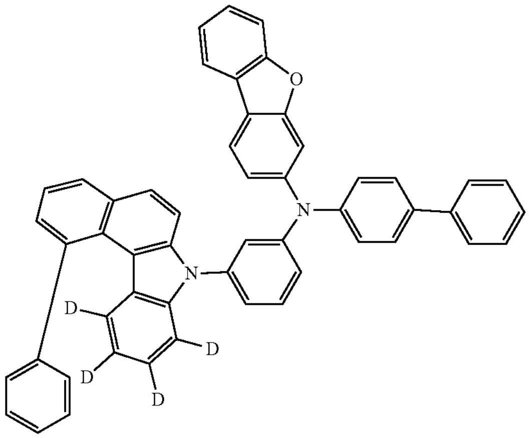
368
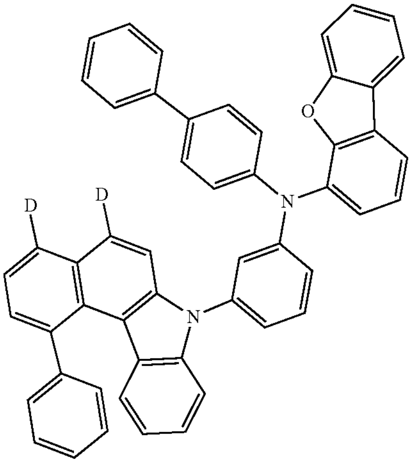
369
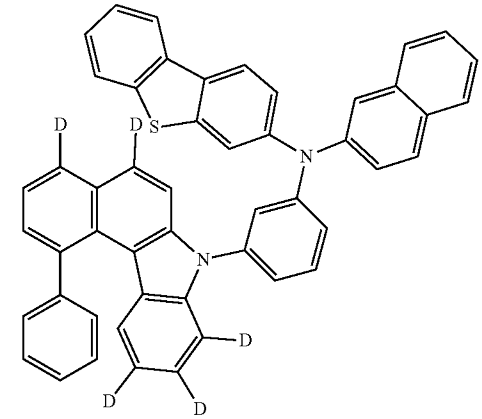

-continued
370
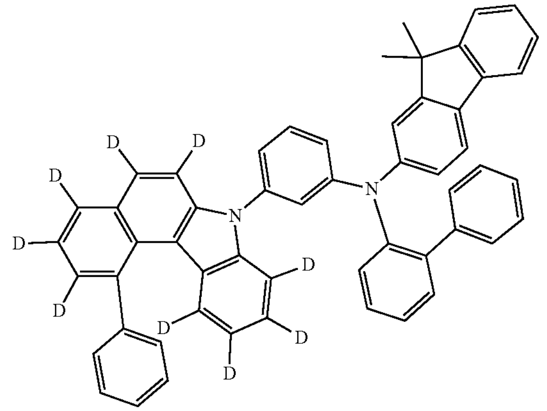
371
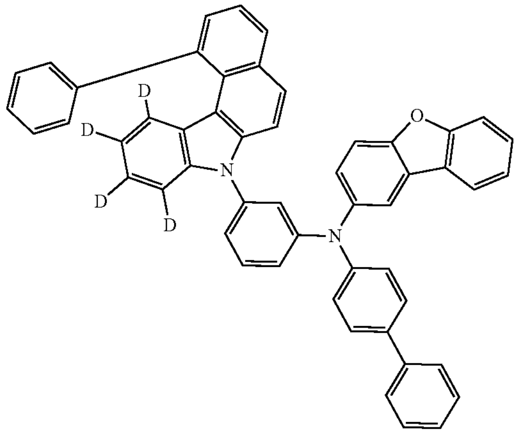
372
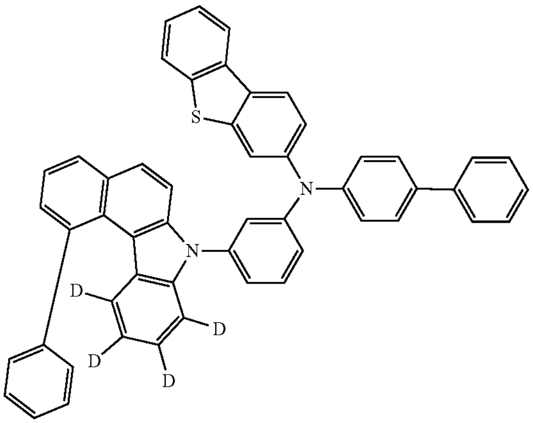
-continued
373
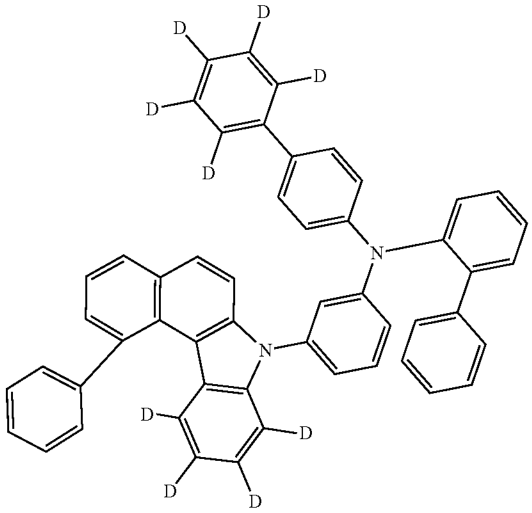
374
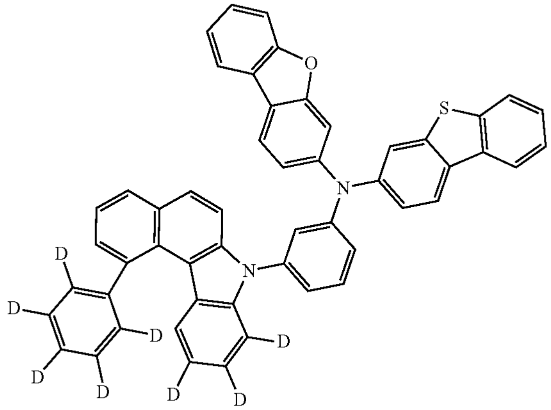
375
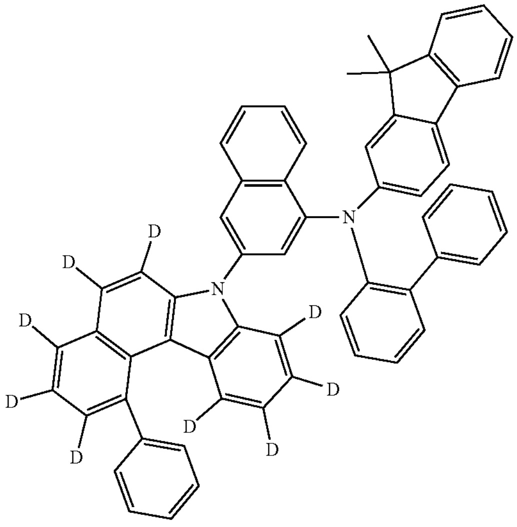

-continued
376
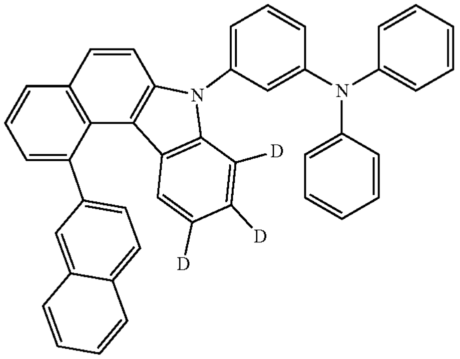
377
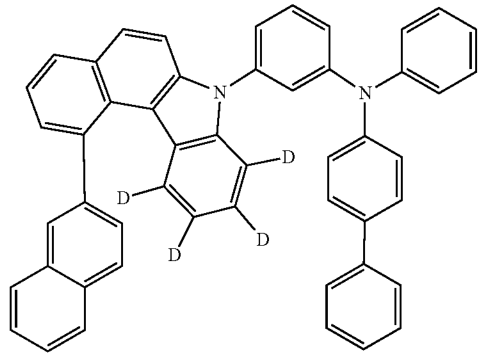
378
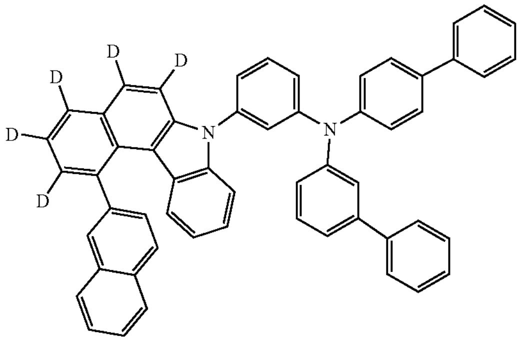
379
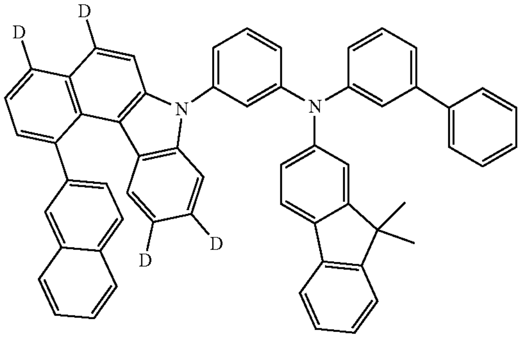
-continued
380
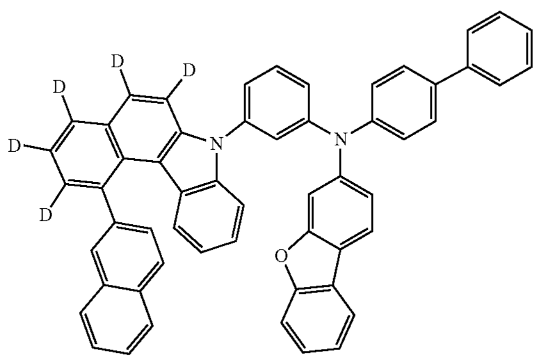
381
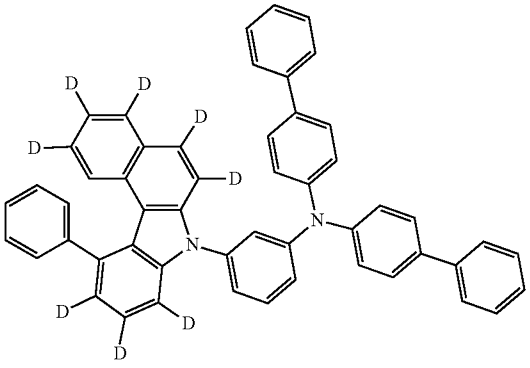
382
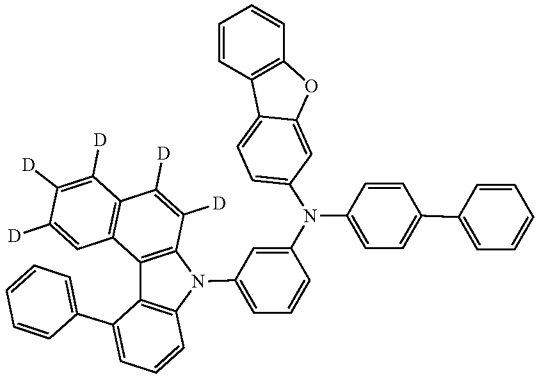
383
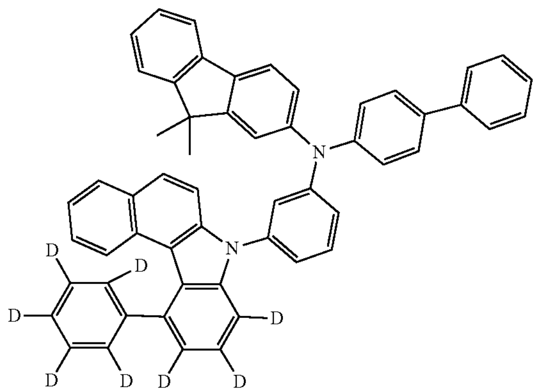

-continued
384
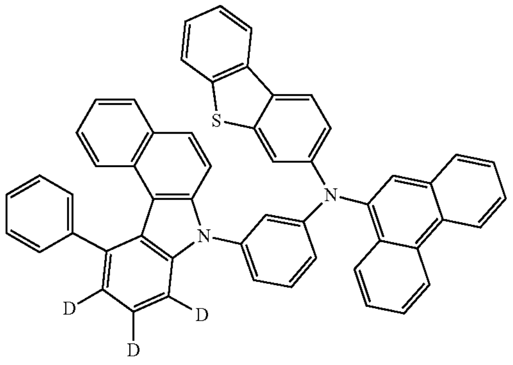
385
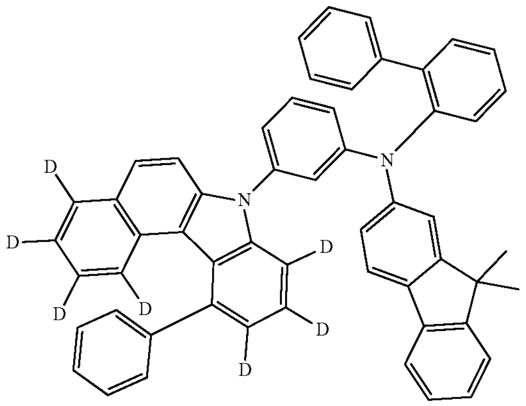
386
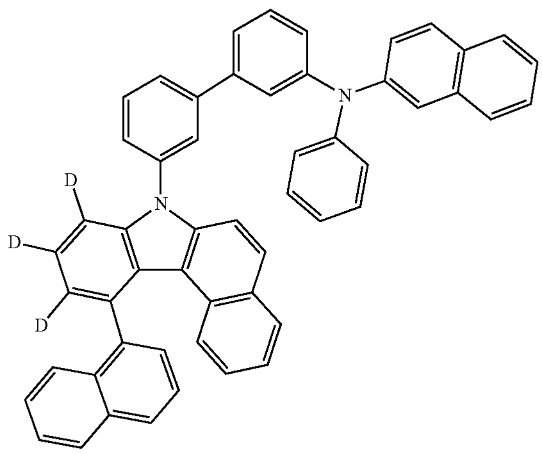
-continued
387
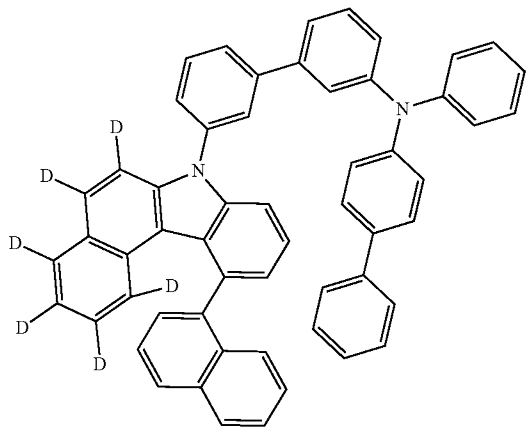
388
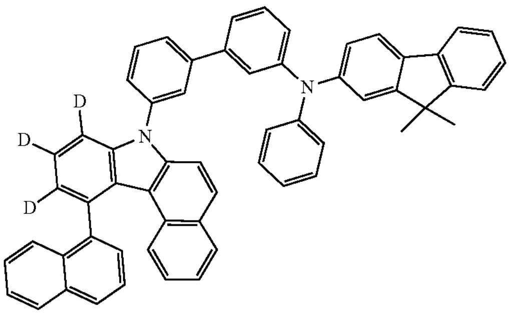
389
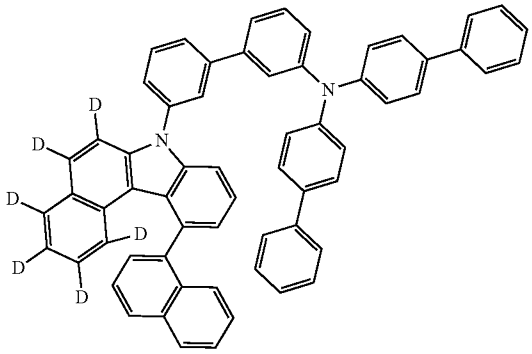
390
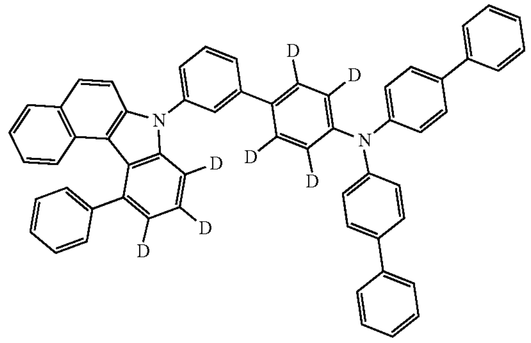

-continued

391

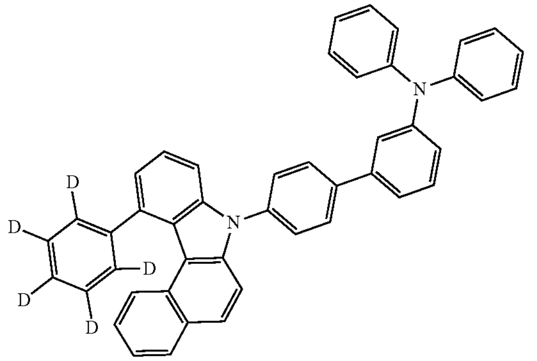

392

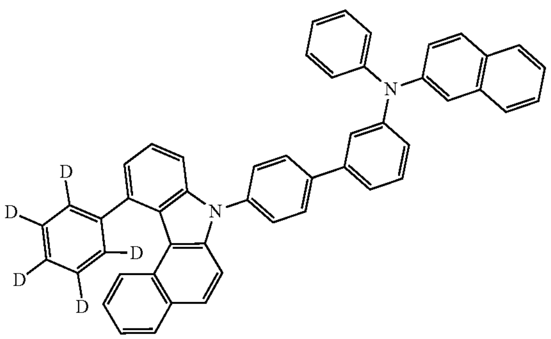

393

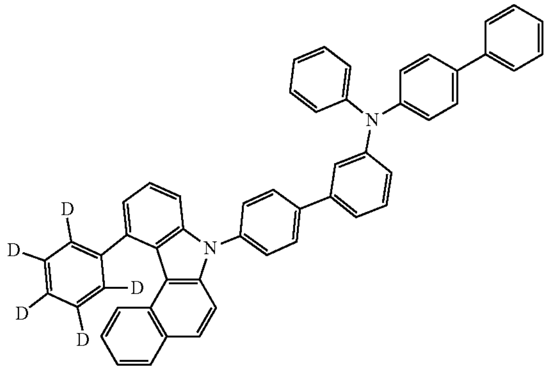

-continued

394

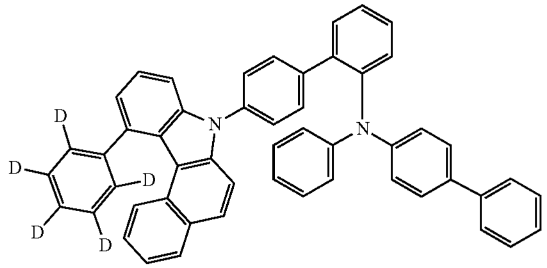

395

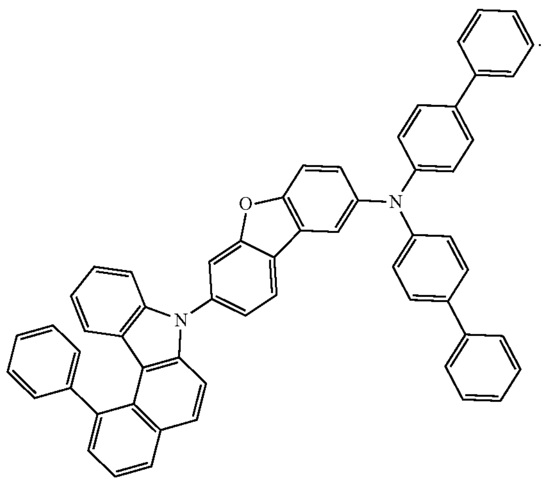

7. An electronic element, comprising an anode and a cathode disposed opposite to each other, and a functional layer disposed between the anode and the cathode; wherein the functional layer comprises the nitrogen-containing compound according to claim 1.

8. The electronic element according to claim 7, wherein the functional layer comprises a hole transport layer, and the hole transport layer comprises the nitrogen-containing compound.

9. The electronic element according to claim 7, wherein the electronic element is an organic electroluminescent device, and the hole transport layer comprises a first hole transport layer and a second hole transport layer that are stacked in sequence, and relative to the second hole transport layer, the first hole transport layer is closer to the anode; wherein the second hole transport layer comprises the nitrogen-containing compound.

10. An electronic device, comprising the electronic element according to claim 7.

11. The electronic element according to claim 7, wherein the electronic element is selected from an organic electroluminescent device and a photoelectric conversion device.

* * * * *